US008604023B2

(12) United States Patent
Glick et al.

(10) Patent No.: US 8,604,023 B2
(45) Date of Patent: Dec. 10, 2013

(54) 1,4-BENZODIAZEPINONE COMPOUNDS AND THEIR USE IN TREATING CANCER

(75) Inventors: Gary D. Glick, Ann Arbor, MI (US); Clarke Bentley Taylor, Ann Arbor, MI (US); Peter Laurence Toogood, Ann Arbor, MI (US); Chad Alan Van Huis, Plymouth, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 60 days.

(21) Appl. No.: 13/263,962

(22) PCT Filed: Apr. 16, 2010

(86) PCT No.: PCT/US2010/031435
§ 371 (c)(1),
(2), (4) Date: Dec. 6, 2011

(87) PCT Pub. No.: WO2010/121164
PCT Pub. Date: Oct. 21, 2010

(65) Prior Publication Data
US 2012/0094982 A1    Apr. 19, 2012

Related U.S. Application Data

(60) Provisional application No. 61/170,176, filed on Apr. 17, 2009.

(51) Int. Cl.
C07D 243/14 (2006.01)
C07D 403/04 (2006.01)
C07D 413/04 (2006.01)
A61K 31/55 (2006.01)
A61K 31/5513 (2006.01)
A61P 35/00 (2006.01)

(52) U.S. Cl.
USPC .......................... 514/221; 540/504

(58) Field of Classification Search
USPC .......................... 540/504; 514/221
See application file for complete search history.

(56) References Cited

U.S. PATENT DOCUMENTS

| 3,261,828 A | 7/1966 | Uskokovic et al. |
| 3,374,264 A | 3/1968 | Uskokovic |
| 3,384,635 A | 5/1968 | Calabateas et al. |
| 3,415,814 A | 12/1968 | Calabateas et al. |
| 3,847,905 A | 11/1974 | Bub |
| 4,076,823 A | 2/1978 | Wade et al. |
| 4,088,756 A | 5/1978 | Voorhees |
| 4,108,852 A | 8/1978 | Bub |
| 4,110,337 A | 8/1978 | Szarvasi et al. |
| RE30,293 E | 6/1980 | Bub |
| 4,495,101 A | 1/1985 | Klaubert et al. |
| 4,551,480 A | 11/1985 | Stiefel et al. |
| 4,560,684 A | 12/1985 | Sugasawa |
| 4,623,646 A | 11/1986 | Casals-Stenzel |
| 4,751,223 A | 6/1988 | Glamkowski et al. |
| 4,820,834 A | 4/1989 | Evans |
| 4,894,366 A | 1/1990 | Okuhara |
| 4,898,861 A | 2/1990 | Morgan et al. |
| 4,916,138 A | 4/1990 | Ueda |
| 4,929,611 A | 5/1990 | Okuhara |
| 4,946,778 A | 8/1990 | Ladner et al. |
| 5,004,741 A | 4/1991 | Evans |
| 5,041,438 A | 8/1991 | Hsu et al. |
| 5,141,930 A | 8/1992 | Nakao et al. |
| 5,147,872 A | 9/1992 | Golwyn |
| 5,216,148 A | 6/1993 | Klaus et al. |
| 5,288,514 A | 2/1994 | Ellman |
| 5,324,726 A | 6/1994 | Bock et al. |
| 5,391,566 A | 2/1995 | Chakravarty |
| 5,444,092 A | 8/1995 | Collins |
| 5,521,170 A | 5/1996 | Setoi |
| 5,545,568 A | 8/1996 | Ellman |
| 5,559,230 A | 9/1996 | Ogawa et al. |
| 5,591,227 A | 1/1997 | Dinh et al. |
| 5,597,915 A | 1/1997 | Chambers et al. |
| 5,599,352 A | 2/1997 | Dinh et al. |
| 5,633,251 A | 5/1997 | Claremon |
| 5,677,282 A | 10/1997 | Oleksyszyn |
| 5,697,967 A | 12/1997 | Dinh et al. |
| 5,763,437 A | 6/1998 | Sato |
| 5,776,946 A | 7/1998 | McGeer et al. |
| 5,861,380 A | 1/1999 | Gyorkos et al. |
| 5,962,337 A | 10/1999 | Ohlmeyer |
| 6,004,942 A | 12/1999 | Firestein et al. |
| 6,074,859 A | 6/2000 | Hirokawa |
| 6,080,588 A | 6/2000 | Glick et al. |

(Continued)

FOREIGN PATENT DOCUMENTS

| CA | 2372150 | 11/2000 |
| CA | 2457405 | 2/2003 |

(Continued)

OTHER PUBLICATIONS

Shoemaker, Hans, et al., "Specific High-Affinity Binding Sites for [3H]Ro 5-4864 in Rat Brain and Kidney," The Journal of Pharmacology and Experimental Therapeutics, vol. 225, No. 1 (1983).
Tarpley, et al., J. Chroni Diseases (1965), 18 (abstract only).
Dourlat, et al., "Novel 1,4-benzodiazepine derivaties with antiproliferative properties on tumor cell lines," Bioorganic & Medicinal Chemistry Letters, 2007, vol. 17, Issue 9, pp. 2527-2530.
Elz et al., 1989 Eur. J. Med Chem. 259-262.
Atwal et al., Tet Lett. 30, 1989, 7313.
Johnson, K.M., et al., Chemistry & Biology, 2005, 12:485-496.
Francis, T.M., et al., "Identification of cytotoxic, T-cell-selective 1,4-benzodiazepine-2,5-diones," Bioorganic & Medicinal Chemistry Letters, Pergamon, Elsevier Science, GB, vol. 16, No. 9, May 1, 2006, pp. 2423-2427.

(Continued)

Primary Examiner — Bruck Kifle
(74) Attorney, Agent, or Firm — Fish & Richardson P.C.

(57) ABSTRACT

The invention provides a family of 1,4-benzodiazepinone compounds and methods for their use as therapeutic agents in treating cancer. Pharmaceutical compositions and methods of making the 1,4-benzodiazepinone compounds are provided.

24 Claims, No Drawings

(56) References Cited

U.S. PATENT DOCUMENTS

| | | |
|---|---|---|
| 6,100,254 A | 8/2000 | Budde et al. |
| 6,239,131 B1 | 5/2001 | Shinozaki |
| 6,277,844 B1 | 8/2001 | Spector et al. |
| 6,319,931 B1 | 11/2001 | Kroemer et al. |
| 6,506,744 B1 | 1/2003 | Alig |
| 6,524,623 B1 | 2/2003 | Hodosh |
| 6,524,832 B1 | 2/2003 | Kufe et al. |
| 6,579,854 B1 | 6/2003 | Mitchell et al. |
| 6,605,593 B1 | 8/2003 | Naicker |
| 6,613,739 B1 | 9/2003 | Naicker |
| 6,767,533 B1 | 7/2004 | Casellas |
| 6,824,561 B2 | 11/2004 | Soykan et al. |
| 6,916,813 B2 | 7/2005 | Atwal |
| 7,109,224 B2 | 9/2006 | Kempson |
| 7,125,866 B1 | 10/2006 | Glick |
| 7,144,880 B2 | 12/2006 | Glick |
| 7,150,433 B2 | 12/2006 | Healy |
| 7,175,953 B2 | 2/2007 | Licha |
| 7,220,739 B2 | 5/2007 | Glick |
| 7,250,410 B2 | 7/2007 | Bourguignon |
| 7,276,348 B2 | 10/2007 | Glick |
| 7,351,421 B2 | 4/2008 | Sung |
| 7,572,788 B2 | 8/2009 | Glick |
| 7,638,624 B2 | 12/2009 | Glick |
| 7,683,046 B2 | 3/2010 | Glick |
| 7,851,465 B2 | 12/2010 | Glick |
| 2002/0025946 A1 | 2/2002 | Buchanan et al. |
| 2002/0048566 A1 | 4/2002 | El-Deiry et al. |
| 2002/0128208 A1 | 9/2002 | Snyder |
| 2003/0044776 A1 | 3/2003 | Dykens et al. |
| 2003/0119029 A1 | 6/2003 | Glick |
| 2004/0009972 A1 | 1/2004 | Ding |
| 2004/0087489 A1 | 5/2004 | Ruiz |
| 2004/0157833 A1 | 8/2004 | Harris |
| 2004/0176358 A1 | 9/2004 | Glick |
| 2005/0113460 A1 | 5/2005 | Glick |
| 2005/0261176 A1 | 11/2005 | Glick |
| 2005/0272723 A1 | 12/2005 | Glick |
| 2006/0025388 A1 | 2/2006 | Glick |
| 2006/0052369 A1 | 3/2006 | Glick |
| 2006/0166975 A1 | 7/2006 | Glick |
| 2007/0036854 A1 | 2/2007 | Glick |
| 2007/0043033 A1 | 2/2007 | Glick |
| 2007/0105844 A1 | 5/2007 | Glick |
| 2007/0111994 A1 | 5/2007 | Glick |
| 2007/0135418 A1 | 6/2007 | Glick |
| 2007/0299059 A1 | 12/2007 | Glick |
| 2008/0064686 A1 | 3/2008 | Durrani |
| 2009/0275099 A1 | 11/2009 | Glick |

FOREIGN PATENT DOCUMENTS

| | | |
|---|---|---|
| CA | 2457405 | 3/2003 |
| CA | 2524394 | 7/2011 |
| DE | 1810423 | 10/1969 |
| EP | 0227539 | 5/1990 |
| EP | 0 349 949 | 10/1990 |
| EP | 0 906 907 | 4/1999 |
| EP | 1143946 | 10/2001 |
| EP | 1423122 | 2/2003 |
| EP | 1398033 | 3/2004 |
| EP | 1622684 | 2/2006 |
| EP | 1742640 | 7/2006 |
| EP | 1778204 | 5/2007 |
| EP | 1786429 | 5/2007 |
| EP | 1845996 | 10/2007 |
| GB | 1363735 | 8/1974 |
| RU | 2096044 | 11/1997 |
| WO | 90/05305 | 5/1990 |
| WO | 90/13332 | 5/1990 |
| WO | 91/12779 | 9/1991 |
| WO | 9201683 | 2/1992 |
| WO | 94/08234 | 4/1994 |
| WO | 97/01560 | 1/1997 |
| WO | 97/30992 | 8/1997 |
| WO | 98/14192 | 4/1998 |
| WO | 98/57161 | 12/1998 |
| WO | 99/19306 | 4/1999 |
| WO | 99/29347 | 6/1999 |
| WO | 99/58117 | 11/1999 |
| WO | 99/66958 | 12/1999 |
| WO | 99/67220 | 12/1999 |
| WO | 00/19200 | 6/2000 |
| WO | 00/66106 | 11/2000 |
| WO | 01/51922 | 7/2001 |
| WO | 02/067988 | 9/2002 |
| WO | 02/098865 | 12/2002 |
| WO | 03/015703 | 2/2003 |
| WO | 03/041658 | 5/2003 |
| WO | 03/045901 | 6/2003 |
| WO | 03/050261 | 6/2003 |
| WO | 03/106628 | 12/2003 |
| WO | 2004/050610 | 6/2004 |
| WO | 2005/004988 | 1/2005 |
| WO | 2006/007532 | 1/2006 |
| WO | 2006014526 | 2/2006 |
| WO | 2006/029245 | 3/2006 |
| WO | 2006002945 | 3/2006 |
| WO | 2006073448 | 7/2006 |
| WO | 2006074358 | 7/2006 |
| WO | 2007050587 | 5/2007 |
| WO | 2007053193 | 5/2007 |
| WO | 2007053725 | 5/2007 |
| WO | 2007146167 | 12/2007 |
| WO | 2008112553 | 9/2008 |
| WO | 2008116156 | 9/2008 |
| WO | 2008/133635 | 11/2008 |
| WO | 2009/036175 | 3/2009 |
| WO | 2009/061916 | 5/2009 |

OTHER PUBLICATIONS

Akssira, M., et al., "New Routes to 1,4-benzodiazepin-2,5-diones," Tetrahedron (1994), vol. 50, No. 30, pp. 9051-9060.

Mohiuddin, G., et al., "A Versatile Synthesis of 3H-1(H), 4(H)-Benzodiazepin-2,5-diones," Indian Journal of Chenmistry, 1985, vol. 24B, pp. 905-907.

Boojamra, Constantine G., et al., "An Expedient and High-Yielding Method for the Solid-Phase Synthesis of Diverse 1,4-Benzodiazepine-2, 5-diones," Journal of Organic Chemistry, 1995, vol. 60, No. 18, pp. 5742-5743.

Keating, Thomas A., et al., "A Remarkable Two-Step Synthesis of Diverse 1, 4-Benzodiazepine-2, 5-diones Using the Ugi Four-Component Condensation," Journal of Organic Chemistry, 1996, vol. 61, No. 25, pp. 8935-8939.

Juaristi, Eusebio, et al., "Enantioselective Synthesis of α-Amino Acids from Chiral 1, 4-enzodiazepine-2, 5-diones Contianing the α-Phenethyl Group," Journal of Organic Chemistry, Mar. 26, 1999, vol. 64, No. 8, pp. 2914-2918.

Marc, Gasper, et al., "High Yield Phase Transfer N-Alkylation of Some Benzodiazepinese by Esters of ω-Halo Acids," Synthetic Communications, 1998, vol. 28, No. 7, pp. 1143-1157.

Bolli, M.H., et al., "Novel Benzo[1,4]diazepin-2-one-Derivatives as Endothelin Receptor Antagonists", Journal of Medicinal Chemistry, vol. 47, No. 11, Apr. 23, 2004, pp. 2776-2795.

Cunha, 2006, "The first bismuth(III)-catalyzed guanylation of thioureas", Tetrahedron Letters 47:6955-56.

Cunha, 2002, "Bismuth nitrate pentahydrate: a new and environmentally benign reagent for guanidylation of N-benzoylthioureas", Tetrahedron Letters 43: 49-52.

Yang, Masafumi, et al., "Effect of Milrinone on Left Ventricular Relaxation and Ca2+ Uptake Function of Cardiac Sarcoplasmic Reticulum," Am. J. Physiol. Heart Circ. Physiol, 279: H1898-H1905 (2000).

Gatza, et al., "Manipulating the Bioenergetics of Alloreactive T Cells Causes Their Selective Apoptosis and Arrests Graft-Versus-Host Disease," Sci. Transl. Med. 3(67ra8): 1-8 (2011).

Shoemaker, et al., "The NC160 Human Tumour Cell Line Anticancer Drug Screen," Nat. Rev. Cancer 6:813-823 (2006).

Solomko, et al., Chemistry of Heterocyclic Compounds, vol. 11, No. 11, Nov. 1975, pp. 1231-1248.

(56) References Cited

OTHER PUBLICATIONS

Algarra, et al., "Application of the Photo-Fries Rearrangement of Aryl N-Chloroacetylanthranylates as Key Step in the . . . ", Heterocycles, vol. 36 1993, pp. 2335-2344.

EP Patent Application No. 06 717616 Supplementary Search Report dated Mar. 26, 2009.

Levitzki, Alexander, "Protein Tyrosine Kinase Inhibitors as Novel Therapeutic Agents," Pharmacol. Ther. vol. 82, Nos. 2-3, pp. 231-239 (1999).

Sanchez, et al., "Tumorigenic activity of the BCR-ABL oncogenes is mediated by BCL2" Proc Natl Acad Sci U S A (Jun. 6, 1995) 92(12) 5287-5291.

Ji Yang, et al., "Prevention of Apoptosis by BCL-2; Release of Cytochrome c from Mitochondria Blocked" Science 275, 1129 (1997).

Prindull, "Apoptosis in the embryo and tumorigenesis" European Journal of Cancer, vol. 31, Issue 1 (1995) pp. 116-123.

Chinese Office Action, CN Patent Application No. 200580029827.4, dated Apr. 17, 2009.

Lowe, "Systemic treatment of severe psoriasis," The New England Journal of Medicine, 324 (5), Feb. 7, 1991, pp. 333-334.

Laupacis, et al., "Cyclosporin A: a powerful immunosuppressant", CMA Journal, May 1, 1982, vol. 126, pp. 1041-1046.

Otto, Michael W., Ph.D., et al., "Benzodiazepine Use, Cognitive Impairment, and Cognitive-Behavioral Therapy for Anxiety Disorders: Issues in the Treatment of a Patient in Need," J. Clin. Psychiatry, 2005, 66 (supp 2).

Yoshi, M., et al., (2005) Nippon Yakurigaku Zasshi 125(1):33-36 (English Abstract attached).

Yasuda, K., (2004) Nippon Rinsho. 62 Suppl. 12:360-363. Abstract not available.

Decaudin, Didier, "Peripheral benzodiazepine receptor and its clinical targeting," Anti-Cancer Drugs, 2004, vol. 15, No. 8.

Bonnot, O., et al., "Exposition in utero au lorazepam et atresie anale: signal epidemiologique," (2003) Encephale. 29(6):553-559.

Lacapere, Jean-Jacques, Vassilios Papadopoulos, "Peripheral-type benzodiazepine receptor: structure and function of a cholesterol-binding protein in steroid and bile acid biosynthesis," Steroids, 68 (2003) 569-585.

Galiegue, S., et al., "The Peripheral Benzodiazepine Receptor: A Promising Therapeutic Drug Target," (2003) Curr. Med. Chem 10(16):1563-1572.

Papadopoulo, V. (2003), Lecture: Peripheral benzodiazepine receptor: structure and function in health and disease, Ann. Pharm. Fr. 61(1):30-50.

Goethals, Ingeborg, et al., "Is central benzodiazepine receptor imaging useful for the identification of epileptogenic foci in localization-related epilepsies?" European Journal of Nuclear Medicine and Molecular Imaging vol. 30, No. 2, Feb. 2003.

Castedo, Marian, et al., "Mitochondrial Apoptosis and the Peripheral Benzodiazepine Receptor: a Novel Target for Viral and Pharmacological Manipulation," The Journal of Experimental Medicine, vol. 196, No. 9, Nov. 4, 2002.

Buffett-Jerrott S.E. et al., "Cognitive and Sedative Effects of Benzodiazepine Use," Current Pharmaceutical Design, 2002, 8, 45-48.

Smyth, W.F., et al. (1998), "A critical evaluation of the application of capillary electrophoresis to the detection and determination of 1,4-benzodiazepine tranquilizers in formulations and body materials," Electrophoresis 19(16-17):2870-2882.

Yoshii, M., et al. (1998) Nihon Shinkeo Seishin Yakurigaku Zasshi, 18(2):49-54.

Varani, et al., (1994), "All-trans Retinoic Acid (RA) Stimulates Events in Organ-cultured Human Skin that Underlie Repair," J. Clin. Invest., 94:1747-1753.

Griffith, C.E., "Editorial Comment: Ascomycin: an advance in the management of atopic dermatitis," Br. J. Dermatol., Apr. 2001; 144(4):679-81.

Stern, R.S. (1995), "Epidemiology of Psoriasis," Dermatologic Clinics, 13:717-722.

Fry, L (1988), "Psoriasis," Brit. J. Dermatol., 119:445-461.

Krueger GC, et al., (1984), "Psoriasis," J. Am. Acad. Dermatol., 11:937-947.

Varani, J., et al. (2001), "Heparin-Binding Epidermal-Growth-Factor-Like Growth Factor Activation of Keratinocyte ErbB . . . ", J. Invest. Dermatol., 117:1335-1341.

Varani, J., et al., "A Novel Benzodiazepine Selectively Inhibits Keratinocyte Proliferation . . . ", The Journal of Pharmacology and Experimental Therapeutics, 2005, vol. 313, No. 1, pp. 56-63.

International Search Report and Written Opinion, PCT/US2008/082629, mailed Jun. 1, 2009.

Bhagavathula, Narasimharao, et al., "7-Chloro-t-(4-hydroxyphenyl_-1-methyl-3-(naphthalen-2-ylmethyl) . . . ", J. Pharmacol & Exp Ther 324: 938-947 (2008).

Borea, "Stereochemical Features Controlling Binding and Intrinsic Activity Properties of Benzodiazepine Receptor Ligands", Molecular Pharmacology, Apr. 1987, 31 (4), pp. 334-344, p. 344, Abstract.

Mahrle, et al., Br. J. Bermatol. 1974, 91, 529-540.

Mui et al. Br. J. Dermatol. 1975, 92, 255-262.

EP Search Report dated Nov. 26, 2009, EP Patent Application No. 09003224.4.

Nadin, Alan, et al., "New Synthesis of 1,3-Dihydro-1,4-benzodiazepin-2(2H)-ones and 3-Amino-1,3-dihydro-1,4-benzodiazepin-2(2H)-ones: Pd-Catalyzed Cross-Coupling of Imidoyl Chlorides with Organoboronic Acids," J. Org. Chem., 2003, 68, pp. 2844-2852.

Reddy, Pavan, et al., "Interleukin-18 Regulates Acute Graft-Versus-Host Disease by Enhancing Fas-mediated Donor T Cell Apoptosis," J. Exp. Med., 2001, 194: 1433-1440.

Bossu, et al., "IL-18 cDNA vaccination protects mice from spontaneous lupus-like automimmune disease," PNAS 2003, 100: 14181-14186.

De Bandt, et al., "Systemic lupus erythematosus induced by anti-tumour necrosis factor alpha therapy: a French national survey," Arthritis Res. & Ther., 2005, 7: R545-R551.

Abunasser, et al., "Etanercept-Induced Lupus Erythematosus Presenting as a Unilateral Pleural Effusion," Chest 2008, 134: 850-853.

Busca, et al., "Recombinant human soluble tumor necrosis factor receptor fusion protein as treatment for steroid refractory graft-versus-host disease following allogeneic hematopoietic stem cell transplatation," Am. J. Hematol., 2007, 82: 45-52.

Kyungjin, Kim, Steven K. Volkkan, and Jonathan A. Ellman, Synthesis of 3-Substituted 1,4-Benzodiazepin-2-ones, J. Braz. Chem. Soc. vol. 9(4), 375-379 (1998).

Kluge, et al., "Kinetics of Inactivation of the F1F0 ATPase of Propionigenium modestum by Dicyclohexylcarbodiimide in Relationship to H+ and Na+ Concentration: Probing the Binding Site for the Coupling Ions," Biochemistry 1993, 32, 10378-10386.

Covelli, Vito, "Stress, Neuropsychiatric Disorders and Immunological Effects Exerted by Benzodiazepines," Immunopharmacology and Immunotoxicology, 20(2), 199-209 (1998).

EP Search Report dated Jun. 23, 2010, EP Patent Application No. 10 003 823.1.

EP Search Report dated Aug. 10, 2010, EP Patent Application No. 08731682.4.

Office Action Mailed Apr. 3, 2009, U.S. Appl. No. 11/176,719, filed Jul. 6, 2005.

Office Action Mailed Aug. 19, 2009, U.S. Appl. No. 11/176,719, filed Jul. 6, 2005.

Office Action Mailed May 24, 2010, U.S. Appl. No. 11/176,719, filed Jul. 6, 2005.

Huse et al., "Generation of a Large Combinatorial Library of the Immunoglobulin Repertoire in Phage Lambda", Science, 246:1275-1281 [1989].

International Search Report and Written Opinion of PCT/US2008/057827 dated Oct. 6, 2008.

IPER and ISR for PCT/us02/31942 mailed Feb. 2, 2007.

Itoh, N., et al., "The Polypeptide Encoded by the cDNA for Human Cell Surface Antigen Fas Can Mediate Apoptosis," Cell 66:233-243 (1991).

(56) References Cited

OTHER PUBLICATIONS

Johnson, et al., "Mechanistic Basis for Therapeutic Targeting of the Mitochondrial FF-ATPase", downloaded from http://pubs.acs.org on Dec. 5, 2008, ASC Chem. Biol. 1 (5), 304-308, Publication Date (WEB): Jun. 9, 2006.

Jones, The non-conalent interaction of pyrrolo[2,1-c][benzodiazepines-5, 11-diones with DNA, Anti-Cancer Drug Design, 5:249-264 (1990).

Kamal, A., "Synthesis of DNA-interactive Pyrrolo[2,1-c][1,4] benzodiazepines by employing polymer-supported reagents . . . ," Synlett, 14,(2004), 2533-35.

Karle Jesper et al., "Diazepam protects against rat hippocampal neuronal cell death induced by antisense oligodeoxynucleotide to GABA-A receptor gamma-2 subunit" Brain Research, vol. 765, No. 1, 1997, pp. 21-29.

Kerver et al, "In situ detection of spontaneous superoxide anion and singlet oxygen production by mitochondria in . . . ", Histochem. J., 29:229-237 [1997] (Abstract only).

Kim et al., "Synthesis of 3-substituted 1,4-benzodiazepin-2-ones," J. Braz. Chem. Soc. 9:375-379 (1998).

Kohler and Milstein, "Continuous cultures of fused cells . . . ", Nature, 256:495-497 [1975].

Koopman, W.J., et al., "The MRL-Ipr/Ipr Mouse. A Model for the Study of Rheumatoid Arthritis," Scan& J. Rheumatolo Suppl 75:284-o289 (1988).

Korsmeyer, S.J., "Bcl-2 Initiates a New Category of Oncogenes: Regulators of Cell Death," Blood 80(4):879-886 (1992).

Kozbor, et al.• "The production of monoclonal antibodies from human lymphocytes", Immunol. Today, 4:72 [1983].

Lee, Sunwoo, et al., "Improved Catalysts for the Palladium-Catalyzed Synthesis of Oxindoles by . . . ", J. Org. Chem. 2001, 66, pp. 3402-3415.

Lewis et al., "Editors' view: Cancer pharmacotherapy: 21st century 'magic bullets' and changing paradigms", British Journal of Clinical Pharmacology, 2006, 62:1,pp. 1-4.

Liu, J.R., et al., "Bclox•. is Expressed in Ovarian Carcinoma and Modulates Chemotherapy-induced Apoptosis," Gynecologic Oncology 70:398-403 (1998).

Los, M., et al., The Role of Caspases in Development, Immunity, and Apoptotic Signal Transduction: Immunity—10:629-639 (1999).

Lowman, et al., "Mutational analysis and protein engineering of receptor-binding determinants in human placental lactogen", J. Biol. Chem. 266:10982 [1991].

Luria,et al., "Tumor Viruses", General Viology 3rd edition,. 436-446 (1978)—Eds. John Wile & Sons, New York.

Malgrange, B., et al., "I•-Carbolines Induce Apoptotic Death of Cerebellar Granule Neurones in Cultures," NeuroReport 7(18):3041-3045 (1996).

Marino, M., et al., "Prevention of Systemic Lupus Erythematosus in MRL/Ipr Mice by Administration of an Immunoglobulin . . . ," Nature Biotechnology—18:735-739 (2000).

MCDonnell'—349:254-256T'J et al., Progression from Lymphoid Hyperplasia to High-Grade . . . Nature-349:254-256 (1991).

Miccoli, et al., "Potentiation of Lonidamine and Diazepam . . . ", Journal of the National Cancer Institute, vol. 90, No. 18, pp. 1400-1406, Sep. 1998.

Miernik et al., "The antimitotic activities of some benzodiazepines", Experientia, 1986, 42, pp. 956-958.

Miller, K.A., et al., "Benzodiazepines Prevent Neuronal Death by Apoptosis & Necrosis . . . ," Society for Neuroscience Abstracts— 24(1-2):979 (1998).

Monks, A., et., Feasibility of High-Flux Anticancer Drug Screen Using a Diverse Panel of Cultured Human Tumor Cell Lines, Journal of the National Cancer Institute, 83:757-766 (1991).

Nagata, S., "Human Autoimmune Lymphoproliferative Syndrome, a Defect in the Apoptosis-Inducing Fas Receptor: A 55 Lesson from the Mouse Model," J. Hum. Genet 43:2-8 (1998).

Okuyama, H., et al., "Analysis of Defective Delayed-Type Hypersensitivity in Autoimmune Mice Bearing Ipr Gene," ClIn. Ex p. ImmunoL 63:87-94 1986.

Okuyama, H., et al., "Effect of Cyclophosphamide Pretreatment on Defective Delayed-Type Hypersensitivity . . . ," Int Arch. Allergy Appl. Immunol. 88:394-401 (1989).

Ozols, R.F., "Paclitaxel Plus Carboplatin in the Treatment of Ovarian Cancer," Seminars in Oncology 26(1) (Supp.2:84-89 (1999).

Paola Costantini et al., "Mitochondrion as Novel Target of Anticancer Chemotherapy", JNCI Journal of the National Cancer Institute 2000 92(13): 1042-1053; doi:10. 1093/jnci/92. 13. 1042.

Parks, Daniel J. "1,4-benzodiazepine-2,5-diones as small molecule antagonists of the HDM2-p53 interaction . . . " Bioorg Med Chem. Ltrs,. 15,(2005), 765-770.

Paull, K.D., et al., "Display and analysis of patterns of differential activity of drugs against human tumor . . . ", J. Natl. Cancer Inst., 81:1088-1092 [1989] (Abstract only).

Pestell, K.E., et al., "Charactehsation of the P53 Status, BCL-2 Expression and Radiation and Platinum Drug Sensitivity of . . . ," Int J. Cancer—77:913-918 (1998).

Giuseppe Piedimonte, et al., "Association of Tyrosine Protein Kinase Activity With Mitochondria in Human Fibroblasts," Journal of Cellular Biochemistry 32:113-123 (1986).

Raboisson, P. "Structure-based design, synthesis and biological evaluative of novel 1,4-diazepines as HDM2 antagonists," Bioorg Med Chem. Ltrs., 15,(2005), 1857-1861.

Ramdas et al., "Benzodiazepine compounds as inhibitors of the Src protein tyrosine kinase . . . " Archives of Biochemistry and Biophysics 368 (1999) 394-400.

Raynaud, F.I., et al., "Intracellular Metabolism of the Orally Active Platinum Drug JM216: Influence of Glutathione Levels," Br. J. Cancer 74(3) :380-?386 (1996).

Russell, J.H., et al., "Mature T Cells of Autoimmune Ipr/Ipr Mice have a Defect in Antigen-Stimulated Suicide," Proc. Nat. Acad. Sci. USA 90:4409-4413 (1993).

Sakata, K., et al., "Role of Fas/FasL Interaction in Physiology and Pathology: The Good and the Bad," Clinical Immunology and Immunopathology 87(1):1-7 (1998).

Sandstrom, P.A., et al., Autocrine Production of Extracellular Catalase Prevents Apoptosis.. Proc. Natl. Acad. Sci. USA—90:4708-4712 (1993).

Schlumpf, M., et al., "Delayed Developmental Immunotoxicity of Prenatal Benzodiazepines," Toxic. In Vitro—8(5):1061-1065(1994).

Schoemaker, H., et al., "Specific High-Affinity Binding Sites for [3H]Ro5—4864 in Rat Brain and Kidney," The J. of Pharmacology and Experimental Therapeutics; vol. 225(1)61-69 (1983).

Schwab, M., et al., "Amplified DNA with Limited Homology to myc Cellular Oncogene is Shared by Human Neuroblastoma Cell Lines and . . . ," Nature—305:245-248 (1983).

Scott, C.F., et al., "Comparison of Antigen-Specific T Cell Responses in Autoimmune MRL/Mp-Ipr/Ipr and MRL/Mp-+/+ Mice," The Journal of Immunology, vol. 132, No. 2, pp. 633-639 (1984).

Sentman, C.L., et al., "bcl-2 Inhibits Multiple Forms of Apoptosis but not Negative Selection in Thymocytes," Cell 67:879-886 (1991).

Shaughnessy, Kevin, H., et al., "Palladium-Catalyzed Inter- and Intramolecular . . . " J. Org. Chem. 1998, 63, pp. 6546-6553.

Sheppard, R.C., et al., "Acid-Labile Resin Linkage Agents for Use in Solid Phase Peptide Synthesis;" Int J. Peptide Protein Res. 20:451-454 (1982).

Snyder, Jane R., et al, "Dissection of melanogenesis with small molecules identifies prohibition as a regulator", Chemistry & Biol. 12:477-484, 4(2005).

Bisaha, S.N., et al., A switch in enantiomer preference between mitochondrial F1F0-ATPase chemotypes, Bioorganic & Medicinal Chemistry Letters, 2005 15(11), pp. 2749-2751.

International Search Report and Written Opinion dated Mar. 27, 2009, PCT/US2008/076021.

Adachi, M., et al., "Aberrant Transcription Caused by the Insertion an Early Transposable Element . . . ," PNAS. USA—90:1756-1760 (1993).

Adelman, N.E., et al., Treatment of (NZB X NZW)F1 Disease with Anti-I-A Monoclonal Antibodies; J. Exp. Med.—158:1350.1355 (1983).

(56) References Cited

OTHER PUBLICATIONS

Appleby, et al., "Murine chronic graft-versus-host disease as a model of osystemic lupus erythematosus: effect of immunosuppressive drugs on disease development," Clin. Exp. Immunol. (1989) 78, 449-453.

Atwal, K.S., et al., "N-(1-Aryl-2-(1-imidazolo)ethyl)-guanidine derivates as potent inhibitors of the bovine mitochondrial F140 ATP hydrolase" Bioorganic & Medicinal Chem. Ltr., vol. 14, pp. 1021-1030 (2004).

Atwal, K.S., et al., "Small Molecule Mitochondrial F1F0 ATPase Huydrolase Inhibitors as Cardioprotective Agents" J. Med. Chem. 47, pp. 1081-1084 (2004).

Baader, S.L., et al., Uptake and Cytotoxicity of Ascorbic Acid and Dehydroascorbic Acid . . . Anticancer Research—14:221-228 (1994).

Bastian, et al., "Casein Interference in Bovine Plasmin Assays Using a Synthetic Substrate," (1991) J Dairy Sci 74:4119-4124.

Beale, P.J., et al., "BCL-2 Family Protein Expression and Platinum Drug Resistance in Ovarian Carcinoma," British Journal of Cancer—82 (2) :436-440 (2000).

Beurdeley-Thomas, et al., "The peripheral benzodiazepine receptors: a review," Journal of Neuro-Oncology 46(2000) 45-56.

Blatt, Neal B., "Benzodiazepine-induced superoxide signals B cell apoptosis: mechanistic insight and potential therapeutic utility", The Journal of Clinical Investigation, Oct. 2002, vol. 110, No. 8., pp. 1123-1132.

Blum, P., et al., "Stiff-Person Syndrome: An Autoimmune Disease," Movement Disorders 6(1):12-20 (1991).

Boitano, Anthony, et al., "Structure activity studies of a novel cytotoxic benzodiazepine", Bioorganic & Medicinal Chemistry Letters, Oxford, GB, vol. 13, No. 19, 2003, pp. 3327-3330.

Bono et al., "Peripheral benzodiazepine receptor agonists exhibit potent antiapoptotic activities," Biochemical and Biophysical Research Communications, 1999, 265, pp. 457-461.

Boojamra, C.G., et al., "Solid-Phase Synthesis of 1,4. Benzodiazepine-2,5-Diones. Library Prep. and Demonstration of Synthesis Generality," J. Org. Chem.—62:1240-1256 (1997).

Bunin et al., "Synthesis and evaluation of 1,4-benzodiazepine libraries", Methods in Enzymology, 1996, 267, pp. 448-465.

Bunin, B.A., et al., "The Combinatorial Synthesis and Chemical and Biological Evaluation of a 1,4-Benzodiazepine Libra ," PNAS USA—91:4708-4712 (1994).

Bunin, BA., et al., "A General and Expedient Method for the Solid-Phase Synthesis of 1,4-Benzodlazepine Derivatives," J. Am. Chem. Soc.—114:10997-10998 (1992).

Chumakov,A.M., et al., "Analysis of p53 Transactivation Through High-Affinity Bindir•g Sites," Oncogene—8:3005o3011 (1993).

Churcher et al., "A new series of potent benzodiazepine y-Secretase inhibitors," Bioorganic & Medicinal Chemistry Letters 13 (2003) 179-.

Cohen, P.L., et al., "Lpr and gld: Single Gen• Models of Systemic Autoimmunity and Lymphoproliferative Disease,"Annu. Rev. Immunol. 9:243-269 (1991).

Cole et al., "The EBV-Hybridoma Technique and its Application to Human Lung Cancer", Monoclonal Antibodies and Cancer Therapy, Alan R. Liss, Inc., pp. 77-96 [1985].

Colosi, et al,"Mutational analysis of the intracellular domain of the human growth hormone recetor", J. Biol. Chem., 268:12617 [1993].

Crabtree, R.H., "A New Type of Hydrogen Bond," Science 282:2000-2001 1998.

Darrow et al., "Structurally similar small molecule photoaffinity CCK-A Agonists and Antagonists as Novel Tools . . . ", Bioorganic & Medicinal Chemistry Letters 8 (1998) 3127-3132.

Desoize, B., "Anticancer Drug Resistance and Inhibition of Apoptosis," Anicancer Research—14:2291-2294 1994.

Dichek, David A., et al., "Seeding of intravascular stents with genetically engineered endothelial cells," Laboratory Investigation, 80:5 pp. 1347-1353 (1989).

Doble, A., et al., "Labelling of Peripheral-Type Benzodiazepine B Human Brain with [aH]l 1195:Anatomical and Subcellular Distribution," Brain Research Bulletin,18:49-61 1987.

Don, A. et al., Cancer Cell, vol. 3, May 2003 497-509.

Donadio, J.V., et al., Immunosuppressive Drug Therapy in Lupus Nephritis, American Journal of Kidney Diseases 21(3):239-250 1993.

EP Search, EP Patent Application No. 05856659.7, dated Dec. 9, 2008.

EP Search, EP Patent Application No. 04 775 923.8, dated Dec. 15, 2008.

Ermak, T.H., et al., "Treatment of Murine Lupus with Monoclonal Antibody to L3T4," Laboratory Investigation 61(4):447-456 1989.

Fuh et al, "Rational design of potent antagonists to the human growth hormone receptor", Science, 256:1677 [1992].

Gallant, J.E., et al.,"Incidence and Natural History of Cytomegalovirus Disease in Patients with Advanced Human . . . " The Journal of Infect. Disease, 166: 1223-1227 (1992).

Garcia-Calvo, M., et al. "Inhibition of Human Caspases by Peptide-Based and Macromolecular Inhibitors," The Journal of Biological Chemistry 273(49):32608-32613 1998.

Gorczyca, W., et al., "Induction of DNA Strand Breaks Associated with Apoptosis During Treatment of Leukemias," Leukemia 7(5):659-670 1993.

Gordon, C., et al.. "Chronic Therapy with Recombinant Tumor Necrosis Factor-α in Autoimmune NZB/NZW Fi Mice," Clinical Immunology and Immunopatholoy, 52:421-434 (1989).

Gordon, E.M., et al., Applications of Combinatorial Technologies to Drug Discovery. 2. Combinatorial Organic 52 Synthesis, Library Screening . . . Journal of Med. Chem. 37(10): (1994).

Grasberger, Bruce L., "Discovery and cocrystal structure of benzodiazepinedione HDM2 antagonists that activate p53 in cells", J. Med. Chem., 48, (2005), 909-912.

Gupta et al., "Psychitripic drugs in dermatology . . . " Database:EMbase (AN:86111413), Journal of the American Academy of Dermatology, 1986, vol. 14, No. 4, pp. 633-645.

Hahn, B.H., et al.; "Influence of Cyclophosphamide and Other Immunosuppressive Drugs on Immune Disorders . . . ," Arthritis and Rheumatism—18(2):145-152 (1975).

Hamann, L.G., et al., "Benzodiazepine-based selective inhibitors of mitochondrial F1F0 ATP hydrolase" Bioorganic & Medicinal Chemistry Ltrs. 14 pp. 1031-1034 (2004).

Hang, L., et al., "A Spontaneous Rheumatoid Arthritis-Like Disease in MR/1 Mice," J. Exp. Mod.—155:1690-1701 1982.

Herranz, R., "Cholesystokinin Antagonists: Pharmacological and Therapeutic Potential", Medicinal Research Reviews 23 (2003) 559-603.

Hirsch, et al., "PK11195, a Ligand of the Mitochondrial Benzodiazepine Receptor, Facilitates the Induction of Apoptosis and Reverses Bcl-2-Mediated Cytoprotection," Experimental Cell Research 241, 426-434 (1998).

Horowitz, R.E., et al., "Cyclophosphamide Treatment of Mouse Systemic Lupus Erythematosus," Laboratory Investigation 21 (3): 199-206 1969.

Hulme, C. J. "Improved procedure for the solution phase preparation of 1,4-benzodiazepine-2,5-dione libraries . . . ", Org. Chem., 63,(1998), 8021-8023.

Brittain, H.G., Polymorphism in Pharmaceutical Solids (1999), published by Marcel Dekker, Inc. (New York, USA), Chapter 5, pp. 205-208.

Byrn, S.R., et al. Solid-State Chemistry of drugs. 2nd ed. (1999), published by SSCI, Inc. (Indiana, USA).

Stevens, S.Y., et al., "Non Nucleic Acid Inhibitors of Protein-DNA Interactions Identified Through Combinatorial Chemistry," J. Am. Chem.Soc.—118:10650-10651 (1996).

Sugimoto, T., et al., Determination of Cell Surface Membrane Antigens . . . JNCI—73: (1):51-57 (1984).

Swanson et al, "Ligand recognition by anti-DNA Autoantibodies," Biochemistry, 35:1624-1633 [1996] (Abstract only).

Swanson, P.C., et al., "Ligand Recognition by Murine Anti-DNA Autoantibodies," J. Clin. Invest 97(7):1748-1760 (1996).

(56) References Cited

OTHER PUBLICATIONS

Swanson, P.C., et al., "High Resolution Ephope Mapping of an Anti-DNA Autoantibody Using Model DNA Ligands," J. Immunology 71 152(5):2601-2612 (1994).
Takahashi, T., et al., "Generalized Lymphoproliferative Disease in Mice, Caused by a Point Mutation in the Fas Ligand;" Cell 76:969-976 (1994).
Tanimoto, Y., et al., Benzodiazepine Receptor Agonists Modulate Thymocyte Apoptosis Through Reduction of the Mitochondrial . . . Jpn. J. Pharmacol. 79:177-183 (1999).
Taupin, V., et al., Endogenous Anxiogenic peptide, ODN-Diazepam-Binding Inhibitor, and Benzodiazepines.. Lymphokine and Cytoklne Research 10(1):7-13 (1991).
Theoffopoulous, AN, et al., "Murine Models of Systemic Lupus Erythematosus," Advances in Immunology 37:269-390 (1985).
Thompson, C.B., "Apoptosis in the Pathogenesis and Treatment of Disease," Science 267:1456-1462 (1995).
Ursini et al., "Synthesis and SAR of New 5-Phenyl-3-ureido-1,5-benzodiazepines as cholecystokinin-B receptor antagonists", J. Med. Chem. 43 (2000) 3596-3613.
Walser, et al., "Quinazolines and 1,4-benzodiazepines. LILX. Preparation of Pyrrolo[2,1-c]-1,4-benzodiazepin-2-ones", J. Org. Chem. 38:3502-3507 (1973).
Watanabe-Fukunaga, R., et al., "Lymphoproliferation Disorder in Mice Explained by Defects in Fas Antigen that Mediates Apoptosis," Nature 356:314-317 (1992).
White, E., "Life, Death, and the Pursuit of Apoptosis," Genes & Development 10:1-15 (1996).
Williams, D. et al, "Identification of compounds the bind mitochondrial F1F0 ATPase by screening a triazine library . . . " Chemistry & Biol. 11:1251-1259, 9(2004).
Wu, G.Y., et al., "Receptor-Mediated in Vitro Gene Transformation by a Soluble DNA Carrier System," The Journal of Biological Chemistry 262(10):4429-4432 (1987).
Wyllie, A.H., "The Genetic Regulation of Apoptosis," Current Opinion in Genetics & Development 5:97-104 (1995).
Zamzami, N., et al., "Mitochondrial Control of Nuclear Apoptosis," J. Exp. Med. 183:1533-1544 1996.
Zoratti, M., et al., "The Mitochondrial Permeability Transition," Biochimica et Biophysica Acta 1241:139-176 (1995).
International Search Report, International Patent Application No. PCT/US02/26171 dated Aug. 8, 2003.
International Search Report, International Patent Application No. PCT/US01/11599 dated Mar. 6, 2001.
International Search Report, International Patent Application No. PCT/US05/031942 dated Sep. 21, 2006.
International Search Report, International Patent Application No. PCT/US04/013455 dated Jan. 6, 2006.
European Search Report, EP Patent Application No. 03 027 484.9-2117 dated May 3, 2004.
European Search Report, EP Patent Application No. 04 775 923.8-2123 dated Nov. 9, 2007.
European Search Report, EP Patent Application No. 00 928 586.7-2117 dated Apr. 23, 2002.
European Search Report, EP Patent Application No. 05 769 345.9 dated Oct. 22, 2007.
International Search Report, PCT/US2006/042753, dated May 6, 2008.
Written Opinion of the International Searching Authority, PCT/US06/21561, dated Aug. 17, 2007.
International Preliminary Report on Patentability, PCT/US2006/041446, mailed May 8, 2008.
International Search Report and Written Opinion, PCT/US2006/00442, mailed May 12, 2006.
International Report on Patentability, PCT/US2006/000442 mailed Jul. 12, 2007.
Puodziunaite, B., et al., "Bromination of Aromatic Ring of Tetrahydro-1,5-Benzodiazepin-2-Ones", Chemistry of Heterocyclic Compounds, vol. 36, No. 6, 2000.
AU Examiner's Report, AU Patent App. No. 2005323519 dated Nov. 27, 2007.
EP Search, EP Patent App. No. 03 027 484.9-2117, dated Jan. 31, 2005.
Nawrocka, et al., Arch. Pharm. (Weinheim) Jan. 2001, 334(1), 3-10.
International Search Report and Written Opinion, PCT/US08/56231, mailed Jun. 24, 2008.
International Search Report and Written Opinion, PCT/US05/14463, mailed Dec. 4, 2006.
International Search Report and Written Opinion, PCT/US07/11422, mailed Nov. 15, 2007.
International Search Report and Written Opinion, PCT/US07/13576, mailed Nov. 23, 2007.
Godic, "New approaches to psoriasis treatment. A review." 2004, Acta Dermatoven APA, vol. 13, No. 2, pp. 50-57.
International Search Report, PCT/US06/042753, mailed Apr. 19, 2007.
Desjardins, P and Stephanie Ledoux, "The Role of Apoptosis in Neurodegenerative Disease," Metabolic Brian Disease, vol. 13, No. 2, pp. 79-96 (1998).
International Search Report, PCT/US06/41446, mailed Aug. 1, 2007.
AU Patent Application No. 2006203946 Examiner's Report dated Sep. 10, 2008.
Iiangumaran, et al., "CD44 Selectively Associates with Active Src Family Protein Tyrosine Kinases Lck and Lyn in Glycosphingolipid-Rich . . . ", Blood, vol. 91, No. 10 (May 15, 1998), pp. 3901-3908.
Sato, et al., "CD22 negatively and positively regulates signal transduction through the B lymphocyte antigen receptor," seminars in Immunology, vol. 10, 1998, pp. 287-297.
Joshi, et al., "Oligomycin Sensitivey-conferring Protein (OSCP) of Mitochodrial ATP Synthase," The Journal of Biological Chemistry, vol. 267, No. 18,m Issue of Jun. 25, pp. 12860-12867, 1992.
EP Supplementary Search Report, EP Application No. 02794914.8 dated Nov. 6, 2008.
Lee, et al., J. Org. Chem. 1999, 64, 3060-3065.
Boitano, Anthony, et al., "The Proapoptotic Benzodiazepine Bz-423 Affects the Growth and Survival of Malignant B Cells," Cancer Research 63, 6870-6876 (Oct. 15, 2003).
Munoz, et al., "Autoimmunity and chronic inflammation—two cleaance-related steps in the etiopathogenesis of SLE", Autoimmunity Reviews 10 (2010) pp. 38-42.
Database Registry (online), Chemical Abstracts Service, Columbus, Ohio, US; Aug. 13, 2001, retrieved from STN, Database Accession No. 351226-10-3.
Database Registry (online), Chemical Abstracts Service, Columbus, Ohio, US; Aug. 13, 2001, retrieved from STN, Database Accession No. 330829-66-8.
Database Registry (online), Chemical Abstracts Service, Columbus, Ohio, US; Apr. 11, 2001, retrieved from STN, Database accession No. 669724-32-7.
Kryl'Skii D V, et al., "Arylbiguanides in Heterocyclization Reactions", Russian Journal of General Chemistry, Nauka/Interperiodica, Mo, vol. 75, No. 2, Feb. 1, 2005, pp. 303-310.
EP Office Communication dated Dec. 7, 2012, related EP Patent Application No. EP 08 831 237.6.

1,4-BENZODIAZEPINONE COMPOUNDS AND THEIR USE IN TREATING CANCER

RELATED APPLICATIONS

This application is a national stage of International (PCT) Patent Application Serial No. PCT/US2010/031435, filed Apr. 16, 2010, and published under PCT Article 21(2) in English, which claims the benefit of and priority to U.S. Provisional Patent Application Ser. No. 61/170,176, filed Apr. 17, 2009, the contents of each of which are hereby incorporated by reference for all purposes.

FIELD OF THE INVENTION

The invention relates to 1,4-benzodiazepinone compounds, pharmaceutical compositions containing 1,4-benzodiazepinone compounds, and their therapeutic use. In particular, the invention relates to 1,4-benzodiazepinone compounds bearing a heterocyclic group at the C5-position, and methods of using such compounds as therapeutic agents to treat cancer.

BACKGROUND OF THE INVENTION

Cancer is a significant health problem throughout the world. Significant resources have been devoted to seeking cures for cancer resulting in important advances in the detection and treatment of cancer. However, there is significant need for new therapeutic agents having increased efficacy and reduced side effects. Current therapies, many of which involve a combination of chemotherapy or surgery and radiation, are inadequate for many patients. One of the early cancer chemotherapy drugs was the alkylating agent cyclophosphamide (Endoxan®), which is an oxazaphosphorin pro-drug activated preferentially in a tumor. The target of alkylating agents like cyclophosphamide is DNA and the concept, that cancer cells with uncontrolled proliferation and a high mitotic index are killed preferentially, has been confirmed. Historically, cancers have been linked to genetic changes caused by chromosomal mutations within the DNA. Mutations, hereditary or acquired, can lead to a loss of gene expression critical for maintaining a healthy state.

Many standard cancer chemotherapeutic drugs kill cancer cells upon induction of programmed cell death ("apoptosis") by targeting basic cellular processes and molecules. These basic cellular processes and molecules include RNA/DNA (alkylating and carbamylating agents, platin analogs and topoisomerase inhibitors), metabolism (drugs of this class are named anti-metabolites and examples are folic acid, purine and pyrimidine antagonists) as well as the mitotic spindle apparatus with α,β-tubulin heterodimers as the essential component (drugs are categorized into stabilizing and destabilizing tubulin inhibitors; examples are Taxol/Paclitaxel®, Docetaxel/Taxotere® and vinca alkaloids). Yet agents such as these are insufficient treatments, as evidenced by the following statistics for breast, prostrate, and lung cancer, for example.

Prostate cancer is the most common form of cancer among males, with an estimated incidence of 30% in men over the age of 50. Moreover, clinical evidence indicates that human prostate cancer has the propensity to metastasize to bone, and the disease appears to progress inevitably from androgen dependent to androgen refractory status, leading to increased patient mortality. This prevalent disease is one of the leading causes of cancer death among men in the United States.

The incidence of breast cancer, a leading cause of death in women, has been gradually increasing in the United States over the last thirty years. Its cumulative risk is relatively high; certain reports indicate that approximately one in eight women are expected to develop some type of breast cancer by age 85 in the United States. In fact, breast cancer is one of the most common cancers in women and still remains a leading cause of cancer death in the United States.

Lung cancer is a leading cause of cancer-related death, and non-small cell lung cancer (NSCLC) accounts for about 80% of these cases. Attempts to use serum protein markers for the early diagnosis of lung cancer have not yielded satisfactory results for routine screening, and newly developed early diagnostic methods using serum DNA as a diagnostic marker await further validation. Moreover, current therapeutic measures are frequently unable to lower the mortality rate of late-stage lung cancer patients. Of the current therapeutic measures, surgical resection is the best cure currently available for early-stage patients. However, a large portion of early-stage patients, defined by the current staging system and available imaging modalities, still develop distant metastases even after surgical removal of the tumor mass.

In view of the foregoing, the need exists for more effective compositions and methods for treating cancers of all types, including prostrate, breast, and lung cancers, as well as colon cancer, ovarian cancer, leukemia, renal cancer, melanoma and central nervous system cancer. The present invention addresses this need and has other related advantages.

SUMMARY

The invention provides 1,4-benzodiazepinone compounds, pharmaceutical compositions, and methods for treating cancer using such compounds and pharmaceutical compositions. In one aspect, the invention provides a compound represented by Formula I or II, wherein the variables are as defined in the detailed description below:

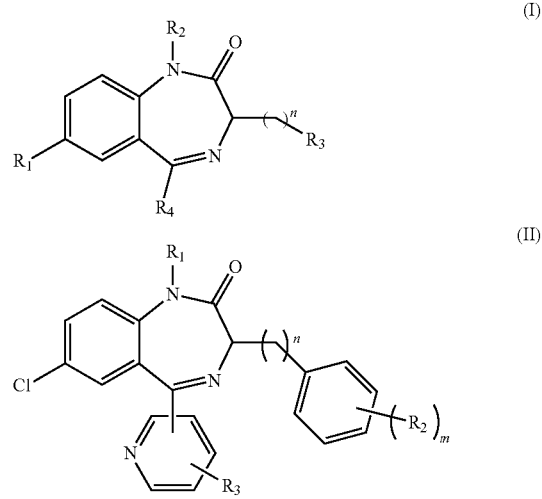

Another aspect of the invention provides a pharmaceutical composition comprising a compound described herein, such as a compound of I, IA, IB, IC, ID, IE, II, or III, as described herein, and a pharmaceutically acceptable carrier. The pharmaceutical compositions may be formulated for a particular mode of administration, such as topical or parenteral administration.

Another aspect of the invention provides a method of treating a subject suffering from cancer. The method comprises administering to a subject in need thereof a therapeutically effective amount of one or more 1,4-benzodiazepinone compounds described herein. The compounds described herein are contemplated to have activity in treating a variety of cancers. For example, the compounds described herein are contemplated to have activity in treating breast cancer, colon cancer, small-cell lung cancer, non-small cell lung cancer, prostate cancer, renal cancer, ovarian cancer, leukemia, melanoma, cancer of the central nervous system tissue, pancreatic cancer, cervical cancer, testicular cancer, bladder cancer, brain cancer, skin cancer, thyroid cancer, Hodgkin's lymphoma, non-Hodgkin's lymphoma, cutaneous T-Cell lymphoma, cutaneous B-Cell lymphoma, and diffuse large B-Cell lymphoma.

In certain embodiments, the compound administered is embraced by formulae I, IA, IB, IC, ID, IE, II, or III, as described herein. In certain other embodiments, the compound is one of the compounds listed in Tables 1-6 herein.

DETAILED DESCRIPTION OF THE INVENTION

The invention provides 1,4-benzodiazepinone compounds, pharmaceutical compositions, and methods for treating cancer using such compounds and pharmaceutical compositions. The practice of the invention employs, unless otherwise indicated, conventional techniques of organic chemistry, pharmacology, biochemistry, and immunology. Such techniques are explained fully in the literature, such as "Comprehensive Organic Synthesis" (B. M. Trost & I. Fleming, eds., 1991-1992); "Handbook of experimental immunology" (D. M. Weir & C. C. Blackwell, eds.); "Gene transfer vectors for mammalian cells" (J. M. Miller & M. P. Calos, eds., 1987); "Current protocols in molecular biology" (F. M. Ausubel et al., eds., 1987, and periodic updates); "PCR: the polymerase chain reaction" (Mullis et al., eds., 1994); and "Current protocols in immunology" (J. E. Coligan et al., eds., 1991), each of which is herein incorporated by reference in its entirety.

Definitions

To facilitate an understanding of the present invention, a number of terms and phrases are defined below.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. In certain other embodiments, a straight chain or branched chain alkyl has 1 to 6 carbon atoms in its backbone. Likewise, cycloalkyls have from about 3 to about 10 carbon atoms in their ring structure, and alternatively about 5, 6 or 7 carbons in the ring structure. Unless specified otherwise, alkyl groups are optionally substituted with halogen, alkoxy, hydroxyl, or amino. In certain embodiments, the alkyl group is not substituted, i.e., it is unsubstituted. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc.

The term "haloalkyl" refers to an alkyl group that is substituted with at least one halogen. For example, —$CH_2F$, —$CHF_2$, —$CF_3$, —$CH_2CF_3$, —$CF_2CF_3$, and the like.

The term "alkylene" as used herein refers a straight or branched, saturated aliphatic, divalent radical. Exemplary alkylene groups include methylene (—$CH_2$—), ethylene (—$CH_2CH_2$—), trimethylene (—$CH_2CH_2CH_2$—), and the like.

The term "aralkyl" refers to an alkyl group substituted with an aryl group.

The term "heteroaralkyl" refers to an alkyl group substituted with a heteroaryl group.

The terms "alkenyl" and "alkynyl" are art-recognized and refer to unsaturated aliphatic groups analogous in length and possible substitution to the alkyls described above, but that contain at least one double or triple bond respectively. Exemplary alkynyl groups include, but are not limited to, ethynyl, propynyl, butynyl, pentynyl, hexynyl, methylpropynyl, 4-methyl-1-butynyl, 4-propyl-2-pentynyl, and 4-butyl-2-hexynyl, etc. The term "cycloalkenyl" is art-recognized and refers to cyclic aliphatic group containing at least 1 C—C double bond. Unless specified otherwise, cycloalkenyl groups are optionally substituted with halogen, alkyl, alkoxy, hydroxyl, or amino. In certain embodiments, the cycloalkenyl group is not substituted, i.e., it is unsubstituted. Exemplary cycloalkenyl groups include cyclohexenyl and cyclopentenyl.

The term "aryl" is art-recognized and refers to a carbocyclic aromatic group. Representative aryl groups include phenyl, naphthyl, anthracenyl, and the like. Unless specified otherwise, the aromatic ring is substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —$CO_2$alkyl, carbonyl, carboxyl, alkylthio, sulfonyl, sulfonamido, sulfonamide, ketone, aldehyde, ester, heterocyclyl, aryl or heteroaryl moieties, —$CF_3$, —CN, or the like. The term "aryl" also includes polycyclic ring systems having two or more carbocyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, and/or aryls. The term "haloaryl" refers to an aryl group that is substituted with at least one halogen. In certain embodiments, the aromatic ring is substituted with halogen, alkoxy, hydroxyl, or amino. In certain embodiments, the aryl group is not substituted, i.e., it is unsubstituted.

The term "monocarbocyclic aryl" is art-recognized and refers to a carbocyclic, single-ring aromatic group, i.e., phenyl. Unless specified otherwise, the monocarbocyclic aryl is optionally substituted with one or two occurrences of halogen, methyl, ethyl, propyl, phenyl, pyridinyl, hydroxyl, amino, or acyl. In certain embodiments, the monocarbocyclic aryl group is not substituted, i.e., it is unsubstituted.

The term "heteroaryl" is art-recognized and refers to aromatic groups that include at least one ring heteroatom. In certain instances, a heteroaryl group contains 1, 2, 3, or 4 ring heteroatoms. Representative examples of heteroaryl groups includes pyrrolyl, furanyl, thiophenyl, imidazolyl, oxazolyl, thiazolyl, triazolyl, pyrazolyl, pyridinyl, pyrazinyl, pyridazinyl and pyrimidinyl, and the like. Unless specified otherwise, the heteroaryl ring is substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —$CO_2$alkyl, carbonyl, carboxyl, alkylthio, sulfonyl, sulfonamido, sulfonamide, ketone, aldehyde, ester, heterocyclyl, aryl or heteroaryl moieties, —$CF_3$, —CN, or the like. The term "heteroaryl" also includes polycyclic ring systems having two or more rings in which two or more carbons are common to two adjoining rings (the rings are "fused rings") wherein at least one of the rings is heteroaromatic, e.g., the other cyclic rings may be cycloalkyls, cycloalkenyls, cycloalkynyls, and/or aryls. In certain embodiments, the heteroaromatic ring is substituted with halogen, alkoxy, hydroxyl, or amino. In certain embodiments, the heteroaryl group is not substituted, i.e., it is unsubstituted.

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

As used herein, the term "heterocyclic" represents, for example, an aromatic or nonaromatic ring containing one or more heteroatoms. The heteroatoms can be the same or different from each other. Examples of heteroatoms include, but are not limited to nitrogen, oxygen and sulfur. Aromatic and nonaromatic heterocyclic rings are well-known in the art. Some nonlimiting examples of aromatic heterocyclic rings include pyridine, pyrimidine, indole, purine, quinoline and isoquinoline. Nonlimiting examples of nonaromatic heterocyclic compounds include piperidine, piperazine, morpholine, pyrrolidine and pyrazolidine. Examples of oxygen containing heterocyclic rings include, but not limited to furan, oxirane, 2H-pyran, 4H-pyran, 2H-chromene, and benzofuran. Examples of sulfur-containing heterocyclic rings include, but are not limited to, thiophene, benzothiophene, and parathiazine. Examples of nitrogen containing rings include, but not limited to, pyrrole, pyrrolidine, pyrazole, pyrazolidine, imidazole, imidazoline, imidazolidine, pyridine, piperidine, pyrazine, piperazine, pyrimidine, indole, purine, benzimidazole, quinoline, isoquinoline, triazole, and triazine. Examples of heterocyclic rings containing two different heteroatoms include, but are not limited to, phenothiazine, morpholine, parathiazine, oxazine, oxazole, thiazine, and thiazole. Unless specified otherwise, the heterocyclic ring is optionally substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like.

The term "heterocycloalkyl" is art-recognized and refers to a saturated cyclic aliphatic group containing at least one N, O, or S ring atom. The term "heterocycloalkyl" also includes bicyclic ring systems in which two or more atoms are common to two adjoining rings, where both rings are saturated and at least one of the rings contains a N, O, or S ring atom. Unless specified otherwise, heterocycloalkyl groups are substituted with 1, 2, or 3, substituents independently selected from the group consisting of alkyl, halogen, alkoxy, hydroxyl, amino, and —C(O)alkyl. In certain embodiments, the heterocycloalkyl group is substituted with 1 substituent selected from the group consisting of alkyl, halogen, alkoxy, hydroxyl, amino, and —C(O)alkyl. In certain embodiments, the heterocycloalkyl group is not substituted, i.e., it is unsubstituted.

The symbol "*" indicates a point of attachment. For example, the symbol "*" in the following structure indicates that the point of attachment is the nitrogen atom:

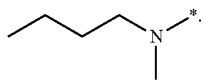

The term "quinolinyl" is art-recognized and refers to a ten-membered bicyclic heteroaromatic group having the formula:

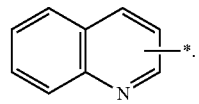

The term "quinazolinyl" is art-recognized and refers to a ten-membered bicyclic heteroaromatic group having the formula:

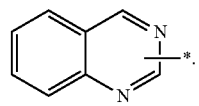

The term "quinoxalinyl" is art-recognized and refers to a ten-membered bicyclic heteroaromatic group having the formula:

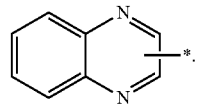

The term "naphthyridinyl" is art-recognized and refers a ten-membered bicyclic heteroaromatic having one nitrogen atom in each ring of the bicyclic ring system. Exemplary naphthyridinyl groups include:

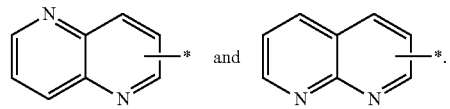

Unless specified otherwise, the quinolinyl, quinazolinyl, quinoxalinyl, and naphthyridinyl groups are optionally substituted with $C_1$-$C_6$alkyl, halogen, hydroxyl, $C_1$-$C_6$alkoxyl, amino, —C(O)—$C_1$-$C_6$alkyl, —CO$_2$—$C_1$-$C_6$alkyl, —C(O)N($C_1$-$C_6$alkyl)$_2$, —C(O)N(H)($C_1$-$C_6$alkyl), or —C(O)NH$_2$. In certain embodiments, the quinolinyl, quinazolinyl, quinoxalinyl, and naphthyridinyl groups are optionally substituted with $C_1$-$C_6$alkyl, halogen, hydroxyl, $C_1$-$C_6$alkoxyl, or amino.

The terms "amine" and "amino" are art-recognized and refer to both unsubstituted and substituted amines, e.g., a moiety that may be represented by the general formulas:

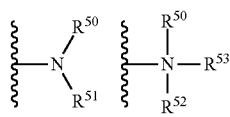

wherein $R^{50}$, $R^{51}$ and $R^{52}$ each independently represent a hydrogen, an alkyl, an alkenyl, —(CH$_2$)$_m$—$R^{61}$, or $R^{50}$ and $R^{51}$, taken together with the N atom to which they are attached complete a heterocycle having from 4 to 8 atoms in the ring structure; $R^{61}$ represents an aryl, a cycloalkyl, a cycloalkenyl, a heterocycle or a polycycle; and m is zero or an integer in the range of 1 to 8. In certain embodiments, only one of $R^{50}$ or $R^{51}$ may be a carbonyl, e.g., $R^{50}$, $R^{51}$ and the nitrogen together do not form an imide. In other embodiments, $R^{50}$ and $R^{51}$ (and optionally $R^{52}$) each independently represent a hydrogen, an alkyl, an alkenyl, or —$(CH_2)_m$—$R^{61}$. Thus, the term "alkylamine" includes an amine group, as defined above, having a substituted or unsubstituted alkyl attached thereto, i.e., at least one of $R^{50}$ and $R^{51}$ is an alkyl group. In certain embodiments, $R^{50}$, $R^{51}$ and $R^{52}$ each independently represent hydrogen or $C_1$-$C_6$alkyl.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—$(CH_2)_m$—R61, where m and R61 are described above.

The term "oxo" refers to a "O=" substituent. For example, a cyclohexanone is a cyclohexane bearing an oxo group.

The term "ketal" refers to a "—O—$(CH_2)_n$—O—" substituent where n is 1, 2, or 3, and both oxygen atoms are attached to the same carbon atom. For example, a ketal (where n is 2) of cyclohexane is shown below:

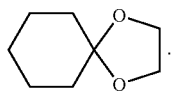

Certain compounds contained in compositions of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

The term "$EC_{50}$" is art-recognized and refers to the concentration of a compound at which 50% of its maximal effect is observed.

The terms "individual," "patient," or "subject" are used interchangeably and include any animal, including mammals, preferably mice, rats, other rodents, rabbits, dogs, cats, swine, cattle, sheep, horses, or primates, and most preferably humans. The compounds of the invention can be administered to a mammal, such as a human, but can also be other mammals such as an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like).

As used herein, the term "effective amount" refers to the amount of a compound (e.g., a compound of the present invention) sufficient to effect beneficial or desired results. An effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. The present invention encompasses various stereoisomers of these compounds and mixtures thereof. Stereoisomers include enantiomers and diastereomers. Mixtures of enantiomers or diastereomers may be designated "(±)" in nomenclature, but the skilled artisan will recognize that a structure may denote a chiral center implicitly.

Individual stereoisomers of compounds of the present invention can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, or (3) direct separation of the mixture of optical enantiomers on chiral chromatographic columns. Stereoisomeric mixtures can also be resolved into their component stereoisomers by well known methods, such as chiral-phase gas chromatography, chiral-phase high performance liquid chromatography, crystallizing the compound as a chiral salt complex, or crystallizing the compound in a chiral solvent. Stereoisomers can also be obtained from stereomerically-pure intermediates, reagents, and catalysts by well known asymmetric synthetic methods.

Geometric isomers can also exist in the compounds of the present invention. The symbol ≈≈≈ denotes a bond that may be a single, double or triple bond as described herein. The present invention encompasses the various geometric isomers and mixtures thereof resulting from the arrangement of substituents around a carbon-carbon double bond or arrangement of substituents around a carbocyclic ring. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers.

Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring are designated as "cis" or "trans." The term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

As a general matter, compositions specifying a percentage are by weight unless otherwise specified. Further, if a variable is not accompanied by a definition, then the previous definition of the variable controls.

I. 1,4-Benzodiazepinone Compounds

One aspect of the invention provides a compound represented by formula I:

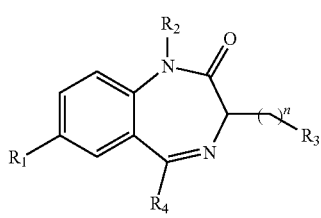

(I)

including pharmaceutically acceptable salts thereof; wherein:

$R_1$ is halogen;

$R_2$ represents independently for each occurrence hydrogen or $C_1$-$C_6$alkyl;

$R_3$ is phenyl or naphthyl, each of which is optionally substituted with one or two substituents independently selected from the group consisting of halogen, $C_1$-$C_6$alkyl, $C_1$-$C_6$alkoxy, amino, —S(O)$R_5$, —SO$_2$$R_5$, —SO$_2$N($R_6$)$_2$, —SO$_2$N($R_6$)C(O)$R_5$, —N($R_6$)SO$_2$$R_5$, —CN, —C(O)$R_5$, —CO$_2$$R_5$, —C(O)N($R_6$)$_2$, —N($R_6$)C(O)$R_5$, and monocarbocyclic aryl;

$R_4$ is

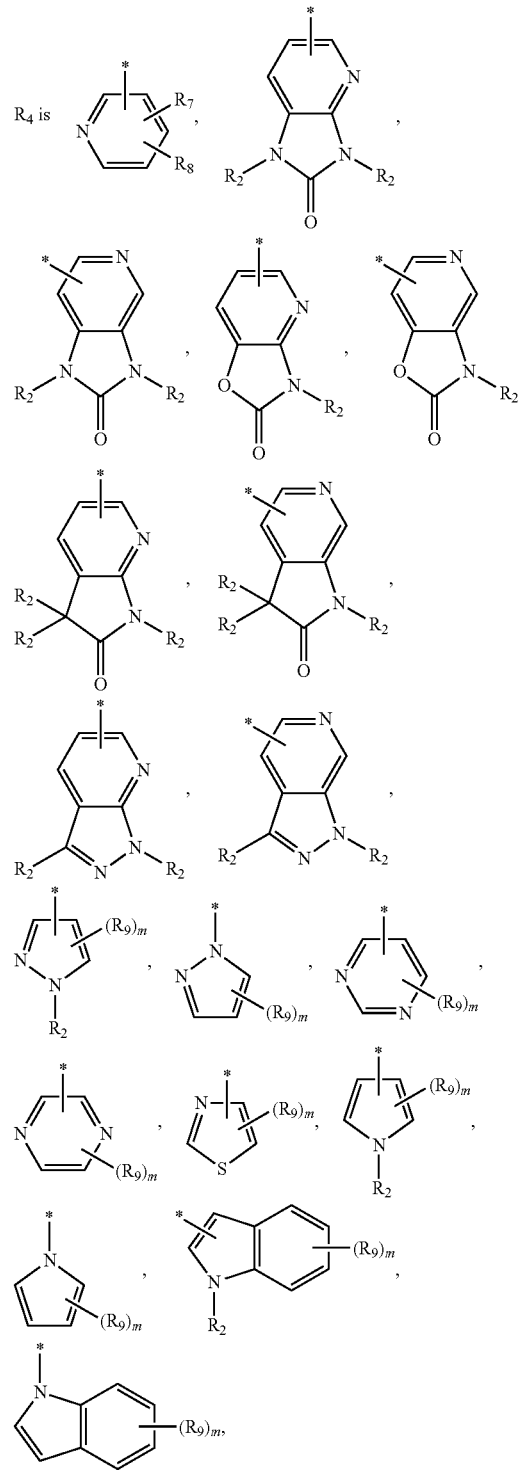

quinolinyl, quinoxalinyl, quinazolinyl, or naphthyridinyl; or $R_4$ is $C_3$-$C_7$heterocycloalkyl optionally substituted with:

(i) a substituent selected from the group consisting of $C_1$-$C_6$alkyl, $C_1$-$C_6$ cycloalkenyl, monocarbocyclic aryl, monocyclic heteroaryl, aralkyl, heteroaralkyl, cyano, halogen, hydroxyl, $C_1$-$C_6$alkoxy, amino, oxo, ketal, —C(O)$R_{10}$, —$CO_2R_{10}$, —C(O)N($R_{10}$)$_2$, —N($R_{10}$)C(O)$R_{10}$, —N($R_{10}$)$CO_2R_{11}$, —$C_1$-$C_6$alkylene-OH, —OC(O)N($R_{10}$)$_2$, —OC(O)$R_5$, —N($R_6$)$SO_2R_{10}$, —$SO_2R_{10}$, —$SO_2$N($R_{10}$)$_2$, —O—($C_1$-$C_6$)alkylene-($C_4$-$C_6$)heterocycloalkyl, —N($R_2$)—($C_1$-$C_6$)alkylene-($C_4$-$C_6$)heterocycloalkyl, and —$OPO_3H_2$; and (ii) a substituent selected from the group consisting of hydrogen, $C_1$-$C_6$alkyl, halogen, and hydroxyl;

$R_5$ represents independently for each occurrence $C_1$-$C_6$alkyl;

$R_6$ represents independently for each occurrence hydrogen or $C_1$-$C_6$alkyl, or two occurrences of $R_6$ attached to the same nitrogen atom are taken together with the nitrogen atom to form a $C_3$-$C_7$ heterocycloalkyl;

$R_7$ is $C_1$-$C_6$alkyl, $C_3$-$C_7$heterocycloalkyl, $C_1$-$C_6$alkoxy, halogen, amino, —N($R_6$)C(O)—$C_1$-$C_6$alkylene-$R_{12}$, —O—($C_1$-$C_6$)alkylene-($C_4$-$C_6$)heterocycloalkyl, or —N($R_2$)—($C_1$-$C_6$)alkylene-($C_4$-$C_6$)heterocycloalkyl;

$R_8$ is hydrogen, halogen, $C_1$-$C_6$alkyl, or $C_1$-$C_6$alkoxy;

$R_9$ represents independently for each occurrence halogen, $C_1$-$C_6$alkyl, $C_1$-$C_6$alkoxy, $C_3$-$C_7$heterocycloalkyl, amino, hydroxyl, —C(O)$R_{10}$, —$CO_2R_{10}$, —C(O)N($R_{10}$)$_2$, —N($R_{10}$)C(O)$R_{10}$, —N($R_{10}$)$CO_2R_{11}$, —OC(O)N($R_{10}$)$_2$, —N($R_6$)C(O)—$C_1$-$C_6$alkylene-$R_{12}$, or —$C_1$-$C_6$alkylene-N($R_2$)C(O)—$C_1$-$C_6$-alkyl;

$R_{10}$ represents independently for each occurrence hydrogen, $C_1$-$C_6$alkyl, aryl, heteroaryl, aralkyl, or heteroaralkyl, or two occurrences of $R_{10}$ attached to the same nitrogen atom are taken together with the nitrogen atom to form a $C_3$-$C_7$ heterocycloalkyl;

$R_{11}$ represents independently for each occurrence $C_1$-$C_6$alkyl, aryl, heteroaryl, aralkyl, or heteroaralkyl;

$R_{12}$ represents independently for each occurrence —$OR_2$, —N($R_2$)$_2$, —OC(O)$R_{11}$, or —N($R_2$)C(O)$R_{11}$;

n is 1 or 2;

m is 0, 1, or 2; and the stereochemical configuration at a stereocenter in a compound represented by formula I is R, S, or a mixture thereof.

In certain embodiments, $R_1$ is chloro. In certain embodiments, $R_2$ is hydrogen. In certain embodiments, $R_2$ is $C_1$-$C_6$ alkyl. In certain other embodiments, $R_2$ is methyl, ethyl, or propyl. In certain embodiments, $R_3$ is phenyl or naphthyl, each of which is optionally substituted with one or two substituents independently selected from the group consisting of halogen, $C_1$-$C_6$alkyl, $C_1$-$C_6$alkoxy, amino, —$SO_2R_5$, —$SO_2$N($R_6$)$_2$, —N($R_6$)$SO_2R_5$, —CN, —C(O)$R_5$, —$CO_2R_5$, —C(O)N($R_6$)$_2$, —N($R_6$)C(O)$R_5$, and monocarbocyclic aryl. In certain other embodiments, $R_3$ is phenyl or naphthyl, each of which is optionally substituted with one or two substituents independently selected from the group consisting of halogen, $C_1$-$C_6$alkyl, —$SO_2R_5$, —$SO_2$N($R_6$)$_2$, —CN, and monocarbocyclic aryl.

In certain other embodiments, $R_3$ is phenyl optionally substituted with one or two substituents independently selected from the group consisting of halogen, $C_1$-$C_6$alkyl, —$SO_2R_5$, —$SO_2$N($R_6$)$_2$, —CN, and monocarbocyclic aryl. In certain other embodiments, $R_3$ is phenyl or naphthyl, each of which is optionally substituted with one or two substituents independently selected from the group consisting of halogen, $C_1$-$C_6$alkyl, —$SO_2R_5$, —$SO_2$N($R_6$)$_2$, —CN, and phenyl. In certain other embodiments, $R_3$ is phenyl or naphthyl, each of which is optionally substituted with one or two substituents independently selected from the group consisting of halogen and $C_1$-$C_6$alkyl. In certain other embodiments, $R_3$ is phenyl optionally substituted with one or two substituents independently selected from the group consisting of chloro, fluoro, bromo, methyl, ethyl, and propyl.

In certain embodiments, $R_4$ is

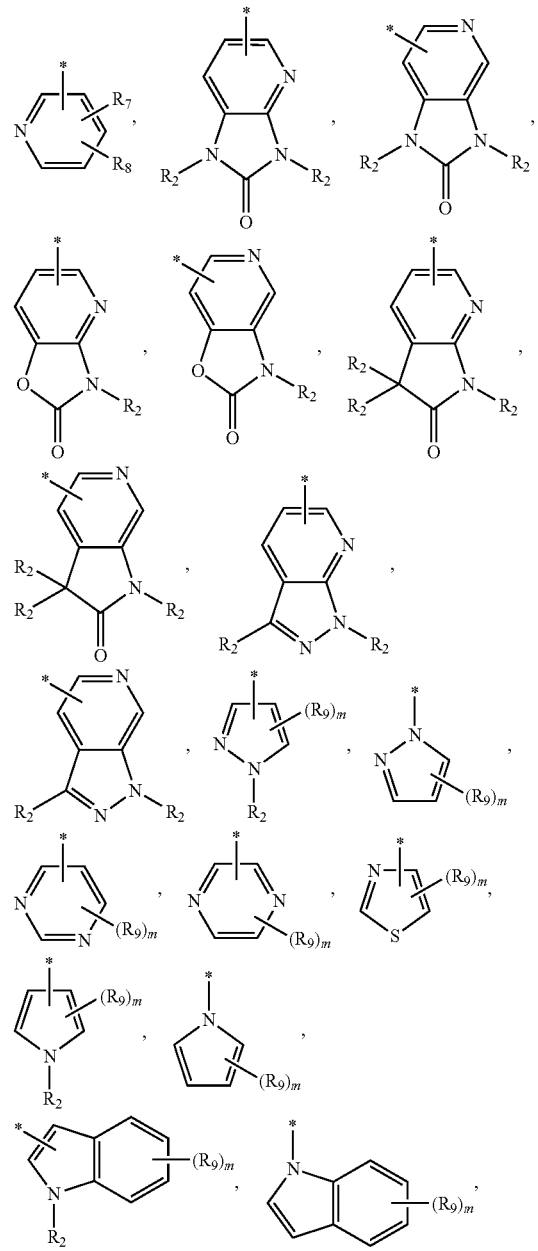

quinolinyl, quinoxalinyl, quinazolinyl, or naphthyridinyl. In certain other embodiments, $R_4$ is

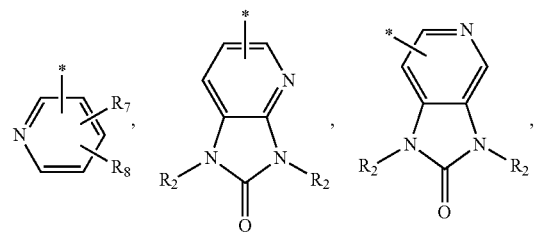

-continued

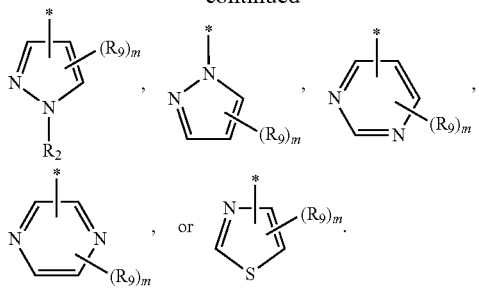

In certain embodiments, $R_4$ is

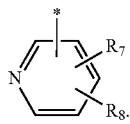

In certain other embodiments, $R_7$ is $C_3$-$C_7$heterocycloalkyl, amino, or —N($R_6$)C(O)—$C_1$-$C_6$alkylene-$R_{12}$. In certain other embodiments, $R_7$ is $C_3$-$C_7$heterocycloalkyl. In certain other embodiments, $R_7$ is aziridinyl, azetidinyl, pyrrolidinyl, piperidinyl, piperazinyl, morpholinyl, hexahydropyrimidinyl, azepanyl, pyrazolidinyl, or imidazolidinyl, each of which is optionally substituted with one or two substituents independently selected from the group consisting of halogen, hydroxyl, amino, $C_1$-$C_6$alkyl, $C_1$-$C_6$alkoxy, and —C(O)—$C_1$-$C_6$alkyl. In certain other embodiments, $R_7$ is azetidinyl, pyrrolidinyl, piperidinyl, piperazinyl, or morpholinyl, each of which is optionally substituted with one or two substituents independently selected from the group consisting of hydroxyl, amino, $C_1$-$C_6$alkyl, and —C(O)—$C_1$-$C_6$alkyl. In certain embodiments, $R_7$ is piperazinyl or morpholinyl, each of which is optionally substituted with one or two substituents independently selected from the group consisting of hydroxyl, amino, $C_1$-$C_6$alkyl, and —C(O)—$C_1$-$C_6$alkyl. In certain other embodiments, $R_7$ is piperazinyl optionally substituted with $C_1$-$C_6$alkyl or —C(O)—$C_1$-$C_6$alkyl. In certain embodiments, $R_8$ is hydrogen.

In certain embodiments, $R_4$ is

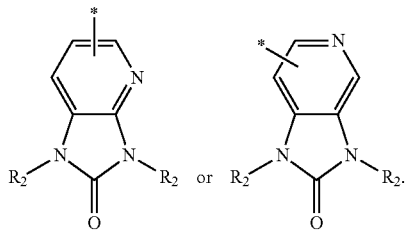

In certain other embodiments, $R_4$ is

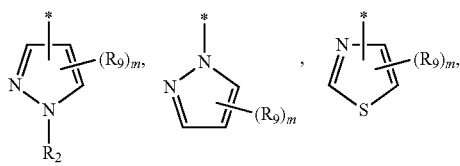

In certain other embodiments, $R_4$ is

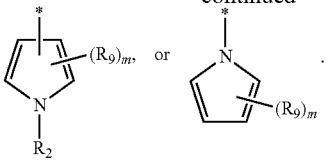

In certain other embodiments, $R_4$ is

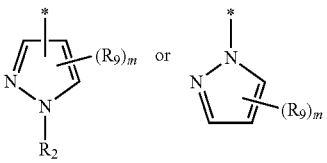

In certain other embodiments, $R_4$ is

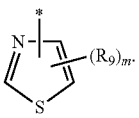

In certain embodiments, $R_4$ is

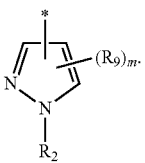

In certain embodiments, $R_9$ is $C_1$-$C_6$alkyl, amino, hydroxyl, —C(O)$R_{10}$, —CO$_2$$R_{10}$, or —C(O)N($R_{10}$)$_2$. In certain embodiments, $R_9$ is methyl, ethyl, or propyl. In certain embodiments, m is 0.

In certain embodiments, $R_4$ is

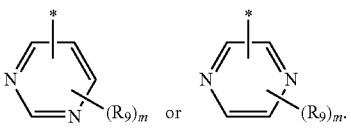

In certain embodiments, $R_9$ is $C_1$-$C_6$alkyl, amino, hydroxyl, —C(O)$R_{10}$, —CO$_2$$R_{10}$, or —C(O)N($R_{10}$)$_2$. In certain embodiments, m is 1.

In certain embodiments, $R_4$ is $C_3$-$C_7$heterocycloalkyl optionally substituted with one or two substituents independently selected from the group consisting of $C_1$-$C_6$alkyl, $C_1$-$C_6$ cycloalkenyl, monocarbocyclic aryl, monocyclic heteroaryl, cyano, halogen, hydroxyl, $C_1$-$C_6$alkoxy, amino, oxo, ketal, —C(O)$R_{10}$, —CO$_2$$R_{10}$, —C(O)N($R_{10}$)$_2$, —N($R_{10}$)C(O)$R_{10}$, —N($R_{10}$)CO$_2$$R_{11}$, —OC(O)N($R_{10}$)$_2$, —N($R_6$)SO$_2$$R_{10}$, —SO$_2$$R_{10}$, and —SO$_2$N($R_{10}$)$_2$. In certain other embodiments, $R_4$ is $C_3$-$C_7$heterocycloalkyl optionally substituted with one or two substituents independently selected from the group consisting of $C_1$-$C_6$alkyl, monocarbocyclic aryl, monocyclic heteroaryl, halogen, hydroxyl, $C_1$-$C_6$alkoxy, amino, oxo, ketal, —C(O)$R_{10}$, —N($R_{10}$)C(O)

$R_{10}$, —N($R_{10}$)CO$_2R_{11}$, and —OC(O)N($R_{10}$)$_2$. In certain other embodiments, $R_4$ is C$_3$-C$_7$heterocycloalkyl optionally substituted with one or two substituents independently selected from the group consisting of C$_1$-C$_6$alkyl, monocarbocyclic aryl, monocyclic heteroaryl, halogen, hydroxyl, amino, oxo, ketal, —N($R_{10}$)C(O)$R_{10}$, and —N($R_{10}$)CO$_2R_{11}$. In certain other embodiments, $R_4$ is C$_3$-C$_7$heterocycloalkyl optionally substituted with one or two substituents independently selected from the group consisting of C$_1$-C$_6$alkyl, hydroxyl, amino, oxo, ketal, —N($R_{10}$)C(O)$R_{10}$, and —N($R_{10}$)CO$_2R_{11}$. In certain other embodiments, $R_4$ is aziridinyl, azetidinyl, pyrrolidinyl, piperidinyl, piperazinyl, morpholinyl, hexahydropyrimidinyl, azepanyl, pyrazolidinyl, or imidazolidinyl, each of which is optionally substituted with one or two substituents independently selected from the group consisting of C$_1$-C$_6$alkyl, monocarbocyclic aryl, monocyclic heteroaryl, halogen, hydroxyl, amino, oxo, ketal, —N($R_{10}$)C(O)$R_{10}$, and —N($R_{10}$)CO$_2R_{11}$. In certain other embodiments, $R_4$ is pyrrolidinyl, piperidinyl, piperazinyl, azepanyl, pyrazolidinyl, morpholinyl, or imidazolidinyl, each of which is optionally substituted with one or two substituents independently selected from the group consisting of C$_1$-C$_6$alkyl, monocarbocyclic aryl, monocyclic heteroaryl, halogen, hydroxyl, amino, oxo, ketal, —N($R_{10}$)C(O)$R_{10}$, and —N($R_{10}$)CO$_2R_{11}$. In certain other embodiments, $R_4$ is pyrrolidinyl, piperidinyl, piperazinyl, or morpholinyl, each of which is optionally substituted with one or two substituents independently selected from the group consisting of C$_1$-C$_6$alkyl, monocarbocyclic aryl, monocyclic heteroaryl, halogen, hydroxyl, amino, oxo, ketal, —N($R_{10}$)C(O)$R_{10}$, and —N($R_{10}$)CO$_2R_{11}$. In certain other embodiments, $R_4$ is pyrrolidinyl, piperidinyl, or piperazinyl, each of which is optionally substituted with one or two substituents independently selected from the group consisting of C$_1$-C$_6$alkyl, halogen, hydroxyl, amino, oxo, ketal, —N($R_{10}$)C(O)$R_{10}$, and —N($R_{10}$)CO$_2R_{11}$. In certain other embodiments, $R_4$ is pyrrolidinyl, piperidinyl, or piperazinyl, each of which is optionally substituted with one or two substituents independently selected from the group consisting of C$_1$-C$_6$alkyl, hydroxyl, oxo, ketal, and —N($R_{10}$)C(O)$R_{10}$.

Another aspect of the invention provides a compound represented by formula IA:

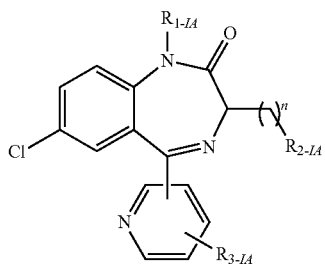

(IA)

including pharmaceutically acceptable salts thereof; wherein: $R_{1-IA}$ represents independently for each occurrence hydrogen, methyl, ethyl, or propyl; $R_{2-IA}$ is phenyl or naphthyl, each of which is optionally substituted with one or two substituents independently selected from the group consisting of halogen, methyl, ethyl, propyl, and monocarbocyclic aryl; $R_{3-IA}$ is C$_3$-C$_7$heterocycloalkyl, C$_1$-C$_6$alkoxy, amino, or —N($R_{1-IA}$)C(O)—C$_1$-C$_6$alkylene-$R_{4-IA}$; $R_{4-IA}$ represents independently for each occurrence —O$R_{1-IA}$ or —OC(O)—C$_1$-C$_6$alkyl; n is 1 or 2; and the stereochemical configuration at a stereocenter in a compound represented by formula IA is R, S, or a mixture thereof.

In certain other embodiments, $R_{2-IA}$ is phenyl or naphthyl, each of which is optionally substituted with one or two substituents independently selected from the group consisting of halogen, methyl, ethyl, and propyl. In certain other embodiments, $R_{3-IA}$ is C$_3$-C$_7$heterocycloalkyl. In certain other embodiments, $R_{3-IA}$ is pyrrolidinyl, piperidinyl, piperazinyl, azepanyl, pyrazolidinyl, morpholinyl, or imidazolidinyl, each of which is optionally substituted with one or two substituents independently selected from the group consisting of C$_1$-C$_6$alkyl, monocarbocyclic aryl, monocyclic heteroaryl, halogen, hydroxyl, amino, oxo, ketal, —N(H)C(O)C$_1$-C$_6$alkyl, —N(C$_1$-C$_6$alkyl)C(O)C$_1$-C$_6$alkyl, —N(H)CO$_2$C$_1$-C$_6$alkyl, and N(C$_1$-C$_6$alkyl)CO$_2$C$_1$-C$_6$alkyl. In certain other embodiments, $R_{3-IA}$ is pyrrolidinyl, piperidinyl, piperazinyl, or morpholinyl, each of which is optionally substituted with one or two substituents independently selected from the group consisting of C$_1$-C$_6$alkyl, halogen, hydroxyl, and amino. In certain other embodiments, $R_{3-IA}$ is pyrrolidinyl, piperidinyl, or piperazinyl, each of which is optionally substituted with one or two substituents independently selected from the group consisting of C$_1$-C$_6$alkyl, halogen, hydroxyl, and amino. In certain other embodiments, $R_{3-IA}$ is pyrrolidinyl, piperidinyl, or piperazinyl, each of which is optionally substituted with methyl, ethyl, or propyl.

Another aspect of the invention provides a compound represented by formula IB:

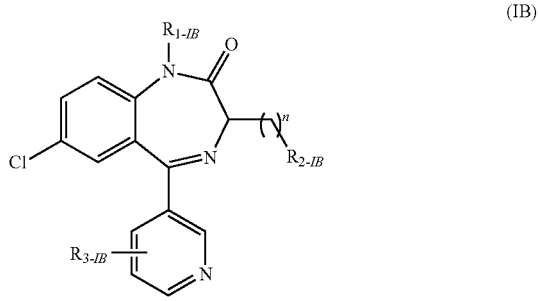

(IB)

including pharmaceutically acceptable salts thereof; wherein: $R_{1-IB}$ represents independently for each occurrence hydrogen, methyl, ethyl, or propyl; $R_{2-IB}$ is phenyl or naphthyl, each of which is optionally substituted with one or two substituents independently selected from the group consisting of halogen, C$_1$-C$_6$ alkyl, and monocarbocyclic aryl; $R_{3-IB}$ is pyrrolidinyl, piperidinyl, piperazinyl, or morpholinyl, each of which is optionally substituted with one or two substituents independently selected from the group consisting of C$_1$-C$_6$alkyl, halogen, hydroxyl, amino, and oxo; n is 1 or 2; and the stereochemical configuration at a stereocenter in a compound represented by formula IB is R, S, or a mixture thereof.

In certain embodiments, $R_{2-IB}$ is phenyl substituted with halogen, methyl, ethyl, or propyl; and $R_{3-IB}$ is pyrrolidinyl, piperidinyl, or piperazinyl. In certain embodiments, $R_{3-IB}$ is piperidinyl optionally substituted with one or two substituents independently selected from the group consisting of C$_1$-C$_6$alkyl, halogen, hydroxyl, amino, and oxo.

Another aspect of the invention provides a compound represented by formula IC:

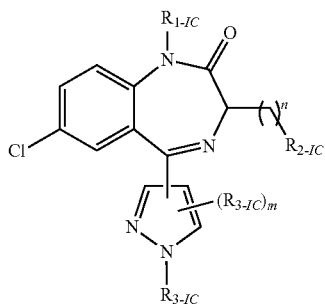

(IC)

including pharmaceutically acceptable salts thereof; wherein: $R_{1\text{-}IC}$ represents independently for each occurrence hydrogen, methyl, ethyl, or propyl; $R_{2\text{-}IC}$ is phenyl or naphthyl, each of which is optionally substituted with one or two substituents independently selected from the group consisting of halogen, $C_1$-$C_6$alkyl, and monocarbocyclic aryl; $R_{3\text{-}IC}$ represents independently for each occurrence hydrogen, methyl, ethyl, or propyl; m and n are independently 1 or 2; and the stereochemical configuration at a stereocenter in a compound represented by formula IC is R, S, or a mixture thereof.

In certain embodiments, $R_{2\text{-}IC}$ is naphthyl; or $R_{2\text{-}IC}$ is phenyl substituted with halogen, methyl, ethyl, or propyl. In certain embodiments, n is 1, and $R_{3\text{-}IC}$ is hydrogen.

Another aspect of the invention provides a compound represented by formula ID:

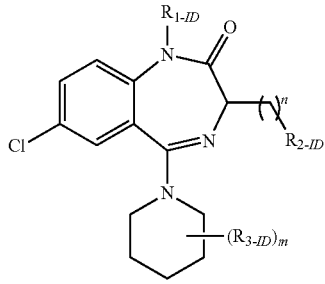

(ID)

including pharmaceutically acceptable salts thereof; wherein: $R_{1\text{-}ID}$ represents independently for each occurrence hydrogen, methyl, ethyl, or propyl; $R_{2\text{-}ID}$ is phenyl or naphthyl, each of which is optionally substituted with one or two substituents independently selected from the group consisting of halogen, $C_1$-$C_6$alkyl, and monocarbocyclic aryl; $R_{3\text{-}ID}$ represents independently for each occurrence monocarbocyclic aryl, monocyclic heteroaryl, hydroxyl, amino, oxo, ketal, or —N($R_{10}$)C(O)$R_{10}$; n and m are independently 1 or 2; and the stereochemical configuration at a stereocenter in a compound represented by formula ID is R, S, or a mixture thereof.

In certain embodiments, $R_{3\text{-}ID}$ represents independently for each occurrence amino, oxo, ketal, or —N($R_{10}$)C(O)$R_{10}$. In certain embodiments, $R_{2\text{-}IC}$ is phenyl substituted with halogen, methyl, ethyl, or propyl.

Another aspect of the invention provides a compound represented by formula IE:

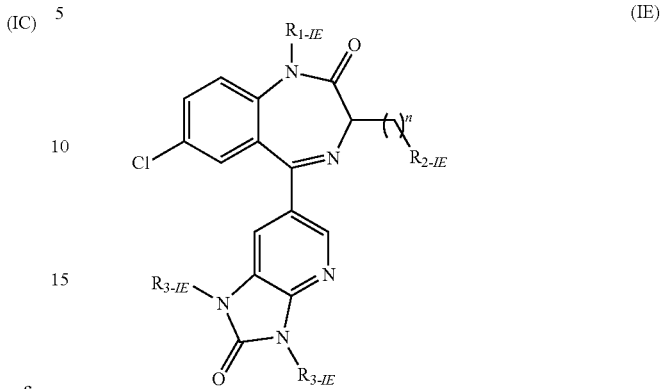

(IE)

including pharmaceutically acceptable salts thereof; wherein: $R_{1\text{-}IE}$ represents independently for each occurrence hydrogen, methyl, ethyl, or propyl; $R_{2\text{-}IE}$ is phenyl or naphthyl, each of which is optionally substituted with one or two substituents independently selected from the group consisting of halogen, $C_1$-$C_6$ alkyl, and monocarbocyclic aryl; $R_{3\text{-}IE}$ represents independently for each occurrence hydrogen or $C_1$-$C_6$alkyl; n is 1 or 2; and the stereochemical configuration at a stereocenter in a compound represented by formula IE is R, S, or a mixture thereof. In certain embodiments, $R_{2\text{-}IE}$ is phenyl optionally substituted with one or two substituents independently selected from the group consisting of halogen, methyl, ethyl, propyl, and phenyl. In certain embodiments, $R_{2\text{-}IE}$ is phenyl optionally substituted with one or two substituents independently selected from the group consisting of chloro and fluoro. In certain embodiments, n is 1, $R_{1\text{-}IE}$ is hydrogen, and $R_{3\text{-}IE}$ represents independently for each occurrence hydrogen, methyl or ethyl.

Another aspect of the invention provides a compound represented by formula II:

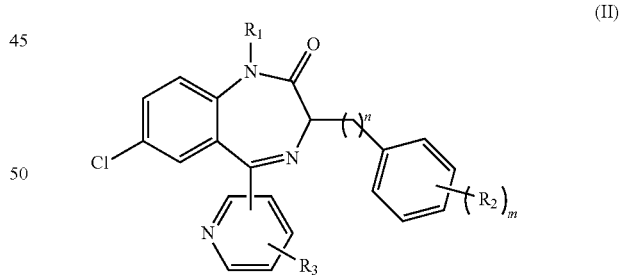

(II)

including pharmaceutically acceptable salts thereof; wherein: $R_1$ represents independently for each occurrence hydrogen or $C_1$-$C_6$alkyl; $R_2$ represents independently for each occurrence chloro, bromo, or fluoro; $R_3$ is $C_3$-$C_7$heterocycloalkyl, $C_1$-$C_6$alkoxy, hydroxyl, amino, —N($R_1$)C(O)—$C_1$-$C_6$alkyl, or —N($R_1$)—($C_1$-$C_6$)alkylene-($C_4$-$C_6$)heterocycloalkyl; m and n are independently 1 or 2; and the stereochemical configuration at a stereocenter in a compound represented by formula II is R, S, or a mixture thereof.

In certain embodiments, $R_3$ is pyrrolidinyl, piperidinyl, or piperazinyl, each of which is optionally substituted with one or two substituents independently selected from the group consisting of $C_1$-$C_6$alkyl, halogen, hydroxyl, and amino. In certain embodiments, $R_3$ is pyrrolidinyl, piperidinyl, or piperazinyl, each of which is optionally substituted with methyl, ethyl, or propyl.

Another aspect of the invention relates to a compound represented by formula III:

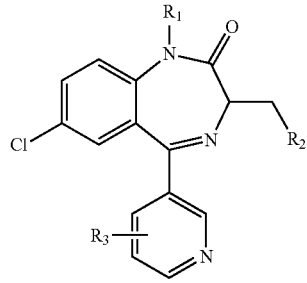
(III)

including pharmaceutically acceptable salts thereof; wherein: $R_1$ represents independently for each occurrence hydrogen or $C_1$-$C_6$alkyl; $R_2$ is

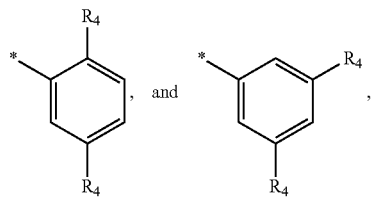

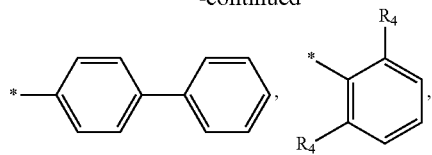

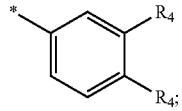

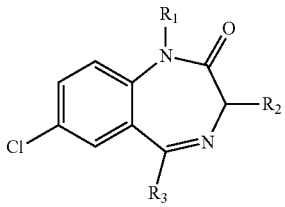

$R_3$ is hydroxyl, amino, —N($R_1$)C(O)—$C_1$-$C_6$alkyl, —O—($C_1$-$C_6$)alkylene-($C_4$-$C_6$)heterocycloalkyl, or —N($R_2$)—($C_1$-$C_6$)alkylene-($C_4$-$C_6$)heterocycloalkyl; $R_4$ represents independently for each occurrence methyl or ethyl; and the stereochemical configuration at a stereocenter in a compound represented by formula III is R, S, or a mixture thereof.

In certain other embodiments, the compound is one of the compounds listed in Tables 1, 2, 3, or 4 herein below, or a pharmaceutically acceptable salt of such compounds.

TABLE 1

| Compound | $R_1$ | $R_2$ | $R_3$ |
|---|---|---|---|
| I-1 | hydrogen | 2-chlorobenzyl | pyridinyl-piperazinyl-NH |
| I-2 | hydrogen | 2-chlorobenzyl | pyridinyl-piperazinyl-N-Me |
| I-3 | hydrogen | 2-chlorobenzyl | pyridinyl-piperazinyl-N-C(O)Me |
| I-4 | hydrogen | 2-chlorobenzyl | pyridinyl-piperazinyl-N-C(O)NH$_2$ |

TABLE 1-continued

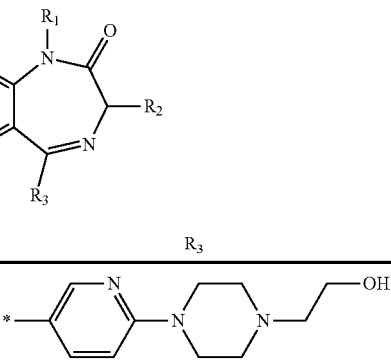

| Compound | R₁ | R₂ | R₃ |
|---|---|---|---|
| I-5 | hydrogen | 2-chlorobenzyl | 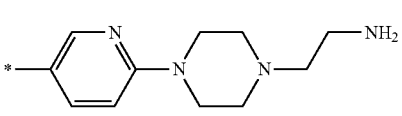 |
| I-6 | hydrogen | 2-chlorobenzyl | 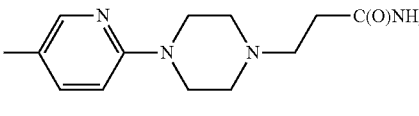 |
| I-7 | hydrogen | 2-chlorobenzyl | 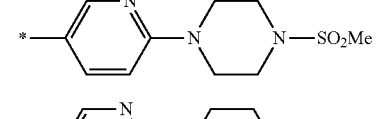 |
| I-8 | hydrogen | 2-chlorophenyl | 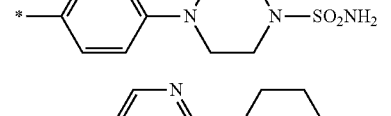 |
| I-9 | hydrogen | 2-chlorophenyl | 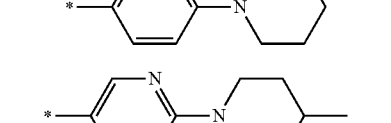 |
| I-10 | hydrogen | 2-chlorophenyl | 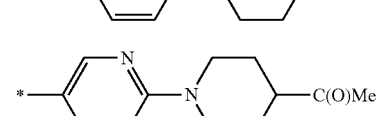 |
| I-11 | hydrogen | 2-chlorophenyl | 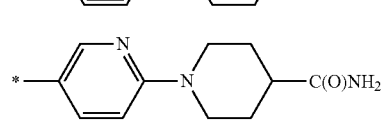 |
| I-12 | hydrogen | 2-chlorobenzyl | 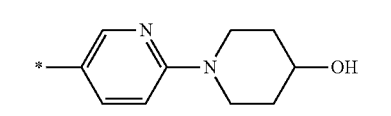 |
| I-13 | hydrogen | 2-chlorobenzyl | 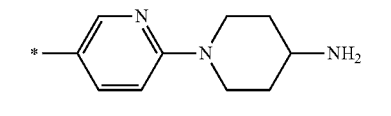 |
| I-14 | hydrogen | 2-chlorobenzyl | 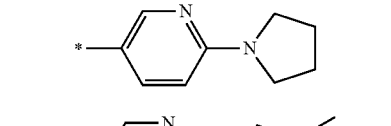 |
| I-15 | hydrogen | 2-chlorobenzyl | 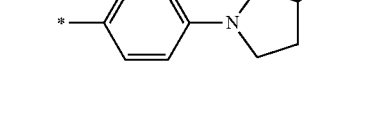 |
| I-16 | hydrogen | 2-chlorobenzyl |  |
| I-17 | hydrogen | 2-chlorobenzyl | |

TABLE 1-continued

| Compound | R₁ | R₂ | R₃ |
|---|---|---|---|
| I-18 | hydrogen | 2-chlorobenzyl | *-pyridine-N-pyrrolidine-C(O)Me |
| I-19 | hydrogen | 2-chlorobenzyl | *-pyridine-N-pyrrolidine-C(O)NH₂ |
| I-20 | hydrogen | 2-chlorobenzyl | *-pyridine-N-pyrrolidine-OH |
| I-21 | hydrogen | 2-chlorobenzyl | *-pyridine-N-pyrrolidine-NH₂ |
| I-22 | hydrogen | 2-chlorobenzyl | *-pyridine-N-(2,2-dimethylimidazolidine)-NH |
| I-23 | hydrogen | 2-chlorobenzyl | *-pyridine-N-(2,2-dimethyl-N-methyl-imidazolidine) |
| I-24 | hydrogen | 2-chlorobenzyl | *-pyridine-N-(2,2-dimethylimidazolidine)-C(O)Me |
| I-25 | hydrogen | 2-chlorobenzyl | *-pyridine-N-(2,2-dimethylimidazolidine)-C(O)NH₂ |
| I-26 | hydrogen | 2-chlorobenzyl | *-pyridine-N-(2,2-dimethylimidazolidine)-NH₂ with NH |
| I-27 | hydrogen | 2-chlorobenzyl | *-pyridine-N-(2,2-dimethyloxazolidine) |
| I-28 | hydrogen | 2-chlorobenzyl | *-pyridine-N-(2,2,5-trimethyloxazolidine) |

TABLE 1-continued
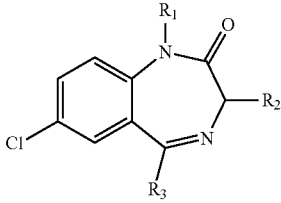
| Compound | R₁ | R₂ | R₃ |
|---|---|---|---|
| I-29 | hydrogen | 2-chlorobenzyl | 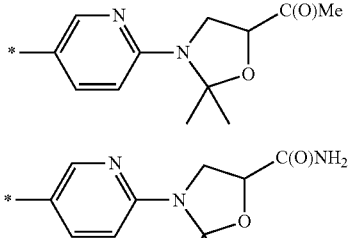 |
| I-30 | hydrogen | 2-chlorobenzyl | 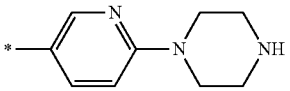 |
| I-31 | hydrogen | 2-methylbenzyl | 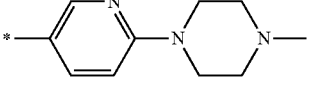 |
| I-32 | hydrogen | 2-methylbenzyl |  |
| I-33 | hydrogen | 2-methylbenzyl |  |
| I-34 | hydrogen | 2-methylbenzyl | 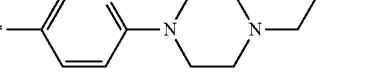 |
| I-35 | hydrogen | 2-methylbenzyl | 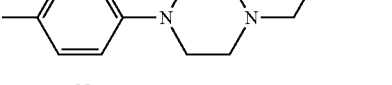 |
| I-36 | hydrogen | 2-methylbenzyl | 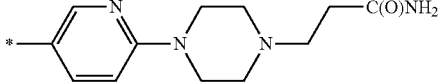 |
| I-37 | hydrogen | 2-methylbenzyl |  |
| I-38 | hydrogen | 2-methylbenzyl |  |
| I-39 | hydrogen | 2-methylbenzyl | 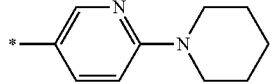 |
| I-40 | hydrogen | 2-methylbenzyl |  |

TABLE 1-continued
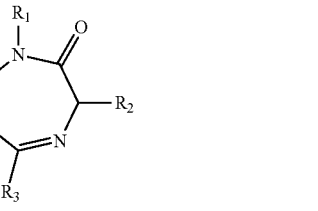
| Compound | R₁ | R₂ | R₃ |
|---|---|---|---|
| I-41 | hydrogen | 2-methylbenzyl | 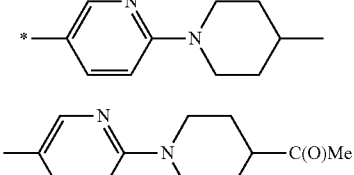 |
| I-42 | hydrogen | 2-methylbenzyl | 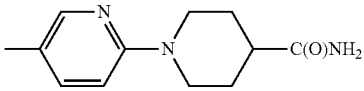 |
| I-43 | hydrogen | 2-methylbenzyl | 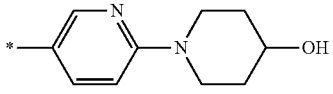 |
| I-44 | hydrogen | 2-methylbenzyl | 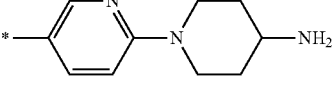 |
| I-45 | hydrogen | 2-methylbenzyl | 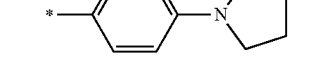 |
| I-46 | hydrogen | 2-methylbenzyl | 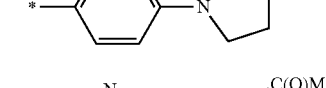 |
| I-47 | hydrogen | 2-methylbenzyl |  |
| I-48 | hydrogen | 2-methylbenzyl | 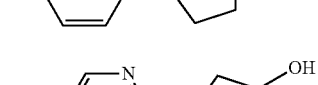 |
| I-49 | hydrogen | 2-methylbenzyl | 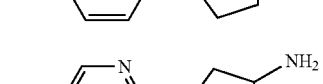 |
| I-50 | hydrogen | 2-methylbenzyl | 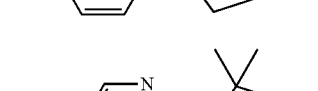 |
| I-51 | hydrogen | 2-methylbenzyl | 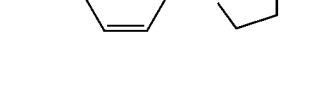 |
| I-52 | hydrogen | 2-methylbenzyl |  |

TABLE 1-continued
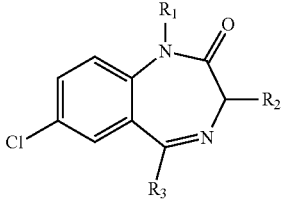
| Compound | R₁ | R₂ | R₃ |
|---|---|---|---|
| I-53 | hydrogen | 2-methylbenzyl | 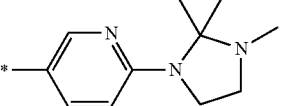 |
| I-54 | hydrogen | 2-methylbenzyl | 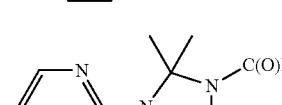 |
| I-55 | hydrogen | 2-methylbenzyl | 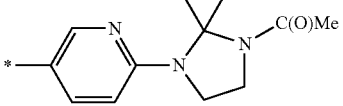 |
| I-56 | hydrogen | 2-methylbenzyl | 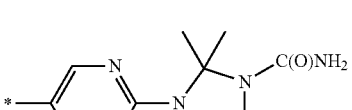 |
| I-57 | hydrogen | 2-methylbenzyl | 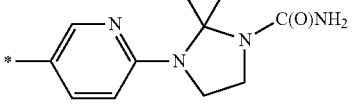 |
| I-58 | hydrogen | 2-methylbenzyl | 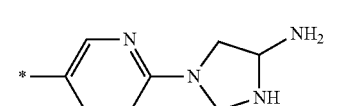 |
| I-59 | hydrogen | 2-methylbenzyl | 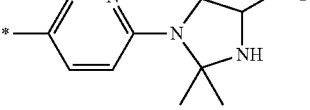 |
| I-60 | hydrogen | 2-methylbenzyl | 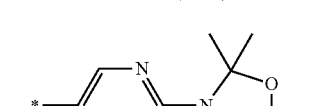 |
| I-61 | methyl | 2-chlorobenzyl | 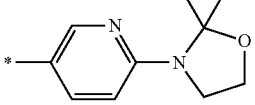 |
| I-62 | methyl | 2-chlorobenzyl | 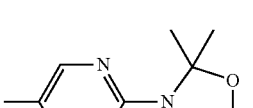 |

TABLE 1-continued
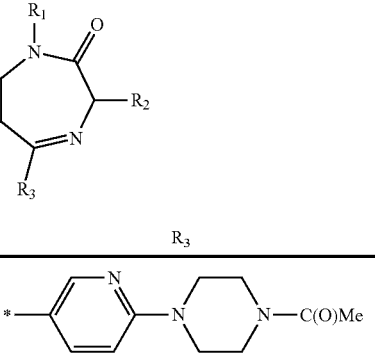
| Compound | R₁ | R₂ | R₃ |
|---|---|---|---|
| I-63 | methyl | 2-chlorobenzyl | 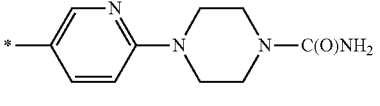 |
| I-64 | methyl | 2-chlorobenzyl | 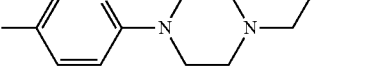 |
| I-65 | methyl | 2-chlorobenzyl | 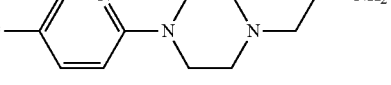 |
| I-66 | methyl | 2-chlorobenzyl | 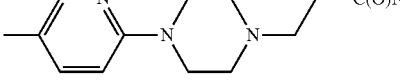 |
| I-67 | methyl | 2-chlorobenzyl | 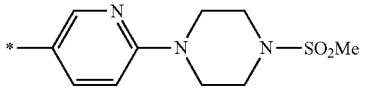 |
| I-68 | methyl | 2-chlorobenzyl | 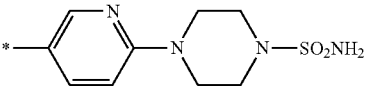 |
| I-69 | methyl | 2-chlorobenzyl | 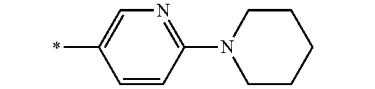 |
| I-70 | methyl | 2-chlorobenzyl | 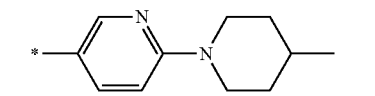 |
| I-71 | methyl | 2-chlorobenzyl | 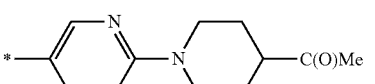 |
| I-72 | methyl | 2-chlorobenzyl | 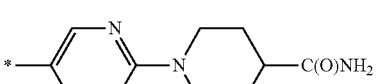 |
| I-73 | methyl | 2-chlorobenzyl | 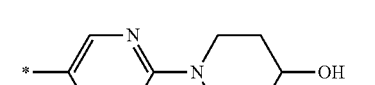 |
| I-74 | methyl | 2-chlorobenzyl | 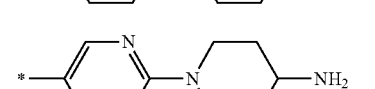 |
| I-75 | methyl | 2-chlorobenzyl | |

TABLE 1-continued
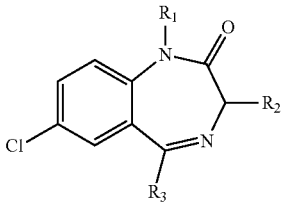
| Compound | R₁ | R₂ | R₃ |
|---|---|---|---|
| I-76 | methyl | 2-chlorobenzyl | 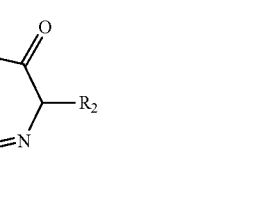 |
| I-77 | methyl | 2-chlorobenzyl | 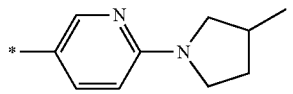 |
| I-78 | methyl | 2-chlorobenzyl | 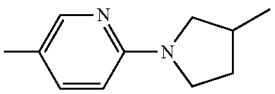 |
| I-79 | methyl | 2-chlorobenzyl | 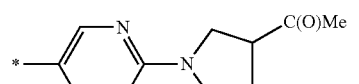 |
| I-80 | methyl | 2-chlorobenzyl | 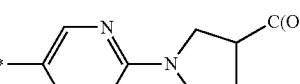 |
| I-81 | methyl | 2-chlorobenzyl | 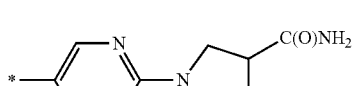 |
| I-82 | methyl | 2-chlorobenzyl | 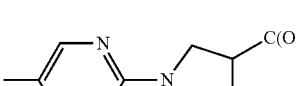 |
| I-83 | methyl | 2-chlorobenzyl | 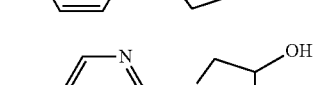 |
| I-84 | methyl | 2-chlorobenzyl |  |
| I-85 | methyl | 2-chlorobenzyl | 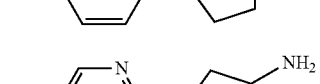 |
| I-86 | methyl | 2-chlorobenzyl |  |

TABLE 1-continued
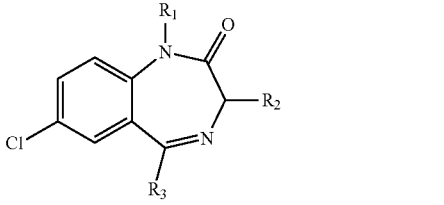
| Compound | R₁ | R₂ | R₃ |
|---|---|---|---|
| I-87 | methyl | 2-chlorobenzyl | 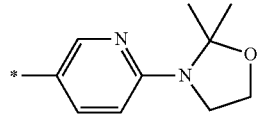 |
| I-88 | methyl | 2-chlorobenzyl | 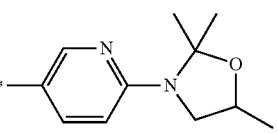 |
| I-89 | methyl | 2-chlorobenzyl | 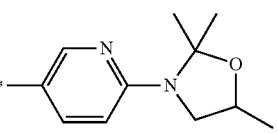 |
| I-90 | methyl | 2-chlorobenzyl | 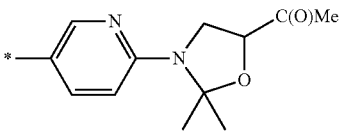 |
| I-91 | hydrogen | 2,4-dichlorobenzyl | 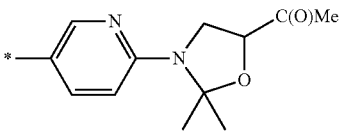 |
| I-92 | hydrogen | 2,4-dichlorobenzyl | 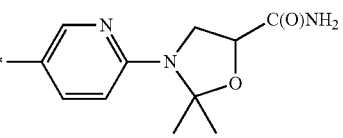 |
| I-93 | hydrogen | 2,4-dichlorobenzyl | 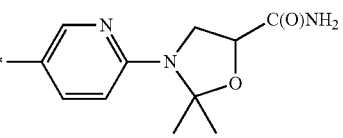 |
| I-94 | hydrogen | 2,4-dichlorobenzyl | 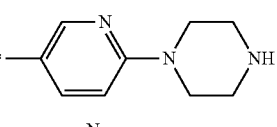 |
| I-95 | hydrogen | 2,4-dichlorobenzyl | 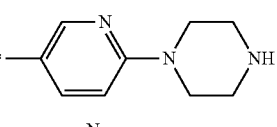 |
| I-96 | hydrogen | 2,4-dichlorobenzyl | 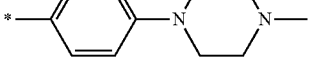 |
| I-97 | hydrogen | 2,4-dichlorobenzyl | 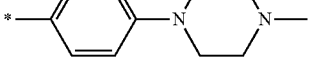 |
| I-98 | hydrogen | 2,4-dichlorobenzyl | 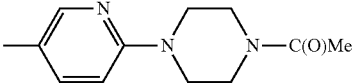 |

TABLE 1-continued

| Compound | R₁ | R₂ | R₃ |
|---|---|---|---|
| I-99 | hydrogen | 2,4-dichlorobenzyl | 5-(4-(sulfamoyl)piperazin-1-yl)pyridin-2-yl |
| I-100 | hydrogen | 2,4-dichlorobenzyl | 5-(piperidin-1-yl)pyridin-2-yl |
| I-101 | hydrogen | 2,4-dichlorobenzyl | 5-(4-methylpiperidin-1-yl)pyridin-2-yl |
| I-102 | hydrogen | 2,4-dichlorobenzyl | 5-(4-acetylpiperidin-1-yl)pyridin-2-yl |
| I-103 | hydrogen | 2,4-dichlorobenzyl | 5-(4-carbamoylpiperidin-1-yl)pyridin-2-yl |
| I-104 | hydrogen | 2,4-dichlorobenzyl | 5-(4-hydroxypiperidin-1-yl)pyridin-2-yl |
| I-105 | hydrogen | 2,4-dichlorobenzyl | 5-(4-aminopiperidin-1-yl)pyridin-2-yl |
| I-106 | hydrogen | 2,4-dichlorobenzyl | 5-(pyrrolidin-1-yl)pyridin-2-yl |
| I-107 | hydrogen | 2,4-dichlorobenzyl | 5-(3-methylpyrrolidin-1-yl)pyridin-2-yl |
| I-108 | hydrogen | 2,4-dichlorobenzyl | 5-(3-acetylpyrrolidin-1-yl)pyridin-2-yl |
| I-109 | hydrogen | 2,4-dichlorobenzyl | 5-(3-carbamoylpyrrolidin-1-yl)pyridin-2-yl |
| I-110 | hydrogen | 2,4-dichlorobenzyl | 5-(3-hydroxypyrrolidin-1-yl)pyridin-2-yl |

TABLE 1-continued
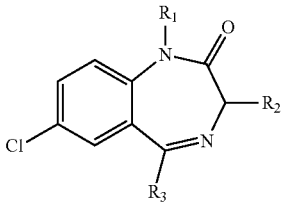
| Compound | R₁ | R₂ | R₃ |
|---|---|---|---|
| I-111 | hydrogen | 2,4-dichlorobenzyl | 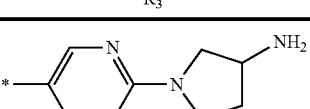 |
| I-112 | hydrogen | 2,4-dichlorobenzyl | 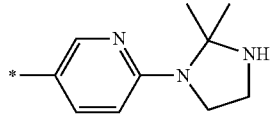 |
| I-113 | hydrogen | 2,4-dichlorobenzyl | 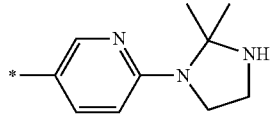 |
| I-114 | hydrogen | 2,4-dichlorobenzyl | 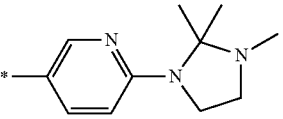 |
| I-115 | hydrogen | 2,4-dichlorobenzyl | 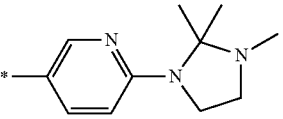 |
| I-116 | hydrogen | 2,4-dichlorobenzyl | 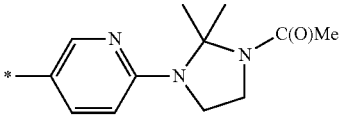 |
| I-117 | hydrogen | 2,4-dichlorobenzyl | 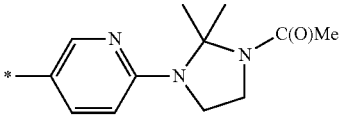 |
| I-118 | hydrogen | 2,4-dichlorobenzyl | 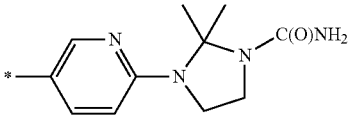 |
| I-119 | hydrogen | 2,4-dichlorobenzyl | 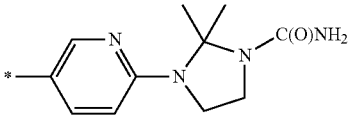 |
| I-120 | hydrogen | 2,4-dichlorobenzyl | 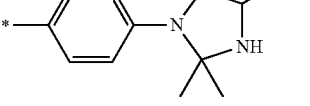 |

TABLE 2

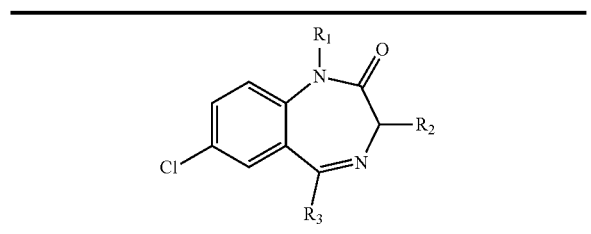

| Compound | R₁ | R₂ | R₃ |
|---|---|---|---|
| II-1 | hydrogen | 2-chlorobenzyl | 4-pyrazolyl (NH) |
| II-2 | hydrogen | 2-chlorobenzyl | 1-methyl-4-pyrazolyl |
| II-3 | hydrogen | 2-chlorobenzyl | 3-methyl-1H-4-pyrazolyl |
| II-4 | hydrogen | 2-chlorobenzyl | 1-C(O)Me-4-pyrazolyl |
| II-5 | hydrogen | 2-chlorobenzyl | 1-C(O)NH₂-4-pyrazolyl |
| II-6 | hydrogen | 2-chlorobenzyl | 3-pyrrolyl (NH) |
| II-7 | hydrogen | 2-chlorobenzyl | 1-methyl-3-pyrrolyl |
| II-8 | hydrogen | 2-chlorobenzyl | 1-C(O)Me-3-pyrrolyl |
| II-9 | hydrogen | 2-chlorobenzyl | 5-C(O)Me-1H-3-pyrrolyl |
| II-10 | hydrogen | 2-chlorobenzyl | 4-thiazolyl |
| II-11 | hydrogen | 2-methylbenzyl | 4-pyrazolyl (NH) |

TABLE 2-continued

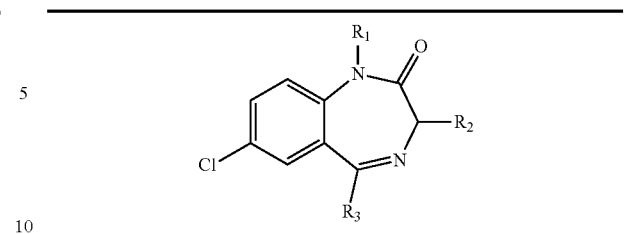

| Compound | R₁ | R₂ | R₃ |
|---|---|---|---|
| II-12 | hydrogen | 2-methylbenzyl | 1-methyl-4-pyrazolyl |
| II-13 | hydrogen | 2-methylbenzyl | 3-methyl-1H-4-pyrazolyl |
| II-14 | hydrogen | 2-methylbenzyl | 1-C(O)Me-4-pyrazolyl |
| II-15 | hydrogen | 2-methylbenzyl | 1-C(O)NH₂-4-pyrazolyl |
| II-16 | hydrogen | 2-methylbenzyl | 3-pyrrolyl (NH) |
| II-17 | hydrogen | 2-methylbenzyl | 1-methyl-3-pyrrolyl |
| II-18 | hydrogen | 2-methylbenzyl | 1-C(O)Me-3-pyrrolyl |
| II-19 | hydrogen | 2-methylbenzyl | 5-C(O)Me-1H-3-pyrrolyl |
| II-20 | hydrogen | 2-methylbenzyl | 4-thiazolyl |
| II-21 | hydrogen | 2,4-dichlorobenzyl | 4-pyrazolyl (NH) |
| II-22 | hydrogen | 2,4-dichlorobenzyl | 1-methyl-4-pyrazolyl |

TABLE 2-continued

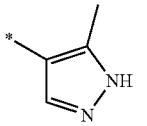

| Compound | R₁ | R₂ | R₃ |
|---|---|---|---|
| II-23 | hydrogen | 2,4-dichlorobenzyl | 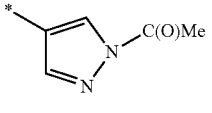 |
| II-24 | hydrogen | 2,4-dichlorobenzyl | 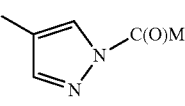 |
| II-25 | hydrogen | 2,4-dichlorobenzyl | 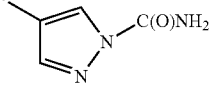 |
| II-26 | hydrogen | 2,4-dichlorobenzyl | 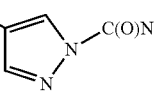 |
| II-27 | hydrogen | 2,4-dichlorobenzyl | 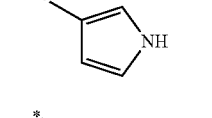 |
| II-28 | hydrogen | 2,4-dichlorobenzyl | 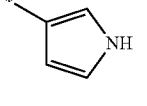 |
| II-29 | hydrogen | 2,4-dichlorobenzyl | 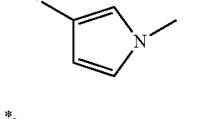 |
| II-30 | hydrogen | 2,4-dichlorobenzyl | 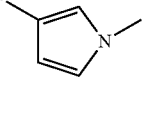 |
| II-31 | methyl | 2-chlorobenzyl | 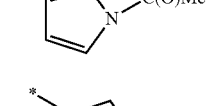 |
| II-32 | methyl | 2-chlorobenzyl | 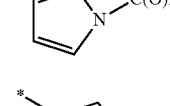 |
| II-33 | methyl | 2-chlorobenzyl | 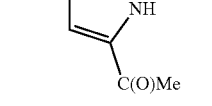 |

TABLE 2-continued

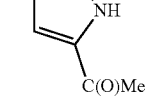

| Compound | R₁ | R₂ | R₃ |
|---|---|---|---|
| II-34 | methyl | 2-chlorobenzyl | 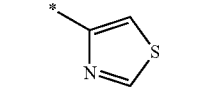 |
| II-35 | methyl | 2-chlorobenzyl | 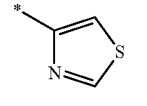 |
| II-36 | methyl | 2-chlorobenzyl | 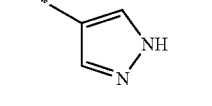 |
| II-37 | methyl | 2-chlorobenzyl | 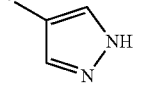 |
| II-38 | methyl | 2-chlorobenzyl | 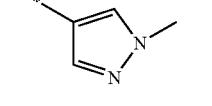 |
| II-39 | methyl | 2-chlorobenzyl | 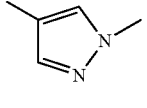 |
| II-40 | methyl | 2-chlorobenzyl | 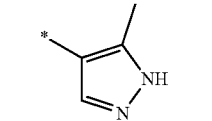 |
| II-41 | hydrogen | naphthalen-2-ylmethyl | 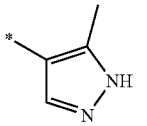 |
| II-42 | hydrogen | naphthalen-2-ylmethyl | 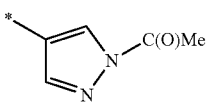 |
| II-43 | hydrogen | naphthalen-2-ylmethyl | 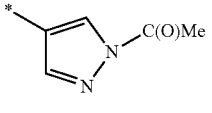 |
| II-44 | hydrogen | naphthalen-2-ylmethyl | 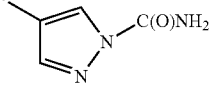 |

TABLE 2-continued

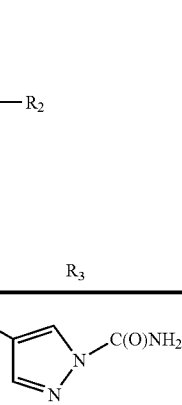

| Compound | R₁ | R₂ | R₃ |
|---|---|---|---|
| II-45 | hydrogen | naphthalen-2-ylmethyl | 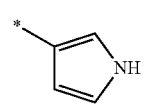 |
| II-46 | hydrogen | naphthalen-2-ylmethyl | 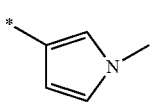 |
| II-47 | hydrogen | naphthalen-2-ylmethyl | 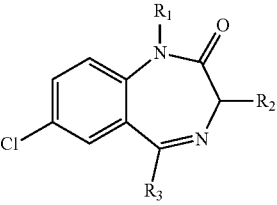 |
| II-48 | hydrogen | naphthalen-2-ylmethyl | 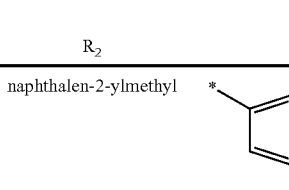 |
| II-49 | hydrogen | naphthalen-2-ylmethyl | 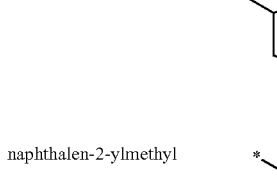 |
| II-50 | hydrogen | naphthalen-2-ylmethyl | 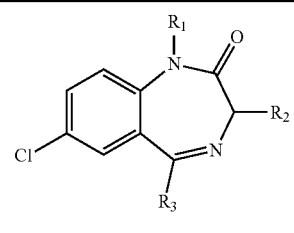 |

TABLE 3

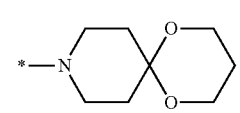

| Compound | R₁ | R₂ | R₃ |
|---|---|---|---|
| III-1 | hydrogen | 2-chlorobenzyl | 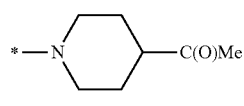 |
| III-2 | hydrogen | 2-chlorobenzyl | 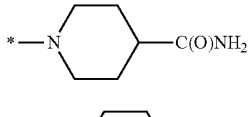 |
| III-3 | hydrogen | 2-chlorobenzyl | *—N⟨piperidine⟩—C(O)Me |
| III-4 | hydrogen | 2-chlorobenzyl | *—N⟨piperidine⟩—C(O)NH₂ |
| III-5 | hydrogen | 2-chlorobenzyl | 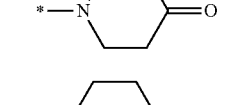 |
| III-6 | hydrogen | 2-chlorobenzyl | 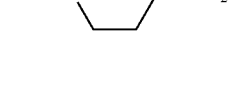 |

TABLE 3-continued

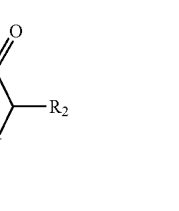

| Compound | R₁ | R₂ | R₃ |
|---|---|---|---|
| III-7 | hydrogen | 2-chlorobenzyl | 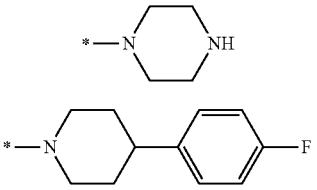 |
| III-8 | hydrogen | 2-chlorobenzyl | 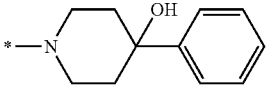 |
| III-9 | hydrogen | 2-chlorobenzyl | 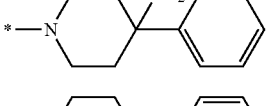 |
| III-10 | hydrogen | 2-chlorobenzyl | 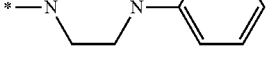 |
| III-11 | hydrogen | 2-chlorobenzyl | 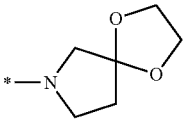 |
| III-12 | hydrogen | 2-chlorobenzyl | 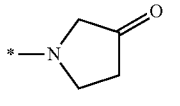 |
| III-13 | hydrogen | 2-chlorobenzyl |  |
| III-14 | hydrogen | 2-methylbenzyl | 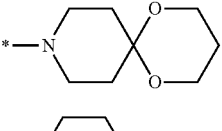 |
| III-15 | hydrogen | 2-methylbenzyl | 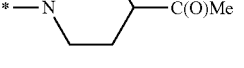 |
| III-16 | hydrogen | 2-methylbenzyl | *—N⟩—C(O)Me |
| III-17 | hydrogen | 2-methylbenzyl | *—N⟩—C(O)NH₂ |
| III-18 | hydrogen | 2-methylbenzyl | 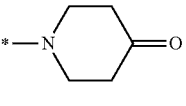 |
| III-19 | hydrogen | 2-methylbenzyl | *—N⟩—NH₂ |

TABLE 3-continued

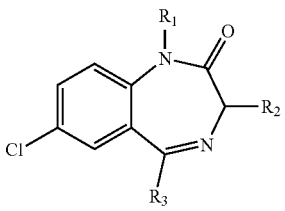

| Compound | R₁ | R₂ | R₃ |
|---|---|---|---|
| III-20 | hydrogen | 2-methylbenzyl | 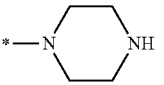 |
| III-21 | hydrogen | 2-methylbenzyl | 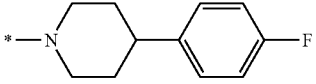 |
| III-22 | hydrogen | 2-methylbenzyl | 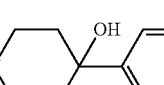 |
| III-23 | hydrogen | 2-methylbenzyl | 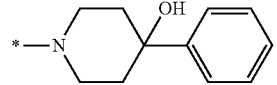 |
| III-24 | hydrogen | 2-methylbenzyl | 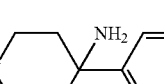 |
| III-25 | hydrogen | 2-methylbenzyl | 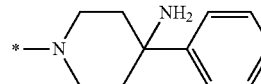 |
| III-26 | hydrogen | 2-methylbenzyl | 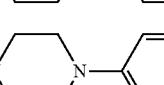 |
| III-27 | hydrogen | 2,4-dichlorobenzyl | 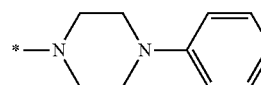 |
| III-28 | hydrogen | 2,4-dichlorobenzyl | 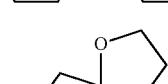 |
| III-29 | hydrogen | 2,4-dichlorobenzyl | 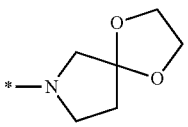 |
| III-30 | hydrogen | 2,4-dichlorobenzyl | 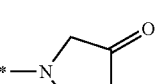 |
| III-31 | hydrogen | 2,4-dichlorobenzyl | 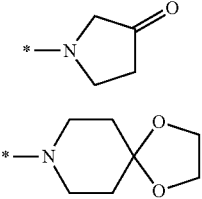 |
| III-32 | hydrogen | 2,4-dichlorobenzyl |  |

TABLE 3-continued

| Compound | R₁ | R₂ | R₃ |
|---|---|---|---|
| III-33 | hydrogen | 2,4-dichlorobenzyl | *—N(piperazine)NH |
| III-34 | hydrogen | 2,4-dichlorobenzyl | *—N(piperidine)-(4-fluorophenyl) |
| III-35 | hydrogen | 2,4-dichlorobenzyl | *—N(piperidine)(OH)(phenyl) |
| III-36 | hydrogen | 2,4-dichlorobenzyl | *—N(piperidine)(NH₂)(phenyl) |
| III-37 | hydrogen | 2,4-dichlorobenzyl | *—N(piperazine)-N-phenyl |
| III-38 | hydrogen | 2,4-dichlorobenzyl | *—N(pyrrolidine-spiro-1,3-dioxolane) |
| III-39 | hydrogen | 2,4-dichlorobenzyl | *—N(3-oxopyrrolidine) |
| III-40 | methyl | 2-chlorobenzyl | *—N(piperidine-spiro-1,3-dioxolane) |
| III-41 | methyl | 2-chlorobenzyl | *—N(piperidine-spiro-1,3-dioxane) |
| III-42 | methyl | 2-chlorobenzyl | *—N(piperidine)-C(O)Me |
| III-43 | methyl | 2-chlorobenzyl | *—N(piperidine)-C(O)NH₂ |
| III-44 | methyl | 2-chlorobenzyl | *—N(4-oxopiperidine) |
| III-45 | methyl | 2-chlorobenzyl | *—N(piperidine)-NH₂ |

TABLE 3-continued
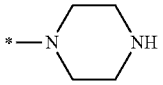
| Compound | R₁ | R₂ | R₃ |
|---|---|---|---|
| III-46 | methyl | 2-chlorobenzyl | 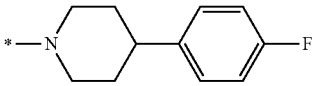 |
| III-47 | methyl | 2-chlorobenzyl | 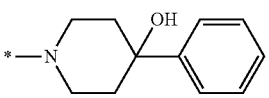 |
| III-48 | methyl | 2-chlorobenzyl | 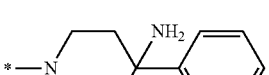 |
| III-49 | methyl | 2-chlorobenzyl | 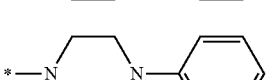 |
| III-50 | methyl | 2-chlorobenzyl | 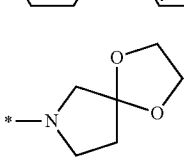 |
| III-51 | methyl | 2-chlorobenzyl | 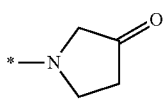 |
| III-52 | methyl | 2-chlorobenzyl | 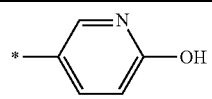 |
TABLE 4
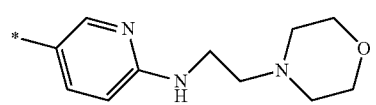
| Compound | R₁ | R₂ | R₃ |
|---|---|---|---|
| IV-1 | hydrogen | 2-chlorobenzyl | (5-pyridinyl-2-ol) |
| IV-2 | hydrogen | 2-chlorobenzyl | (5-pyridinyl-2-NH-CH₂CH₂-morpholine) |

TABLE 4-continued

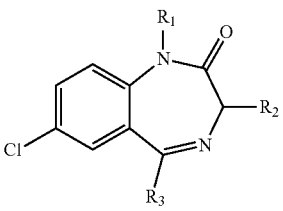

| Compound | R₁ | R₂ | R₃ |
|---|---|---|---|
| IV-3 | hydrogen | 2-chlorobenzyl | 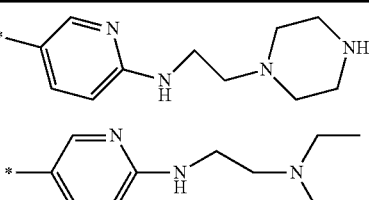 |
| IV-4 | hydrogen | 2-chlorobenzyl | 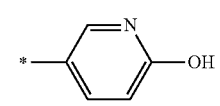 |
| IV-5 | cyclopropyl | 2-chlorobenzyl | 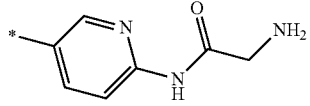 |
| IV-6 | hydrogen | 2-chlorobenzyl | 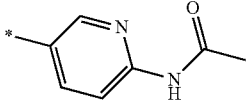 |
| IV-7 | hydrogen | 2-chlorobenzyl | 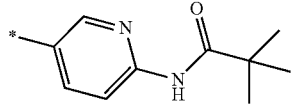 |
| IV-8 | hydrogen | 2-chlorobenzyl | 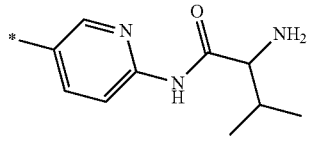 |
| IV-9 | hydrogen | 2-chlorobenzyl | 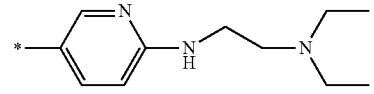 |
| IV-10 | hydrogen | 2-(methylsulfonyl)benzyl | 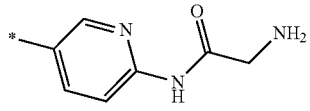 |
| IV-11 | hydrogen | 2-chloro-3-fluorobenzyl | 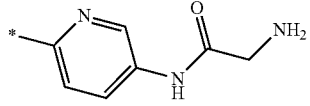 |
| IV-12 | hydrogen | 2-chloro-3-fluorobenzyl | 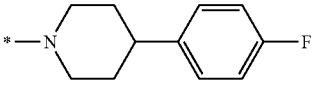 |
| IV-13 | hydrogen | 2-(methylsulfonyl)benzyl | 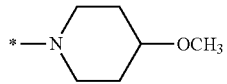 |
| IV-14 | hydrogen | 2-chlorobenzyl | *—N⟨piperidine⟩—OCH₃ |

TABLE 4-continued

| Compound | R₁ | R₂ | R₃ |
|---|---|---|---|
| IV-15 | hydrogen | 2-chlorobenzyl | 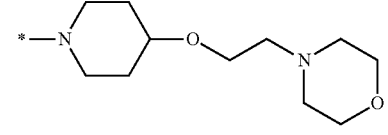 |
| IV-16 | hydrogen | 2-chlorobenzyl | 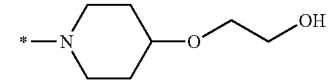 |
| IV-17 | hydrogen | 2-chlorobenzyl | 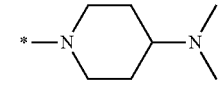 |
| IV-18 | hydrogen | 2-chlorobenzyl | 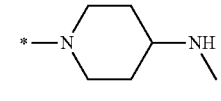 |
| IV-19 | hydrogen | 2-chlorobenzyl | 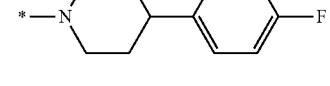 |
| IV-20 | hydrogen | 2-(methylsulfonyl)benzyl | 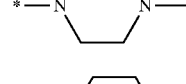 |
| IV-21 | hydrogen | 2-chlorobenzyl | 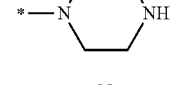 |
| IV-22 | hydrogen | 2-chlorobenzyl | 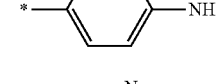 |
| IV-23 | hydrogen | 2-chlorobenzyl | 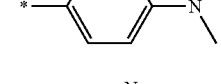 |
| IV-24 | hydrogen | 2-chlorobenzyl | 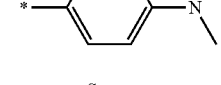 |
| IV-25 | hydrogen | 2-(N,N-dimethylsulfamoyl)benzyl | 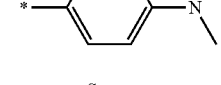 |
| IV-26 | hydrogen | 2-chlorobenzyl | 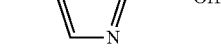 |

TABLE 4-continued

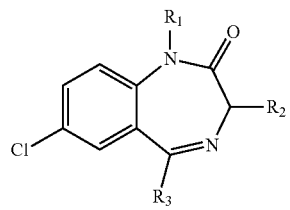

| Compound | R₁ | R₂ | R₃ |
|---|---|---|---|
| IV-27 | hydrogen | 2-chlorobenzyl | 2-methylpyridin-4-yl |
| IV-28 | hydrogen | 2-chlorobenzyl | 2-(methylamino)pyrimidin-5-yl |
| IV-29 | hydrogen | 2-chlorobenzyl | 2-((methylamino)methyl)thiazol-4-yl |
| IV-30 | hydrogen | 2-chlorobenzyl | 2-((2-aminoacetamido)methyl)thiazol-4-yl |
| IV-31 | hydrogen | 2-fluorobenzyl | 2-methylpyridin-4-yl |
| IV-32 | hydrogen | 2-fluorobenzyl | 2-(hydroxymethyl)pyridin-4-yl |
| IV-33 | hydrogen | 2-chlorobenzyl | 4-(phosphonooxy)piperidin-1-yl |
| IV-34 | hydrogen | 2-cyanobenzyl | 2,6-dimethylpyridin-4-yl |
| IV-35 | hydrogen | 2-chlorobenzyl | 3-(methylamino)pyrrolidin-1-yl |
| IV-36 | hydrogen | 2-chlorobenzyl | 3-hydroxypyrrolidin-1-yl |
| IV-37 | hydrogen | 2-chlorobenzyl | 3,4-dihydroxypyrrolidin-1-yl |

TABLE 4-continued

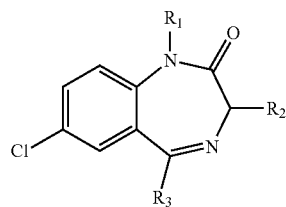

| Compound | $R_1$ | $R_2$ | $R_3$ |
|---|---|---|---|
| IV-38 | hydrogen | 2-chlorobenzyl | octahydropyrrolo[3,4-c]pyrrol-2-yl |
| IV-39 | hydrogen | 2-chloro-3-fluorobenzyl | 1H-pyrazol-4-yl |
| IV-40 | methyl | 2-chlorobenzyl | 1H-pyrazol-4-yl |
| IV-41 | —$(CH_2)_2$OH | 2-chlorobenzyl | 1H-pyrazol-4-yl |
| IV-42 | cyclopropyl | 2-chlorobenzyl | 1H-pyrazol-4-yl |
| IV-43 | —$(CH_2)_2$N$(CH_3)_2$ | 2-chlorobenzyl | 1H-pyrazol-4-yl |
| IV-44 | —$(CH_2)_2$N$(CH_3)_2$ | 2-(methylsulfonyl)benzyl | 1H-pyrazol-4-yl |
| IV-45 | cyclopropyl | 2-cyanobenzyl | 1H-pyrazol-4-yl |
| IV-46 | —$(CH_2)_2$OH | 2-methylbenzyl | 1H-pyrazol-4-yl |
| IV-47 | —$(CH_2)_2$OH | 2-phenylbenzyl | 1H-pyrazol-4-yl |
| IV-48 | Methyl | 2-methylbenzyl | 1H-pyrazol-4-yl |
| IV-49 | hydrogen | 2-phenylbenzyl | 1H-pyrazol-4-yl |
| IV-50 | hydrogen | 2-t-butylbenzyl | 1H-pyrazol-4-yl |

TABLE 4-continued

| Compound | $R_1$ | $R_2$ | $R_3$ |
|---|---|---|---|
| IV-51 | hydrogen | 2-chloro-3-fluorobenzyl | 5-(1H-pyrazolo[3,4-b]pyridinyl) |
| IV-52 | hydrogen | 2-chlorobenzyl | 5-(1H-pyrazolo[3,4-b]pyridinyl) |
| IV-53 | hydrogen | 2-chlorobenzyl | 6-(oxazolo[4,5-b]pyridin-2(3H)-one) |
| IV-54 | hydrogen | 2-chlorobenzyl | 5-(2-(methylsulfonamido)pyridinyl) |
| IV-55 | hydrogen | 2-chlorobenzyl | 4-(2-(methylsulfonamido)pyridinyl) |
| IV-56 | hydrogen | 2-chlorobenzyl | 5-(1H-pyrrolo[2,3-b]pyridin-2(3H)-one) |
| IV-57 | hydrogen | 2-chlorobenzyl | 5-(3,3-dimethyl-1H-pyrrolo[2,3-b]pyridin-2(3H)-one) |

Methods for preparing 1,4-benzodiazepinone compounds described herein are illustrated in the following synthetic schemes. The following schemes are given for the purpose of illustrating the invention, but not for limiting the scope or spirit of the invention. Consistent with this purpose, Scheme 1 shows methods of preparing 1,4-benzodiazepinone compounds having an heteroaromatic group at the C5-position of the benzodiazepinone ring.

SCHEME 1

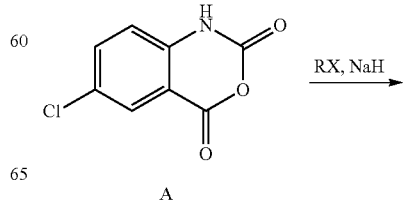

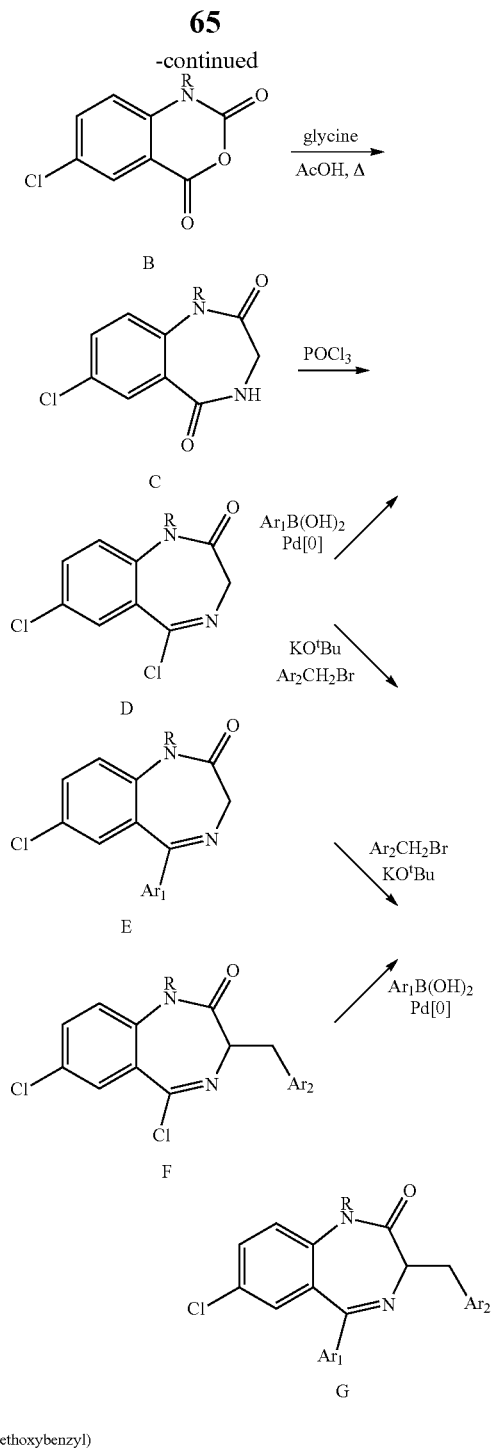

B1 (R = Me)
B2 (R = p-methoxybenzyl)
E1 (R = Me, Ar₁ = heteroaryl)
E2 (R = Ar₁ = heteroaryl)

N-alkylation of isatoic anhydride A can be carried out by treating compound A with sodium hydride and an alkyl or benzyl halide. Reaction of compound A with a benzyl halide, such as a p-methoxybenzyl halide, can be performed to install a protecting group, while reaction of compound A with various alkyl halides, e.g., methyl iodide or ethyl iodide, can be performed to install alkyl substitution on the N1-position of the benzodiazepinone ring. Isatoic anhydride B can be converted to benzodiazepinone C upon reaction with glycine. See *Indian J. Chem. Sect. B.* 1985, 24, 905-907. This procedure provides benzodiazepinone C, which can be subsequently treated with POCl₃ to provide imidoyl chloride D.

A heteroaromatic group (substituent Ar₁) can be installed at the C5-position of the benzodiazepinone core by Suzuki coupling of a heteroaryl boronic acid, in accordance with procedures described by Nadin and co-workers. See *J. Org. Chem.* 2003, 68, 2844-2852. The "eastern" aryl ring (substituent Ar₂) can be installed by alkylation at the C3-position of the benzodiazepinone ring. Deprotonation at C-3 using a strong base, such as potassium tert-butoxide, followed by addition of a substituted benzyl halide provides benzodiazepinone G. Benzyl halides for this reaction can be obtained commercially or prepared from the corresponding benzyl alcohol using known procedures, such as treating a benzyl alcohol with thionyl chloride. A variety of benzyl alcohols are commercially available. In addition, a variety of benzyl alcohols can be prepared using any one of the following methods: i) reduction of a commercially available carboxylic acid (e.g., reduction using lithium aluminum hydride); ii) conversion of a dibromo-benzyl alcohol to a dialkyl-benzyl alcohol using, for example, a dialkylzinc reagent in the presence of a palladium catalyst, such as PdCl₂(dppf); iii) conversion of a dibromobenzyl acetate to a dialkyl benzyl acetate followed by hydrolysis; iv) formylation of the appropriate aromatic compound followed by reduction; or v) conversion of a reactive chlorobenzoate ester to the respective alkyl benzoate ester using, for example, a Grignard reagent in the presence of an iron catalyst, such as Fe(acac)₃, followed by reduction.

Substituents on the "eastern" aromatic ring can be installed following C3-alkylation of the benzodiazepine ring. For example, C3-alkylation with 3-bromobenzyl bromide, followed by Pd-catalyzed attachment of an alkyl group to the aromatic ring.

As illustrated in Scheme 1 above, benzodiazepinone G can also be prepared using a synthetic strategy involving C3-alkylation of imidoyl chloride D followed by a palladium-coupling reaction to install a "southern" heteroaromatic ring. This synthetic strategy should be amenable to wide a variety of substrates. The heteroaryl boronates used in this palladium-coupling reaction can be obtained from commercial sources or they can be easily prepared. For example, a heteroaryl boronate can be prepared by treating a heteroaryl bromide with bis(pinacolato)diboron in the presence of a palladium catalyst.

In situations where protecting groups are used during the synthesis, protecting groups on compound G can be removed using standard procedures known in the art. For example, N-deprotection of a p-methoxybenzyl group can be performed using cerium (IV) ammonium nitrate, according to literature procedures.

The synthetic approach illustrated in Scheme 1 is amenable to making 1,4-benzodiazepines have a heterocycloalkyl group at the C5-position of the benzodiazepinone ring. The synthetic procedure for making such compounds utilizes a heterocycloalkyl boronic acid in place of the heteroaryl boronic acid shown in Scheme 1. A variety of heterocycloalkyl boronic acids are known in the art and/or could be purchased from commercial sources.

To further illustrate synthetic methods for making compounds described herein, Scheme 2 shows the synthesis of a specific 1,4-benzodiazepinone compound having an aminopyridinyl group at the C5-position of the 1,4-benzodiazepinone ring.

SCHEME 2
SCHEME 3
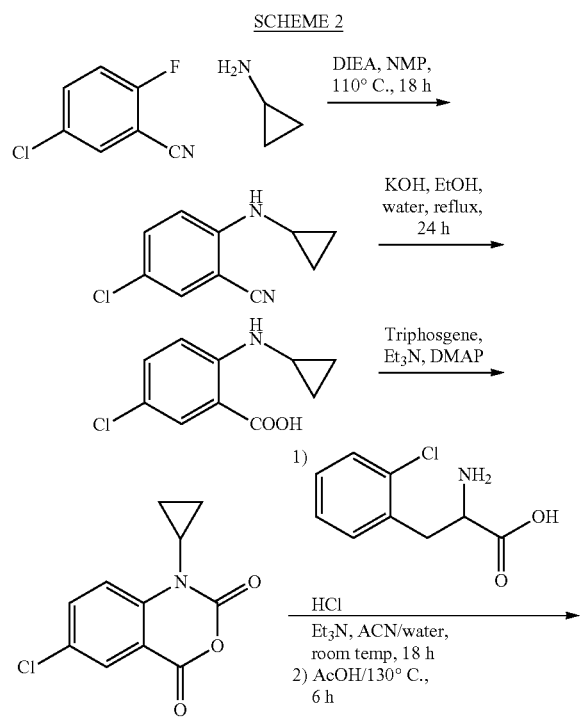
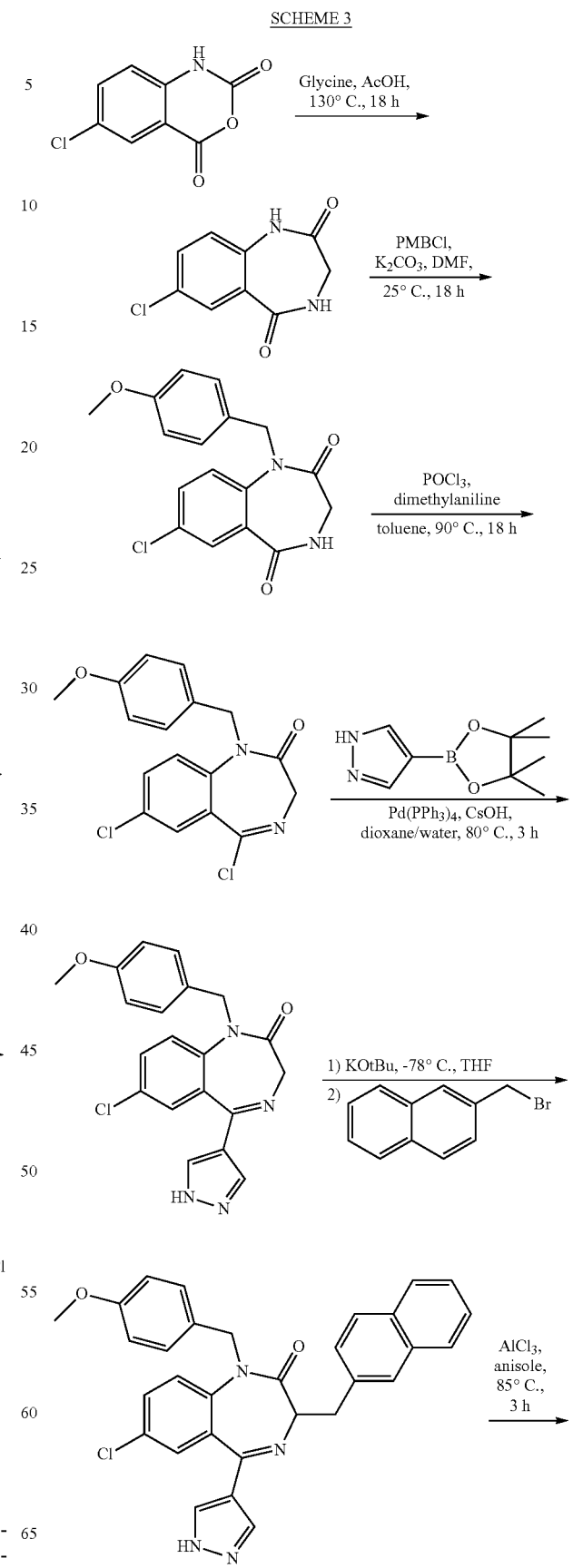
Scheme 3 shows the synthesis of a specific 1,4-benzodiazepinone compound having a pyrazolyl group at the C5-position of the 1,4-benzodiazepinone ring.

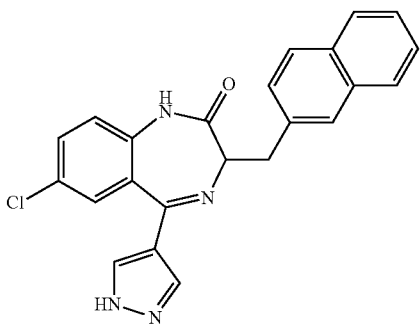

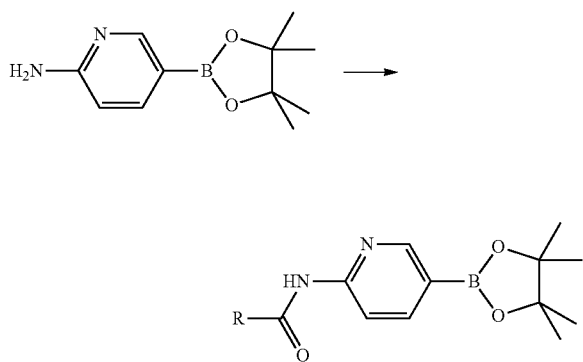

A wide variety of heterocyclic boronic acids or boranes are commercially available or can be readily prepared commercial boronates or aryl halides using procedures known in the art. For example, acylation of 5-(4,4,5,5-tetramethyl-1,3,2-dioxaborolan-2-yl)pyridin-2-amine may be performed with a variety of acylating agents and coupling conditions such as acetic anhydride in pyridine, or Boc-glycine and dicyclohexylcarbodiimide (Scheme 4). In some cases it is desirable to deprotect this side chain fragment after the Suzuki coupling, for example to remove a nitrogen protecting group such as a Boc group.

SCHEME 4

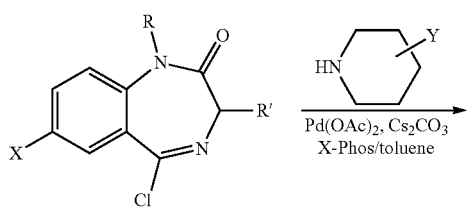

1,4-Benzodiazepinone compounds having a heteroalkyl group at the C5-position can also be prepared by coupling an imidoyl chloride with a heteroalkyl group, such as depicted in Scheme 5 for an optionally substituted piperidine group. The coupling reaction is catalyzed using palladium acetate or a similar palladium (II) catalyst in the presence of a base (such as cesium carbonate) and a phosphine ligand, such as X-phos. Typical reaction conditions utilize a non-polar solvent (e.g., toluene) and involve heating the reaction mixture.

SCHEME 5

Y is alkyl, alkoxy, fluoro, etc.
X is chloro, fluoro, etc.
R is alkyl, aralkyl (e.g., methoxybenzyl)
R' is aralkyl Additional synthetic procedures are described in detail in the examples below. Further, additional synthetic procedures can be found in, for example, "Comprehensive Organic Synthesis" (B. M. Trost & I. Fleming, eds., 1991-1992); Carey, F. A. and Sundberg, R. J. Advanced Organic Chemistry Part B: Reactions and Synthesis, $3^{rd}$ Ed.; Plenum Press: New York, 1990; and J. March, Advanced Organic Chemistry, McGraw Hill Book Company, New York, (1992, $4^{th}$ edition); each of which is hereby incorporated by reference.

II. Therapeutic Applications

It is contemplated that the 1,4-benzodiazepinone compounds of formula I and related benzodiazepinone compounds, for example, those embraced by formula II, provide therapeutic benefits to patients suffering from cancer. Accordingly, one aspect of the invention relates to a method of treating a subject suffering from cancer. The method comprises administering to a subject in need thereof a therapeutically effective amount of one or more 1,4-benzodiazepinone compounds described herein. The compounds described herein are contemplated to have activity in treating a variety of cancers. For example, the compounds described herein are contemplated to have activity in treating a hematological cancer or solid tumor malignancy. In certain embodiments, the cancer is breast cancer, colon cancer, small-cell lung cancer, non-small cell lung cancer, prostate cancer, renal cancer, ovarian cancer, leukemia, melanoma, cancer of the central nervous system tissue, pancreatic cancer, cervical cancer, testicular cancer, bladder cancer, brain cancer, skin cancer, thyroid cancer, Hodgkin's lymphoma, non-Hodgkin's lymphoma, cutaneous T-Cell lymphoma, cutaneous B-Cell lymphoma, or diffuse large B-Cell lymphoma. In certain other embodiments, the cancer is breast cancer, colon cancer, small-cell lung cancer, non-small cell lung cancer, prostate cancer, renal cancer, ovarian cancer, leukemia, melanoma, or cancer of the central nervous system tissue. In certain other embodiments, the cancer is colon cancer, small-cell lung cancer, non-small cell lung cancer, renal cancer, ovarian cancer, renal cancer, or melanoma.

Additional exemplary cancers include fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, epithelial carcinoma, glioma, astrocytoma, medulloblastoma, hemangioblastoma, acoustic neuroma, oligodendroglioma, meningioma, neuroblastoma, and retinoblastoma.

In certain embodiments, the cancer is a neuroblastoma, meningioma, hemangiopericytoma, multiple brain metastase, glioblastoma multiforms, glioblastoma, brain stem glioma, poor prognosis malignant brain tumor, malignant glioma, anaplastic astrocytoma, anaplastic oligodendroglioma, neuroendocrine tumor, rectal adeno carcinoma, Dukes C & D colorectal cancer, unresectable colorectal carcinoma, metastatic hepatocellular carcinoma, Kaposi's sarcoma, karotype acute myeloblastic leukemia, Hodgkin's lymphoma, non-Hodgkin's lymphoma, cutaneous T-Cell lymphoma, cutaneous B-Cell lymphoma, diffuse large B-Cell lymphoma, low grade follicular lymphoma, metastatic melanoma, localized melanoma, malignant mesothelioma, malignant pleural effusion mesothelioma syndrome, peritoneal carcinoma, papillary serous carcinoma, gynecologic sarcoma, soft tissue sarcoma, sceleroderma, cutaneous vasculitis, Langerhans cell histiocytosis, leiomyosarcoma, fibrodysplasia ossificans progressive, hormone refractory prostate cancer, resected high-risk soft tissue sarcoma, unrescectable hepatocellular carcinoma, Waidenstrom's macroglobulinemia, smoldering myeloma, indolent myeloma, fallopian tube cancer, androgen independent prostate cancer, androgen dependent stage 1V non-metastatic prostate cancer, hormone-insensitive prostate cancer, chemotherapy-insensitive prostate cancer, papillary thyroid carcinoma, follicular thyroid carcinoma, medullary thyroid carcinoma, or leiomyoma.

The compounds administered to the patient for treating cancer may be any of the generic, subgeneric or specific compounds described herein, including all the particular embodiments specified in relation to formulae I, IA, IB, IC, ID, IE, II, and III above. In certain embodiments, the subject treated is a human.

Procedures for testing the efficacy of the compounds described herein against various cancers are known in the art.

IV. Pharmaceutical Compositions and Dosing Considerations

Another aspect of the invention provides pharmaceutical compositions which comprise a therapeutically-effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations. (See e.g., Martin, Remington's Pharmaceutical Sciences, 15th Ed., Mack Publ. Co., Easton, Pa. [1975]).

As set out above, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1-19)

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product. In certain embodiments, the invention provides for the use of a compound described herein in the manufacture of a medicament for the treatment of a disease or disorder described herein.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes.

The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc.

administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient, when used for the indicated analgesic effects, will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms. Preferred dosing is one administration per day.

While it is possible for a compound of the present invention to be administered alone, it is preferable to administer the compound as a pharmaceutical formulation (composition).

The compounds according to the invention may be formulated for administration in any convenient way for use in human or veterinary medicine, by analogy with other pharmaceuticals.

In another aspect, the present invention provides pharmaceutically acceptable compositions which comprise a therapeutically-effective amount of one or more of the subject compounds, as described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin, lungs, or mucous membranes; or (4) intravaginally or intrarectally, for example, as a pessary, cream or foam; (5) sublingually or buccally; (6) ocularly; (7) transdermally; or (8) nasally.

In some embodiments, in vivo administration is effected in one dose, continuously or intermittently throughout the course of treatment. Methods of determining the most effective means and dosage of administration are well known to those of skill in the art and vary with the composition used for therapy, the purpose of the therapy, the target cell being treated, and the subject being treated. Single or multiple administrations are carried out with the dose level and pattern being selected by the treating physician.

Suitable dosage formulations and methods of administering the agents are readily determined by those of skill in the art. Preferably, the compounds are administered at about 0.01 mg/kg to about 200 mg/kg, more preferably at about 0.1 mg/kg to about 100 mg/kg, even more preferably at about 0.5 mg/kg to about 50 mg/kg. When the compounds described herein are co-administered with another agent (e.g., as sensitizing agents), the effective amount may be less than when the agent is used alone.

The pharmaceutical compositions can be administered orally, intranasally, parenterally or by inhalation therapy, and may take the form of tablets, lozenges, granules, capsules, pills, ampoules, suppositories or aerosol form. They may also take the form of suspensions, solutions and emulsions of the active ingredient in aqueous or non-aqueous diluents, syrups, granulates or powders. In addition to an agent of the present invention, the pharmaceutical compositions can also contain other pharmaceutically active compounds or a plurality of compounds of the invention.

EXAMPLES

The invention now being generally described, will be more readily understood by reference to the following examples, which are included merely for purposes of illustration of certain aspects and embodiments of the present invention, and are not intended to limit the invention.

Example 1

Representative Procedure for Synthesis of Benzo[e][1,4]diazepin-2(3H)-ones from Imidoyl Chlorides Part I: Palladium-Coupling of a Heteroaryl Boronic Acid and an Imidoyl Chloride

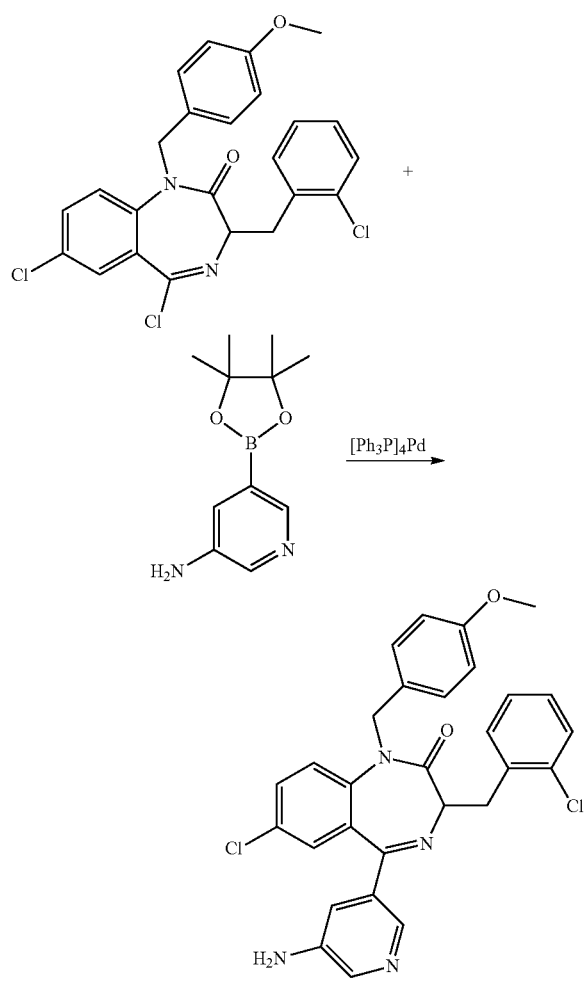

5-(5-Aminopyridin-3-yl)-7-chloro-3-(2-chlorobenzyl)-1-(4-methoxybenzyl)-1H-benzo[e][1,4]diazepin-2(3H)-one 5,7-Dichloro-3-(2-chlorobenzyl)-1-(4-methoxybenzyl)-1H-benzo[e][1,4]diazepin-2(3H)-one (240 mg) and 5-(4,4,5,5-tetramethyl-1,3,2-dioxaborolan-2-yl)pyridin-3-amine (134 mg, 1.2 eq) were suspended in dioxane/water (6 mL/2 mL), and then cesium hydroxide (170 mg, 2 eq) was added and the mixture was degassed by pulling vacuum until bubbling occurred, and then introducing nitrogen gas. The degassing procedure was repeated twice, and then tetrakis(triphenylphosphine)palladium(0) (30 mg, 0.05 eq) was added. The degassing procedure was repeated once, and then the reaction was heated to 90° C. for three hours. The crude mixture was then diluted with EtOAc (20 mL) and then washed with water, then brine, and then it was dried over sodium sulfate, and concentrated onto silica gel. The product was purified by chromatography (gradient: 75:25 hexanes:EtOAc to EtOAc) delivering the product as a solid (90 mg, 33% yield). MS (ES+) m/z 531.0 (M+1).

Part II: Removal of Methoxybenzyl Protecting Group

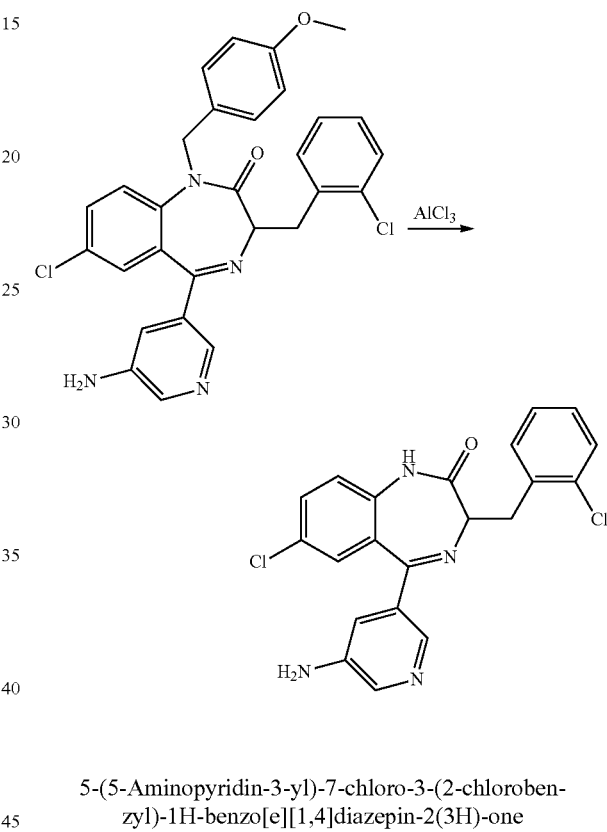

5-(5-Aminopyridin-3-yl)-7-chloro-3-(2-chlorobenzyl)-1H-benzo[e][1,4]diazepin-2(3H)-one 5-(5-Aminopyridin-3-yl)-7-chloro-3-(2-chlorobenzyl)-1-(4-methoxybenzyl)-1H-benzo[e][1,4]diazepin-2(3H)-one (90 mg) was dissolved in anisole (5 mL) and aluminum chloride (90 mg, 4 eq) was then added. The suspension was heated to 85° C. under nitrogen gas for two hours, and then it was cooled to room temperature and poured onto ice water/EtOAc 1:1 (30 mL:30 g). The slurry was stirred vigorously for 1 hour, and the organic phase was then separated and washed with brine. The organic phase was dried over sodium sulfate, then concentrated, and purified by chromatography (gradient: DCM to 8:2 DCM:MeOH) delivering the title compound as a solid (23 mg, 34% yield). $^1$H-NMR (300 MHz, DMSO-$d_6$) δ 10.80 (s, 1H), 7.98 (d, 1H), 7.65 (m, 2H), 7.47 (dd, 2H), 7.30-7.20 (m, 4H), 6.85 (s, 1H) 5.47 (bs, 2H), 3.77 (t, 1H), 3.45 (d, 2H). HRMS (ES+) m/z calcd for $C_{21}H_{16}Cl_2N_4O$ $[M+H]^+$, 411.0779. found, 411.0770.

The following compounds were prepared by making appropriate substitutions to the above procedures.

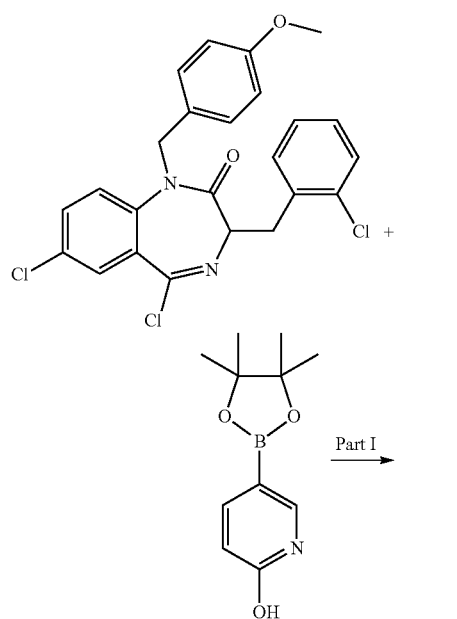

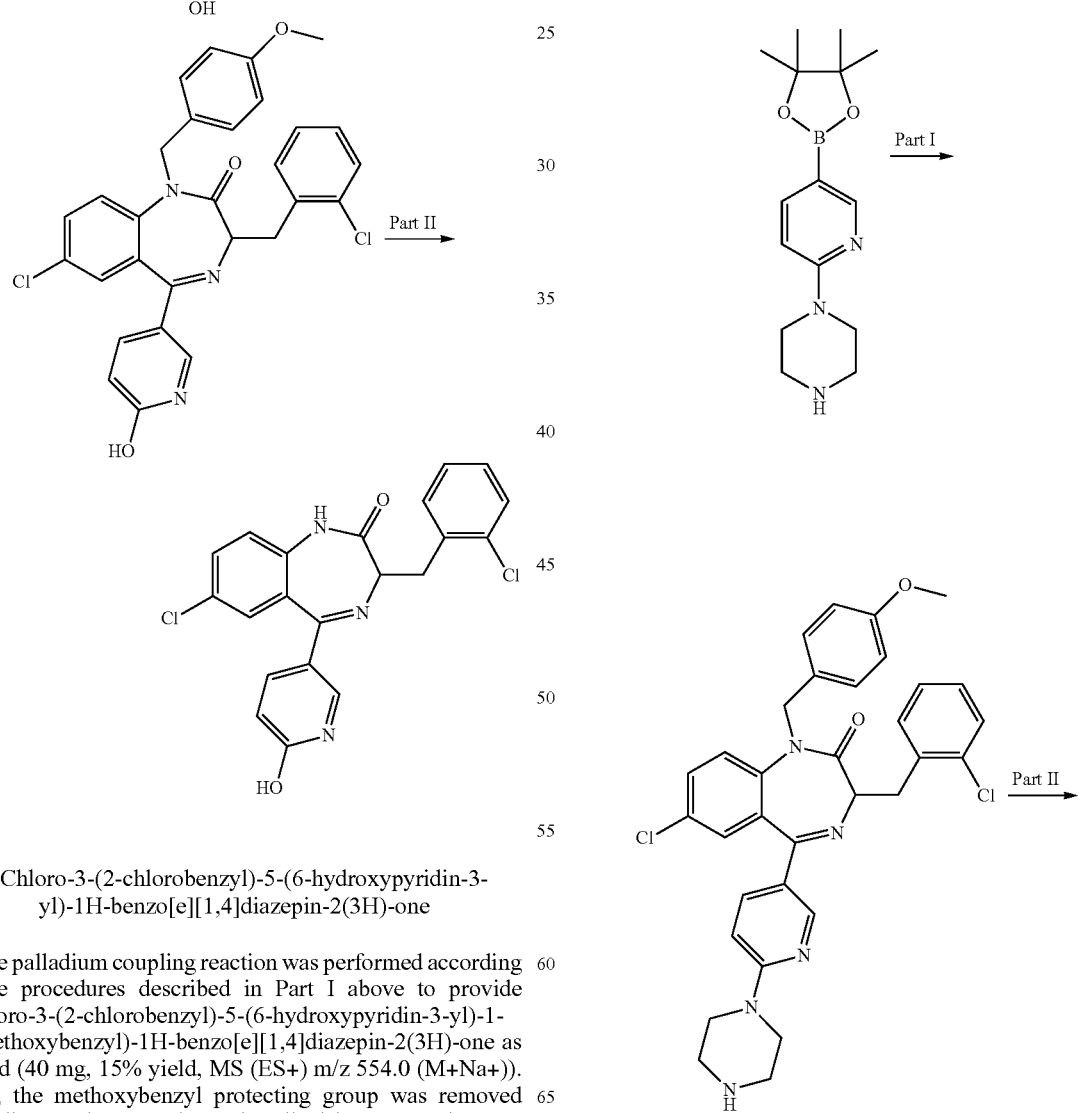

¹H-NMR (300 MHz, DMSO-d₆) δ 11.73 (bs, 1H), 10.72 (bs, 1H), 7.68-7.60 (m, 2H), 7.53 (s, 1H), 7.45 (d, 1H), 7.36 (d, 1H), 7.27-7.18 (m, 4H), 6.35 (d, 1H), 3.70 (m, 1H), 3.40 (m, 2H). HRMS (ES+) m/z calcd for $C_{21}H_{16}Cl_2N_3O_2$ [M+H]⁺, 412.0620. found, 412.0606.

7-Chloro-3-(2-chlorobenzyl)-5-(6-hydroxypyridin-3-yl)-1H-benzo[e][1,4]diazepin-2(3H)-one The palladium coupling reaction was performed according to the procedures described in Part I above to provide 7-chloro-3-(2-chlorobenzyl)-5-(6-hydroxypyridin-3-yl)-1-(4-methoxybenzyl)-1H-benzo[e][1,4]diazepin-2(3H)-one as a solid (40 mg, 15% yield, MS (ES+) m/z 554.0 (M+Na+)). Then, the methoxybenzyl protecting group was removed according to the procedures described in Part II above to provide the title compound as a solid (11.4 mg, 37% yield).

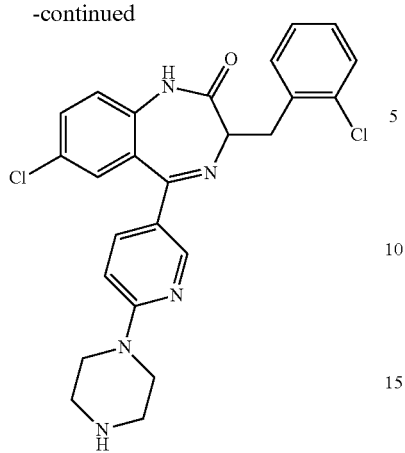

7-Chloro-3-(2-chlorobenzyl)-5-(6-(piperazin-1-yl)pyridin-3-yl)-1H-benzo[e][1,4]diazepin-2(3H)-one The palladium coupling reaction was performed according to the procedures described in Part I above to provide 7-chloro-3-(2-chlorobenzyl)-1-(4-methoxybenzyl)-5-(6-(piperazin-1-yl)pyridin-3-yl)-1H-benzo[e][1,4]diazepin-2(3H)-one as a solid (130 mg, 40% yield). MS (ES+) m/z 600.1 (M+1). Then, the methoxybenzyl protecting group was removed according to the procedures described in Part II above to provide the title compound as a solid (63 mg, 60% yield). $^1$H-NMR (300 MHz, DMSO-d$_6$) δ 10.70 (bs, 1H), 8.00 (s, 1H), 7.62-7.18 (m, 8H), 6.80 (d, 1H), 3.75 (m, 1H), 3.60-3.40 (m, 6H), 2.78 (bs, 4H). HRMS (ES+) m/z calcd for $C_{25}H_{23}Cl_2N_5O$ [M+H]$^+$, 480.1358. found, 480.1350.

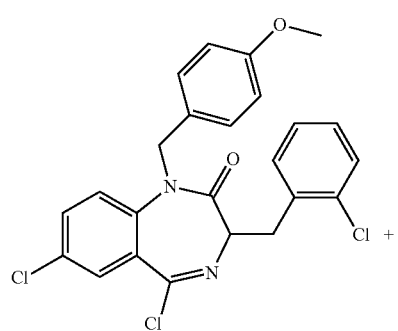

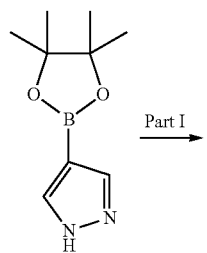

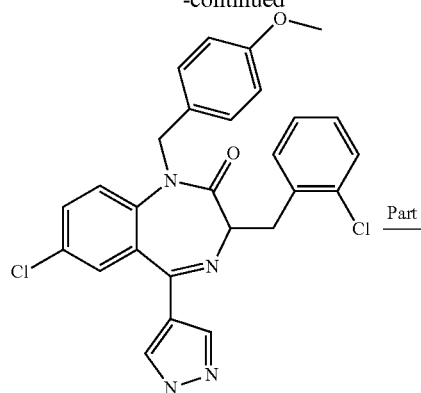

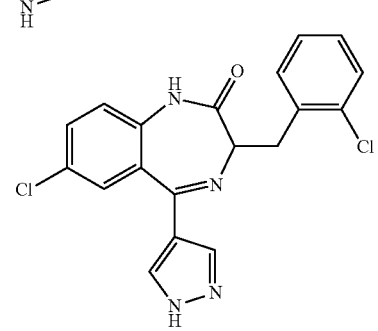

7-Chloro-3-(2-chlorobenzyl)-5-(1H-pyrazol-4-yl)-1H-benzo[e][1,4]diazepin-2(3H)-one The palladium coupling reaction was performed according to the procedures described in Part I above to provide 7-chloro-3-(2-chlorobenzyl)-1-(4-methoxybenzyl)-5-(1H-pyrazol-4-yl)-1H-benzo[e][1,4]diazepin-2(3H)-one as a solid (100 mg, 38% yield). MS (ES+) m/z 527.1 (M+Na+). Then, the methoxybenzyl protecting group was removed according to the procedures described in Part II above to provide the title compound as a solid (8 mg, 10% yield). $^1$H-NMR (300 MHz, DMSO-d$_6$) δ 13.12 (bs, 1H), 10.65 (s, 1H), 7.82 (m, 1H), 7.70-7.40 (m, 14H), 7.38 (d, 1H), 7.20 (m, 3H), 3.70 (m, 1H), 3.40 (m, 2H). HRMS (ES+) m/z calcd for $C_{19}H_{14}Cl_2N_4O$ [M+H]$^+$, 385.0623. found, 385.0614.

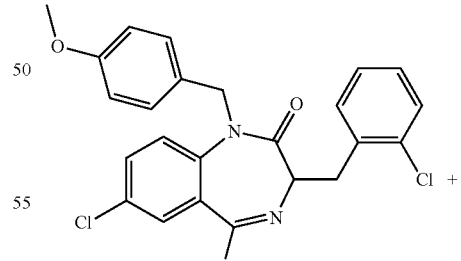

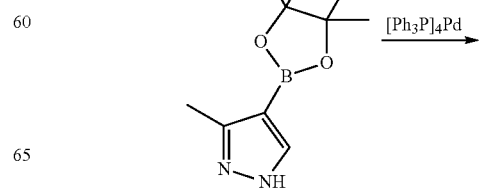

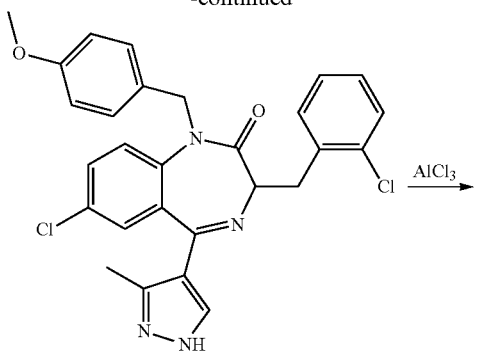

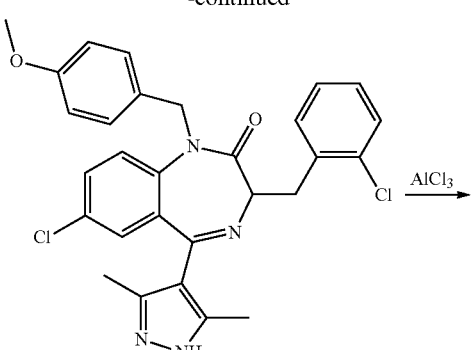

7-Chloro-3-(2-chlorobenzyl)-5-(3-methyl-1H-pyrazol-4-yl)-1H-benzo[e][1,4]diazepin-2(3H)-one The palladium coupling reaction was performed according to the procedures described in Part I above to provide 7-chloro-3-(2-chlorobenzyl)-1-(4-methoxybenzyl)-5-(3-methyl-1H-pyrazol-4-yl)-1H-benzo[e][1,4]diazepin-2(3H)-one as a solid (30 mg, 10% yield). MS (ES+) m/z 518.9 (M+1). Then, the methoxybenzyl protecting group was removed according to the procedures described in Part II above to provide the title compound as a solid (18.5 mg, 80% yield). $^1$H-NMR (300 MHz, DMSO-$d_6$) δ 12.90-12.70 (m, 1H), 10.65 (s, 1H), 7.58 (d, 1H), 7.42-7.30 (m, 3H), 7.25-7.10 (m, 4H), 3.79 (m, 1H), 3.50-3.35 (m, 2H), 2.05 (s, 3H). HRMS (ES+) m/z calcd for $C_{20}H_{16}Cl_2N_4O$ [M+H]$^+$, 399.0799. found, 399.0782.

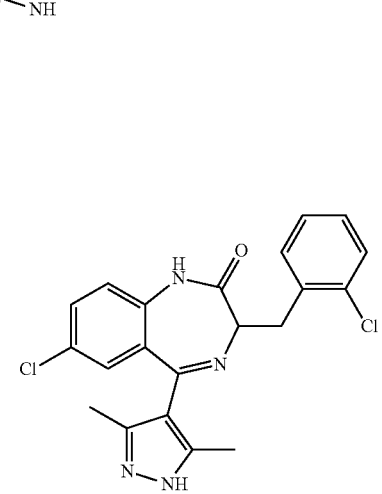

7-Chloro-3-(2-chlorobenzyl)-5-(3,5-dimethyl-1H-pyrazol-4-yl)-1H-benzo[e][1,4]diazepin-2(3H)-one The palladium coupling reaction was performed according to the procedures described in Part I above to provide 7-chloro-3-(2-chlorobenzyl)-5-(3,5-dimethyl-1H-pyrazol-4-yl)-1-(4-methoxybenzyl)-1H-benzo[e][1,4]diazepin-2(3H)-one as a solid (70 mg, 24% yield). MS (ES+) m/z 532.9 (M+1). Then, the methoxybenzyl protecting group was removed according to the procedures described in Part II above to provide the title compound as a solid (9.7 mg, 18% yield). $^1$H-NMR (300 MHz, CDCl$_3$) δ 9.20 (s, 1H), 7.53-7.43 (m, 2H), 7.34-7.04 (m, 6H), 4.00 (m, 1H), 3.65 (m, 2H), 1.85 (s, 6H). HRMS (ES+) m/z calcd for $C_{21}H_{18}Cl_2N_4O$ [M+H]$^+$, 413.0936. found, 413.0927.

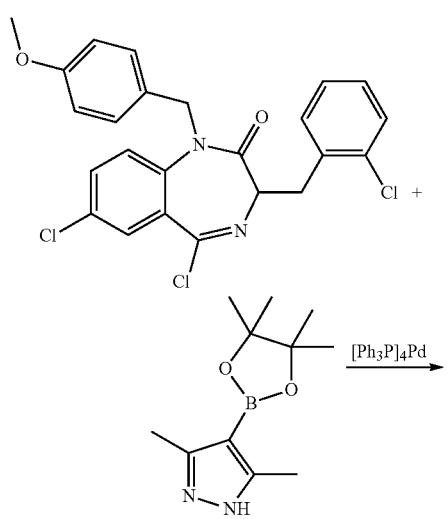

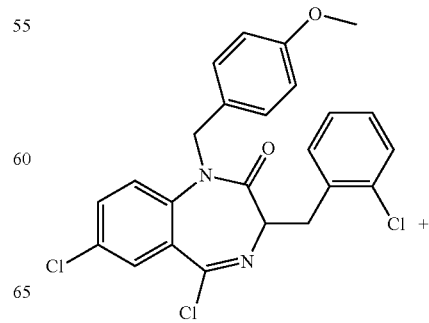

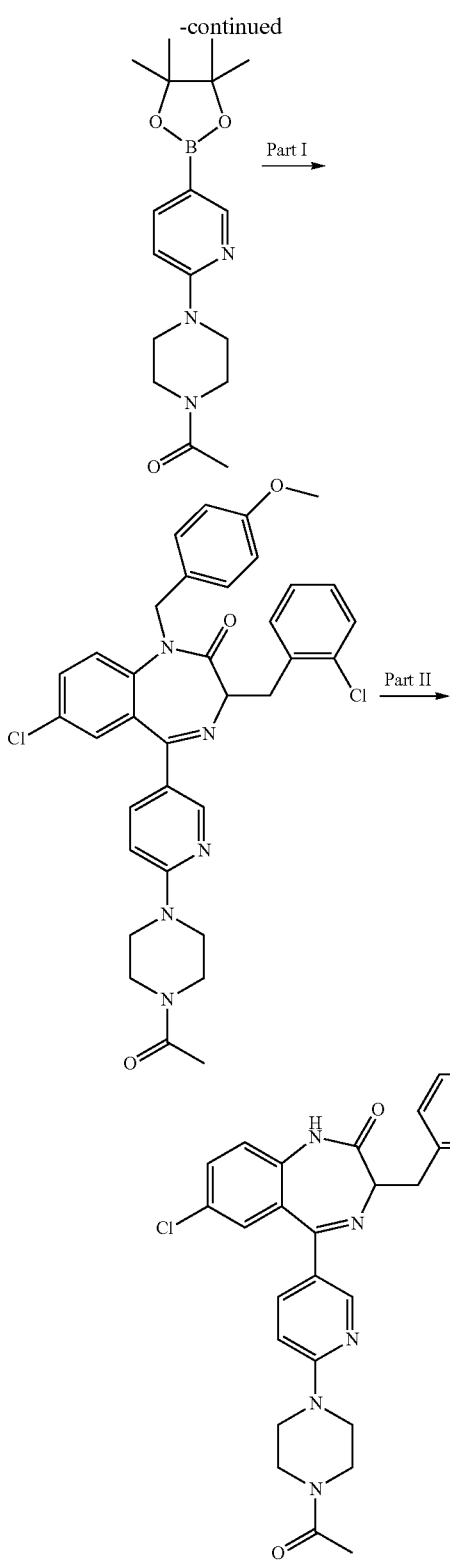

5-(6-(4-Acetylpiperazin-1-yl)pyridin-3-yl)-7-chloro-3-(2-chlorobenzyl)-1H-benzo[e][1,4]diazepin-2(3H)-one The palladium coupling reaction was performed according to the procedures described in Part I above to provide 5-(6-(4-acetylpiperazin-1-yl)pyridin-3-yl)-7-chloro-3-(2-chlorobenzyl)-1-(4-methoxybenzyl)-1H-benzo[e][1,4]diazepin-2(3H)-one as a solid (340 mg, 95% yield). MS (ES+) m/z 663.9 (M+Na+). Then, the methoxybenzyl protecting group was removed according to the procedures described in Part II above to provide the title compound as a solid (110 mg, 40% yield). $^1$H-NMR (300 MHz, DMSO-$d_6$) δ 10.73 (s, 1H), 8.04 (s, 1H), 7.60 (dd, 1H), 7.54 (dd, 1H), 7.45 (d, 1H), 7.36 (d, 1H), 7.30-7.20 (m, 4H), 6.82 (d, 1H), 3.70 (m, 1H), 3.65-3.40 (m, 10H), 2.02 (s, 3H). HRMS (ES+) m/z calcd for $C_{27}H_{25}Cl_2N_5O_2$ [M+H]$^+$, 522.1464. found, 522.1455.

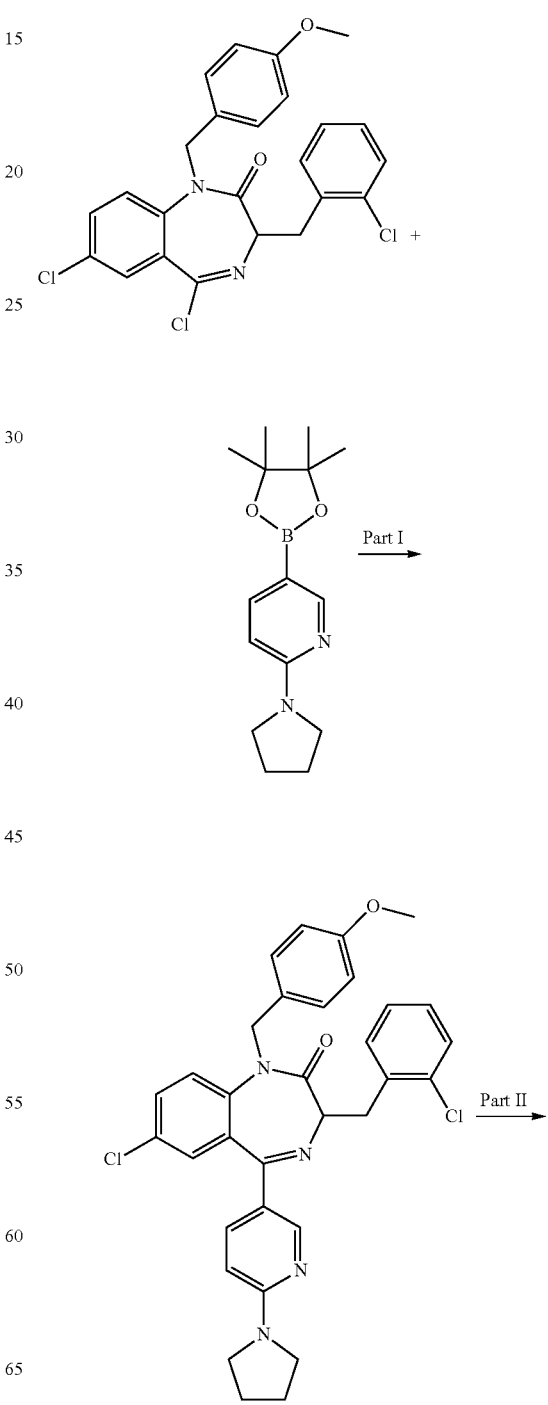

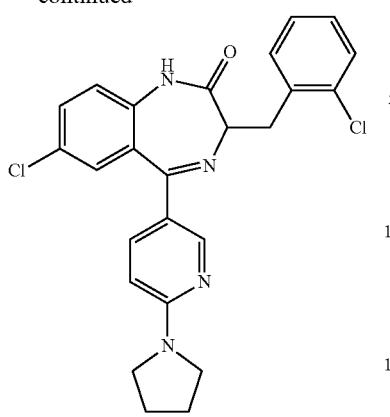

7-Chloro-3-(2-chlorobenzyl)-5-(6-(pyrrolidin-1-yl)pyridin-3-yl)-1H-benzo[e][1,4]diazepin-2(3H)-one The palladium coupling reaction was performed according to the procedures described in Part I above to provide 7-chloro-3-(2-chlorobenzyl)-1-(4-methoxybenzyl)-5-(6-(pyrrolidin-1-yl)pyridin-3-yl)-1H-benzo[e][1,4]diazepin-2(3H)-one as a solid (450 mg, 73% yield). MS (ES+) m/z 585.0 (M+1). Then, the methoxybenzyl protecting group was removed according to the procedures described in Part II above to provide the title compound as a solid (274 mg, 77% yield). $^1$H-NMR (400 MHz, DMSO-$d_6$) δ 10.70 (s, 1H), 7.96 (s, 1H), 7.60 (d, 1H), 7.48 (m, 2H), 7.35 (d, 1H), 7.30-7.18 (m, 4H), 6.39 (d, 1H), 3.72 (m, 1H), 3.50-3.32 (m, 6H), 1.90 (m, 4H). HRMS (ES+) m/z calcd for $C_{25}H_{22}Cl_2N_4O$ [M+H]$^+$, 465.1249. found, 465.1262.

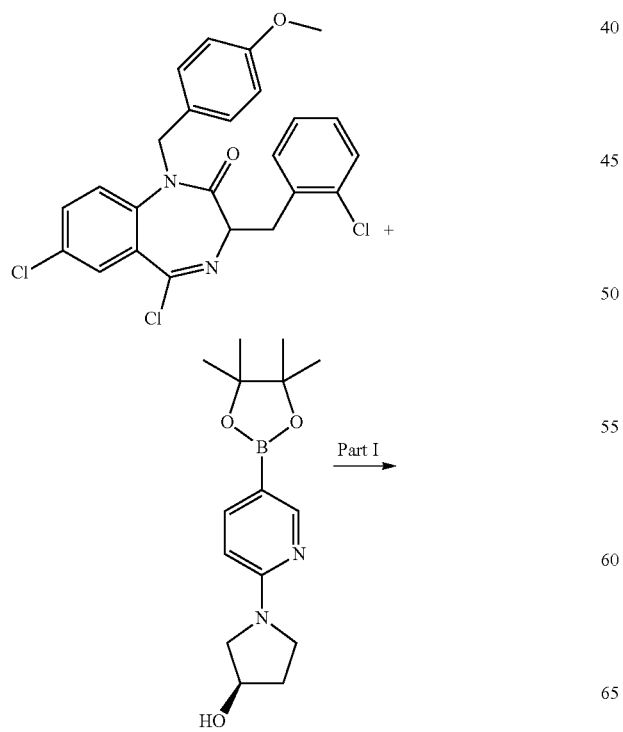

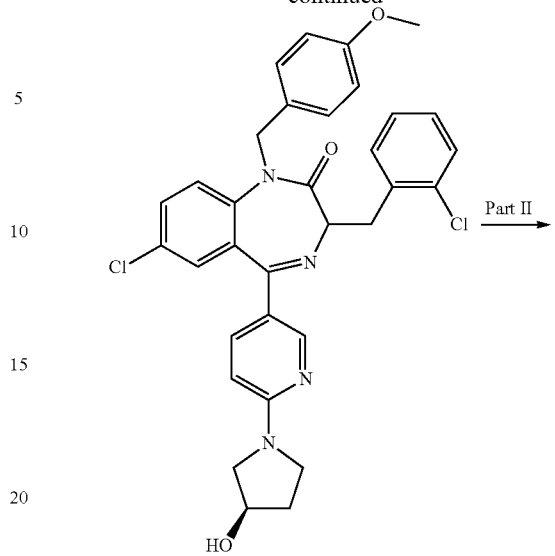

7-Chloro-3-(2-chlorobenzyl)-5-(6-((R)-3-hydroxypyrrolidin-1-yl)pyridin-3-yl)-1H-benzo[e][1,4]diazepin-2(3H)-one The palladium coupling reaction was performed according to the procedures described in Part I above to provide 7-chloro-3-(2-chlorobenzyl)-5-((6-(R)-3-hydroxypyrrolidin-1-yl)pyridin-3-yl)-1-(4-methoxybenzyl)-1H-benzo[e][1,4]diazepin-2(3H)-one as a solid (520 mg, 82% yield). MS (ES+) m/z 601.0 (M+1). Then, the methoxybenzyl protecting group was removed according to the procedures described in Part II above to provide the title compound as a solid (227 mg, 54% yield). $^1$H-NMR (400 MHz, DMSO-$d_6$) δ 10.69 (s, 1H), 7.98 (s, 1H), 7.60 (d, 1H), 7.48 (m, 2H), 7.37 (d, 1H), 7.29-7.19 (m, 4H), 6.42 (d, 1H), 4.96, (d, 1H), 4.38 (bs, 1H), 3.70 (m, 1H), 3.53-3.40 (m, 5H), 3.35 (m, 3H), 3.18 (d, 1H), 2.05-1.82 (m, 2H). HRMS (ES+) m/z calcd for $C_{25}H_{22}Cl_2N_4O_2$ [M+H]$^+$, 481.1198. found, 481.1212.

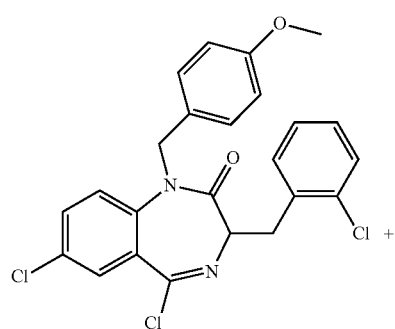 +

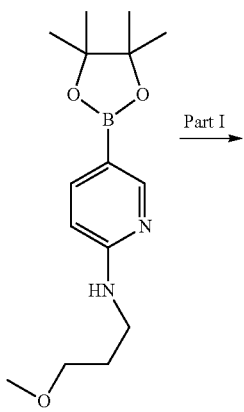  Part I

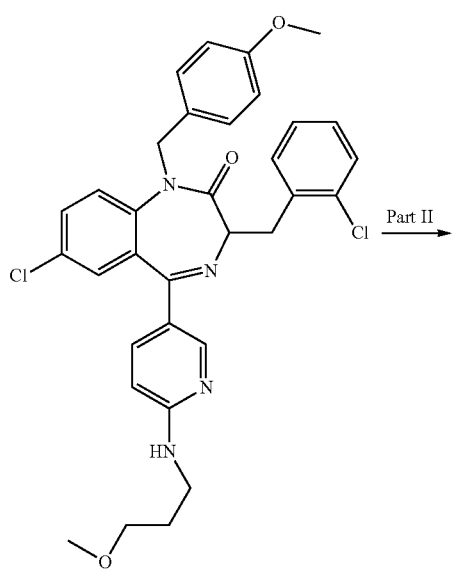  Part II

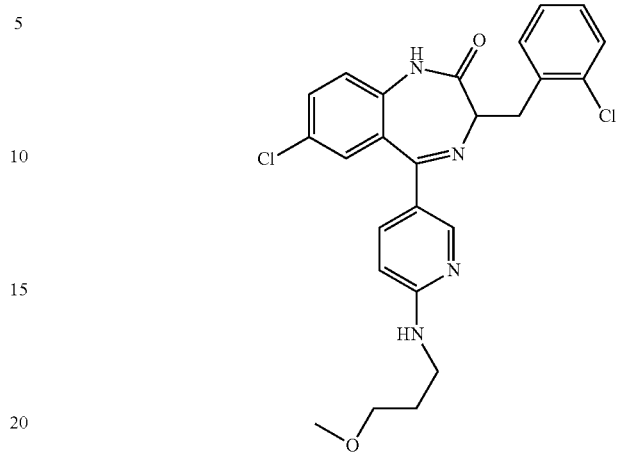

7-Chloro-3-(2-chlorobenzyl)-5-(6-(2-methoxyethylamino)pyridin-3-yl)-1H-benzo[e][1,4]diazepin-2(3H)-one The palladium coupling reaction was performed according to the procedures described in Part I above to provide 7-chloro-3-(2-chlorobenzyl)-1-(4-methoxybenzyl)-5-(6-(2-methoxyethylamino)pyridin-3-yl)-1H-benzo[e][1,4]diazepin-2(3H)-one as a solid (540 mg, 87% yield). MS (ES+) m/z 589.0 (M+1). Then, the methoxybenzyl protecting group was removed according to the procedures described in Part II above to provide the title compound as a solid (251 mg, 58% yield). $^1$H-NMR (400 MHz, DMSO-d$_6$) δ 10.68 (s, 1H), 7.89 (s, 1H), 7.60 (d, 1H), 7.50-7.40 (m, 2H), 7.38-7.18 (m, 5H), 7.13 (bs, 1H), 6.48 (d, 1H), 3.69 (m, 1H), 3.43 (m, 6H), 3.32 (s, 2H), 3.23 (s, 3H). HRMS (ES+) m/z calcd for $C_{24}H_{22}Cl_2N_4O_2$ [M+H]$^+$, 469.1198. found, 469.1213.

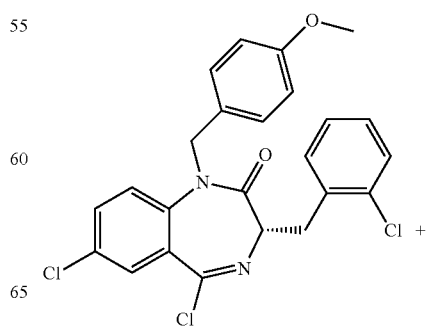 +

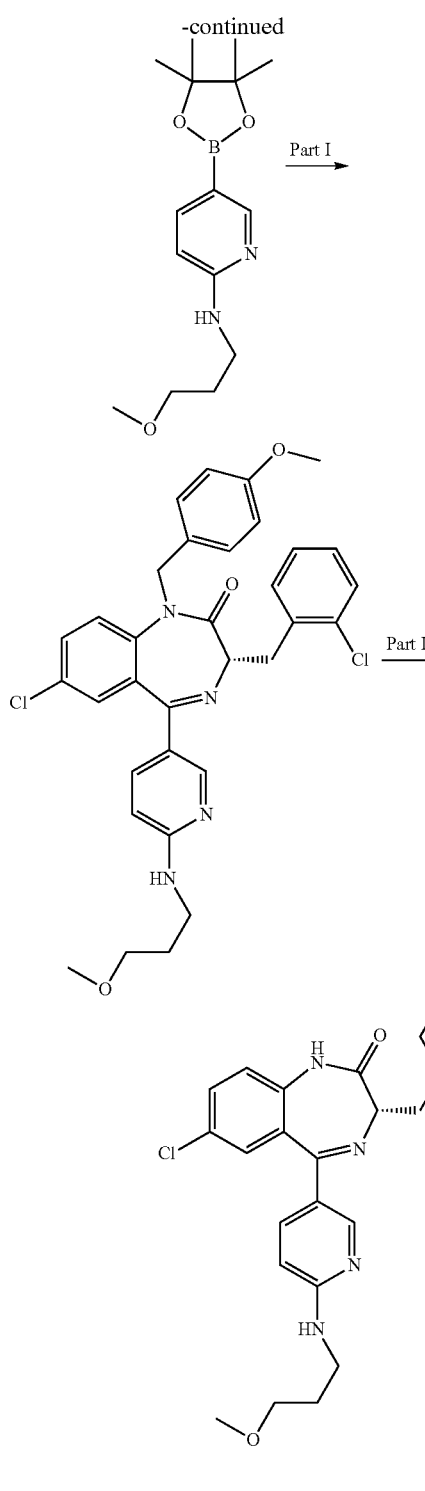

(S)-7-Chloro-3-(2-chlorobenzyl)-5-(6-(2-methoxy-ethylamino)pyridin-3-yl)-1H-benzo[e][1,4]diazepin-2(3H)-one The palladium coupling reaction was performed according to the procedures described in Part I above to provide (S)-7-chloro-3-(2-chlorobenzyl)-1-(4-methoxybenzyl)-5-(6-(2-methoxyethylamino)pyridin-3-yl)-1H-benzo[e][1,4]diazepin-2(3H)-one as a solid (210 mg, 82% yield). Then, the methoxybenzyl protecting group was removed according to the procedures described in Part II above to provide the title compound as a solid (71 mg, 43% yield). $^1$H-NMR (300 MHz, DMSO-d$_6$) δ 10.70 (s, 1H), 7.88 (s, 1H), 7.60 (dd, 1H), 7.50-7.10 (m, 8H), 6.49 (d, 1H), 3.70 (m, 1H), 3.40 (s, 6H), 3.30 (s, 5H), 3.21 (s, 3H), 1.04 (s, 3H). HRMS (ES+) m/z calcd for C$_{24}$H$_{22}$Cl$_2$N$_4$O$_2$ [M+H]$^+$, 469.1198. found, 469.1208.

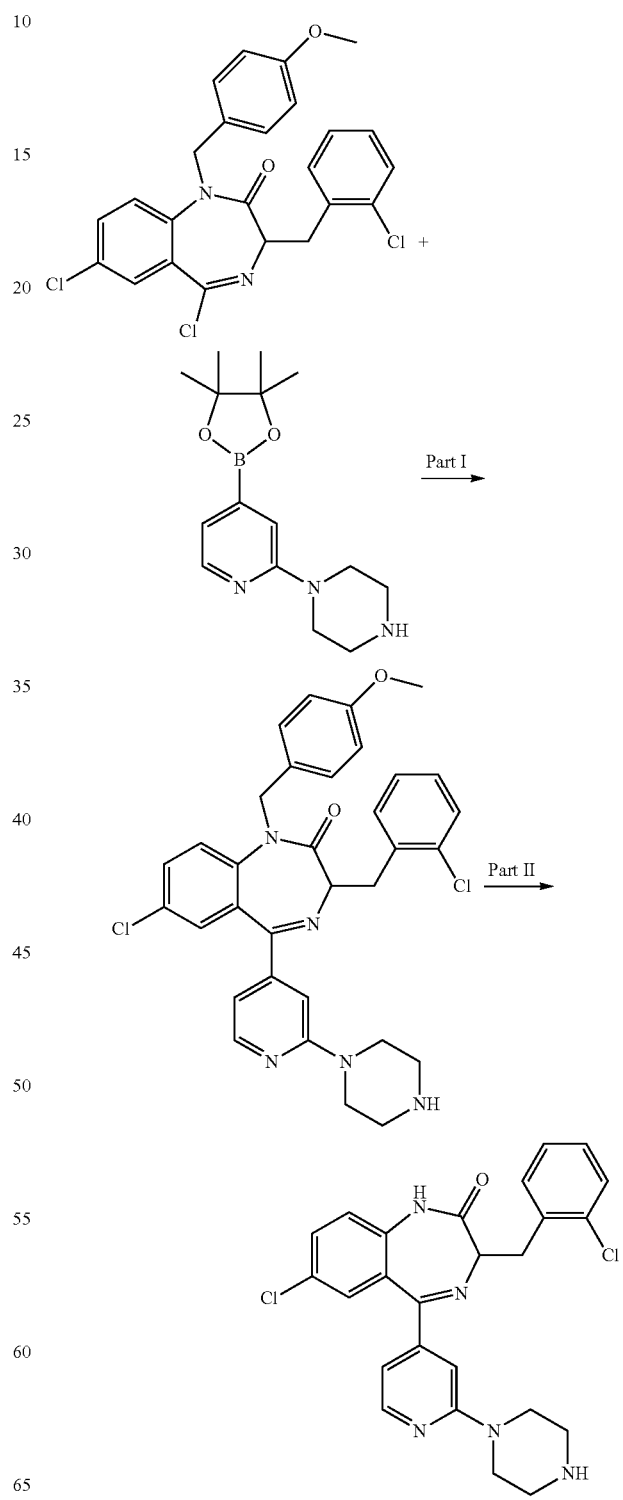

7-Chloro-3-(2-chlorobenzyl)-5-(2-(piperazin-1-yl)
pyridin-4-yl)-1H-benzo[e][1,4]diazepin-2(3H)-one The palladium coupling reaction was performed according to the procedures described in Part I above to provide 7-chloro-3-(2-chlorobenzyl)-1-(4-methoxybenzyl)-5-(2-(piperazin-1-yl)pyridin-4-yl)-1H-benzo[e][1,4]diazepin-2(3H)-one (68 mg, 36% yield). MS (ES+) m/z 600.2 (M+1). Then, the methoxybenzyl protecting group was removed according to the procedures described in Part II above to provide the title compound (14 mg, 26% yield). $^1$H-NMR (300 MHz, CDCl$_3$) δ 9.55 (bs, 1H), 8.20 (d, 1H), 7.50 (t, 2H), 7.38-7.10 (m, 5H), 6.70-6.52 (m, 2H), 3.90 (t, 1H), 3.81-3.62 (m, 6H), 3.48 (t, 1H), 3.30-3.10 (m, 4H). HRMS (ES+) m/z calcd for $C_{25}H_{23}Cl_2N_5O$ [M+H]$^+$, 480.1358. found, 480.1361.

Example 2

Representative Procedures for the Synthesis of a 1,4-Benzodiazepinone bearing a C5-1H-Imidazo[4,5-b]pyridin-2(3H)-one Group Part I: Synthesis of Imidazo[4,5-b]pyridin-2(3H)-one Boronic Acid Step 1

5-Bromopyridine-2,3-diamine

5-Bromo-3-nitropyridin-2-amine (3 g) was dissolved in isopropyl alcohol (56 mL) and water (28 mL). Ammonium chloride (1.47 g, 2 eq) was added followed by iron powder (2.31 g, 3 eq). The reaction was heated to 90° C. for 45 minutes. The solution was then cooled, and diluted with EtOAc, filtered, and the layers were separated. The organic layer was then washed with brine, dried over sodium sulfate, and concentrated delivering product as a solid (2.45 g, 95% yield). $^1$H-NMR (300 MHz, DMSO-d$_6$) δ 7.25 (d, 1H), 6.77 (d, 1H), 5.70-5.40 (bs, 2H), 5.20-4.80 (bs, 2H).

Step 2

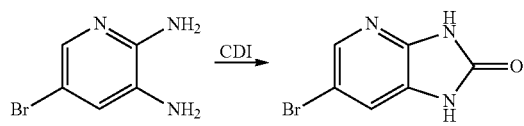

6-Bromo-1H-imidazo[4,5-b]pyridin-2(3H)-one

5-Bromopyridine-2,3-diamine (2.45 g) was dissolved in THF (25 mL) and 1,1'-carbonyldiimidazole (2.54 g, 1.2 eq) was added. The reaction was stirred at room temperature under nitrogen gas overnight. Water was then added to the mixture and the product was collected by filtration. The solid was dried under vacuum delivering product (2.57 g, 92% yield). $^1$H-NMR (300 MHz, DMSO-d$_6$) δ 11.50 (s, 1H), 11.00 (s, 1H), 7.93 (s, 1H), 7.39 (s, 1H). MS (ES+) m/z 213.1 (M+1).

Step 3

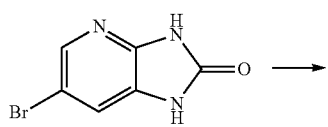

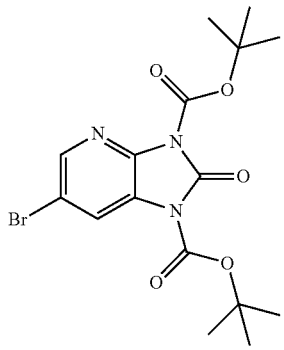

di-tert-Butyl-6-bromo-2-oxo-1H-imidazo[4,5-b]pyridine-1,3(2H)-dicarboxylate

A THF (10 mL) solution of di-tert butyl dicarbonate (4.69 g, 2.2 eq) was added dropwise to a solution of 6-bromo-1H-imidazo[4,5-b]pyridin-2(3H)-one (2.09 g) and DMAP (119 mg, 0.1 eq) in THF (40 mL). The reaction was stirred at reflux for 1 h, then cooled and concentrated. The product was purified by chromatography (gradient: 95:5 hexanes:EtOAc to 80:20 hexanes:EtOAc) delivering the product (1.48 g, 37% yield). $^1$H-NMR (300 MHZ, CDCl$_3$) δ 8.32 (s, 1H), 8.24 (s, 1H), 1.65 (s, 20H).

Step 4

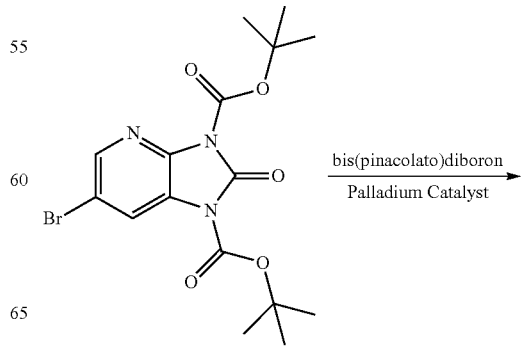

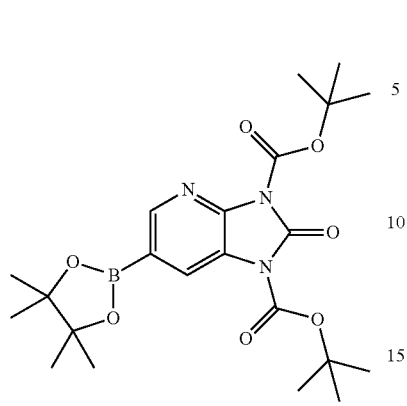

di-tert-Butyl 2-oxo-6-(4,4,5,5-tetramethyl-1,3,2-dioxaborolan-2-yl)-1H-imidazo[4,5-b]pyridine-1,3(2H)-dicarboxylate di-tert-butyl 6-Bromo-2-oxo-1H-imidazo[4,5-b]pyridine-1,3(2H)-dicarboxylate (1.48 g), bis(pinacolato)diboron (1.089 g, 1.2 eq), and potassium acetate (526 mg, 1.5 eq) were put in a flask and dissolved in dioxane (36 mL). The mixture was subjected to vacuum until bubbling occurred, and nitrogen gas was then introduced. The degassing procedure was repeated twice, and then (1,1'-bis(diphenylphosphino)ferrocene)-dichloropalladium(II)dichloromethane adduct (129 mg, 0.05 eq) was added. The reaction was heated to 80° C. for 3 h. The mixture was then cooled, then diluted with EtOAc, and washed with water, then brine, then dried over sodium sulfate, and then concentrated. The product was purified by chromatography delivering product (1.30 g, 79% yield). $^1$H-NMR (300 MHz, CDCl$_3$) δ 8.60 (s, 1H), 8.40 (s, 1H), 3.68 (s, 1H), 1.65 (s, 21H), 1.45 (d, 6H), 1.32 (s, 16H), 1.25 (s, 12H).

Part II: Palladium-Coupling of Imidoyl Chloride and Heteroaryl Boronic Acid

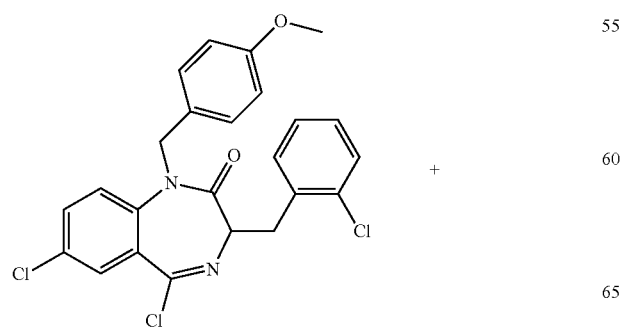

+

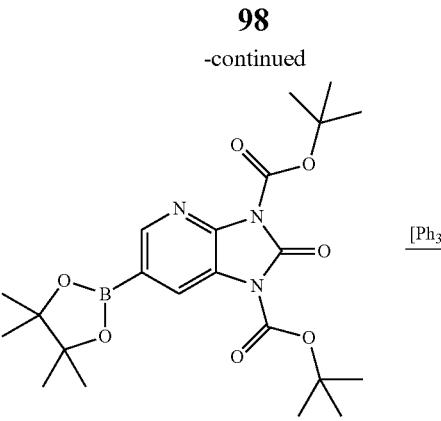

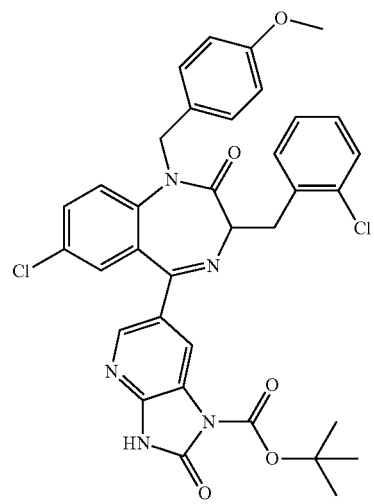

tert-Butyl 6-(7-chloro-3-(2-chlorobenzyl)-1-(4-methoxybenzyl)-2-oxo-2,3-dihydro-1H-benzo[e][1,4]diazepin-5-yl)-2-oxo-2,3-dihydro-1H-imidazo[4,5-b]pyridine-1-carboxylate The reaction was performed according to the procedures described in Part I of Example 1 to provide a mixture of bis-Boc protected product and a mono-Boc protected product (308 mg, 45% yield). MS (ES+) m/z 694.2 (M+Na⁺). This mixture was used in the deprotection reaction below.

Part III: Deprotection of Boc Protecting Group(s)

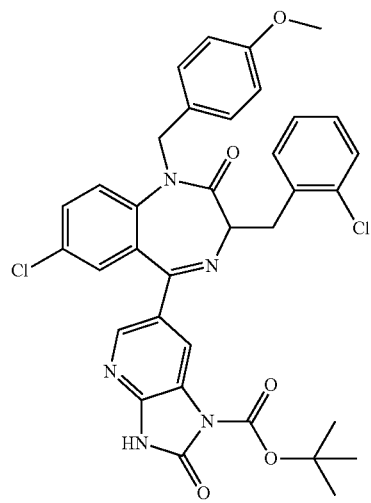

7-Chloro-3-(2-chlorobenzyl)-1-(4-methoxybenzyl)-
5-(2-oxo-2,3-dihydro-1H-imidazo[4,5-b]pyridin-6-
yl)-1H-benzo[e][1,4]diazepin-2(3H)-one tert-Butyl 6-(7-chloro-3-(2-chlorobenzyl)-1-(4-methoxy-benzyl)-2-oxo-2,3-dihydro-1H-benzo[e][1,4]diazepin-5-yl)-2-oxo-2,3-dihydro-1H-imidazo[4,5-b]pyridine-1-carboxylate (308 mg) was dissolved in 4 N HCl in dioxane (20 mL) and it was held at room temperature for an hour, then partitioned between aqueous sodium bicarbonate and EtOAc. The organic fraction was washed with brine, then dried over sodium sulfate, then concentrated and used further without purification (250 mg, 95% yield). $^1$H-NMR (300 MHz, CDCl$_3$) δ 8.60 (bs, 1H), 8.10 (s, 1H), 7.80-7.10 (m, 14H), 6.90 (d, 2H), 6.62 (d, 2H), 5.65 (d, 1H), 4.55 (d, 1H), 3.95 (m, 1H), 3.80-3.60 (m, 8H), 1.60 (bs, 2H).

Part IV: Deprotection of Methoxybenzyl Protecting Group

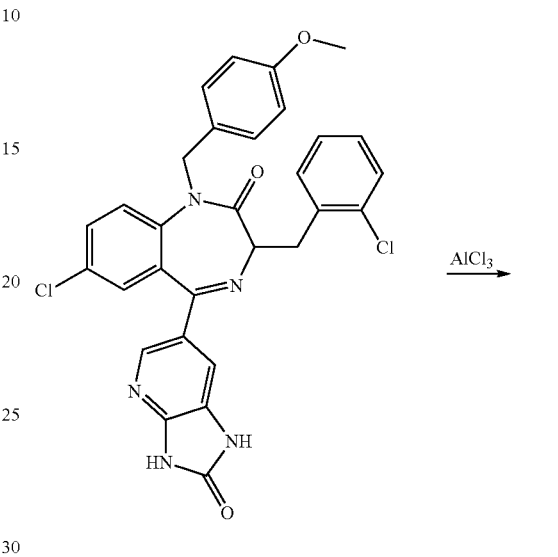

7-Chloro-3-(2-chlorobenzyl)-5-(2-oxo-2,3-dihydro-
1H-imidazo[4,5-b]pyridin-6-yl)-1H-benzo[e][1,4]
diazepin-2(3H)-one The reaction was performed according to the procedures described in Part II of Example I to provide the title compound as a solid (71 mg, 36% yield). $^1$H-NMR (300 MHz, DMSO-d$_6$) δ 11.55 (s, 1H), 10.90 (s, 1H), 10.75 (s, 1H), 7.75 (s, 1H), 7.65 (d, 1H), 7.50-7.20 (m, 7H), 4.07 (q, 1H), 3.80 (m, 1H), 3.60-3.38 (m, 2H), 3.15 (s, 1H). HRMS (ES+) m/z calcd for $C_{22}H_{15}Cl_2N_5O_2$ [M+H]$^+$, 452.0681. found, 452.0686.

Example 3

Procedures for the Synthesis of a 1,4-Benzodiazepinone bearing a C5-Pyridin-2-yl)piperazine Group Part I: Synthesis of 6-(4-Methylpiperazin-1-yl)pyridinyl Boronic Acid Step 1

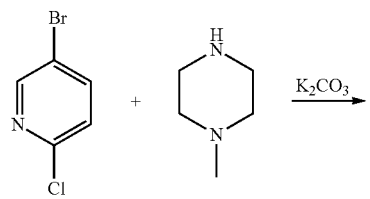

1-(5-Bromopyridin-2-yl)-4-methylpiperazine

5-Bromo-2-chloropyridine (1.0 g), N-methylpiperazine (1.56 g, 3 eq), and potassium carbonate (2.16 g, 3 eq) were combined in N-methylpyrrolidinone (5 mL) and heated to 120° C. overnight. The crude mixture was then cooled to room temperature and diluted with water. The solid product was collected by filtration, then washed with more water and dried under vacuum (824 mg, 62% yield). $^1$H-NMR (300 MHz, CDCl$_3$) δ 8.18 (d, 1H), 7.50 (dd, 1H), 6.53 (d, 1H), 3.50 (m, 4H), 2.50 (m, 4H), 2.33 (s, 3H).

Step 2

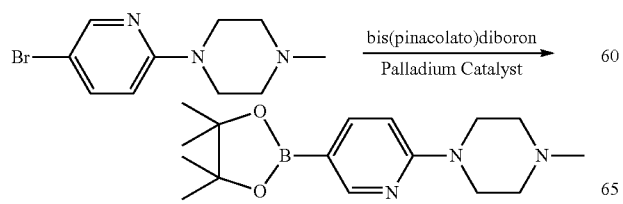

1-Methyl-4-(5-(4,4,5,5-tetramethyl-1,3,2-dioxaborolan-2-yl)pyridin-2-yl)piperazine The reaction was carried out as described in the borylation reaction in Part I of Example 2 to provide the title compound (132 mg, 14% yield). MS (ES+) m/z 304.2 (M+1).

Part II: Palladium-Coupling of Imidoyl Chloride and Heteroaryl Boronic Acid

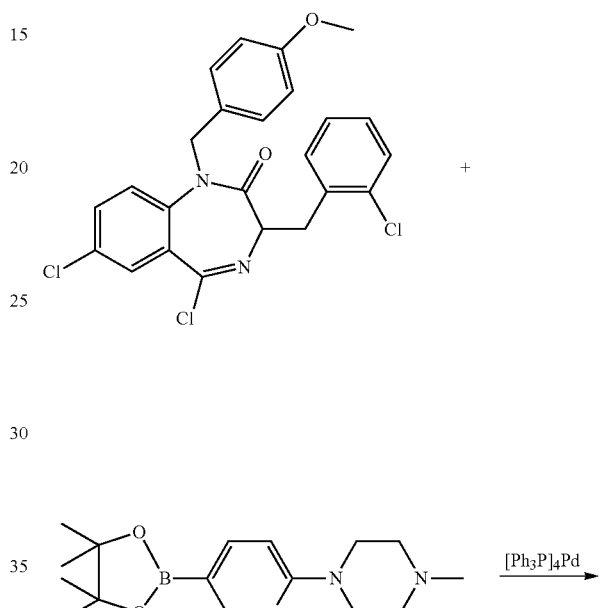

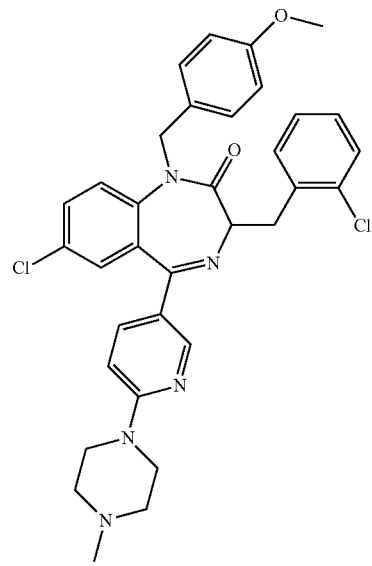

7-Chloro-3-(2-chlorobenzyl)-1-(4-methoxybenzyl)-5-(6-(4-methylpiperazin-1-yl)pyridin-3-yl)-1H-benzo[e][1,4]diazepin-2(3H)-one The reaction was performed according to the procedures described in Part I of Example 1 to provide the title compound (99 mg, 51% yield). MS (ES+) m/z 614.2 (M+1).

Part III: Deprotection of Methoxybenzyl Protecting Group

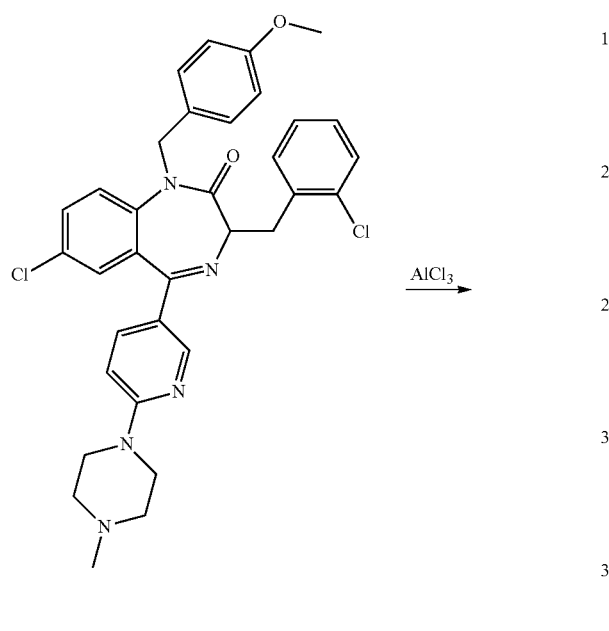

7-Chloro-3-(2-chlorobenzyl)-5-(6-(4-methylpiperazin-1-yl)pyridin-3-yl)-1H-benzo[e][1,4]diazepin-2(3H)-one The reaction was performed according to the procedure described in Part II of Example 1 to provide the title compound (13 mg, 16% yield). $^1$H-NMR (300 MHz, CDCl$_3$) δ 8.65 (s, 1H), 8.15 (s, 1H), 7.65 (dd, 1H), 7.58 (d, 1H), 7.45 (dd, 1H), 7.35-7.07 (m, 5H), 6.60 (d, 1H), 3.85 (m, 1H), 3.75-3.55 (m, 7H), 3.50 (s, 1H), 2.50 (m, 4H), 2.36 (s, 3H). HRMS (ES+) m/z calcd for C$_{26}$H$_{25}$Cl$_2$N$_5$O [M+H]$^+$, 494.1514. found, 494.1519.

Example 4

Palladium Coupling Procedures for the Synthesis of Benzo[e][1,4]diazepin-2(3H)-ones having a 1H-Pyrazolyl Group at the C5-Position

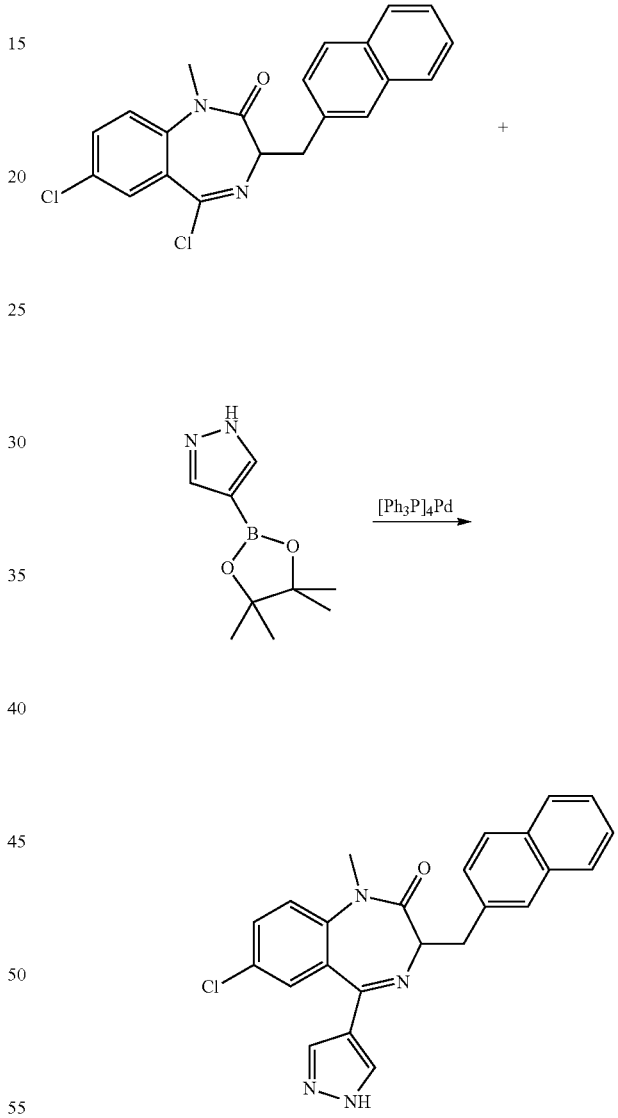

7-Chloro-1-methyl-3-(naphthalen-2-ylmethyl)-5-(1H-pyrazol-4-yl)-1H-benzo[e][1,4]diazepin-2(3H)-one The reaction was performed according to the procedure described in Part I of Example 1 to provide the title compound (150 mg, 35% yield). $^1$H-NMR (400 MHz, DMSO-d$_6$) δ 13.20 (s, 1H), 7.93 (s, 1H), 7.84-7.72 (m, 5H), 7.68-7.59 (m, 2H), 7.54 (d, 1H), 7.50-7.39 (m, 4H), 3.79 (dd, 1H), 3.49 (qd, 2H), 3.30 (s, 3H). HRMS (ES+) m/z calcd for $C_{24}H_{19}ClN_4O$ [M+H]⁺, 415.1326. found, 415.1323.

Example 5

Procedures for the Synthesis of Benzo[e][1,4]diazepin-2(3H)-ones having a 1H-Pyrazolyl Group at the C5-Position

Part I: Palladium Coupling of an Imidoyl Chloride and a Boronic Acid

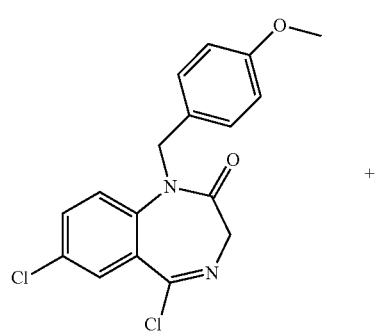
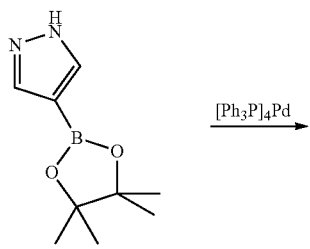
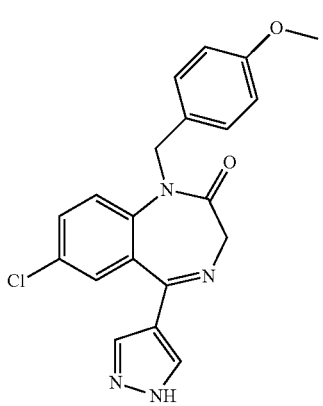

7-Chloro-1-(4-methoxybenzyl)-5-(1H-pyrazol-4-yl)-1H-benzo[e][1,4]diazepin-2(3H)-one The reaction was performed according to the procedure described in Part I of Example 1 to provide the title compound as a yellow solid (163 mg, 18% yield). MS (ES+) m/z 381.3 (M+1).

Part II: Base-induced Alkylation of a Functionalized 1,4-Benzodiazepinone

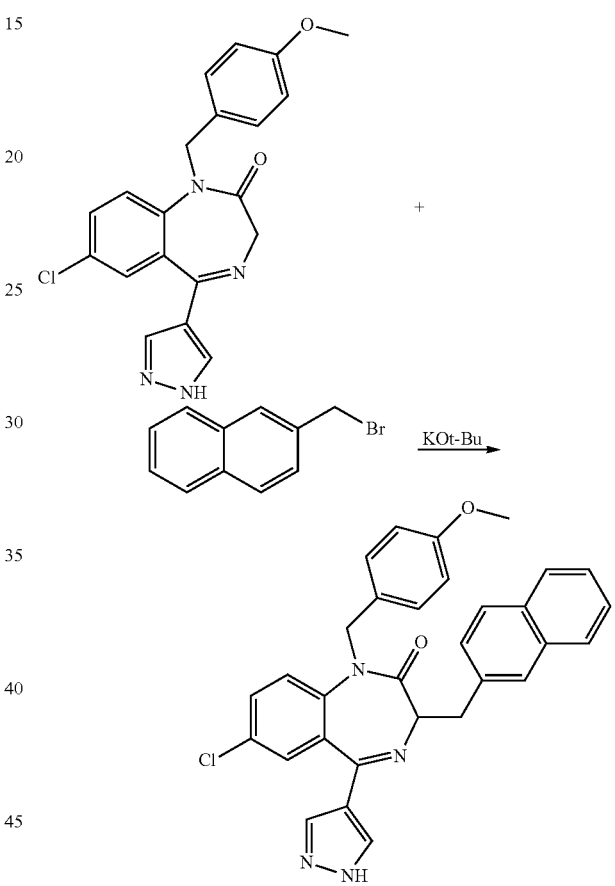

7-Chloro-1-(4-methoxybenzyl)-3-(naphthalen-2-ylmethyl)-5-(1H-pyrazol-4-yl)-1H-benzo[e][1,4]diazepin-2(3H)-one 7-Chloro-1-(4-methoxybenzyl)-5-(1H-pyrazol-4-yl)-1H-benzo[e][1,4]diazepin-2(3H)-one (163 mg) was dissolved in THF (3 mL) and the solution was cooled to −78° C. A solution of KOtBu in THF (1 M, 1.1 mL, 2.6 eq) was then added dropwise and the anion was stirred for 10 minutes. 2-Bromomethyl naphthalene (123 mg, 1.3 eq) was then added and the reaction was allowed to warm to room temperature where it was held for 2 hours. The reaction was then quenched with saturated aqueous ammonium chloride and the crude product was partitioned between water and EtOAc. The organic fraction was washed with brine, then dried over sodium sulfate, and concentrated onto silica gel then purified by flash chromatography (gradient: 3:1 hexanes:EtOAc to EtOAc) delivering the product as a solid (106 mg, 48% yield). MS (ES+) m/z 521.2 (M+1).

Part III: Removal of Methoxybenzyl Protecting Group

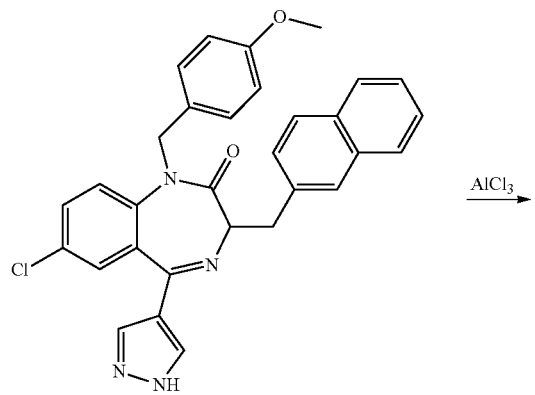

7-Chloro-3-(naphthalen-2-ylmethyl)-5-(1H-pyrazol-4-yl)-1H-benzo[e][1,4]diazepin-2(3H)-one The reaction was carried out as described in Part II of Example 1 above to provide the title compound as a solid (20 mg, 25% yield). $^1$H-NMR (300 MHz, DMSO-d$_6$) δ 13.15 (s, 1H), 10.60 (s, 1H), 7.90-7.35 (m, 11H), 7.20 (d, 1H), 3.70 (m, 1H), 3.50-3.40 (m, 2H). HRMS (ES+) m/z calcd for $C_{23}H_{17}ClN_4O$ [M+H]$^+$, 401.1169. found, 401.1171.

Example 6

Procedures for the Synthesis of Benzo[e][1,4]diazepin-2(3H)-ones having a 1H-Pyrazolyl Group at the C5-Position Part I: Synthesis of Heteroaryl Boronic Acid Step 1

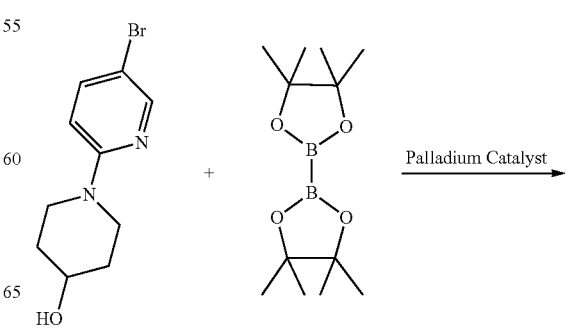

1-(5-Bromopyridin-2-yl)piperidin-4-ol

The reaction was carried out as described in Step 1 of Part I of Example 3 to provide the title compound as a solid (1.10 g, 82% yield). $^1$H-NMR (300 MHz, DMSO-d$_6$) δ 8.10 (d, 1H), 7.60 (dd, 1H), 6.80 (d, 1H), 4.66 (d, 1H), 3.95-3.85 (m, 2H), 3.65 (sextet, 1H), 3.15-3.00 (m, 2H), 1.80-1.65 (m, 2H), 1.40-1.23 (m, 2H).

Step 2

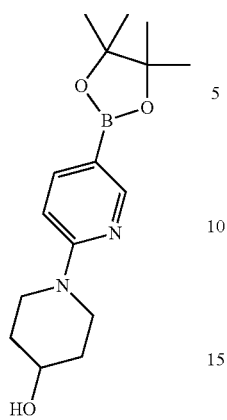

1-(5-(4,4,5,5-Tetramethyl-1,3,2-dioxaborolan-2-yl)
pyridin-2-yl)piperidin-4-ol

The reaction was carried out as described in Step 4 of Part I of Example 2 to provide the title compound as a solid (350 mg, 27% yield). MS (ES+) m/z 305.2 (M+1).

Part II: Palladium Coupling of an Imidoyl Chloride and a Heteroaryl Boronic Acid

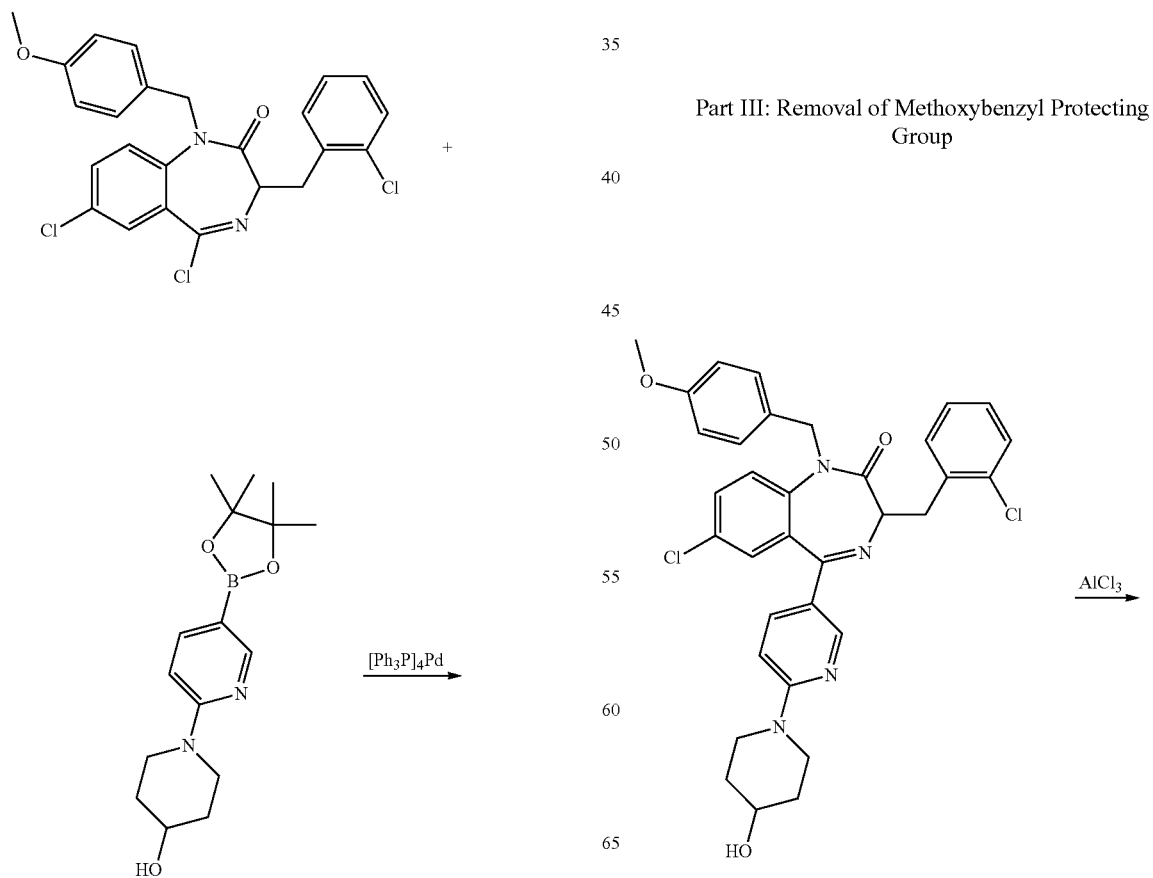

7-Chloro-3-(2-chlorobenzyl)-5-(6-(4-hydroxypiperidin-1-yl)pyridin-3-yl)-1-(4-methoxybenzyl)-1H-benzo[e][1,4]diazepin-2(3H)-one The reaction was carried out as described in Part I of Example 1 to provide the title compound as a solid (310 mg, 95% yield). MS (ES+) m/z 615.2 (M+1).

Part III: Removal of Methoxybenzyl Protecting Group

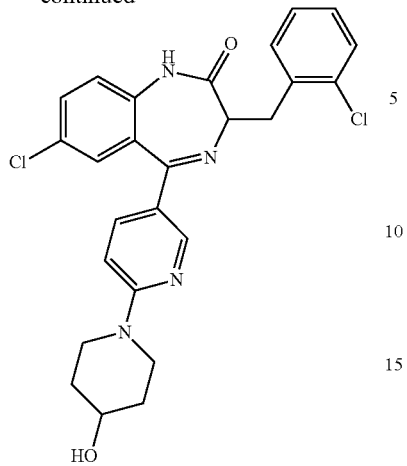

7-Chloro-3-(2-chlorobenzyl)-5-(6-(4-hydroxypiperidin-1-yl)pyridin-3-yl)-1H-benzo[e][1,4]diazepin-2(3H)-one The reaction was carried out as described in Part II of Example 1 to provide the title compound as a solid (72.6 mg, 29% yield). $^1$H-NMR (300 MHz, DMSO-d$_6$) δ 10.72 (s, 1H), 8.00 (s, 1H), 7.60 (d, 1H), 7.46 (t, 2H), 7.40-7.20 (m, 5H), 6.81 (d, 1H), 4.70 (d, 1H), 4.04 (m, 2H), 3.71 (m, 2H), 3.42 (m, 2H), 3.23-3.08 (m, 4H), 1.77 (m, 2H), 1.32 (m, 2H). HRMS (ES+) m/z calcd for C$_{26}$H$_{24}$Cl$_2$N$_4$O$_2$ [M+H]$^+$, 495.1355. found, 495.1371.

The following compounds were prepared by making appropriate substitutions to the above procedures.

Example 6A

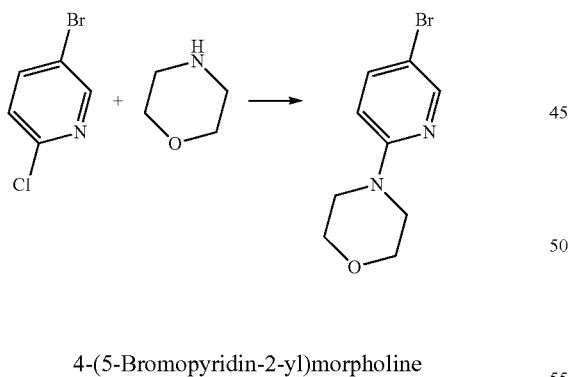

4-(5-Bromopyridin-2-yl)morpholine

The reaction was carried out as described in Step 1 of Part I of Example 3 to provide the title compound as a crystalline white solid (1.02 g, 81% yield). $^1$H-NMR (300 MHz, DMSO-d$_6$) δ 8.16 (d, 1H), 7.69 (dd, 1H), 6.80 (d, 1H), 3.65 (m, 4H), 3.38 (m, 4H).

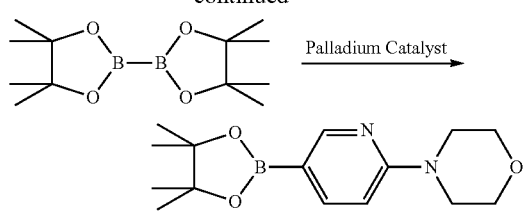

4-(5-(4,4,5,5-Tetramethyl-1,3,2-dioxaborolan-2-yl)pyridin-2-yl)morpholine

The reaction was carried out as described in Step 4 of Part I of Example 2 to provide the title compound as a solid (400 mg, 39% yield). MS (ES+) m/z 291.2 (M+1).

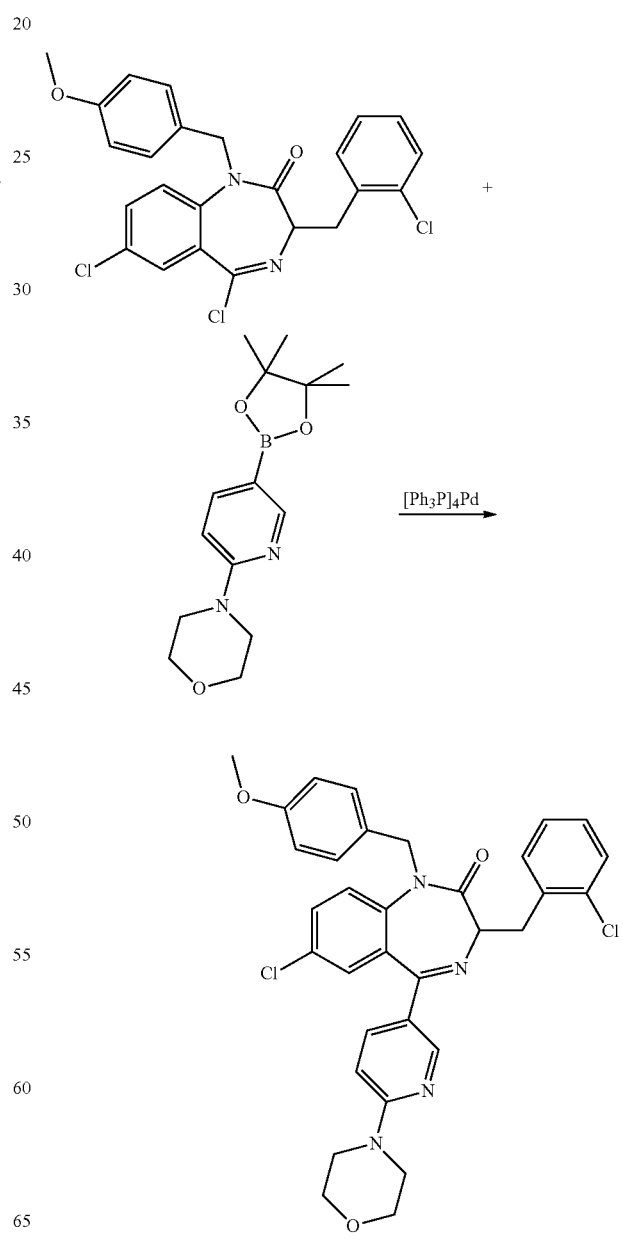

7-Chloro-3-(2-chlorobenzyl)-1-(4-methoxybenzyl)-5-(6-morpholinopyridin-3-yl)-1H-benzo[e][1,4]diazepin-2(3H)-one The reaction was carried out as described in Part I of Example 1 to provide the title compound as a solid (300 mg, 95% yield). MS (ES+) m/z 601.1 (M+1).

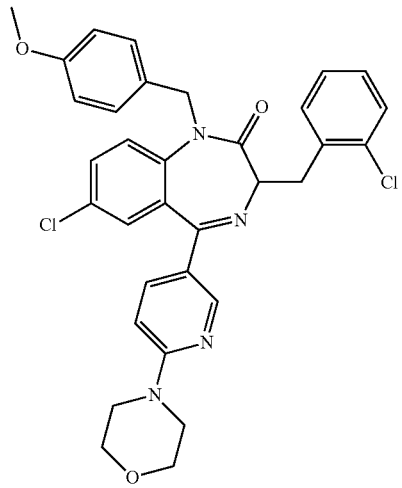

7-Chloro-3-(2-chlorobenzyl)-5-(6-morpholinopyridin-3-yl)-1H-benzo[e][1,4]diazepin-2(3H)-one The reaction was carried out as described in Part II of Example 1 to provide the title compound as a solid (61 mg, 25% yield). $^1$H-NMR (300 MHz, DMSO-$d_6$) δ 10.73 (s, 1H), 8.02 (s, 1H), 7.60 (dd, 1H), 7.55 (dd, 1H), 7.46 (dd, 1H), 7.35 (d, 1H), 7.30-7.20 (m, 4H), 6.82 (d, 1H), 3.75-3.62 (m, 5H), 3.55-3.37 (m, 6H). HRMS (ES+) m/z calcd for $C_{25}H_{22}Cl_2N_4O_2$ [M+H]$^+$, 481.1198. found, 481.1198.

Example 6B

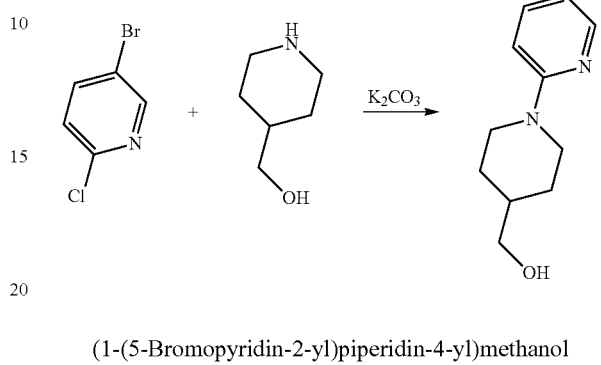

(1-(5-Bromopyridin-2-yl)piperidin-4-yl)methanol

The reaction was carried out as described in Step 1 of Part I of Example 3 to provide the title compound as a solid (1.40 g, 99% yield). $^1$H-NMR (300 MHz, DMSO-$d_6$) δ 8.10 (d, 1H), 7.60 (dd, 1H), 6.79 (d, 1H), 4.44 (t, 1H), 4.21 (bd, 2H), 3.22 (t, 2H), 2.75 (t, 2H), 1.72-1.50 (m, 3H), 1.20-1.00 (m, 2H).

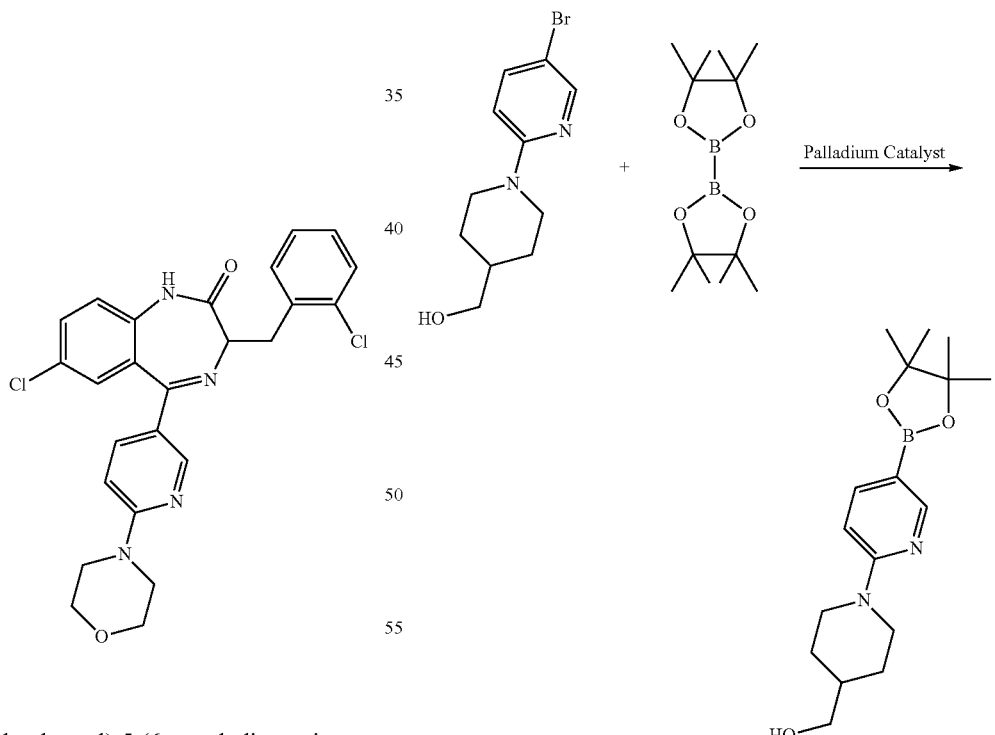

(1-(5-(4,4,5,5-Tetramethyl-1,3,2-dioxaborolan-2-yl)pyridin-2-yl)piperidin-4-yl)methanol The reaction was carried out as described in Step 4 of Part I of Example 2 to provide the title compound as a solid (260 mg, 16% yield). MS (ES+) m/z 319.2 (M+1).

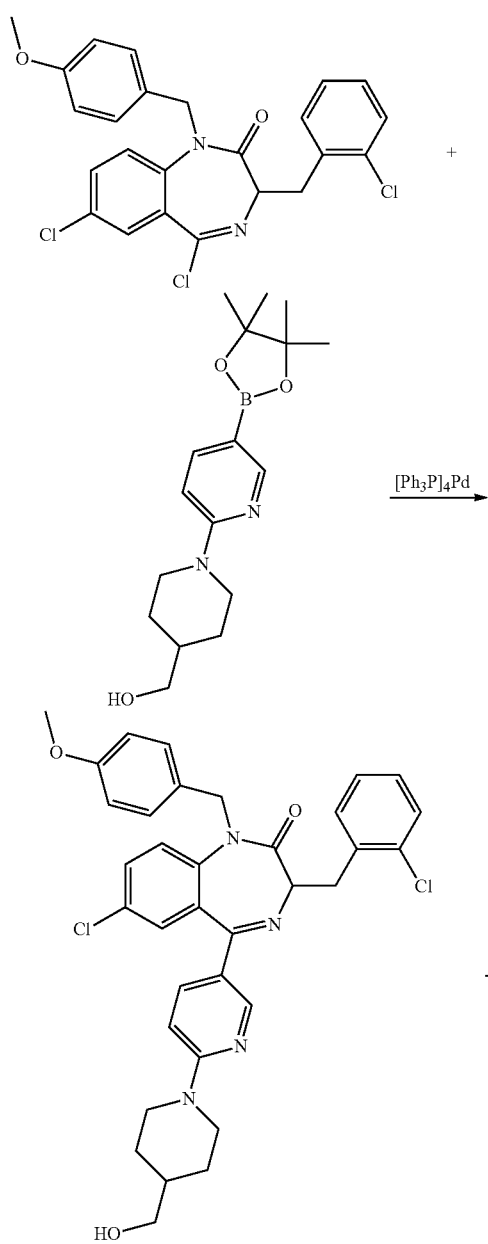

7-Chloro-3-(2-chlorobenzyl)-5-(6-(4-(hydroxymethyl)piperidin-1-yl)pyridin-3-yl)-1H-benzo[e][1,4]diazepin-2(3H)-one The reaction was carried out as described in Part I of Example 1 to provide 7-chloro-3-(2-chlorobenzyl)-5-(6-(4-(hydroxymethyl)piperidin-1-yl)pyridin-3-yl)-1-(4-methoxybenzyl)-1H-benzo[e][1,4]diazepin-2(3H)-one as a solid (220 mg, 59% yield). Then, the methoxybenzyl protecting group was removed according to the procedures described in Part II of Example 1 to provide the title compound as a solid (25 mg, 14% yield). HRMS (ES+) m/z calcd for $C_{27}H_{26}Cl_2N_4O_2$ [M+H]$^+$, 509.1511. found, 509.1511.

Example 7

Procedures for the Synthesis of 7-Chloro-3-(2-chlorophenethyl)-5-(2-oxo-2,3-dihydro-1H-imidazo[4,5-b]pyridin-6-yl)-1H-benzo[e][1,4]diazepin-2(3H)-one Beginning with 2-Chloro-iodobenzene and Allyl Alcohol

Step 1

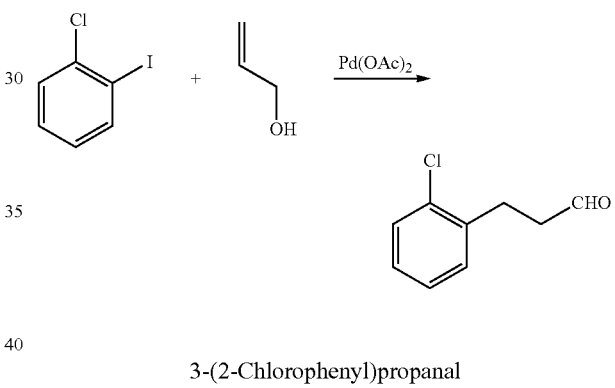

3-(2-Chlorophenyl)propanal

2-Chloro-iodobenzene (700 mg), allyl alcohol (256 mg, 1.5 eq.), palladium acetate (13 mg, 0.02 eq), sodium bicarbonate (616 mg, 2.5 eq), and tetrabutylammonium chloride (816 mg, 1 eq) were mixed together in anhydrous DMF (12 mL). The mixture was stirred at 30° C. for 24 h, then diluted with water. The crude mixture was extracted into EtOAc 3×, and the organic layer was washed with water twice, then brine, and then dried over sodium sulfate, and concentrated. The residue was purified by chromatography (gradient: 88:12 hexanes:EtOAc to 1:1 hexanes:EtOAc) delivering the product (200 mg, 40% yield). $^1$H-NMR (300 MHz, CDCl$_3$) δ 9.80 (s, 1H), 7.38-7.30 (m, 1H), 7.28-7.10 (m, 3H), 3.10-3.02 (m, 2H), 2.84-2.68 (m, 2H).

Step 2

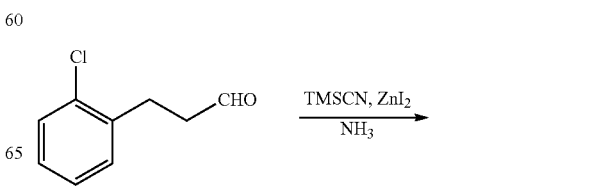

-continued

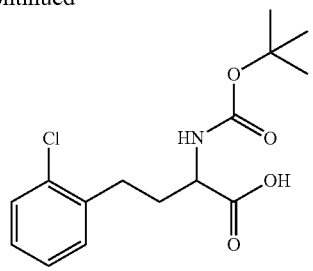

2-(tert-Butoxycarbonylamino)-4-(2-chlorophenyl)
butanoic acid

In a glass bomb was placed trimethylsilyl-cyanide (2.65 g, 1.5 eq), zinc iodide (284 mg, 0.05 eq), 3-(2-chlorophenyl) propanal (3.00 g, 1 eq), and THF (32 mL). The mixture was stirred at room temperature for 15 minutes, then a 7 M solution of ammonia in methanol (51 mL, 20 eq) was added. The tube was sealed and heated to 60° C. for three hours. The solution was then concentrated, and hydrochloric acid (6 M, 5.93 mL, 30 eq) was added and the mixture was heated to reflux for 8 h. The mixture was then cooled to room temperature and slowly neutralized with aqueous sodium bicarbonate. Additional sodium bicarbonate was added (15 mL), followed by 1,4-dioxane (323 mL) and Boc anhydride (15.53 g, 4 eq). The reaction was stirred for another 4 h, and the mixture was partitioned with EtOAc 3×, discarding the organic layer each time. The pH was then carefully adjusted to 5 with HCl (2N) and the product was extracted into EtOAc 3×. The combined organic extracts were then washed with water, then brine, then dried over sodium sulfate and concentrated delivering a tan oil which was used further without purification (2.27 g, 41% yield). $^1$H-NMR (300 MHz, CDCl$_3$) δ 7.35-7.29 (m, 2H), 7.24-7.10 (m, 3H), 6.97-6.88 (m, 1H), 5.15 (d, 1H), 4.35 (bs, 1H), 3.81 (s, 1H), 3.70 (s, 9H), 2.82 (t, 2H), 2.20 (bs, 1H), 1.95 (q, 1H), 1.46 (s, 9H).

Step 3

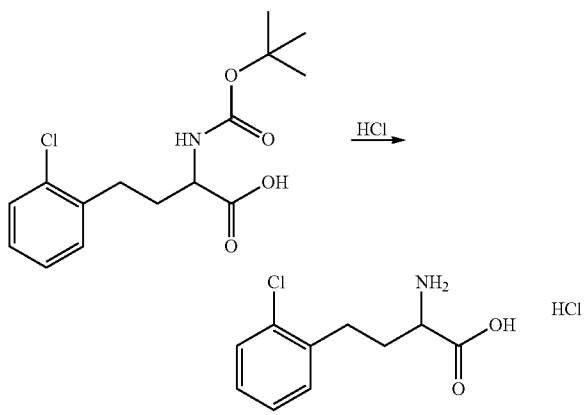

2-Amino-4-(2-chlorophenyl)butanoic acid
hydrochloride 2-(tert-Butoxycarbonylamino)-4-(2-chlorophenyl)butanoic acid (2.25 g) was dissolved in 4 N HCl in dioxane (20 mL, 11 eq) and stirred at room temperature for 1 h. The solution was then concentrated delivering product as a yellow solid (1.49 g, 83% yield).

Step 4

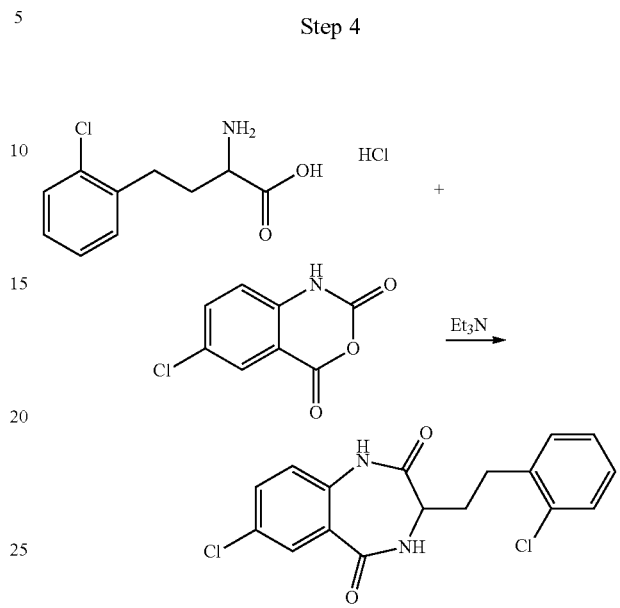

7-Chloro-3-(2-chlorophenethyl)-3,4-dihydro-1H-
benzo[e][1,4]diazepine-2,5-dione

2-Amino-4-(2-chlorophenyl)butanoic acid hydrochloride (1.49 g, 1 eq) was dissolved in water/acetonitrile 1:1 (24 mL:24 mL), and triethylamine (1.67 mL, 2 eq) was then added. 5-Chloroisatoic anhydride (1.18 g, 1 eq) was added in about 10 portions giving time between each addition for the previous portion to dissolve. After all of the anhydride was added the reaction was stirred at room temperature overnight. Any solids present after reaction were filtered off. The filtrate was concentrated in vacuo, azeotroped with acetonitrile, redissolved in AcOH (60 mL) and heated to 130° C. for 6 h. The crude mixture was then concentrated, and the residue was rinsed with NaHCO$_3$(aq), stirring the slurry for 30 minutes before collecting the solid by filtration. The crude solid was washed with acetonitrile. $^1$H-NMR (300 MHz, DMSO-d$_6$) δ 10.50 (s, 1H), 8.74 (d, 1H), 7.68 (s, 1H), 7.59 (d, 1H), 7.40-7.03 (m, 5H), 3.66 (q, 1H), 2.75 (m, 2H), 2.03 (m, 1H), 1.83 (m, 1H). MS (ES+) m/z 371.0 (M+Na).

Step 5

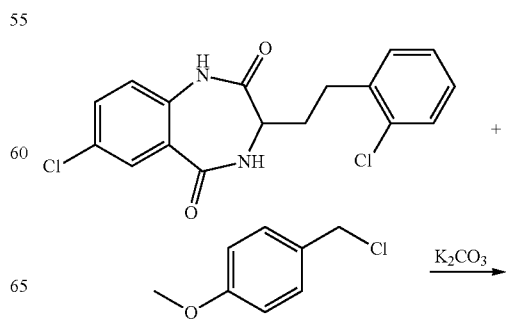

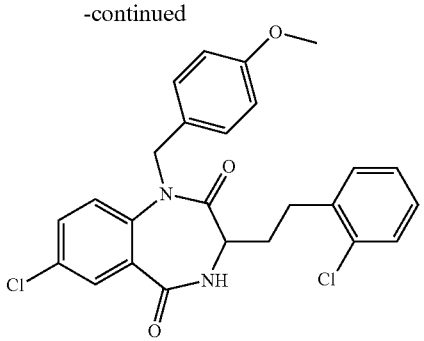

7-Chloro-3-(2-chlorophenethyl)-1-(4-methoxybenzyl)-3,4-dihydro-1H-benzo[e][1,4]diazepine-2,5-dione 7-Chloro-3-(2-chlorophenethyl)-3,4-dihydro-1H-benzo[e][1,4]diazepine-2,5-dione (1.0 g, 1 eq), 1-(chloromethyl)-4-methoxybenzene (448 mg, 1 eq), and potassium carbonate (1.19 g, 3 eq) were suspended in DMF (11.5 mL), and the mixture was stirred at room temperature overnight. Water was then added and the mixture was stirred for 30 minutes. The solid was collected by filtration, and the solid was returned to a flask and concentrated from toluene to remove water. The crude material was purified by chromatography (gradient: 9:1 hexanes:EtOAc to 1:1 hexanes:EtOAc) yielding a white solid (970 mg, 72% yield). $^1$H-NMR (300 MHz, DMSO-d$_6$) δ 8.90 (d, 1H), 7.60-7.50 (m, 3H), 7.38-7.17 (m, 4H), 6.97 (d, 2H), 6.78 (d, 2H), 5.32 (d, 1H), 4.81 (d, 1H), 3.80 (m, 1H), 3.65 (s, 3H), 2.74 (t, 2H), 2.10 (m, 1H), 1.90 (m, 1H). MS (ES+) m/z 490.9 (M+Na).

Step 6

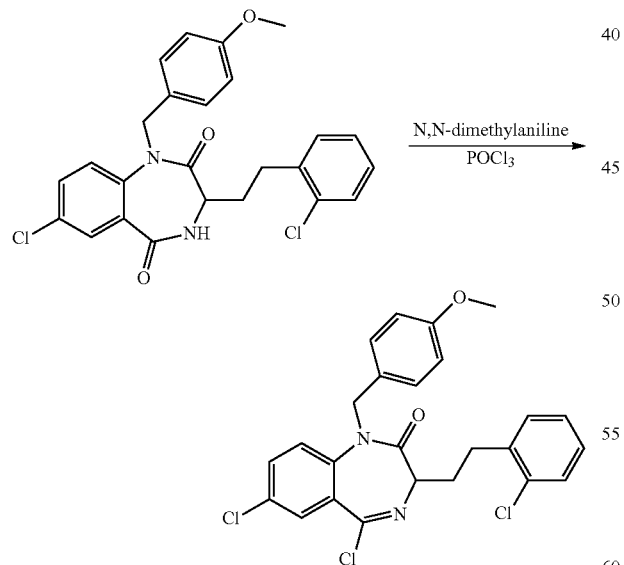

5,7-Dichloro-3-(2-chlorophenethyl)-1-(4-methoxybenzyl)-1H-benzo[e][1,4]diazepin-2(3H)-one 7-Chloro-3-(2-chlorophenethyl)-1-(4-methoxybenzyl)-3,4-dihydro-1H-benzo[e][1,4]diazepine-2,5-dione (950 mg) was dissolved in toluene (20 mL) and then N,N-dimethylaniline (564 mg, 2.3 eq) was added followed by phosphorousoxychloride (403 mg, 1.3 eq). The reaction was heated to 90° C. overnight, then cooled to room temperature and washed with ice cold water, then cold 0.5 M HCl, then cold sodium bicarbonate, then cold water, then brine, and then it was dried over sodium sulfate, and filtered through a plug of silica gel (eluting with 1:1 hexanes:EtOAc), and concentrated, and held under vacuum for 24 h. Crude product was a viscous purple oil. $^1$H-NMR (300 MHz, CDCl$_3$) δ 7.70 (d, 1H), 7.40 (dd, 1H), 7.30-7.22 (m, 2H), 7.20-7.07 (m, 2H), 7.00 (d, 2H), 6.81-6.70 (m, 3H), 5.28 (d, 1H), 4.82 (d, 1H), 3.75 (s, 3H), 3.55 (t, 1H), 2.95 (s, 2H), 2.90-2.79 (m, 2H), 2.55-2.45 (m, 2H).

Step 7

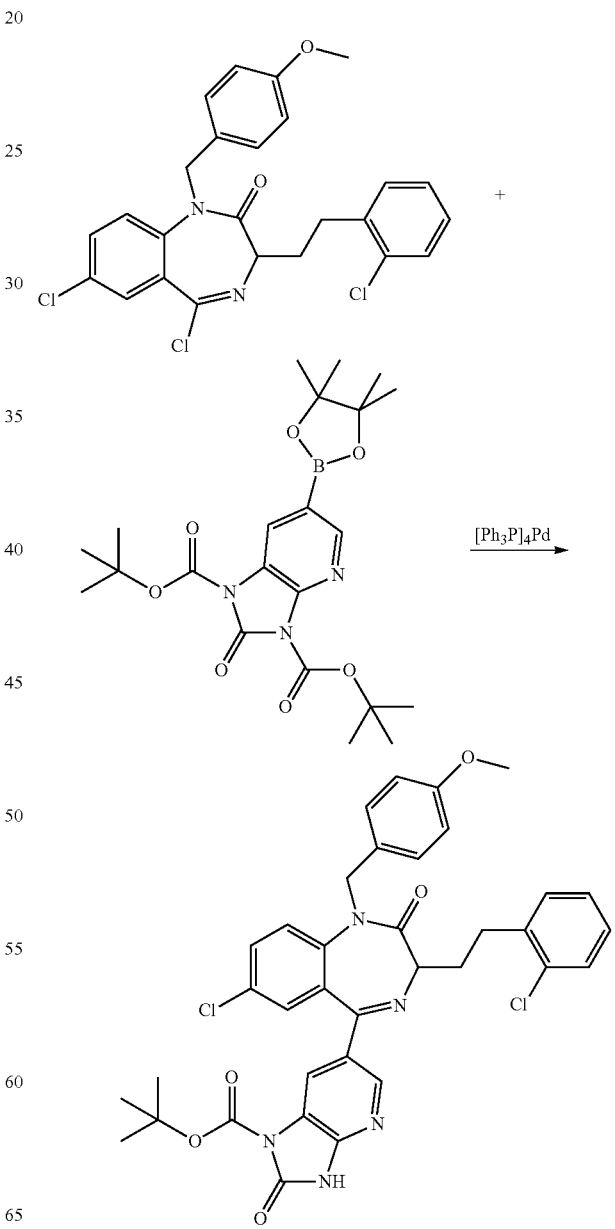

121 tert-Butyl 6-(7-chloro-3-(2-chlorophenethyl)-1-(4-methoxybenzyl)-2-oxo-2,3-dihydro-1H-benzo[e][1,4]diazepin-5-yl)-2-oxo-2,3-dihydro-1H-imidazo[4,5-b]pyridine-1-carboxylate 5,7-Dichloro-3-(2-chlorophenethyl)-1-(4-methoxybenzyl)-1H-benzo[e][1,4]diazepin-2(3H)-one (245 mg) and di-tert-butyl 2-oxo-6-(4,4,5,5-tetramethyl-1,3,2-dioxaborolan-2-yl)-1H-imidazo[4,5-b]pyridine-1,3(2H)-dicarboxylate (255 mg, 1.1 eq) were dissolved in dioxane/water (2 mL:0.65 mL), and cesium carbonate (327 mg, 2 eq) was added followed by lithium chloride (64 mg, 3 eq). The mixture was degassed with nitrogen and then tetrakis-triphenylphosphine palladium (0) (58 mg, 0.1 eq) was added. The mixture was degassed again, and the reaction was then heated to 80° C. for three hours. The crude mixture was partitioned between water and EtOAc and the organic fraction was then washed with brine, then dried over sodium sulfate and concentrated onto silica gel and purified by chromatography (gradient: 9:1 hexanes:EtOAc to EtOAc) delivering both the product 90 mg, 23% yield). MS (ES+) m/z 707.9 (M+Na) and m/z 807.9 (M+Na+Boc) and doubly Boc-protected material.

Step 8

122

7-Chloro-3-(2-chlorophenethyl)-1-(4-methoxybenzyl)-5-(2-oxo-2,3-dihydro-1H-imidazo[4,5-b]pyridin-6-yl)-1H-benzo[e][1,4]diazepin-2(3H)-one tert-Butyl 6-(7-chloro-3-(2-chlorophenethyl)-1-(4-methoxybenzyl)-2-oxo-2,3-dihydro-1H-benzo[e][1,4]diazepin-5-yl)-2-oxo-2,3-dihydro-1H-imidazo[4,5-b]pyridine-1-carboxylate (90 mg) was dissolved in 4 N HCl in dioxane (10 mL), and stirred at room temperature for 2 h, then concentrated delivering pure product (50 mg, 75% yield). MS (ES+) m/z 607.9 (M+Na).

Step 9

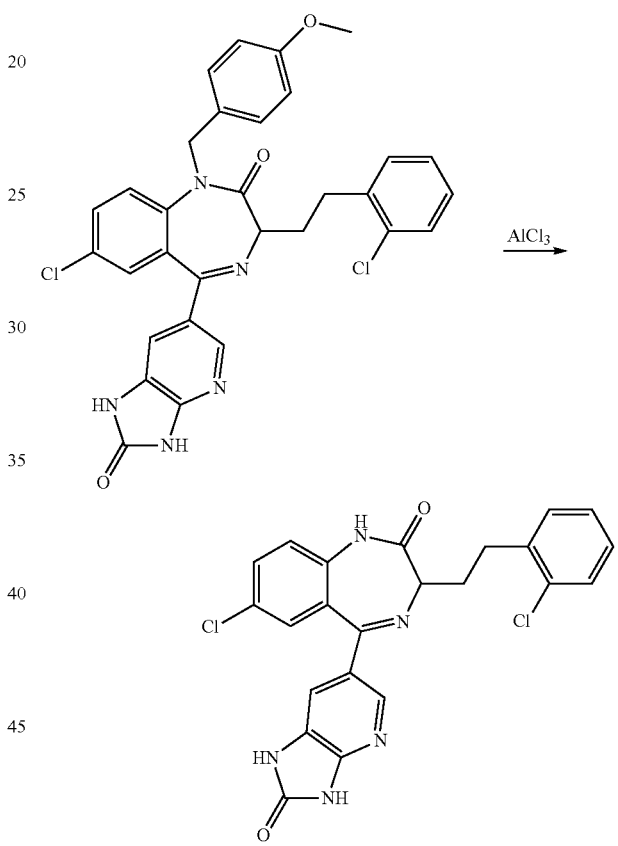

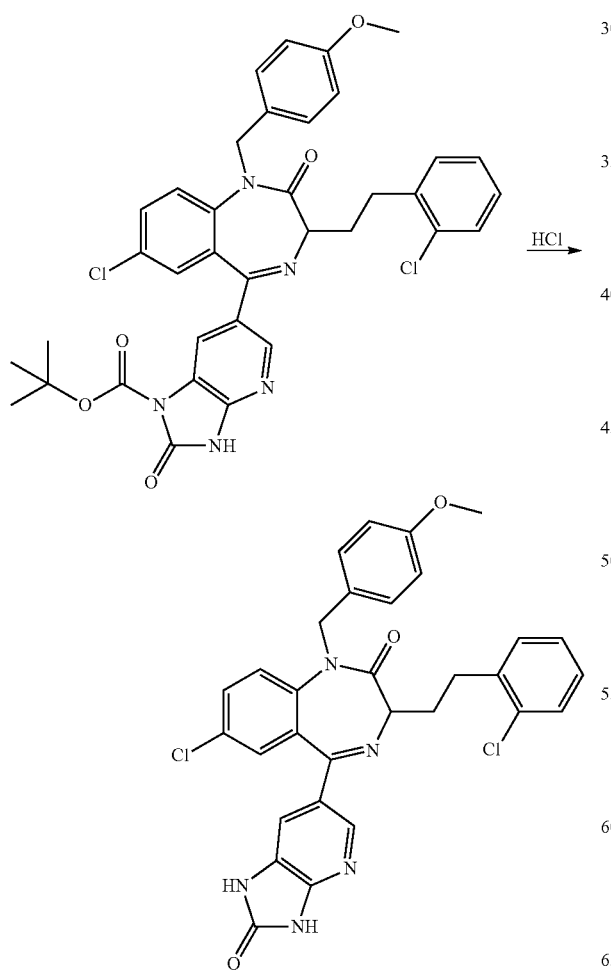

7-Chloro-3-(2-chlorophenethyl)-5-(2-oxo-2,3-dihydro-1H-imidazo[4,5-b]pyridin-6-yl)-1H-benzo[e][1,4]diazepin-2(3H)-one 7-Chloro-3-(2-chlorophenethyl)-1-(4-methoxybenzyl)-5-(2-oxo-2,3-dihydro-1H-imidazo[4,5-b]pyridin-6-yl)-1H-benzo[e][1,4]diazepin-2(3H)-one (50 mg) was dissolved in anisole (2.1 mL) and aluminum chloride (46 mg, 4 eq) was added. The reaction was stirred at 85° C. for 2 h, then poured into ice:EtOAc (1:1). The quenched reaction was stirred vigorously for 1 h, then the organic layer was separated, washed with brine, dried over sodium sulfate, and then concentrated onto silica gel and purified by chromatography (gradient:

DCM to 9:1 DCM:MeOH) delivering product (10 mg, 25% yield). HRMS (ES+) m/z calcd for $C_{23}H_{17}Cl_2N_5O_2$ [M+H]$^+$, 466.0838. found, 466.0838.

Example 8

Procedures for the Synthesis of 5-(6-Aminopyridin-3-yl)-7-chloro-3-(2-chlorobenzyl)-1-cyclopropyl-1H-benzo[e][1,4]diazepin-2(3H)-one Beginning with 3-Chloro-6-fluorobenzonitrile and Cyclopropylamine Step 1

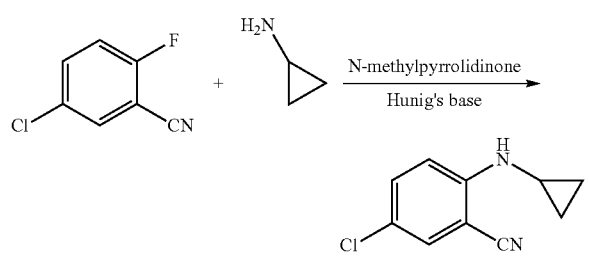

5-Chloro-2-(cyclopropylamino)benzonitrile

A solution of 3-chloro-6-fluorobenzonitrile (5 g), Hunig's base (5.60 mL, 1 eq), and cyclopropylamine (3.34 mL, 1.5 eq) in anhydrous N-methylpyrrolidinone (16 mL) was heated to 110° C. for 18 h in a sealed tube. The mixture was then cooled to room temperature and partitioned between ethyl acetate and aqueous sodium bicarbonate. The organic layer was washed once with water, then brine, then concentrated and the residue was washed with hexanes delivering the product as a crystalline white solid (4.66 g, 75% yield). $^1$H-NMR (300 MHz, DMSO-$d_6$) δ 7.58 (s, 1H), 7.46 (dd, 1H), 7.02 (d, 1H), 6.70 (s, 1H), 2.40 (m, 1H), 0.75 (m, 2H), 0.50 (m, 2H).

Step 2

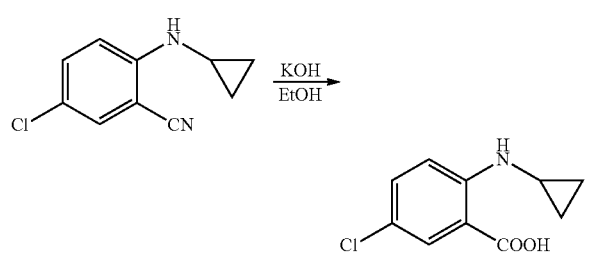

5-Chloro-2-(cyclopropylamino)benzoic acid

5-Chloro-2-(cyclopropylamino)benzonitrile (4.66 g) was dissolved in a solution of KOH (4.75 g, 3.5 eq) in EtOH (12 mL) and water (2.5 mL). The solution was refluxed for 24 h, cooled, and acidified with concentrated HCl. The precipitate was filtered, washed with water, and dried by multiple concentrations from toluene delivering pure product (4.70 g, 92% yield). $^1$H-NMR (400 MHz, DMSO-$d_6$) δ 7.88 (bs, 1H), 7.70 (d, 1H), 7.42 (dd, 1H), 7.09 (d, 1H), 2.47 (m, 1H), 0.78 (m, 2H), 0.45 (m, 2H).

Step 3

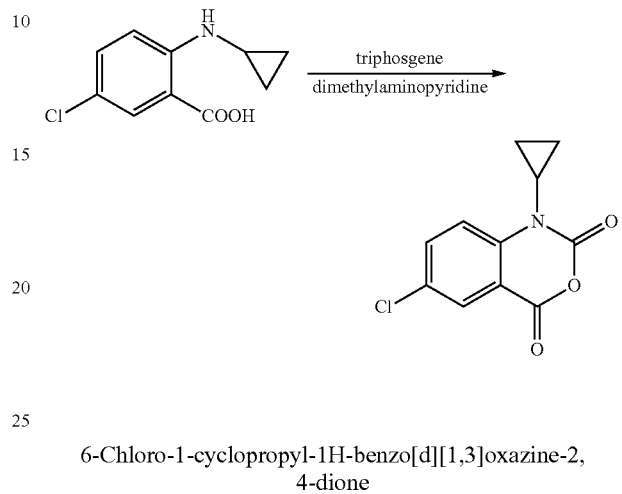

6-Chloro-1-cyclopropyl-1H-benzo[d][1,3]oxazine-2,4-dione

A solution of 5-chloro-2-(cyclopropylamino)benzoic acid (4.70 g) and triethylamine (3.12 mL, 1 eq) in DCM (111 mL) was cooled to 0° C. and treated with triphosgene (2.31 g, 0.35 eq) in small portions. Dimethylaminopyridine (271 mg, 0.1 eq) was then added and the reaction was stirred at room temperature overnight. The crude was washed with cold 1 N HCl, and the organic portion was dried over sodium sulfate, and concentrated, then held under vacuum for 18 h delivering product (5.00 g, 95% yield). $^1$H-NMR (400 MHz, DMSO-$d_6$) δ 7.88 (m, 2H), 7.68 (d, 1H), 2.90 (m, 1H), 1.16 (m, 2H), 0.80 (m, 2H). MS (ES+) m/z 260.0 (M+Na).

Step 4

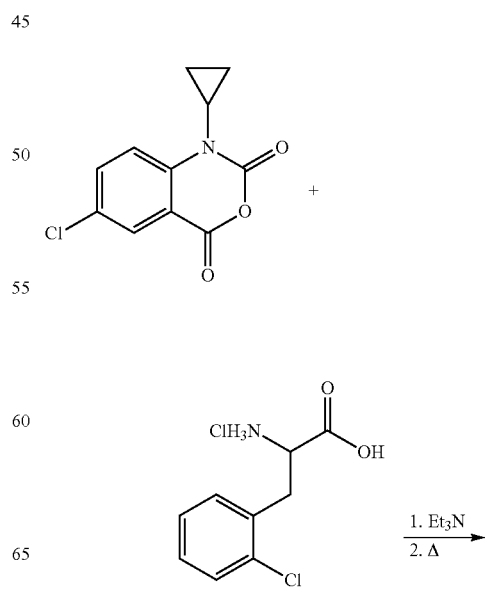

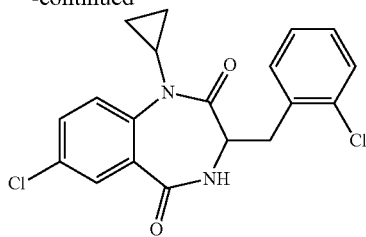

7-Chloro-3-(2-chlorobenzyl)-1-cyclopropyl-3,4-dihydro-1H-benzo[e][1,4]diazepine-2,5-dione 2-Amino-3-(2-chlorophenyl)propanoic acid hydrochloride (4.97 g, 1 eq) was dissolved in water/acetonitrile (84 mL/84 mL) and triethylamine (5.91 mL, 2 eq) was then added. 1-Cyclopropyl-5-chloroisatoic anhydride (5.00 g, 1 eq) was then added in about 10 portions giving time between each addition for the previous portion to dissolve. After all of the anhydride was added the reaction was stirred at room temperature overnight. Any solids present after reaction were filtered off. The filtrate was concentrated in vacuo, azeotroped with acetonitrile, re-dissolved in AcOH (210 mL) and heated to 130° C. for 6 h. The crude mixture was then concentrated, and the residue was washed with NaHCO₃(aq), stirring the mixture for a while before collecting the solid by filtration. The crude product was chromatographed (gradient: 3:1 hex:EtOAc to EtOAc) delivering the product (126 mg, 2% yield).

Step 5

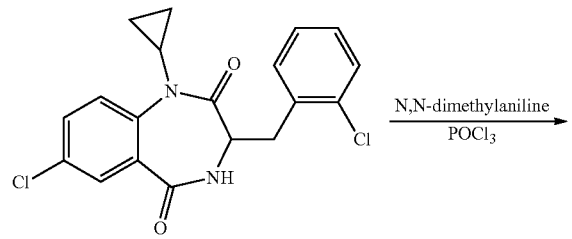

5,7-Dichloro-3-(2-chlorobenzyl)-1-cyclopropyl-1H-benzo[e][1,4]diazepin-2(3H)-one The reaction was carried out according to the procedure described in step 6 of Example 4 delivering product (50 mg, 100% yield) which was carried into the next reaction without purification.

Step 6

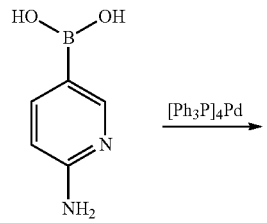

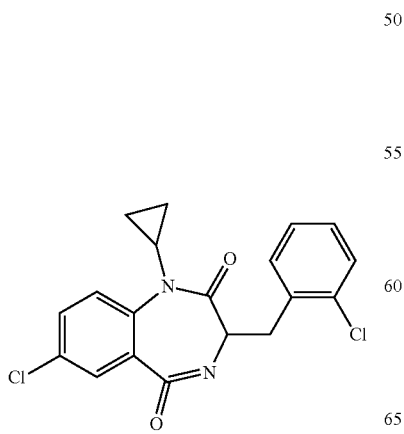

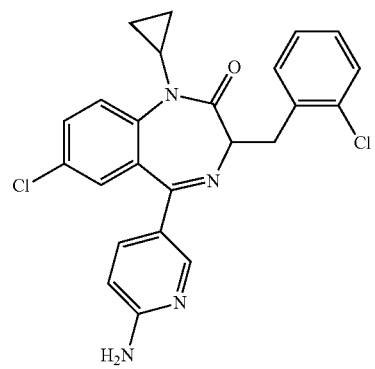

127

5-(6-Aminopyridin-3-yl)-7-chloro-3-(2-chlorobenzyl)-1-cyclopropyl-1H-benzo[e][1,4]diazepin-2(3H)-one The reaction was carried out according to the procedure described in Part I of Example 1 to provide the title compound after chromatography (3.4 mg, 4% yield). MS (ES+) m/z 450.9 (M+1).

Example 9

Procedures for the Synthesis of N-(5-(7-Chloro-3-(2-chlorobenzyl)-2-oxo-2,3-dihydro-1H-benzo[e][1,4]diazepin-5-yl)pyridin-2-yl)acetamide Beginning with Tetramethyl-1,3,2-dioxaborolan-2-yl)pyridin-2-amine

Step 1

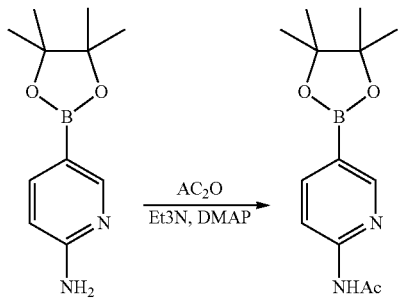

N-(5-(4,4,5,5-Tetramethyl-1,3,2-dioxaborolan-2-yl)pyridin-2-yl)acetamide 5-(4,4,5,5-Tetramethyl-1,3,2-dioxaborolan-2-yl)pyridin-2-amine (0.3 g, 1.36 mmol) was dissolved in dichloromethane (5 mL) and 4-dimethylaminopyridine 17 mg, 0.136 mmol) was added, followed by triethylamine (0.38 mL, 2.73 mmol) then acetic anhydride (0.153, 1.5 mmol). The mixture was stirred at room temperature for 3.5 h then diluted with dichloromethane and washed with NH₄Cl (sat aq) then brine. The organic layer was dried (MgSO₄), filtered and concentrated. Chromatography eluting with ethyl acetate gave the desired product (187 mg, 52% yield). ¹H-NMR (300 MHz, CDCl₃) δ 9.3 (s, 1H), 8.6 (s, 1H), 8.2 (d, 1H), 8.05 (d, 1H), 2.2 (s, 3H), 1.2 (s, 12H).

Step 2

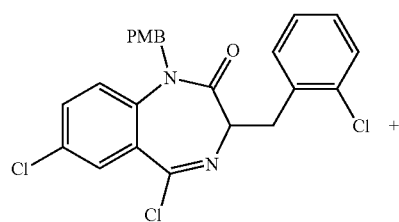

128

-continued

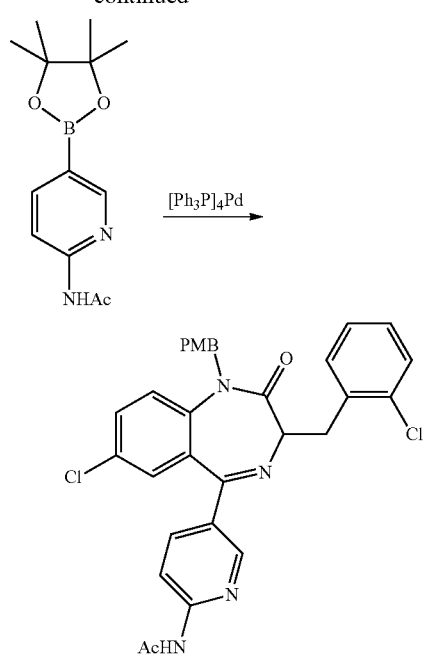

N-(5-(7-Chloro-3-(2-chlorobenzyl)-1-(4-methoxybenzyl)-2-oxo-2,3-dihydro-1H-benzo[e][1,4]diazepin-5-yl)pyridin-2-yl)acetamide 5,7-Dichloro-3-(2-chlorobenzyl)-1-(4-methoxybenzyl)-1H-benzo[e][1,4]diazepin-2(3H)-one (208 mg, 0.439 mmol), LiCl (56 mg, 1.32 mmol), and CsOH (221 mg, 1.32 mmol) were combined, then a solution of N-(5-(4,4,5,5-tetramethyl-1,3,2-dioxaborolan-2-yl)pyridin-2-yl)acetamide (115 mg, 0.439 mmol) in 1,4-dioxane (3 mL) was added followed by water (300 uL). The mixture was purged with nitrogen, then tetrakis(triphenylphosphinepalladium(0) (51 mg, 0.044 mmol) was added and the flask was lowered into a 100° C. oil bath and heated at 100° C. for 3 h. The mixture was allowed to cool, then diluted with ethyl acetate and rinsed with water 2× then brine and dried (MgSO₄). Chromatography eluting with 40-50% ethyl acetate in hexanes to give a colorless oil (210 mg, 83% yield). MS (ES+) m/z 573.1 (M+1).

Step 3

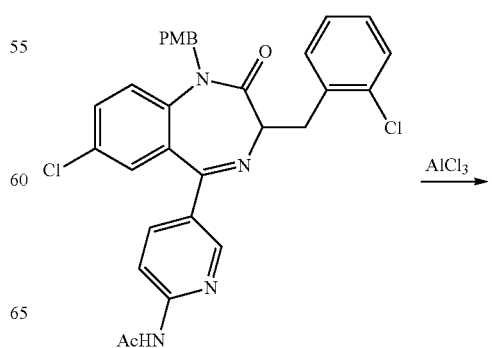

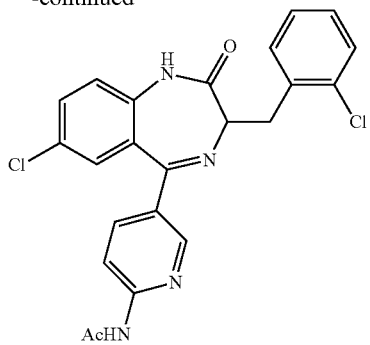

N-(5-(7-Chloro-3-(2-chlorobenzyl)-2-oxo-2,3-dihydro-1H-benzo[e][1,4]diazepin-5-yl)pyridin-2-yl)acetamide N-(5-(7-Chloro-3-(2-chlorobenzyl)-1-(4-methoxybenzyl)-2-oxo-2,3-dihydro-1H-benzo[e][1,4]diazepin-5-yl)pyridin-2-yl)acetamide (210 mg, 0.366 mmol) was dissolved in anisole (1 mL) under nitrogen and AlCl$_3$ (195 mg, 1.465 mmol) was added in one portion. The resulting orange solution was heated to 85° C. for 2 h then allowed to cool. Ice and ethyl acetate were added and the mixture was stirred for 30 min then partitioned and the organic layer was washed with water then brine and dried (MgSO$_4$). Chromatography on silica gel eluting with 10%-50%-70% ethyl acetate in hexanes gave the product (120 mg, 72% yield). $^1$H-NMR (300 MHz, CDCl$_3$) δ 7.62-7.5 (m, 3H), 7.5-7.20 (m, 7H), 6.49 (s, 1H), 6.47 (s, 1H), 4.31 (dd, 1H), 4.25-4.17 (m, 2H), 3.59 (dd, 1H), 3.35 (dd, 1H). HRMS (ES+) m/z calcd for C$_{23}$H$_{18}$Cl$_2$N$_4$O$_2$ [M+H]$^+$, 453.0885. found, 453.0872.

Example 10

Procedures for the Synthesis of N-(5-(3-(Biphenyl-2-ylmethyl)-7-chloro-1-methyl-2-oxo-2,3-dihydro-1H-benzo[e][1,4]diazepin-5-yl)pyridin-2-yl)pivalamide Beginning with Tetramethyl-1,3,2-dioxaborolan-2-yl)pyridin-2-amine Step 1

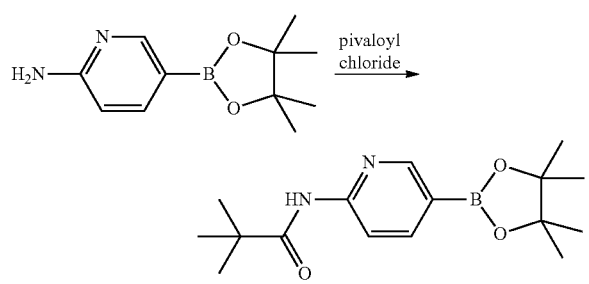

N-(5-(4,4,5,5-Tetramethyl-1,3,2-dioxaborolan-2-yl)pyridin-2-yl)pivalamide 5-(4,4,5,5-Tetramethyl-1,3,2-dioxaborolan-2-yl)pyridin-2-amine (0.5 g, 2.27 mmol), pivaloyl chloride (0.277 g, 2.20 mmol) and triethylamine (0.248 g, 2.45 mmol) in pyridine (10 mL) were stirred at room temperature overnight. The mixture was diluted with ethyl acetate and ice/water and the layers were separated. The aqueous phase was extracted with ethyl acetate and the combined extracts dried over sodium sulfate. Purification by chromatography (1:1 ethyl acetate in hexanes) gave the product (0.385 g, 56% yield) as a white solid. $^1$H-NMR (300 MHz, CDCl$_3$) δ 8.60 (s, 1H), 8.23 (d, 1H), 8.06 (d, 2H), 1.33 (s, 12H), 1.31 (s, 9H). MS (ES+) m/z 305 (M+1).

Step 2

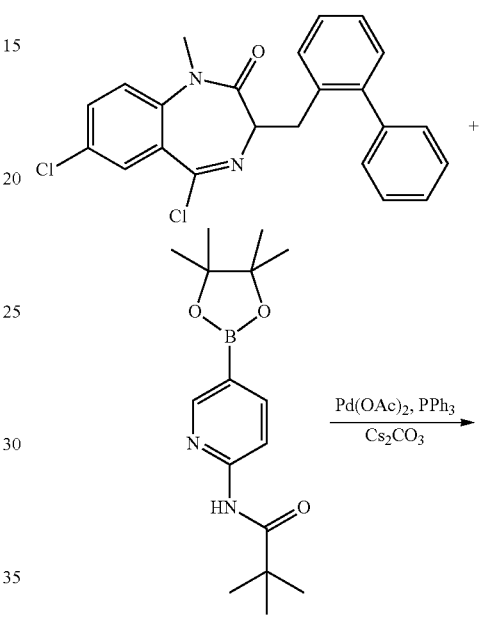

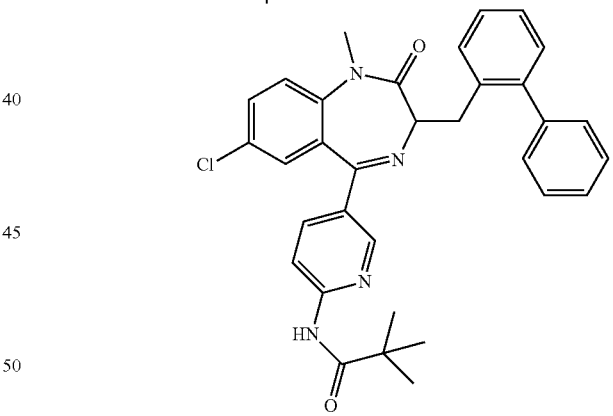

N-(5-(3-(Biphenyl-2-ylmethyl)-7-chloro-1-methyl-2-oxo-2,3-dihydro-1H-benzo[e][1,4]diazepin-5-yl)pyridin-2-yl)pivalamide 3-(Biphenyl-2-ylmethyl)-5,7-dichloro-1-methyl-1H-benzo[e][1,4]diazepin-2(3H)-one (0.192 g, 0.469 mmol), N-(5-(4,4,5,5-tetramethyl-1,3,2-dioxaborolan-2-yl)pyridin-2-yl)pivalamide (0.214 g, 0.703 mmol, 1.2 eq), Palladium (II) acetate (0.2 eq), triphenyl phosphine (0.2 eq) and cesium carbonate (2 eq) were heated at 100° C. in DMF (3 mL) under an atmosphere of nitrogen in a sealed tube for 1.5 h. The mixture was cooled then diluted with ethyl acetate and water (2:1) then filtered through a pad of celite. The layers were separated and the organic phase was washed with brine then dried over sodium sulfate. Chromatography eluting with 1:1 ethyl acetate in hexanes gave an oil which was dissolved in a 2:1 mixture of acetonitrile and water and freeze-dried to give product as an off-white solid (0.096 g, 37% yield). $^1$H-NMR (300 MHz, CDCl$_3$) δ 8.29-8.22 (m, 2H), 8.09 (s, 1H), 7.71 (dd, 1H), 7.51-7.47 (m, 2H), 7.32-7.28 (m, 2H), 7.20-7.12 (m, 8H), 3.69-3.55 (m, 2H), 3.41-3.36 (m, 1H), 3.31 (s, 3H), 1.33 (s, 9H). MS (APCI) m/z 551 (M+1).

Example 11

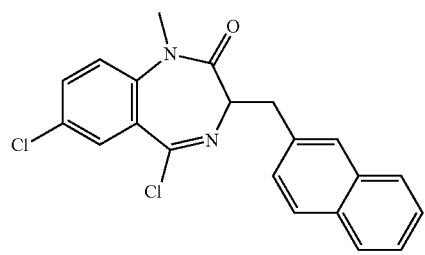

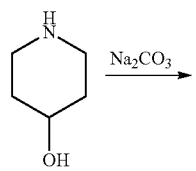

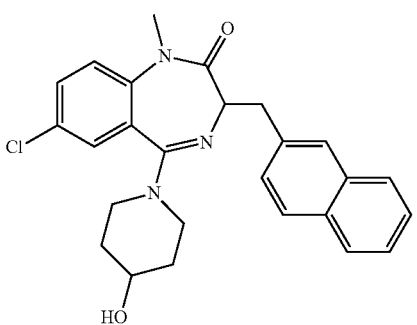

7-Chloro-5-(4-hydroxypiperidin-1-yl)-1-methyl-3-(naphthalen-2-ylmethyl)-1H-benzo[e][1,4]diazepin-2(3H)-one 5,7-Dichloro-1-methyl-3-(naphthalen-2-ylmethyl)-1H-benzo[e][1,4]diazepin-2(3H)-one (0.36 g, 0.94 mmol), 4-hydroxypiperidine (0.38 g, 3.8 mmol), sodium carbonate (0.40 g, 3.8 mmol), and tetrabutylammonium iodide (0.09 g, 0.24 mmol) were combined in toluene (5 mL) and heated to 100° C. for 24 hours. The solution was cooled, diluted with ethyl acetate, washed with water, brine, dried with magnesium sulfate, filtered and concentrated in vacuo. Column chromatography eluting with a gradient of 25-100% ethyl acetate in hexanes provided 7-chloro-5-(4-hydroxypiperidin-1-yl)-1-methyl-3-(naphthalen-2-ylmethyl)-1H-benzo[e][1,4]diazepin-2(3H)-one. (35 mg, 8% yield) ESI m/z measured 448.1794 [M+H]$^+$. calculated 448.1792.

Example 12

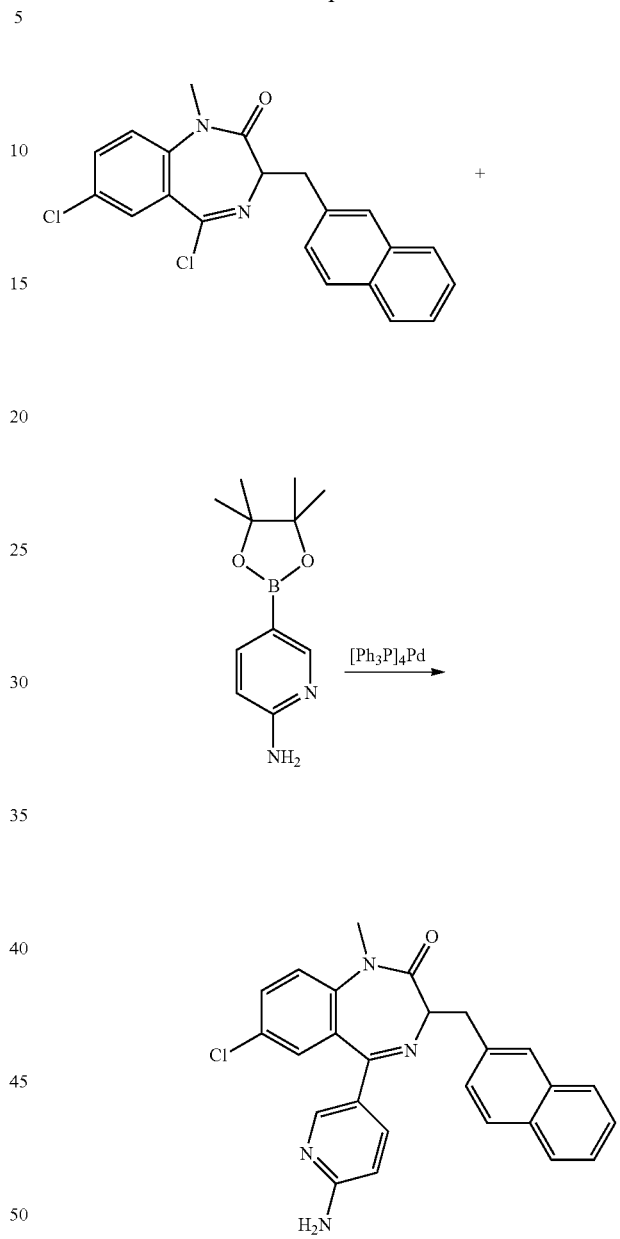

5-(6-Aminopyridin-3-yl)-7-chloro-1-methyl-3-(naphthalen-2-ylmethyl)-1H-benzo[e][1,4]diazepin-2(3H)-one 5,7-Dichloro-1-methyl-3-(naphthalen-2-ylmethyl)-1H-benzo[e][1,4]diazepin-2(3H)-one (0.40 g, 1.04 mmol), 2-aminopyridine-5-boronic acid pinacol ester (0.28 g, 1.25 mmol) and lithium chloride (0.13 g, 3.1 mmol) were added to 1,4-dioxane (4 mL). Nitrogen was bubbled into solution as reagents were added. Tetrakis(triphenylphosphine) palladium(0) (0.12 g, 0.10 mmol) was added followed by cesium hydroxide monohydrate (0.53 g, 3.1 mmol) and water (1 mL). After bubbling through nitrogen for 5 minutes the reaction was heated to 100° C. for 1 h under a nitrogen atmosphere.

The mixture was cooled to ambient temperature, diluted with ethyl acetate (25 mL), washed with water (2×20 mL), brine (20 mL), dried with sodium sulfate, decanted then concentrated in the presence of silica. Chromotography eluting with a gradient of 30-100% ethyl acetate in hexanes provided 5-(6-aminopyridin-3-yl)-7-chloro-1-methyl-3-(naphthalen-2-ylmethyl)-1H-benzo[e][1,4]diazepin-2(3H)-one (140 mg, 30% yield). $^1$H NMR (300 MHz, $d_6$-DMSO) δ 3.47 (m, 2H) 3.75 (m, 1H), 6.43 (m, 1H), 6.50 (s, 2H), 7.27 (m, 1H), 7.40-7.67 (m, 6H), 7.75-7.82 (m, 4H), 7.92 (m, 1H); ESI m/z measured 441.1487 [M+H]$^+$. calculated 441.1482.

The following compounds were prepared according to the above procedure.

5-(5-Aminopyrazin-2-yl)-7-chloro-1-methyl-3-(naphthalen-2-ylmethyl)-1H-benzo[e][1,4]diazepin-2(3H)-one (60 mg, 10% yield) $^1$H NMR (300 MHz, $d_6$-DMSO) δ 3.52 (m, 2H) 3.84 (m, 1H), 6.95 (s, 2H), 7.31 (s, 1H) 7.40-7.69 (m, 6H), 7.75-7.86 (m, 4H), 8.48 (s, 1H); ESI m/z measured 442.1435 [M+H]$^+$. calculated 442.1435.

5-(5-Aminopyridin-2-yl)-7-chloro-1-methyl-3-(naphthalen-2-ylmethyl)-1H-benzo[e][1,4]diazepin-2(3H)-one (26 mg, 26% yield) $^1$H NMR (300 MHz, $d_6$-DMSO) δ 3.3 (m, 5H, buried), 3.78 (m, 1H), 7.18 (m, 1H), 7.4-7.85 (m, 10H), 8.1 (m, 2H), 8.7 (m, 1H), 9.08 (s, 1H); ESI m/z measured 441.1481 [M+H]$^+$. calculated 441.1482.

7-Chloro-5-(4-(hydroxymethyl)pyridin-2-yl)-1-methyl-3-(naphthalen-2-ylmethyl)-1H-benzo[e][1,4]diazepin-2(3H)-one (11 mg, 11% yield) $^1$H NMR (300 MHz, $d_6$-DMSO) δ 3.3 (m, 5H, buried), 3.76 (m, 1H), 5.24 (q, 2H), 7.36-7.5 (m, 6H), 7.65-7.82 (m, 6H), 8.45 (m, 1H); ESI m/z measured 456.1474 [M+H]$^+$. calculated 456.1479.

7-Chloro-5-(5-methoxypyridin-2-yl)-1-methyl-3-(naphthalen-2-ylmethyl)-1H-benzo[e][1,4]diazepin-2(3H)-one (98 mg, 51% yield) $^1$H NMR (300 MHz, $d_6$-DMSO) δ 3.3 (s, 3H), 3.52 (m, 2H) 3.86 (s, 3H), 3.91 (m, 1H), 7.3 (m, 1H), 7.4-7.64 (m, 6H), 7.7-7.85 (m, 4H), 8.0 (m, 1H), 8.23 (m, 1H); ESI m/z measured 456.1475 [M+H]$^+$. calculated 456.1479.

7-Chloro-3-(2-chlorobenzyl)-5-(pyridin-4-yl)-1H-benzo[e][1,4]diazepin-2(3H)-one The title compound was prepared according to the above procedure, followed deprotection with aluminum chloride in anisole according to the procedures described in Part II of Example 1 (98 mg, 51%). $^1$H NMR (300 MHz, $d_6$-DMSO) δ 3.5 (m, 2H) 3.87 (m, 1H), 7.23-7.34 (m, 5H), 7.40 (dd, 1H), 7.48 (dd, 4H), 7.67 (dd, 1H), 8.63 (d, 2H), 10.89 (s, 1H); ESI m/z measured 396.0669 [M+H]$^+$. calculated 396.0670.

7-Chloro-5-(2-(hydroxymethyl)thiazol-4-yl)-1-methyl-3-(naphthalen-2-ylmethyl)-1H-benzo[e][1,4]diazepin-2(3H)-one (32 mg, 15% yield) ESI m/z measured 462.1038 [M+H]$^+$. calculated 462.1043.

7-Chloro-5-(5-(hydroxymethyl)pyridin-2-yl)-1-methyl-3-(naphthalen-2-ylmethyl)-1H-benzo[e][1,4]diazepin-2(3H)-one (16 mg, 17% yield) ESI m/z measured 456.1481 [M+H]$^+$. calculated 456.1479.

Example 13

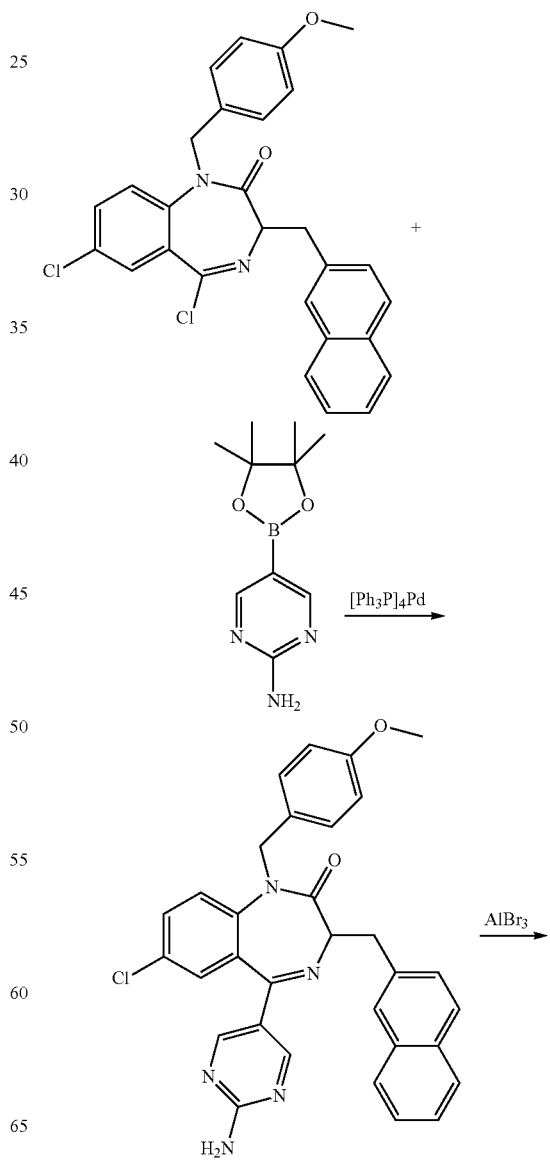

-continued

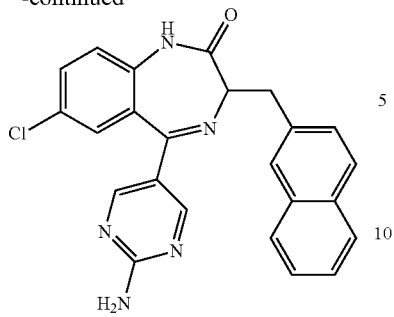

5-(6-Aminopyridin-3-yl)-7-chloro-3-(naphthalen-2-ylmethyl)-1H-benzo[e][1,4]diazepin-2(3H)-one 5,7-Dichloro-1-(4-methoxybenzyl)-3-(naphthalen-2-ylmethyl)-1H-benzo[e][1,4]diazepin-2(3H)-one (0.10 g, 0.20 mmol) and 2-aminopyridine-5-boronic acid pinacol ester were reacted according to the corresponding procedure described in Example 12 to yield intermediate 5-(6-aminopyridin-3-yl)-7-chloro-1-(4-methoxybenzyl)-3-(naphthalen-2-ylmethyl)-1H-benzo[e][1,4]diazepin-2(3H)-one. (77 mg, 69%). 5-(6-Aminopyridin-3-yl)-7-chloro-1-(4-methoxybenzyl)-3-(naphthalen-2-ylmethyl)-1H-benzo[e][1,4]diazepin-2(3H)-one (77 mg, 0.14 mmol) was dissolved in anhydrous anisole (2 mL) under a nitrogen atmosphere, and aluminum bromide (1M in dichloromethane, 0.70 mL, 0.70 mmol) was added. The mixture was heated to 80° C. for 1 hour then cooled to ambient temperature and an additional amount of aluminum bromide (1M in dichloromethane, 0.70 mL, 0.70 mmol) was added. The solution was heated to 80° C. for 1 hour, cooled, poured into ice, diluted with ethyl acetate and saturated sodium bicarbonate. The layers were separated and the organic layer dried with sodium sulfate, decanted and concentrated in the presence of silica gel. Column chromatography eluting with a gradient of 70-100% ethyl acetate in hexanes provided 5-(6-aminopyridin-3-yl)-7-chloro-3-(naphthalen-2-ylmethyl)-1H-benzo[e][1,4]diazepin-2(3H)-one (25 mg, 42% yield). $^1$H NMR (300 MHz, d$_6$-DMSO) δ 3.47 (m, 2H) 3.71 (m, 1H), 6.40-6.46 (m, 2H), 7.20-7.26 (m, 2H), 7.42-7.62 (m, 5H), 7.78-7.87 (m, 4H), 10.64 (s, 1H); ESI m/z measured 427.1324 [M+H]$^+$. calculated 427.1326.

Example 14

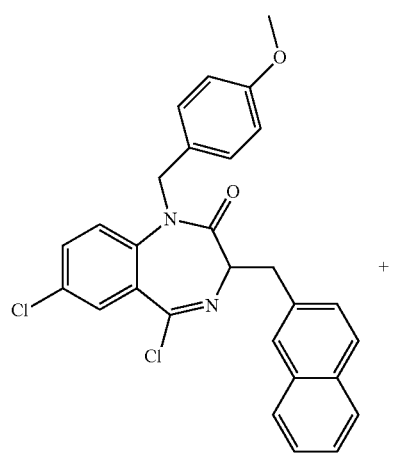

+

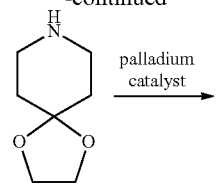

palladium catalyst
→

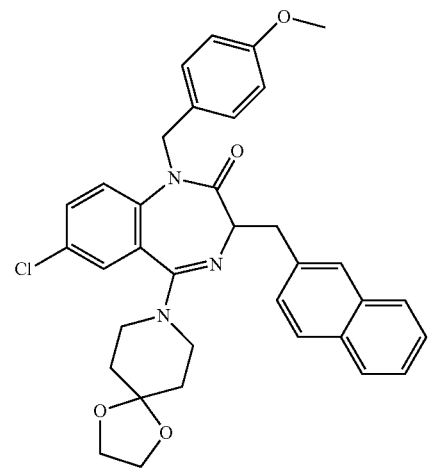

7-Chloro-1-(4-methoxybenzyl)-3-(naphthalen-2-ylmethyl)-5-(1,4-dioxa-8-azaspiro[4.5]decan-8-yl)-1H-benzo[e][1,4]diazepin-2(3H)-one Palladium acetate (8 mg, 0.038 mmol), X-Phos (18 mg, 0.038 mmol), and cesium carbonate (270 mg, 0.83 mmol) were combined in anhydrous toluene (2 mL), and nitrogen bubbled through the solution for 5 minutes. A solution of 5,7-dichloro-1-(4-methoxybenzyl)-3-(naphthalen-2-ylmethyl)-1H-benzo[e][1,4]diazepin-2(3H)-one (370 mg, 0.76 mmol) and 1,4-dioxa-8-azaspiro[4.5]decane (0.12 mL, 0.91 mmol) in toluene (2 mL) was added and then heated to 120° C. under a nitrogen blanket for 14 hours. The solution was cooled, diluted with ethyl acetate, washed with water, brine, dried with sodium sulfate, decanted, then concentrated in the presence of silica. Column chromatography eluting with a gradient of 10-70% ethyl acetate in hexanes provided 7-chloro-1-(4-methoxybenzyl)-3-(naphthalen-2-ylmethyl)-5-(1,4-dioxa-8-azaspiro[4.5]decan-8-yl)-1H-benzo[e][1,4]diazepin-2(3H)-one. (345 mg, 77% yield). ESI m/z measured 596.2321 [M+H]$^+$. calculated 596.2316.

The following compounds were prepared according to the above procedure.

7-Chloro-1-methyl-3-(naphthalen-2-ylmethyl)-5-(1,4-dioxa-8-azaspiro[4.5]decan-8-yl)-1H-benzo[e][1,4]diazepin-2(3H)-one (65 mg, 15%) ESI m/z measured 490.1893 [M+H]$^+$. calculated 490.1897.

137 tert-Butyl 1-(7-chloro-1-methyl-3-(naphthalen-2-ylmethyl)-2-oxo-2,3-dihydro-1H-benzo[e][1,4]diazepin-5-yl)piperidin-4-ylcarbamate (116 mg, 28% yield) ESI m/z measured 547.2478 [M+H]⁺. calculated 547.2476.

Example 15

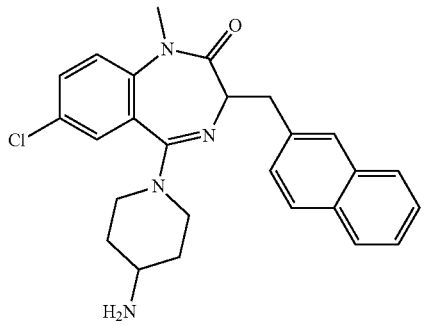 [SMILES: CN1C(=O)C(Cc2ccc3ccccc3c2)N=C(N2CCC(N)CC2)c2cc(Cl)ccc21]

5-(4-Aminopiperidin-1-yl)-7-chloro-1-methyl-3-(naphthalen-2-ylmethyl)-1H-benzo[e][1,4]diazepin-2(3H)-one 5,7-Dichloro-1-methyl-3-(naphthalen-2-ylmethyl)-1H-benzo[e][1,4]diazepin-2(3H)-one (170 mg, 0.44 mmol) and tert-butyl piperidin-4-ylcarbamate (89 mg, 0.44 mmol) were coupled according to the corresponding procedure described in Example 14 to yield intermediate tert-butyl 1-(7-chloro-1-methyl-3-(naphthalen-2-ylmethyl)-2-oxo-2,3-dihydro-1H-benzo[e][1,4]diazepin-5-yl)piperidin-4-ylcarbamate. (85 mg, 35%). Tert-butyl 1-(7-chloro-1-methyl-3-(naphthalen-2-ylmethyl)-2-oxo-2,3-dihydro-1H-benzo[e][1,4]diazepin-5-yl)piperidin-4-ylcarbamate (85 mg, 0.16 mmol) was dissolved in dichloromethane (1 mL) and trifluoroacetic acid (1 mL) and stirred at ambient temperature for 2 hours. The solution was concentrated, redissolved in ethyl acetate and extracted into 1 M aqueous hydrochloric acid (3×10 mL). The extracts were neutralized with saturated sodium bicarbonate, extracted with dichloromethane (3×25 mL), then dried with sodium sulfate, filtered, and concentrated to yield 5-(4-ami-

138 nopiperidin-1-yl)-7-chloro-1-methyl-3-(naphthalen-2-ylmethyl)-1H-benzo[e][1,4]diazepin-2(3H)-one (20 mg, 29% yield). MS (M+H)⁺447.2.

Example 16

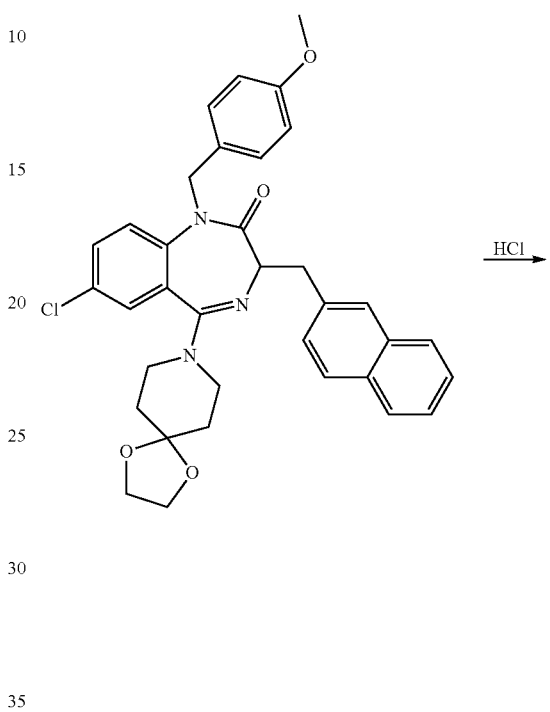

7-Chloro-3-(naphthalen-2-ylmethyl)-5-(4-oxopiperidin-1-yl)-1H-benzo[e][1,4]diazepin-2(3H)-one 7-Chloro-1-(4-methoxybenzyl)-3-(naphthalen-2-ylmethyl)-5-(1,4-dioxa-8-azaspiro[4.5]decan-8-yl)-1H-benzo[e][1,4]diazepin-2(3H)-one (0.14 g, 0.24 mmol) was dissolved in 1,4-dioxane (4 mL), and concentrated aqueous hydrochloric acid (4 mL) was added. The reaction mixture was stirred at 60° C. for 5 hours, then the temperature increased to 80° C. for 2 hours. The solution was cooled, diluted with ethyl acetate, washed with saturated sodium bicarbonate solution, brine, dried with sodium sulfate, decanted and concentrated in the presence of silica. Chromatography provided 7-chloro-3-(naphthalen-2-ylmethyl)-5-

(4-oxopiperidin-1-yl)-1H-benzo[e][1,4]diazepin-2(3H)-one (22 mg, 22% yield). ESI m/z measured 432.1487 [M+H]+. calculated 432.1479.

Example 17

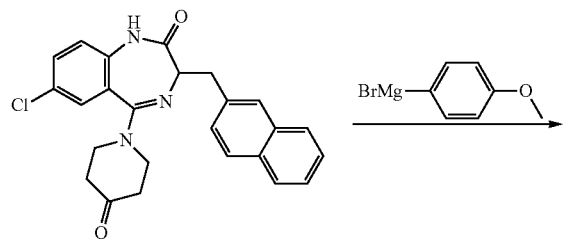

7-Chloro-5-(4-hydroxy-4-(4-methoxyphenyl)piperidin-1-yl)-3-(naphthalen-2-ylmethyl)-1H-benzo[e][1,4]diazepin-2(3H)-one 7-Chloro-3-(naphthalen-2-ylmethyl)-5-(4-oxopiperidin-1-yl)-1H-benzo[e][1,4]diazepin-2(3H)-one (18 mg, 0.04 mmol) was dissolved in anhydrous tetrahydrofuran (0.2 mL) under nitrogen, 4-methoxyphenylmagnesium bromide (0.5M solution in tetrahydrofuran, 0.5 mL, 0.25 mmol) was added dropwise. After stirring at ambient temperature for 1 hour the reaction was quenched with water (1 mL), diluted with ethyl acetate, separated, washed with water, dried with sodium sulfate, decanted, and concentrated. The residue was redissolved in ethyl acetate (0.5 mL) and hexanes added slowly (total of 6 mL). A solid precipitated and was collected by filtration. Washing with hexanes provided 7-chloro-5-(4-hydroxy-4-(4-methoxyphenyl)piperidin-1-yl)-3-(naphthalen-2-ylmethyl)-1H-benzo[e][1,4]diazepin-2(3H)-one (10 mg, 43% yield). ESI m/z measured 540.2062 [M+H]+. calculated 540.2054.

Example 18

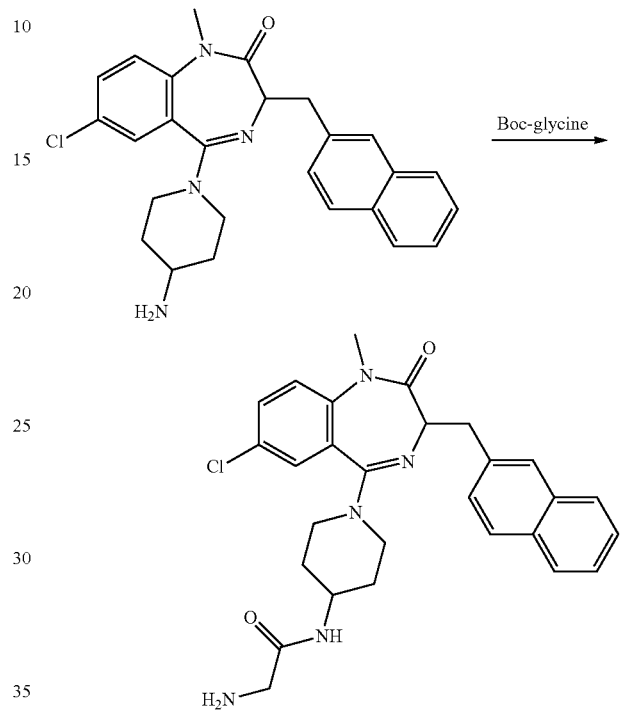

2-Amino-N-(1-(7-chloro-1-methyl-3-(naphthalen-2-ylmethyl)-2-oxo-2,3-dihydro-1H-benzo[e][1,4]diazepin-5-yl)piperidin-4-yl)acetamide 5-(4-Aminopiperidin-1-yl)-7-chloro-1-methyl-3-(naphthalen-2-ylmethyl)-1H-benzo[e][1,4]diazepin-2(3H)-one (15 mg, 0.034 mmol) was dissolved in anhydrous N,N-dimethylformamide (0.3 mL), and Boc-glycine (7 mg, 0.037 mmol), and then 1-ethyl-3-[3-(dimethylamino)propyl]-carbodiimide hydrochloride (8 mg, 0.04 mmol), 1-hydroxybenztriazole (5 mg, 0.04 mmol), and triethylamine (6 µL, 0.04 mmol) were added. The reaction was stirred at ambient temperature for 24 hours. The solution was diluted with ethyl acetate (5 mL), washed with saturated sodium bicarbonate (3×1 mL), dried with sodium sulfate, decanted and concentrated in vacuo. Column chromatography eluting with a gradient of 70-100% ethyl acetate in hexanes provided tert-butyl 2-(1-(7-chloro-1-methyl-3-(naphthalen-2-ylmethyl)-2-oxo-2,3-dihydro-1H-benzo[e][1,4]diazepin-5-yl)piperidin-4-ylamino)-2-oxoethylcarbamate (3 mg, 15%). This material was dissolved in dichloromethane (0.2 mL) and trifluoroacetic acid (0.1 mL) and stirred at ambient temperature for 1 hour then concentrate in vacuo. Azeotroping four times with dichloromethane provided 2-amino-N-(1-(7-chloro-1-methyl-3-(naphthalen-2-ylmethyl)-2-oxo-2,3-dihydro-1H-benzo[e][1,4]diazepin-5-yl)piperidin-4-yl)acetamide as the trifluoroacetate salt (3 mg, quant. yield). ESI m/z measured 504.2173 [M+H]+. calculated 504.2166.

Example 19

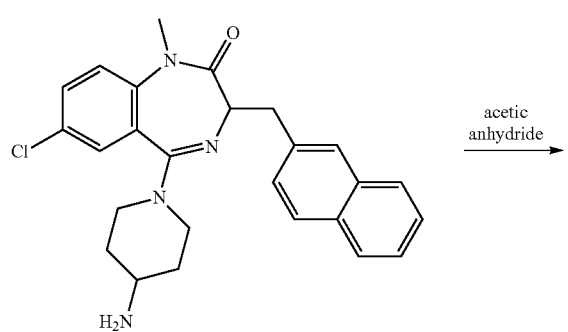

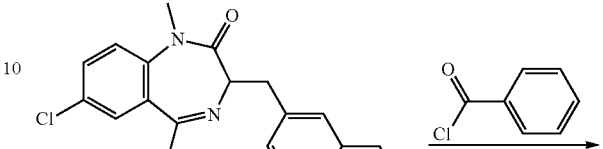

N-(1-(7-chloro-1-methyl-3-(naphthalen-2-ylmethyl)-2-oxo-2,3-dihydro-1H-benzo[e][1,4]diazepin-5-yl)piperidin-4-yl)acetamide 5-(4-Aminopiperidin-1-yl)-7-chloro-1-methyl-3-(naphthalen-2-ylmethyl)-1H-benzo[e][1,4]diazepin-2(3H)-one (50 mg, 0.11 mmol) was dissolved in dichloromethane (0.5 mL) and triethylamine (31 μL, 0.22 mmol), acetic anhydride (11 μL, 0.11 mmol) was added and the mixture was stirred at ambient temperature for 1 hour. To the solution was added silica and concentrated in vacuo. Column chromatography eluting with a gradient of 70-100% ethyl acetate in hexanes then 0-15% methanol in ethyl acetate provided N-(1-(7-chloro-1-methyl-3-(naphthalen-2-ylmethyl)-2-oxo-2,3-dihydro-1H-benzo[e][1,4]diazepin-5-yl)piperidin-4-yl)acetamide (30 mg, 55% yield). ESI m/z measured 489.2043 [M+H]+. calculated 489.2057.

Example 20

N-(1-(7-chloro-1-methyl-3-(naphthalen-2-ylmethyl)-2-oxo-2,3-dihydro-1H-benzo[e][1,4]diazepin-5-yl)piperidin-4-yl)benzamide 5-(4-Aminopiperidin-1-yl)-7-chloro-1-methyl-3-(naphthalen-2-ylmethyl)-1H-benzo[e][1,4]diazepin-2(3H)-one (50 mg, 0.11 mmol) was dissolved in dichloromethane (2 mL) and triethylamine (31 μL, 0.22 mmol), a solution of benzoyl chloride (10 μL, 0.11 mmol) in dichloromethane (0.2 mL) was added dropwise, and stirred at ambient temperature for 30 minutes. To the solution was added silica gel and the mixture was concentrated. Column chromatography eluting with a gradient of 50-100% ethyl acetate in hexanes provided N-(1-(7-chloro-1-methyl-3-(naphthalen-2-ylmethyl)-2-oxo-2,3-dihydro-1H-benzo[e][1,4]diazepin-5-yl)piperidin-4-yl)

benzamide (35 mg, 57% yield). ESI m/z measured 551.2224 [M+H]⁺. calculated 551.2214.

Example 21

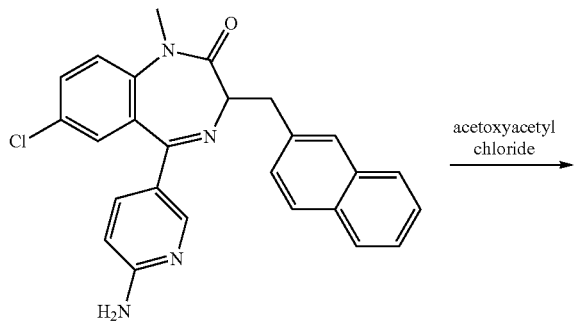

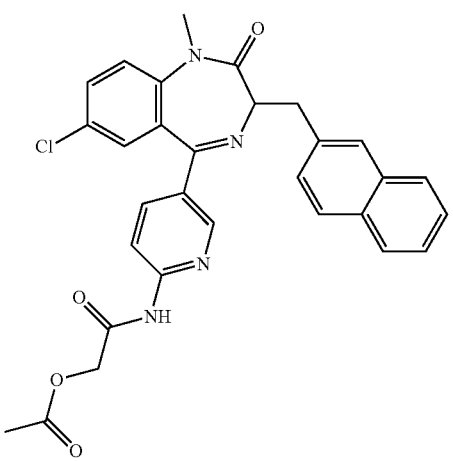

2-(5-(7-Chloro-1-methyl-3-(naphthalen-2-ylmethyl)-2-oxo-2,3-dihydro-1H-benzo[e][1,4]diazepin-5-yl)pyridin-2-ylamino)-2-oxoethyl acetate 5-(6-Aminopyridin-3-yl)-7-chloro-1-methyl-3-(naphthalen-2-ylmethyl)-1H-benzo[e][1,4]diazepin-2(3H)-one (50 mg, 0.11 mmol) was dissolved in dichloromethane (0.5 mL), and triethylamine (19 μL, 0.14 mmol) was added followed by acetoxyacetyl chloride (13 μL, 0.12 mmol). A slightly exothermic reaction occurred. This mixture as stirred at ambient temperature overnight. Additional triethylamine (46 μL, 0.33 mmol) was added followed by acetoxyacetyl chloride (30 μL, 0.22 mmol) and stirring continued at ambient temperature for 4 days. Concentration in the presence of silica, then column chromatography eluting with a step gradient of 20-80% ethyl acetate in hexanes in 5% increments every 3 minutes provided 2-(5-(7-chloro-1-methyl-3-(naphthalen-2-ylmethyl)-2-oxo-2,3-dihydro-1H-benzo[e][1,4]diazepin-5-yl)pyridin-2-ylamino)-2-oxoethyl acetate (45 mg, 73%). $^1$H NMR (300 MHz, d$_6$-DMSO) δ 2.10 (s, 3H), 3.3 (s, 3H), 3.53 (d, 2H) 3.83 (t, 1H), 4.72 (s, 2H), 7.30 (m, 1H), 7.4-7.5 (m, 3H), 7.60 (m, 2H), 7.65 (m, 1H), 7.77-7.88 (m, 4H), 8.03 (m, 1H), 8.36, (m, 1H), 10.94 (s, 1H); ESI m/z measured 541.1646 [M+H]⁺. calculated 541.1643.

Example 22

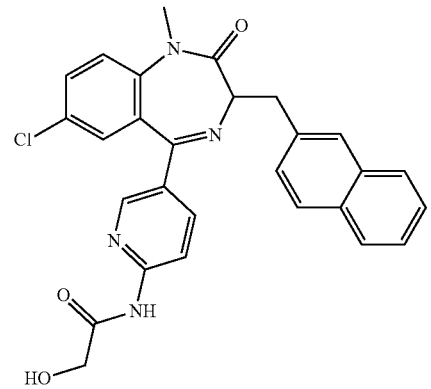 [SMILES: CN1C(=O)C(Cc2ccc3ccccc3c2)N=C(c2ccc(NC(=O)CO)nc2)c2cc(Cl)ccc21]

N-(5-(7-chloro-1-methyl-3-(naphthalen-2-ylmethyl)-2-oxo-2,3-dihydro-1H-benzo[e][1,4]diazepin-5-yl)pyridin-2-yl)-2-hydroxyacetamide 2-(5-(7-Chloro-1-methyl-3-(naphthalen-2-ylmethyl)-2-oxo-2,3-dihydro-1H-benzo[e][1,4]diazepin-5-yl)pyridin-2-ylamino)-2-oxoethyl acetate (20 mg, 0.04 mmol) was dissolved in methanol (0.5 mL) and water (0.1 mL), potassium carbonate was added and the mixture was stirred at ambient temperature for 45 minutes. The crude mixture as partitioned between ethyl acetate and water, the layers were separated, and the organic layer was dried with sodium sulfate, decanted, then concentrated in the presence of silica gel. Column chromatography eluting with a step gradient of 20-80% ethyl acetate in hexanes in 5% increments every 3 minutes provided N-(5-(7-chloro-1-methyl-3-(naphthalen-2-ylmethyl)-2-oxo-2,3-dihydro-1H-benzo[e][1,4]diazepin-5-yl)pyridin-2-yl)-2-hydroxyacetamide (8 mg, 43% yield). ESI m/z measured 521.1348 [M+H]⁺. calculated 521.1356.

Example 23

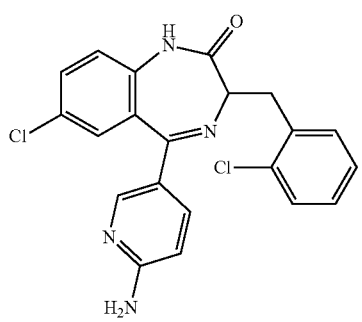 [SMILES: Nc1ccc(C2=NC(Cc3ccccc3Cl)C(=O)Nc3ccc(Cl)cc32)cn1]

5-(6-Aminopyridin-3-yl)-7-chloro-3-(2-chlorobenzyl)-1H-benzo[e][1,4]diazepin-2(3H)-one 5-(6-Aminopyridin-3-yl)-7-chloro-3-(2-chlorobenzyl)-1-(4-methoxybenzyl)-1H-benzo[e][1,4]diazepin-2(3H)-one was prepared following the procedure for the corresponding reaction in Example 12. 5-(6-Aminopyridin-3-yl)-7-chloro-3-(2-chlorobenzyl)-1-(4-methoxybenzyl)-1H-benzo[e][1,4]diazepin-2(3H)-one (175 mg, 0.33 mmol) was then dissolved in anhydrous anisole (4 mL), aluminum chloride (263 mg, 1.98 mmol) was added and the mixture was heated to 85° C. for one hour. The solution was cooled to ambient temperature, poured onto ice, and ethyl acetate added then slurried for 10 minutes. The layers were separated, and the aqueous layer extracted with ethyl acetate. The combined organic layers were washed with brine, dried with sodium sulfate, decanted and concentrated in vacuo. Column chromatography eluting with a gradient of 0-5% methanol in ethyl acetate provided 5-(6-aminopyridin-3-yl)-7-chloro-3-(2-chlorobenzyl)-1H-benzo[e][1,4]diazepin-2(3H)-one (113 mg, 83% yield). $^1$H NMR (300 MHz, d$_6$-DMSO) δ 3.44 (m, 2H) 3.72 (m, 1H), 6.40 (m, 1H), 6.48 (s, 2H), 7.18-7.64 (m, 9H), 7.83 (m, 1H), 10.70 (s, 1H); ESI m/z measured 411.0783 [M+H]$^+$. calculated 411.0779.

Example 24

Procedures for the Synthesis of 5-(2-Aminopyrimidin-5-yl)-7-chloro-3-(2-chlorobenzyl)-1H-benzo[e][1,4]diazepin-2(3H)-one Step 1

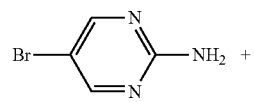 +

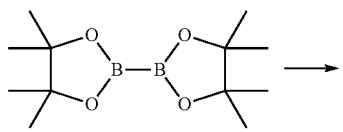 →

5-(4,4,5,5-Tetramethyl-1,3,2-dioxaborolan-2-yl)pyrimidin-2-amine

The reaction was carried out according to the procedure described in Step 4 of Part I of Example 2 to provide the title compound (658 mg, 52% yield). $^1$HNMR (300 MHz, CDCl$_3$) δ 8.59 (s, 2H), 5.56 (bs, 1H), 1.32 (s, 12H).

Step 2

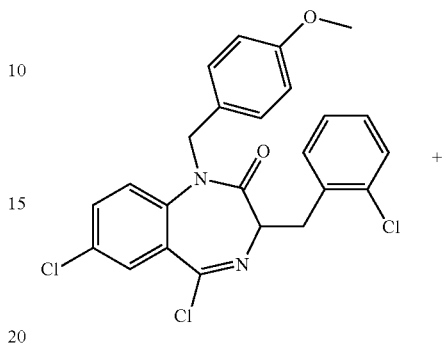 +

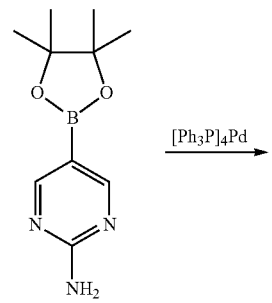

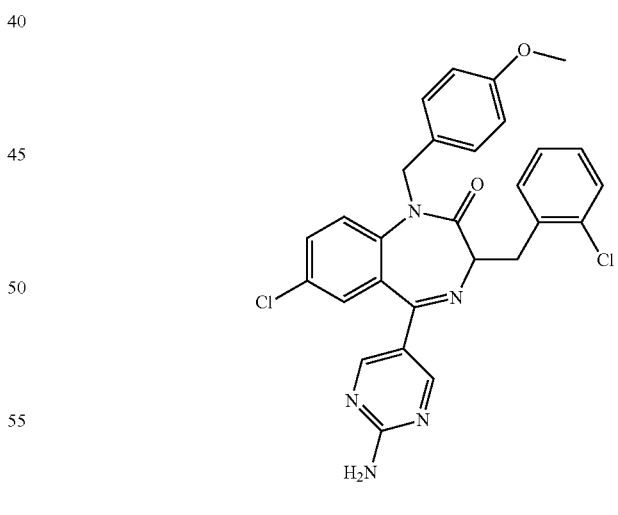

5-(2-Aminopyrimidin-5-yl)-7-chloro-3-(2-chlorobenzyl)-1-(4-methoxybenzyl)-1H-benzo[e][1,4]diazepin-2(3H)-one The reaction was carried out according to the procedure described in Part I of Example 1 to provide the title compound (360 mg, 43% yield). $^1$HNMR (300 MHz, CDCl$_3$) δ8.16 (s, 2H), 7.57 (d, 1H), 7.45-7.08 (m, 6H), 6.85 (d, 2H), 6.63 (d, 2H), 5.62 (d, 1H), 5.30 (bs, 2H), 4.59 (d, 1H), 3.90 (m, 1H), 3.78-3.60 (m, 5H).

Step 3

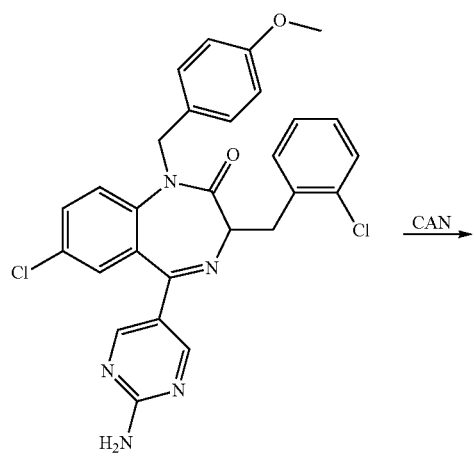

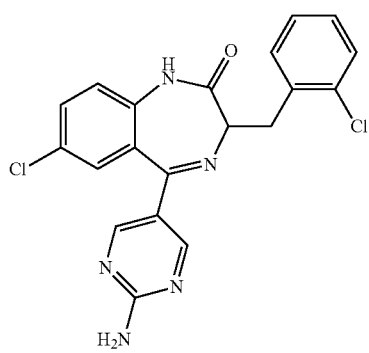

5-(2-Aminopyrimidin-5-yl)-7-chloro-3-(2-chlorobenzyl)-1H-benzo[e][1,4]diazepin-2(3H)-one Ceric ammonium nitrate (201 mg, 2.6 eq) was added portionwise to a stirred solution of 5-(2-aminopyrimidin-5-yl)-7-chloro-3-(2-chlorobenzyl)-1-(4-methoxybenzyl)-1H-benzo[e][1,4]diazepin-2(3H)-one (75 mg) in 9:1 acetonitrile:water (9 mL:1 mL). The reaction was stirred at room temperature overnight, and then another 200 mg of ceric ammonium nitrate was added. The reaction was stirred another 3 h, and then concentrated in vacuo. The crude was partitioned between EtOH and saturated potassium carbonate. The aqueous layer was re-extracted with ethanol 4×. The combined extracts were then dried over sodium sulfate, then concentrated and purified by chromatography (Gradient: 3:1 hexanes:EtOAc to EtOAc) yielding product (44 mg, 76% yield). $^1$HNMR (300 MHz, DMSO-d6) δ10.78 (s, 1H), 8.18 (s, 2H), 7.62 (d, 1H), 7.50-7.13 (m, 8H), 3.70 (m, 1H), 3.50-3.32 (m, 2H). HRMS (ES+) m/z calcd for $C_{20}H_{15}Cl_2N_5O$ [M+H]$^+$, 412.0732. found, 412.0726.

Example 25

Procedures for the Synthesis of 5-(2-Aminopyrimidin-5-yl)-7-chloro-3-(3,4-diethylbenzyl)-1H-benzo[e][1,4]diazepin-2(3H)-one Part I: Synthesis of 4-(Bromomethyl)-1,2-diethylbenzene Synthetic Intermediate

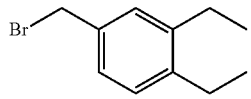

4-(Bromomethyl)-1,2-diethylbenzene 1,2-Diethylbenzene (3.4 g, 23.3 mmol) and paraformaldehyde (2.5 g, 84 mmol) were suspended in glacial acetic acid (60 mL), hydrobromic acid (38% in acetic acid, 8 mL) was added, the reaction flask was sealed with a rubber septum and heated to 80° C. After 4 hours the solution was cooled to ambient temperature and paraformaldehyde (2.5 g, 84 mmol) and hydrobromic acid (38% in acetic acid, 8 mL) were added. The mixture was reheated to 80° C. for 4 hours. Further paraformaldehyde (2.5 g, 84 mmol) and hydrobromic acid (38% in acetic acid, 8 mL) were and the reaction let stir at 80° C. overnight. After a total of 24 hours of reaction time the solution was cooled, diluted with water and diethyl ether, then the layers separated. The organic layers were washed carefully with saturated sodium bicarbonate (4×50 mL), brine, then dried with sodium sulfate, filtered and concentrated in the presence of silica. Purified by column chromatography eluting with 100% hexanes. Concentrated fractions to a yield 4-(bromomethyl)-1,2-diethylbenzene (4.05 g, 77%) $^1$H NMR (300 MHz, CDCl$_3$) δ 1.21 (m, 6H) 2.64 (m, 4H), 4.47 (s, 2H), 7.1-7.2 (m, 3H).

Part II: Synthesis of Heteroaryl Boronic Acid

Step 1

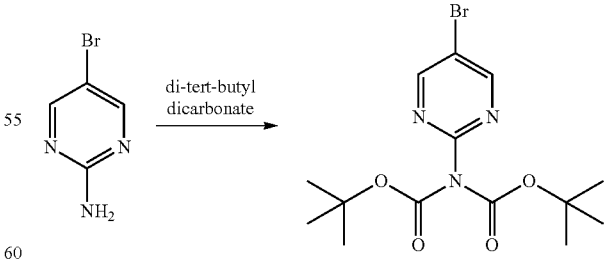

N,N-di-t-Butoxycarbonyl-5-bromopyrimidin-2-amine

Di-tert-butyl dicarbonate (5.52 g, 2.2 eq) was added to a solution of 2-amino-5-bromopyrimidine (2.0 g,) and 4-dimethylaminopyridine (140 mg, 0.1 eq) in anhydrous THF (18 mL). The reaction was stirred at room temperature under a nitrogen atmosphere overnight. A few drops of water were then added to the reaction to quench it, and the crude was then concentrated and purified by chromatography (gradient: 95:5 hexanes:EtOAc to 80:20 hexanes:EtOAc) delivering the product (3.70 g, 86% yield). ¹HNMR (300 MHz, CDCl₃) δ 8.78 (s, 2H), 1.44 (s, 18H).

Step 2

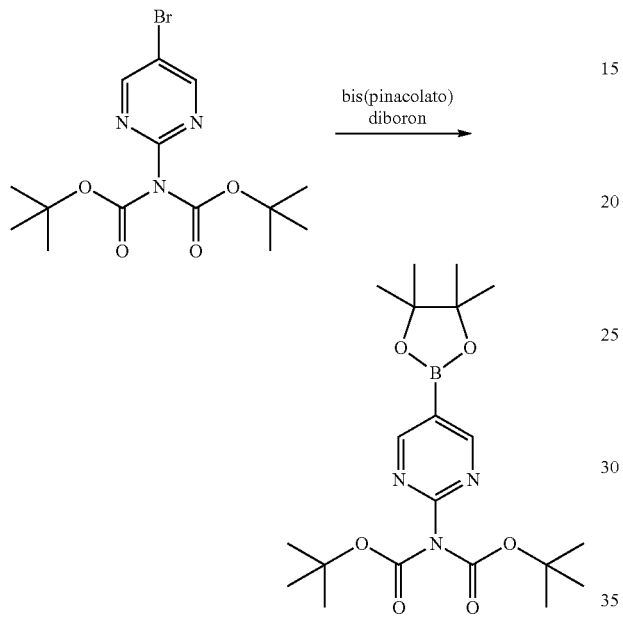

N,N-di-t-Butoxycarbonyl-5-(4,4,5,5-tetramethyl-1,3,2-dioxaborolan-2-yl)pyrimidin-2-amine The reaction was carried out according to the procedure described in Step 4 of Part 1 of Example 2 to provide the title compound (2.23 g, 54% yield). ¹HNMR (300 MHz, CDCl₃) δ 9.00 (s, 2H), 1.44 (s, 18H), 1.38 (s, 12H), 1.25 (s, 12H).

Part III: Synthesis of 5-(2-Aminopyrimidin-5-yl)-7-chloro-3-(3,4-diethylbenzyl)-1H-benzo[e][1,4]diazepin-2(3H)-one Step 1

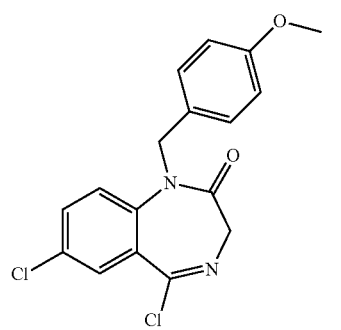

+

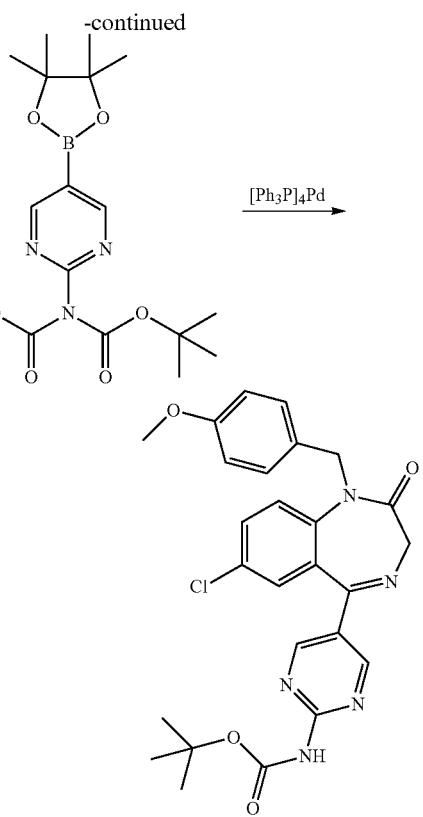

tert-Butyl 5-(7-chloro-1-(4-methoxybenzyl)-2-oxo-2,3-dihydro-1H-benzo[e][1,4]diazepin-5-yl)pyrimidin-2-ylcarbamate The reaction was carried out according to the procedure for described in Part I of Example 1 to provide the title compound (320 mg, 14% yield). ¹HNMR (300 MHz, CDCl₃) δ 8.64 (s, 2H), 7.45 (dd, 1H), 7.36 (d. 1H), 7.15 (s, 1H), 6.90 (d, 2H), 6.65 (d, 2H), 5.50 (d, 1H), 4.90 (d, 1H), 4.65 (d, 1H), 3.80 (d, 1H), 3.70 (s, 3H), 1.53 (s, 9H). MS (ES+) m/z 530.2 (M+Na).

Step 2

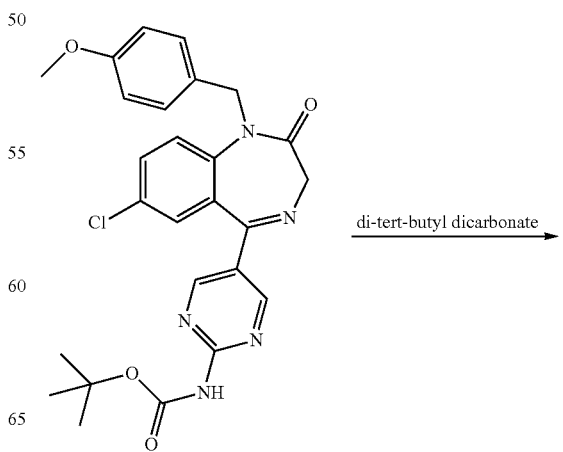

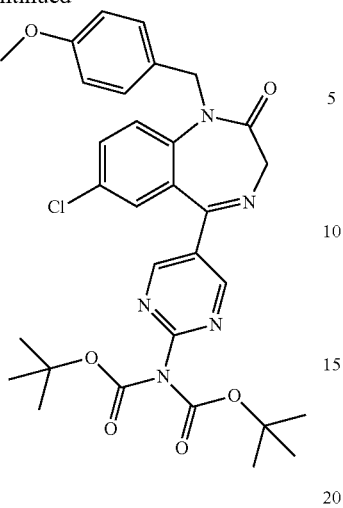

Bis-tert-butyl-5-(7-chloro-1-(4-methoxybenzyl)-2-oxo-2,3-dihydro-1H-benzo[e][1,4]diazepin-5-yl) pyrimidin-2-yl-bis-carbamate Di-tert-butyl dicarbonate (158 mg, 1.2 eq) was added to a solution of tert-butyl 5-(7-chloro-1-(4-methoxybenzyl)-2-oxo-2,3-dihydro-1H-benzo[e][1,4]diazepin-5-yl)pyrimidin-2-ylcarbamate (306 mg) and 4-dimethylaminopyridine (7.4 mg, 0.1 eq) in anhydrous THF (10 mL). The reaction was stirred at room temperature under a nitrogen atmosphere overnight. A few drops of water were added to the reaction to quench it, and the crude was then concentrated and purified by chromatography (gradient; 9:1 hexanes:EtOAc to 6:4 hexanes:EtOAc) delivering the product pure (178 mg, 49% yield). $^1$HNMR (300 MHz, CDCl$_3$) δ 8.64 (s, 2H), 7.50-7.35 (m, 2H), 7.08 (d, 1H), 6.90 (d, 2H), 6.63 (d, 2H), 5.56 (d, 1H), 4.95 (d, 1H), 4.60 (d, 1H), 3.85 (d, 1H), 3.70 (s, 3H), 1.49 (s, 18H).

Step 3

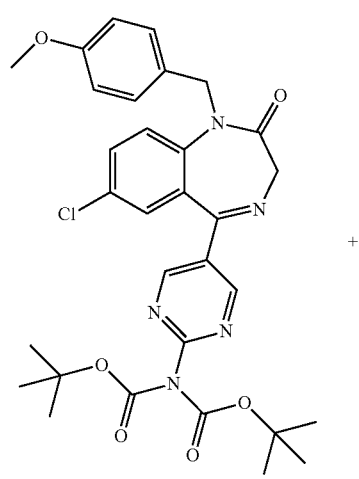

+

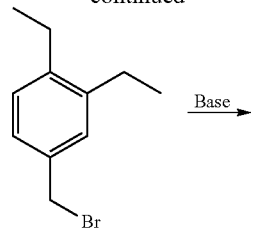

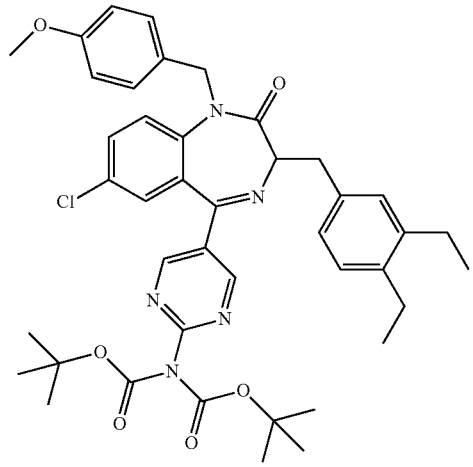

Bis-tert-butyl 5-(7-chloro-3-(3,4-diethylbenzyl)-1-(4-methoxybenzyl)-2-oxo-2,3-dihydro-1H-benzo[e][1,4]diazepin-5-yl)pyrimidin-2-yl(methyl)-bis-carbamate The starting material (178 mg) was dissolved in THF (10 mL) and cooled to −78° C. Potassium t-butoxide (49.3 mg, 1.5 eq) was then added, and the deprotonation was allowed to evolve for 10 minutes. A solution of diethylbenzylbromide (100 mg, 1.5 eq) in THF (2 mL) was then added dropwise and the reaction was allowed to warm to room temperature where it was held for an hour. The reaction was quenched with aqueous ammonium chloride, partitioned between EtOAc and water, and then the organic solution was washed with brine, and dried over sodium sulfate. The solution was then concentrated onto silica gel and purified by chromatography (gradient: 15:85 EtOAc:hexanes to 60:40 EtOAc:hexanes) delivering the product which was taken on to the next reaction without purification. MS (ES+) m/z 776.3 (M+Na).

Step 4

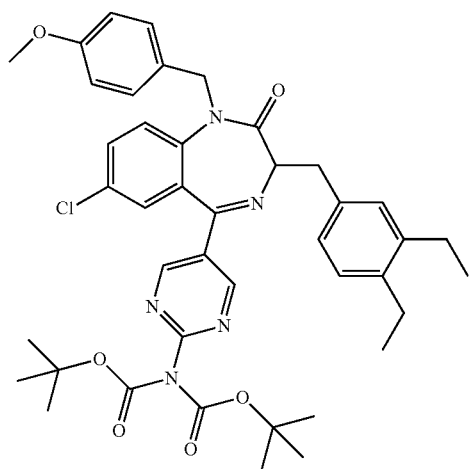

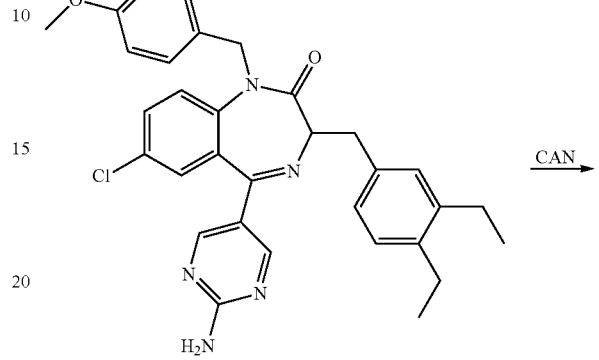

Step 5 unidentified contaminant (20 mg, 12% yield). The crude was taken on to the next step without purification. MS (ES+) m/z 554.19 (M+1).

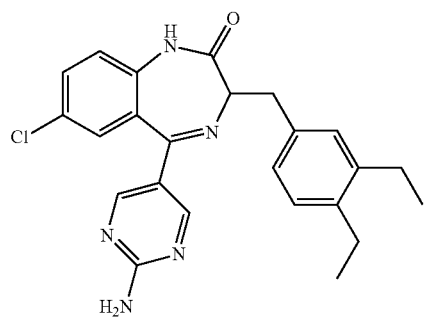

5-(2-Aminopyrimidin-5-yl)-7-chloro-3-(3,4-diethyl-benzyl)-1H-benzo[e][1,4]diazepin-2(3H)-one The reaction was carried out according to the deprotection procedure described in Step 3 of Example 24 above to provide the title compound (0.8 mg, 5% yield). $^1$HNMR (300 MHz, CDCl$_3$) δ 8.45 (s, 1H), 8.40 (s, 1H), 8.08-7.90 (m, 1H), 7.48 (d, 1H), 7.35-7.00 (m, 6H), 5.30 (bs, 2H), 3.70 (m, 1H), 3.60-3.45 (m, 2H), 2.70-2.50 (m, 4H), 1.40-1.10 (m, 6H). HRMS (ES+) m/z calcd for $C_{24}H_{24}ClN_5O$ [M+H]$^+$, 434.1748. found, 434.1732.

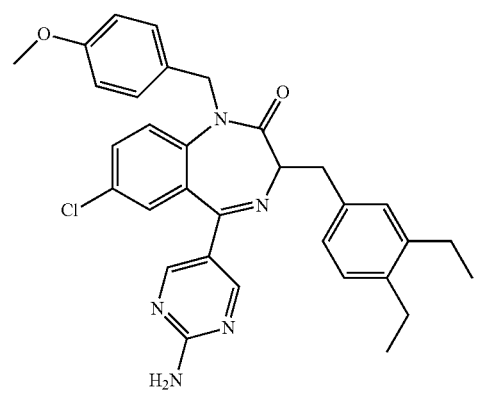

5-(2-Aminopyrimidin-5-yl)-7-chloro-3-(3,4-diethyl-benzyl)-1-(4-methoxybenzyl)-1H-benzo[e][1,4]diaz-epin-2(3H)-one The substrate was dissolved in 4 N HCl in dioxane and the reaction was held at room temperature for 2 days, then concentrated in vacuo delivering a mixture of product and an Example 26

The compounds listed in Table 5 were tested for cytotoxicity in Ramos cells. The assay was conducted as described in K. M. Johnson et al. *Chemistry & Biology* 2005, 12, 485-496. The symbol "+++" indicates an EC$_{50}$≤5 μM, "++" indicates an EC$_{50}$ between 5 μM and 25 μM, and "+" indicates an EC$_{50}$≥25 μM.

TABLE 5

| Compound | Chemical Structure | EC$_{50}$ Value |
|---|---|---|
| V-1 | 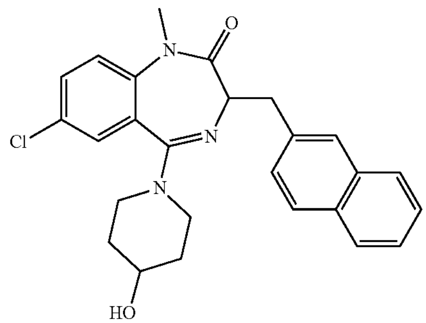 [SMILES: CN1C(=O)C(Cc2ccc3ccccc3c2)N=C(N2CCC(O)CC2)c2cc(Cl)ccc21] | + |
| V-2 | 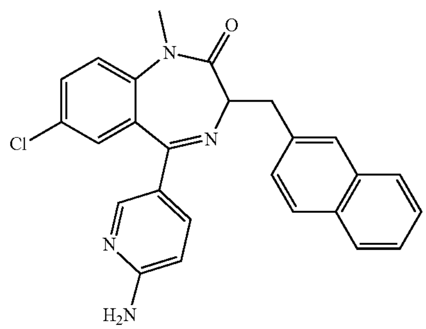 [SMILES: CN1C(=O)C(Cc2ccc3ccccc3c2)N=C(c2ccc(N)nc2)c2cc(Cl)ccc21] | ++ |
| V-3 | 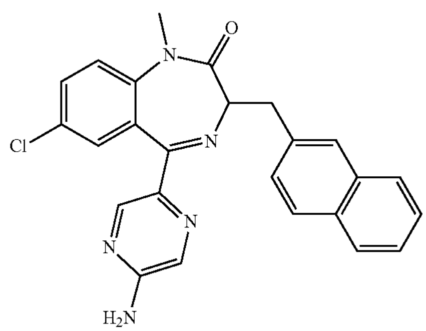 [SMILES: CN1C(=O)C(Cc2ccc3ccccc3c2)N=C(c2cnc(N)cn2)c2cc(Cl)ccc21] | + |
| V-4 | 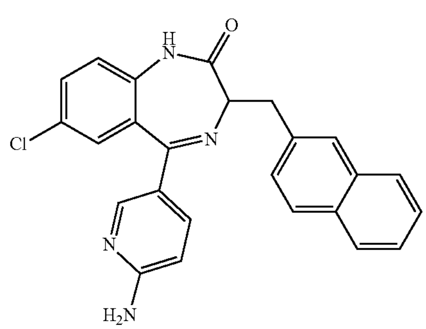 [SMILES: Nc1ccc(C2=NC(Cc3ccc4ccccc4c3)C(=O)Nc3ccc(Cl)cc32)cn1] | ++ |

TABLE 5-continued

| Compound | Chemical Structure | EC$_{50}$ Value |
|---|---|---|
| V-5 | 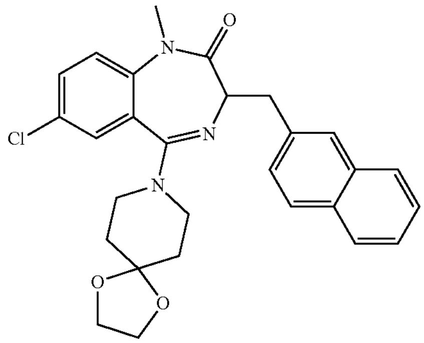 [SMILES: CN1C(=O)C(Cc2ccc3ccccc3c2)N=C(N2CCC3(CC2)OCCO3)c2cc(Cl)ccc21] | +++ |
| V-6 | 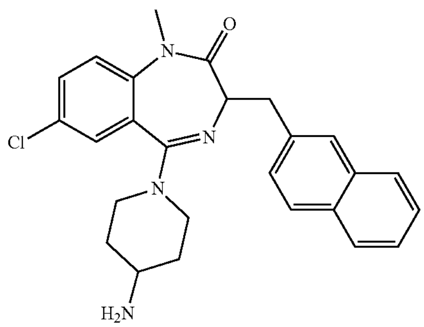 [SMILES: CN1C(=O)C(Cc2ccc3ccccc3c2)N=C(N2CCC(N)CC2)c2cc(Cl)ccc21] | ++ |
| V-7 | 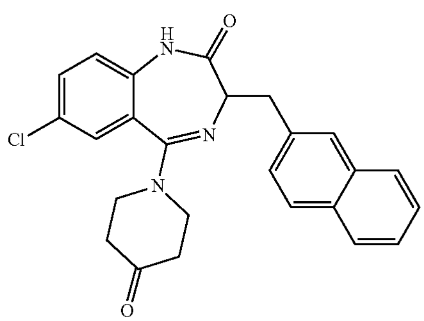 [SMILES: O=C1CCN(C2=NC(Cc3ccc4ccccc4c3)C(=O)Nc3ccc(Cl)cc32)CC1] | ++ |
| V-8 | 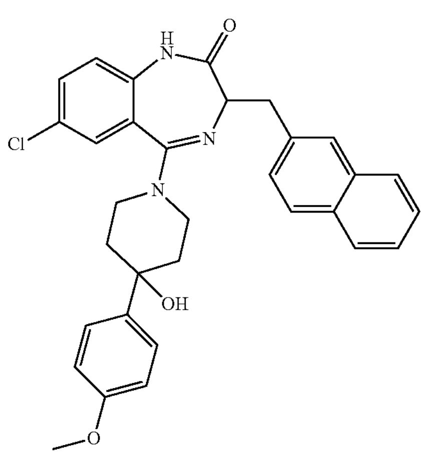 [SMILES: COc1ccc(C2(O)CCN(C3=NC(Cc4ccc5ccccc5c4)C(=O)Nc4ccc(Cl)cc43)CC2)cc1] | +++ |

TABLE 5-continued

| Compound | Chemical Structure | EC$_{50}$ Value |
|---|---|---|
| V-9 | 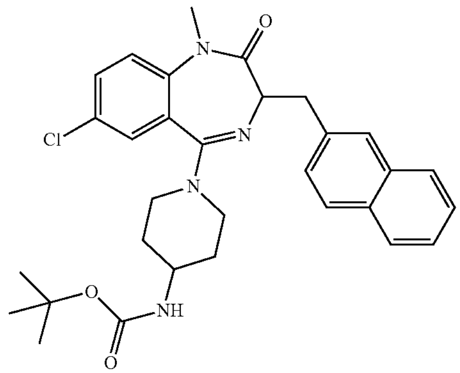 [SMILES: CN1C(=O)C(Cc2ccc3ccccc3c2)N=C(N2CCC(NC(=O)OC(C)(C)C)CC2)c2cc(Cl)ccc21] | + |
| V-10 | 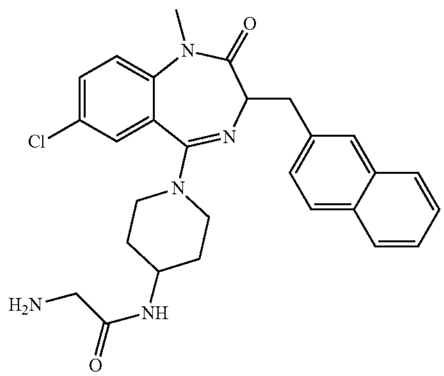 [SMILES: CN1C(=O)C(Cc2ccc3ccccc3c2)N=C(N2CCC(NC(=O)CN)CC2)c2cc(Cl)ccc21] | +++ |
| V-11 | 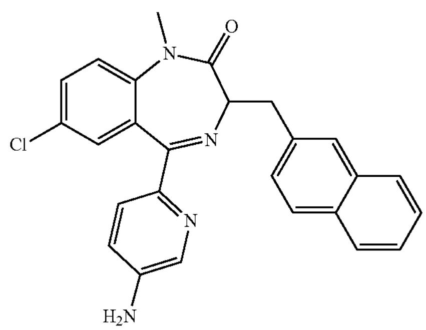 [SMILES: CN1C(=O)C(Cc2ccc3ccccc3c2)N=C(c2ccc(N)cn2)c2cc(Cl)ccc21] | +++ |
| V-12 | 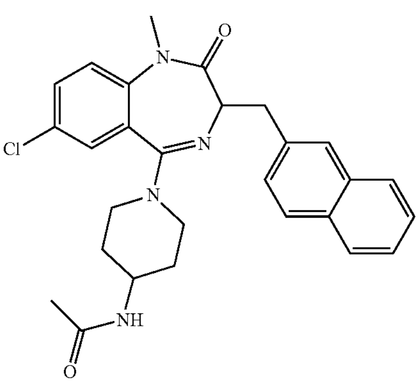 [SMILES: CC(=O)NC1CCN(C2=NC(Cc3ccc4ccccc4c3)C(=O)N(C)c3ccc(Cl)cc32)CC1] | ++ |

TABLE 5-continued
| Compound | Chemical Structure | EC$_{50}$ Value |
|---|---|---|
| V-13 | 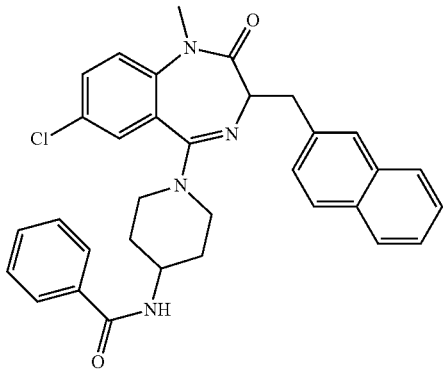 [SMILES: CN1C(=O)C(Cc2ccc3ccccc3c2)N=C(N2CCC(NC(=O)c3ccccc3)CC2)c2cc(Cl)ccc21] | + |
| V-14 | 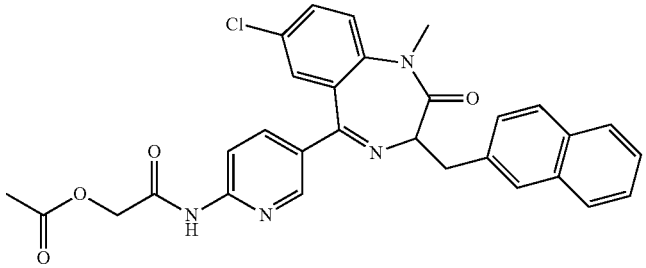 [SMILES: CC(=O)OCC(=O)Nc1ccc(C2=NC(Cc3ccc4ccccc4c3)C(=O)N(C)c3ccc(Cl)cc32)cn1] | +++ |
| V-15 | 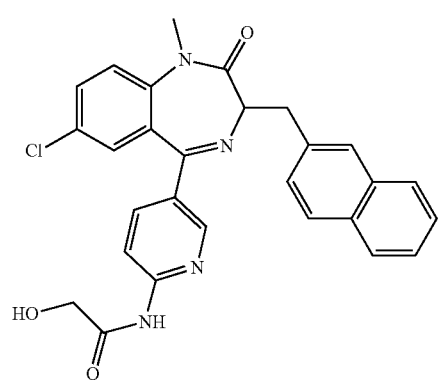 [SMILES: CN1C(=O)C(Cc2ccc3ccccc3c2)N=C(c2ccc(NC(=O)CO)nc2)c2cc(Cl)ccc21] | ++ |
| V-16 | 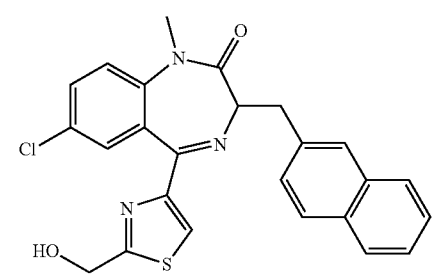 [SMILES: CN1C(=O)C(Cc2ccc3ccccc3c2)N=C(c2csc(CO)n2)c2cc(Cl)ccc21] | +++ |

TABLE 5-continued

| Compound | Chemical Structure | EC$_{50}$ Value |
| --- | --- | --- |
| V-17 | 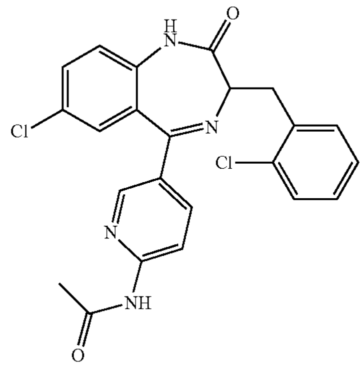 [SMILES: CC(=O)Nc1ccc(C2=NC(Cc3ccccc3Cl)C(=O)Nc3ccc(Cl)cc32)cn1] | ++ |
| V-18 | 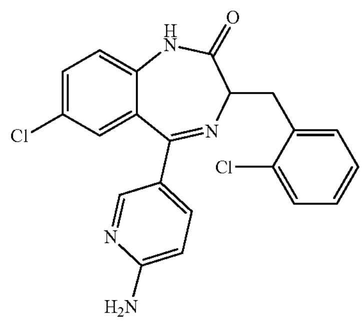 [SMILES: Nc1ccc(C2=NC(Cc3ccccc3Cl)C(=O)Nc3ccc(Cl)cc32)cn1] | ++ |
| V-19 | 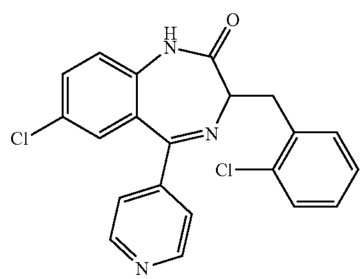 [SMILES: O=C1Nc2ccc(Cl)cc2C(c2ccncc2)=NC1Cc1ccccc1Cl] | ++ |
| V-20 | 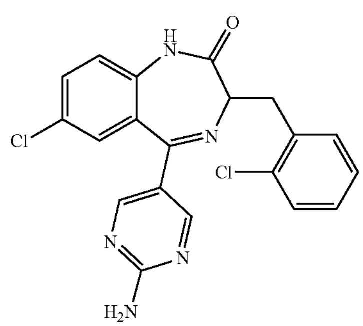 [SMILES: Nc1ncc(C2=NC(Cc3ccccc3Cl)C(=O)Nc3ccc(Cl)cc32)cn1] | ++ |
| V-21 | 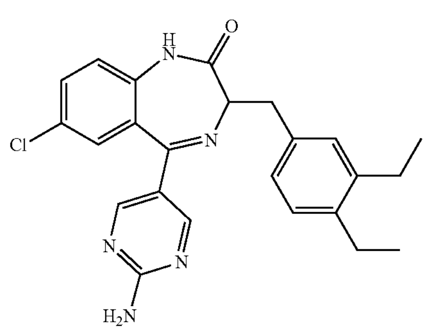 [SMILES: CCc1ccc(CC2N=C(c3cnc(N)nc3)c3cc(Cl)ccc3NC2=O)cc1CC] | ++ |

TABLE 5-continued

| Compound | Chemical Structure | EC₅₀ Value |
|---|---|---|
| V-22 | 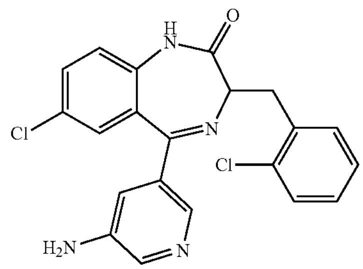 [SMILES: Nc1cncc(C2=NC(Cc3ccccc3Cl)C(=O)Nc3ccc(Cl)cc32)c1] | + |
| V-23 | 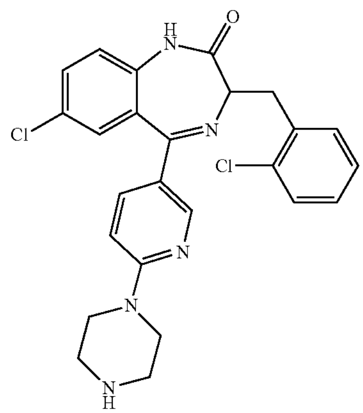 [SMILES: O=C1Nc2ccc(Cl)cc2C(c2ccc(N3CCNCC3)nc2)=NC1Cc1ccccc1Cl] | +++ |
| V-24 | 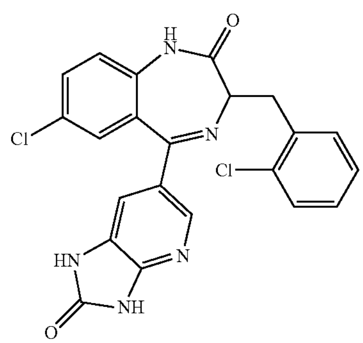 [SMILES: O=C1Nc2ccc(Cl)cc2C(c2cnc3[nH]c(=O)[nH]c3c2)=NC1Cc1ccccc1Cl] | +++ |
| V-25 | 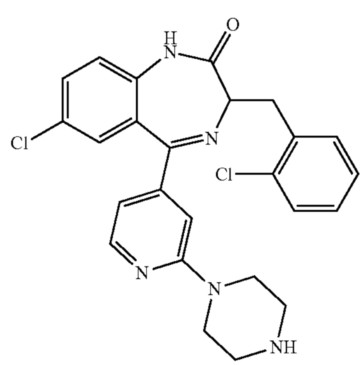 [SMILES: O=C1Nc2ccc(Cl)cc2C(c2ccnc(N3CCNCC3)c2)=NC1Cc1ccccc1Cl] | ++ |

TABLE 5-continued

| Compound | Chemical Structure | EC$_{50}$ Value |
|---|---|---|
| V-26 | 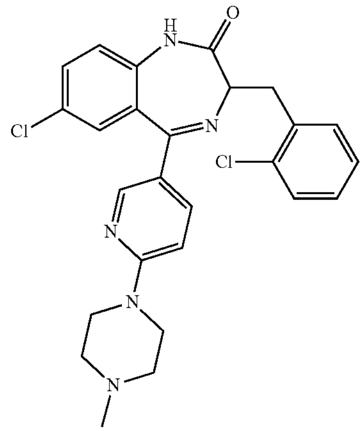 [SMILES: CN1CCN(c2ccc(C3=NC(Cc4ccccc4Cl)C(=O)Nc4ccc(Cl)cc43)cn2)CC1] | +++ |
| V-27 | 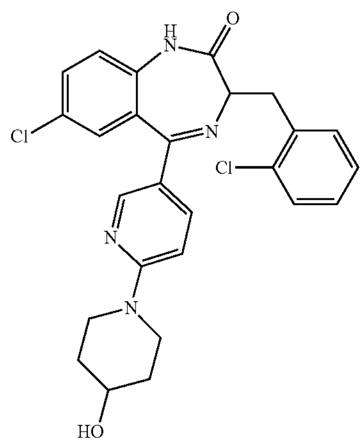 [SMILES: O=C1Nc2ccc(Cl)cc2C(c2ccc(N3CCC(O)CC3)nc2)=NC1Cc1ccccc1Cl] | +++ |
| V-28 | 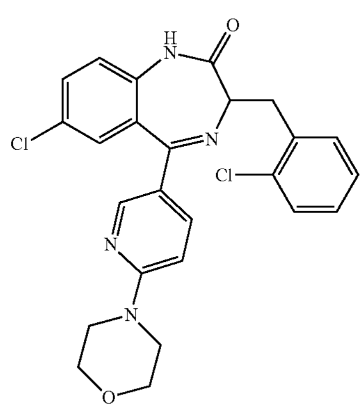 [SMILES: O=C1Nc2ccc(Cl)cc2C(c2ccc(N3CCOCC3)nc2)=NC1Cc1ccccc1Cl] | +++ |

TABLE 5-continued

| Compound | Chemical Structure | EC$_{50}$ Value |
|---|---|---|
| V-29 | 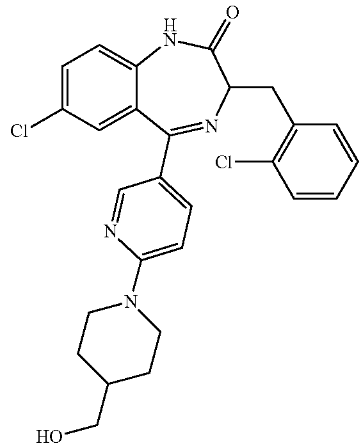 [SMILES: O=C1Nc2ccc(Cl)cc2C(c2ccc(N3CCC(CO)CC3)nc2)=NC1Cc1ccccc1Cl] | +++ |
| V-30 | 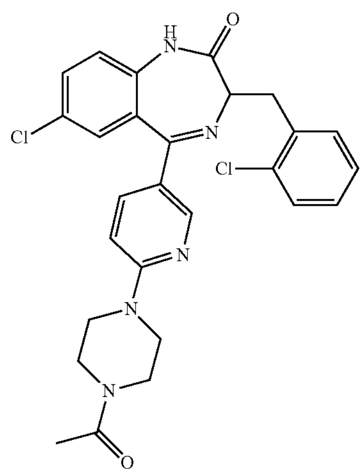 [SMILES: CC(=O)N1CCN(c2ccc(C3=NC(Cc4ccccc4Cl)C(=O)Nc4ccc(Cl)cc43)cn2)CC1] | +++ |
| V-31 | 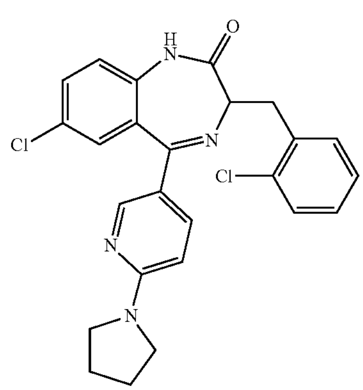 [SMILES: O=C1Nc2ccc(Cl)cc2C(c2ccc(N3CCCC3)nc2)=NC1Cc1ccccc1Cl] | +++ |

TABLE 5-continued

| Compound | Chemical Structure | EC$_{50}$ Value |
|---|---|---|
| V-32 | 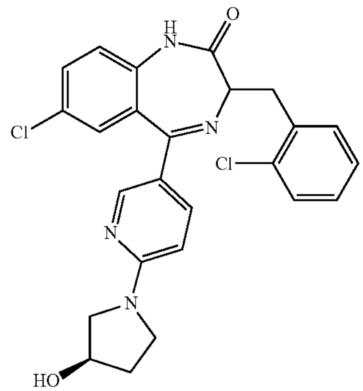 [SMILES: O=C1Nc2ccc(Cl)cc2C(c2ccc(N3CC[C@@H](O)C3)nc2)=NC1Cc1ccccc1Cl] | ++ |
| V-33 | 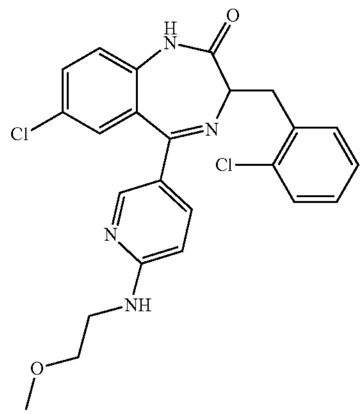 [SMILES: COCCNc1ccc(C2=NC(Cc3ccccc3Cl)C(=O)Nc3ccc(Cl)cc32)cn1] | ++ |
| V-34 | 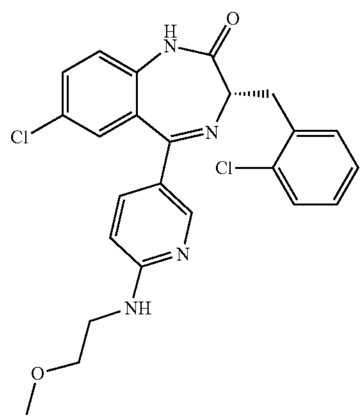 [SMILES: COCCNc1ccc(C2=N[C@@H](Cc3ccccc3Cl)C(=O)Nc3ccc(Cl)cc32)cn1] | ++ |
| V-35 | 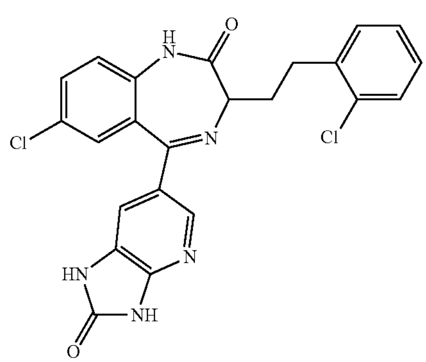 [SMILES: O=C1Nc2ccc(Cl)cc2C(c2cnc3[nH]c(=O)[nH]c3c2)=NC1CCc1ccccc1Cl] | ++ |

TABLE 5-continued

| Compound | Chemical Structure | EC$_{50}$ Value |
|---|---|---|
| V-36 | 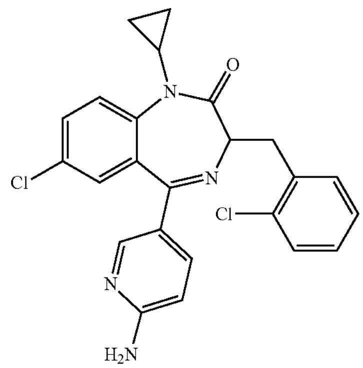 [SMILES: Nc1ccc(C2=NC(Cc3ccccc3Cl)C(=O)N(C3CC3)c3ccc(Cl)cc32)cn1] | ++ |
| V-37 | 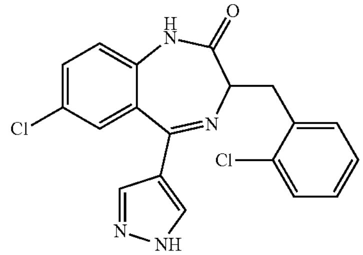 [SMILES: O=C1Nc2ccc(Cl)cc2C(c2cn[nH]c2)=NC1Cc1ccccc1Cl] | ++ |
| V-38 | 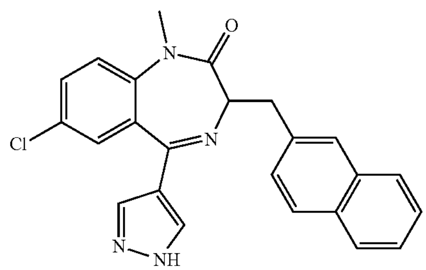 [SMILES: CN1C(=O)C(Cc2ccc3ccccc3c2)N=C(c2cn[nH]c2)c2cc(Cl)ccc21] | +++ |
| V-39 | 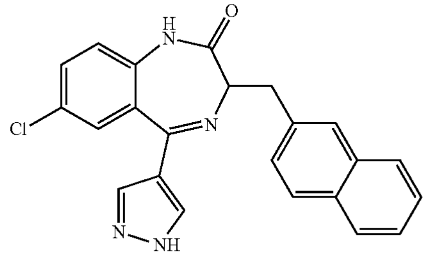 [SMILES: O=C1Nc2ccc(Cl)cc2C(c2cn[nH]c2)=NC1Cc1ccc2ccccc2c1] | +++ |
| V-40 | 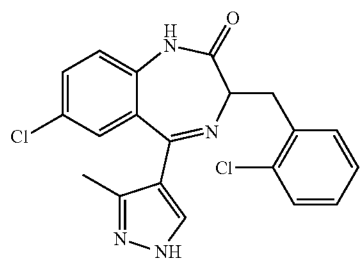 [SMILES: Cc1n[nH]cc1C1=NC(Cc2ccccc2Cl)C(=O)Nc2ccc(Cl)cc21] | ++ |

TABLE 5-continued

| Compound | Chemical Structure | EC$_{50}$ Value |
|---|---|---|
| V-41 | (structure: benzodiazepinone with Cl, chlorophenyl, and dimethylpyrazole substituents) | ++ |

Example 27

The compounds described herein can be tested for activity against various forms of cancer by testing for inhibition of cancer cell growth using in vitro assays. For example, compounds V-23 and V-38 (See Table 5 in Example 26) where tested for efficacy in inhibiting the growth of human cancer cells using the general procedure described below. The test evaluated compound activity for inhibiting cancer cell growth in over 50 cancer cell lines, which included non-small cell lung cancer, colon cancer, breast cancer, ovarian cancer, leukemia, renal cancer, melanoma, prostate cancer, and cancer of the central nervous system tissue. Results from this test are shown in Table 6.

General Procedure for In Vitro Testing:

Human tumor cell lines are grown in RPMI 1640 medium containing 5% fetal bovine serum and 2 mM L-glutamine. For the screening experiment, cells are inoculated into 96 well microtiter plates in 100 µL at plating densities ranging from 5,000 to 40,000 cells/well depending on the doubling time of individual cell lines. After cell inoculation, the microtiter plates are incubated at 37° C., 5% CO$_2$, 95% air and 100% relative humidity for 24 h prior to addition of test compound.

After 24 h, two plates of each cell line are fixed in situ with TCA, to represent a measurement of the cell population for each cell line at the time of addition (Tz) of the test compound. The test compound is solubilized in dimethyl sulfoxide at a concentration equal to twice the desired final maximum test concentration with complete medium containing 50 µg/ml gentamicin. Additional four, 10-fold or ½ log serial dilutions are made to provide a total of five concentrations of test compound plus control. Aliquots of 100 µL of these different test compound dilutions are added to the appropriate microtiter wells already containing 100 µL of medium, resulting in the required final concentrations of test compound.

Following addition of the test compound, the plates are incubated for an additional 48 h at 37° C., 5% CO$_2$, 95% air, and 100% relative humidity. For adherent cells, the assay is terminated by the addition of cold TCA. Cells are fixed in situ by the gentle addition of 50 µL of cold 50% (w/v) TCA (final concentration, 10% TCA) and incubated for 60 minutes at 4° C. The supernatant is discarded, and the plates are washed five times with tap water and air dried. Sulforhodamine B (SRB) solution (100 µL) at 0.4% (w/v) in 1% acetic acid is added to each well, and plates are incubated for 10 minutes at room temperature. After staining, unbound dye is removed by washing five times with 1% acetic acid and the plates are air dried. Bound stain is then solubilized with 10 mM trizma base, and the absorbance is read on an automated plate reader at a wavelength of 515 nm. For suspension cells, the procedure is the same except that the assay is terminated by fixing settled cells at the bottom of the wells by gently adding 50 µL of 80% TCA (final concentration, 16% TCA). Using seven absorbance measurements [time zero, (Tz), control growth, (C), and test growth in the presence of drug at the five concentration levels (Ti)], the percentage growth is calculated at each of the drug concentrations levels.

The percentage of growth inhibition caused by the test compounds on the cancer cell lines can be calculated using the following formulae:

$[(Ti-Tz)/(C-Tz)] \times 100$ for concentrations for which $Ti \geq Tz$ $[(Ti-Tz)/Tz] \times 100$ for concentrations for which $Ti < Tz$ Three dose response parameters can be calculated for each test compound. Growth inhibition of 50% (GI$_{50}$) is calculated from $[(Ti-Tz)/(C-Tz)] \times 100 = 50$, which is the drug concentration resulting in a 50% reduction in the net protein increase (as measured by SRB staining) in control cells during the drug incubation. The concentration of test compound resulting in total growth inhibition (TGI) is calculated from Ti=Tz. The LC$_{50}$ (concentration of drug resulting in a 50% reduction in the measured protein at the end of the drug treatment as compared to that at the beginning) indicating a net loss of cells following treatment is calculated from $[(Ti-Tz)/Tz] \times 100 = -50$. Values are calculated for each of these three parameters if the level of activity is reached. However, if the effect is not reached or is exceeded, the value for that parameter is expressed as greater or less than the maximum or minimum concentration tested.

Results:

Cancer cell growth inhibition for compounds V-23 and V-38 (see Table 5 for compound structures) is provided below in Table 6. The symbol "+++" indicates administration of the test compound resulted in at least 75% growth inhibition of the cancer cells, "++" indicates that administration of the test compound resulted in 40%-75% growth inhibition of the cancer cells, "+" indicates administration of the test compound resulted in less than 40% growth inhibition of the cancer cells, "NT" indicates that the compound was not tested against this particular cell line, "−" indicates an apparent increase in cancer cell growth upon administration of the test compound.

TABLE 6

| Panel/Cell One | Compound V-23 | Compound V-38 |
|---|---|---|
| Non-Small Cell Lung Cancer | | |
| A549/ATCC | +++ | ++ |
| EKVX | +++ | ++ |

TABLE 6-continued

| Panel/Cell One | Compound V-23 | Compound V-38 |
|---|---|---|
| HOP-62 | +++ | +++ |
| HOP-92 | ++ | ++ |
| NCI-H226 | + | ++ |
| NCI-H23 | ++ | +++ |
| NCI-H322M | + | + |
| NCI-H460 | +++ | ++ |
| NCI-H522 | +++ | ++ |
| Colon Cancer | | |
| COLO 205 | ++ | ++ |
| HCC-2998 | +++ | +++ |
| HCT-116 | +++ | +++ |
| HCT-15 | +++ | ++ |
| HT29 | +++ | + |
| KM12 | +++ | +++ |
| SW-620 | +++ | +++ |
| Breast Cancer | | |
| BT-549 | +++ | +++ |
| HS 578T | ++ | + |
| MCF7 | +++ | ++ |
| MDA-MB-231/ATCC | +++ | + |
| MDA-MB-435 | +++ | + |
| MDA-MB-468 | NT | ++ |
| NCI/ADR-RES | + | + |
| T-47D | ++ | + |
| Ovarian Cancer | | |
| IGROV1 | +++ | +++ |
| OVCAR-3 | +++ | +++ |
| OVCAR-4 | ++ | ++ |
| OVCAR-5 | +++ | + |
| OVCAR-8 | ++ | + |
| SK-OV-3 | ++ | + |
| Leukemia | | |
| CCRF-CEM | ++ | + |
| HL-60(TB) | +++ | + |
| K-562 | +++ | + |
| MOLT-4 | ++ | + |
| RPMI-8226 | ++ | + |
| SR | ++ | − |
| Renal Cancer | | |
| 786-0 | +++ | +++ |
| A498 | + | +++ |
| ACHN | +++ | +++ |
| CAKI-1 | +++ | + |
| RXF 393 | +++ | +++ |
| SN12C | +++ | ++ |
| TK-10 | +++ | +++ |
| UO-31 | +++ | +++ |
| Melanoma | | |
| LOXIMVI | +++ | +++ |
| M14 | +++ | +++ |
| MALME-3M | +++ | +++ |
| SK-MEL-2 | ++ | ++ |
| SK-MEL-28 | +++ | +++ |
| SK-MEL-5 | +++ | +++ |
| UACC-257 | +++ | +++ |
| UACC-62 | ++ | +++ |
| Prostate Cancer | | |
| DU-145 | +++ | +++ |
| PC-3 | ++ | + |
| CNS Cancer | | |
| SF-268 | ++ | +++ |
| SF-295 | +++ | + |
| SF-539 | +++ | +++ |
| SNB-19 | ++ | ++ |
| SNB-75 | ++ | +++ |
| U251 | +++ | +++ |

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

We claim:

1. A compound represented by formula I:

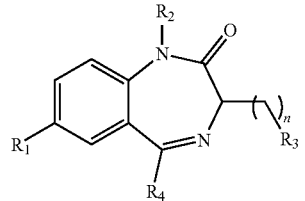

or a pharmaceutically acceptable salt thereof; wherein:

$R_1$ is halogen;

$R_2$ represents independently for each occurrence hydrogen or $C_1$-$C_6$alkyl;

$R_3$ is phenyl or naphthyl, each of which is optionally substituted with one or two substituents independently selected from the group consisting of halogen, $C_1$-$C_6$alkyl, $C_1$-$C_6$alkoxy, amino, —S(O)$R_5$, —SO$_2$R$_5$, —SO$_2$N(R$_6$)$_2$, —SO$_2$N(R$_6$)C(O)R$_5$, —N(R$_6$)SO$_2$R$_5$, —CN, —C(O)R$_5$, —CO$_2$R$_5$, —C(O)N(R$_6$)$_2$, —N(R$_6$)C(O)R$_5$, and monocarbocyclic aryl;

$R_4$ is

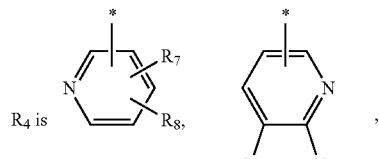

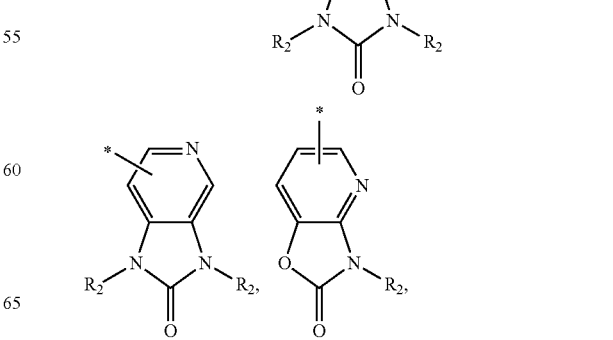

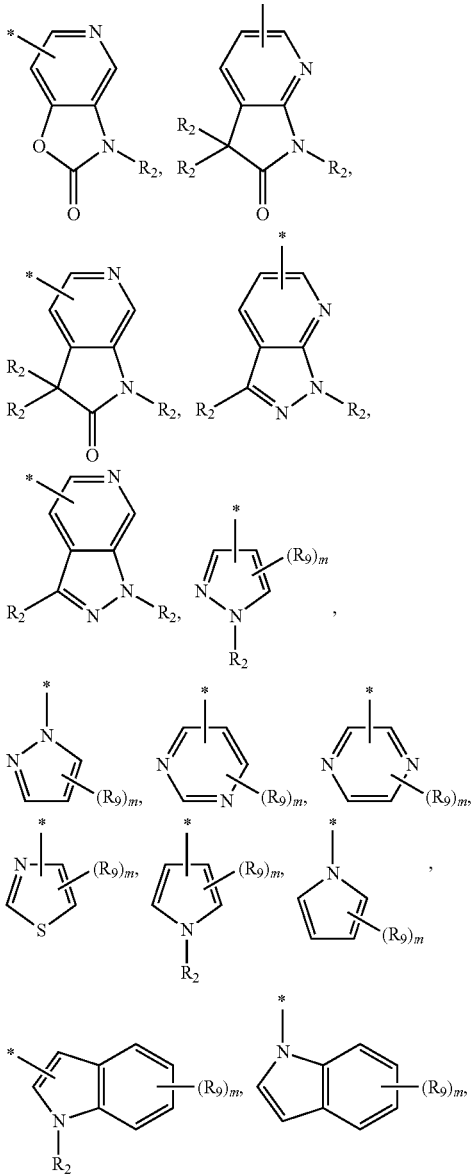

quinolinyl, quinoxalinyl, quinazolinyl, or naphthyridinyl; or $R_4$ is piperazinyl, piperidinyl, or pyrrolidinyl, each of which is optionally substituted with:
(i) a substituent selected from the group consisting of $C_1$-$C_6$alkyl, $C_1$-$C_6$cycloalkenyl, monocarbocyclic aryl, monocyclic heteroaryl, aralkyl, heteroaralkyl, cyano, halogen, $C_1$-$C_6$alkoxy, amino, —C(O)$R_{10}$, —CO$_2$$R_{10}$, —C(O)N($R_{10}$)$_2$, —N($R_{10}$)C(O)$R_{10}$, —N($R_{10}$)CO$_2$$R_{11}$, —$C_1$-$C_6$alkylene-OH, —OC(O)N($R_{10}$)$_2$, —OC(O)$R_5$, —N($R_6$)SO$_2$$R_{10}$, —SO$_2$$R_{10}$, —SO$_2$N($R_{10}$)$_2$, —O—($C_1$-$C_6$)alkylene-($C_4$-$C_6$)heterocycloalkyl, —N($R_2$)—($C_1$-$C_6$)alkylene-($C_4$-$C_6$) heterocycloalkyl, and —OPO$_3$H$_2$; and
(ii) a substituent selected from the group consisting of hydrogen, $C_1$-$C_6$alkyl, and halogen;

$R_5$ represents independently for each occurrence $C_1$-$C_6$alkyl;

$R_6$ represents independently for each occurrence hydrogen or $C_1$-$C_6$alkyl, or two occurrences of $R_6$ attached to the same nitrogen atom are taken together with the nitrogen atom to form a $C_3$-$C_7$ heterocycloalkyl;

$R_7$ is $C_1$-$C_6$alkyl, $C_3$-$C_7$heterocycloalkyl, $C_1$-$C_6$alkoxy, halogen, amino, —N($R_6$)C(O)—$C_1$-$C_6$alkylene-$R_{12}$, —O—($C_1$-$C_6$)alkylene-($C_4$-$C_6$)heterocycloalkyl, or —N($R_2$)—($C_1$-$C_6$)alkylene-($C_4$-$C_6$)heterocycloalkyl;

$R_8$ is hydrogen, halogen, $C_1$-$C_6$alkyl, or $C_1$-$C_6$alkoxy;

$R_9$ represents independently for each occurrence halogen, $C_1$-$C_6$alkyl, $C_1$-$C_6$alkoxy, $C_3$-$C_7$heterocycloalkyl, amino, hydroxyl, —C(O) $R_{10}$, —CO$_2$$R_{10}$, —C(O)N($R_{10}$)$_2$, —N($R_{10}$)C(O)$R_{10}$, —N($R_{10}$)CO$_2$$R_{11}$, —OC(O)N($R_{10}$)$_2$, —N($R_6$)C (O)—$C_1$-$C_6$alkylene-$R_{12}$, or —$C_1$-$C_6$alkylene-N($R_2$) C(O)—$C_1$-$C_6$-alkyl;

$R_{10}$ represents independently for each occurrence hydrogen, $C_1$-$C_6$alkyl, aryl, heteroaryl, aralkyl, or heteroaralkyl, or two occurrences of $R_{10}$ attached to the same nitrogen atom are taken together with the nitrogen atom to form a $C_3$-$C_7$ heterocycloalkyl;

$R_{11}$ represents independently for each occurrence $C_1$-$C_6$alkyl, aryl, heteroaryl, aralkyl, or heteroaralkyl;

$R_{12}$ represents independently for each occurrence —OR$_2$, —N($R_2$)$_2$, —OC(O)$R_{11}$, or —N($R_2$)C(O) $R_{11}$;

n is 1 or 2;

m is 0, 1, or 2;

wherein $C_3$-$C_7$heterocycloalkyl is a heterocycloalkyl group containing at least one N, O, or S ring atom and 3-7 ring carbon atoms; heteroaryl is a monocyclic aromatic group containing 1, 2, 3, or 4 ring heteroatoms; and the stereochemical configuration at a stereocenter in a compound represented by formula I is R, S, or a mixture thereof.

2. The compound of claim 1, wherein $R_1$ is chloro.

3. The compound of claim 1, wherein $R_2$ is hydrogen.

4. The compound of claim 1, wherein $R_2$ is methyl, ethyl, or propyl.

5. The compound of claim 1, wherein $R_3$ is phenyl optionally substituted with one or two substituents independently selected from the group consisting of halogen, $C_1$-$C_6$alkyl, —SO$_2$$R_5$, —SO$_2$N($R_6$)$_2$, —CN, and monocarbocyclic aryl.

6. The compound of claim 1, wherein $R_4$ is

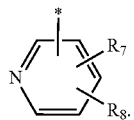

7. The compound of claim 6, wherein $R_7$ is aziridinyl, azetidinyl, pyrrolidinyl, piperidinyl, piperazinyl, morpholinyl, hexahydropyrimidinyl, azepanyl, pyrazolidinyl, or imidazolidinyl, each of which is optionally substituted with one or two substituents independently selected from the group consisting of halogen, hydroxyl, amino, $C_1$-$C_6$alkyl, $C_1$-$C_6$alkoxy, and —C(O)—$C_1$-$C_6$alkyl.

8. The compound of claim 7, wherein $R_8$ is hydrogen.

9. The compound of claim 1, wherein $R_4$ is

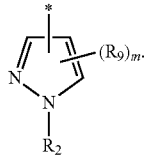

10. The compound of claim 1, wherein the compound is represented by formula IA:

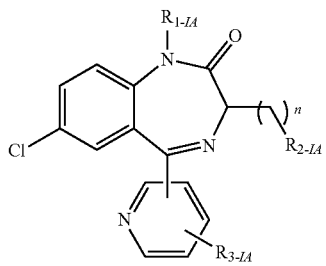

(IA)

or a pharmaceutically acceptable salt thereof; wherein:
$R_{1-IA}$ represents independently for each occurrence hydrogen, methyl, ethyl, or propyl;
$R_{2-IA}$ is phenyl or naphthyl, each of which is optionally substituted with one or two substituents independently selected from the group consisting of halogen, methyl, ethyl, propyl, and monocarbocyclic aryl;
$R_{3-IA}$ is $C_3$-$C_7$heterocycloalkyl, $C_1$-$C_6$alkoxy, amino, or —N($R_{1-IA}$)C(O)—$C_1$-$C_6$alkylene-$R_{4-IA}$;
$R_{4-IA}$ represents independently for each occurrence —O$R_{1-IA}$ or —OC(O)—$C_1$-$C_6$alkyl;
n is 1 or 2; and
the stereochemical configuration at a stereocenter in a compound represented by formula IA is R, S, or a mixture thereof.

11. The compound of claim 10, wherein $R_{3-IA}$ is $C_3$-$C_7$heterocycloalkyl.

12. The compound of claim 10, wherein $R_{3-IA}$ is pyrrolidinyl, piperidinyl, piperazinyl, or morpholinyl, each of which is optionally substituted with one or two substituents independently selected from the group consisting of $C_1$-$C_6$alkyl, halogen, hydroxyl, and amino.

13. The compound of claim 10, wherein $R_{3-IA}$ is pyrrolidinyl, piperidinyl, or piperazinyl, each of which is optionally substituted with methyl, ethyl, or propyl.

14. The compound of claim 1, wherein the compound is represented by formula IB:

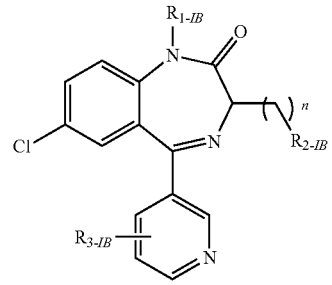

(IB)

or a pharmaceutically acceptable salt thereof; wherein:
$R_{1-IB}$ represents independently for each occurrence hydrogen, methyl, ethyl, or propyl;
$R_{2-IB}$ is phenyl or naphthyl, each of which is optionally substituted with one or two substituents independently selected from the group consisting of halogen, $C_1$-$C_6$ alkyl, and monocarbocyclic aryl;
$R_{3-IB}$ is pyrrolidinyl, piperidinyl, piperazinyl, or morpholinyl, each of which is optionally substituted with one or two substituents independently selected from the group consisting of $C_1$-$C_6$alkyl, halogen, hydroxyl, amino, and oxo;
n is 1 or 2; and
the stereochemical configuration at a stereocenter in a compound represented by formula IB is R, S, or a mixture thereof.

15. The compound of claim 14, wherein $R_{3-IB}$ is piperidinyl optionally substituted with one or two substituents independently selected from the group consisting of $C_1$-$C_6$alkyl, halogen, hydroxyl, amino, and oxo.

16. The compound of claim 1, wherein the compound is represented by formula IC:

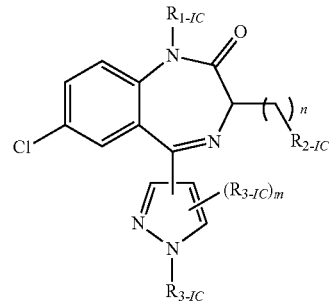

(IC)

or a pharmaceutically acceptable salt thereof; wherein:
$R_{1-IC}$ represents independently for each occurrence hydrogen, methyl, ethyl, or propyl;
$R_{2-IC}$ is phenyl or naphthyl, each of which is optionally substituted with one or two substituents independently selected from the group consisting of halogen, $C_1$-$C_6$alkyl, and monocarbocyclic aryl;
$R_{3-IC}$ is hydrogen, methyl, ethyl, or propyl;
m and n are independently 1 or 2; and
the stereochemical configuration at a stereocenter in a compound represented by formula IC is R, S, or a mixture thereof.

17. The compound of claim 16, wherein $R_{2-IC}$ is naphthyl; or $R_{2-IC}$ is phenyl substituted with halogen, methyl, ethyl, or propyl.

18. The compound of claim 17, wherein n is 1, and $R_{3\text{-}IC}$ is hydrogen.

19. A compound represented by formula ID:

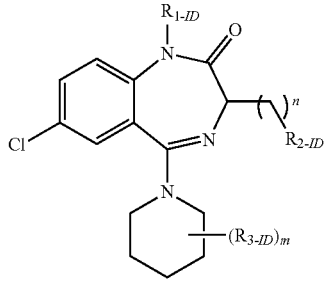

(ID)

or a pharmaceutically acceptable salt thereof; wherein:
- $R_{1\text{-}ID}$ represents independently for each occurrence hydrogen, methyl, ethyl, or propyl;
- $R_{2\text{-}ID}$ is phenyl or naphthyl, each of which is optionally substituted with one or two substituents independently selected from the group consisting of halogen, $C_1$-$C_6$alkyl, and monocarbocyclic aryl;
- $R_{3\text{-}ID}$ represents independently for each occurrence monocarbocyclic aryl, monocyclic heteroaryl, hydroxyl, amino, oxo, ketal, or —N($R_{10}$)C(O)$R_{10}$;
- m and n are independently 1 or 2;
- wherein the monocyclic heteroaryl contains 1, 2, 3, or 4 ring heteroatoms; and
- the stereochemical configuration at a stereocenter in a compound represented by formula ID is R, S, or a mixture thereof.

20. A compound represented by formula II:

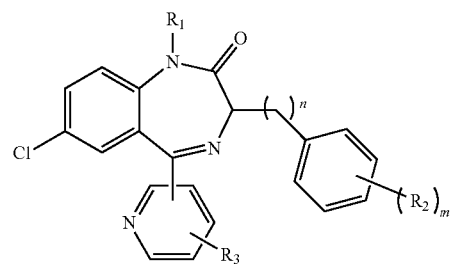

(II)

or a pharmaceutically acceptable salt thereof; wherein:
- $R_1$ represents independently for each occurrence hydrogen or $C_1$-$C_6$alkyl;
- $R_2$ represents independently for each occurrence chloro, bromo, or fluoro;
- $R_3$ is $C_3$-$C_7$heterocycloalkyl, $C_1$-$C_6$alkoxy, hydroxyl, amino, —N($R_1$)C(O)—$C_1$-$C_6$alkyl, or —N($R_1$)—($C_1$-$C_6$)alkylene-($C_4$-$C_6$)heterocycloalkyl;
- m and n are independently 1 or 2;
- wherein $C_3$-$C_7$heterocycloalkyl is a heterocycloalkyl group containing at least one N, O, or S ring atom and 3-7 ring carbon atoms; and
- the stereochemical configuration at a stereocenter in a compound represented by formula II is R, S, or a mixture thereof.

21. A compound in any one of Tables 1-5 below,

TABLE 1

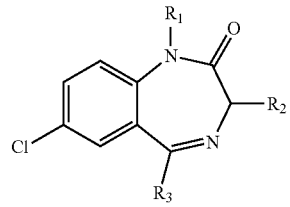

| Compound | $R_1$ | $R_2$ | $R_3$ |
|---|---|---|---|
| I-1 | hydrogen | 2-chlorobenzyl | *-pyridyl-piperazinyl-NH |
| I-2 | hydrogen | 2-chlorobenzyl | *-pyridyl-piperazinyl-N—Me |
| I-3 | hydrogen | 2-chlorobenzyl | *-pyridyl-piperazinyl-N—C(O)Me |
| I-4 | hydrogen | 2-chlorobenzyl | *-pyridyl-piperazinyl-N—C(O)NH$_2$ |
| I-5 | hydrogen | 2-chlorobenzyl | *-pyridyl-piperazinyl-N—CH$_2$CH$_2$—OH |

TABLE 1-continued

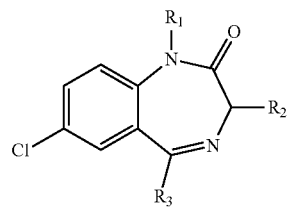

| Compound | R₁ | R₂ | R₃ |
|---|---|---|---|
| I-6 | hydrogen | 2-chlorobenzyl | *-pyridine-piperazine-CH₂CH₂NH₂ |
| I-7 | hydrogen | 2-chlorobenzyl | *-pyridine-piperazine-CH₂CH₂C(O)NH₂ |
| I-8 | hydrogen | 2-chlorophenyl | *-pyridine-piperazine-SO₂Me |
| I-9 | hydrogen | 2-chlorophenyl | *-pyridine-piperazine-SO₂NH₂ |
| I-10 | hydrogen | 2-chlorophenyl | *-pyridine-piperidine |
| I-11 | hydrogen | 2-chlorophenyl | *-pyridine-piperidine-Me |
| I-12 | hydrogen | 2-chlorobenzyl | *-pyridine-piperidine-C(O)Me |
| I-13 | hydrogen | 2-chlorobenzyl | *-pyridine-piperidine-C(O)NH₂ |
| I-14 | hydrogen | 2-chlorobenzyl | *-pyridine-piperidine-OH |
| I-15 | hydrogen | 2-chlorobenzyl | *-pyridine-piperidine-NH₂ |
| I-16 | hydrogen | 2-chlorobenzyl | *-pyridine-pyrrolidine |
| I-17 | hydrogen | 2-chlorobenzyl | *-pyridine-pyrrolidine-Me |

TABLE 1-continued

| Compound | R₁ | R₂ | R₃ |
|---|---|---|---|
| I-18 | hydrogen | 2-chlorobenzyl | *-pyridin-2-yl-pyrrolidin-3-yl-C(O)Me |
| I-19 | hydrogen | 2-chlorobenzyl | *-pyridin-2-yl-pyrrolidin-3-yl-C(O)NH₂ |
| I-20 | hydrogen | 2-chlorobenzyl | *-pyridin-2-yl-pyrrolidin-3-yl-OH |
| I-21 | hydrogen | 2-chlorobenzyl | *-pyridin-2-yl-pyrrolidin-3-yl-NH₂ |
| I-22 | hydrogen | 2-chlorobenzyl | *-pyridin-2-yl-(2,2-dimethyl)imidazolidin-NH |
| I-23 | hydrogen | 2-chlorobenzyl | *-pyridin-2-yl-(2,2-dimethyl)imidazolidin-N-Me |
| I-24 | hydrogen | 2-chlorobenzyl | *-pyridin-2-yl-(2,2-dimethyl)imidazolidin-N-C(O)Me |
| I-25 | hydrogen | 2-chlorobenzyl | *-pyridin-2-yl-(2,2-dimethyl)imidazolidin-N-C(O)NH₂ |
| I-26 | hydrogen | 2-chlorobenzyl | *-pyridin-2-yl-(2,2-dimethyl)imidazolidin-4-NH₂ |
| I-27 | hydrogen | 2-chlorobenzyl | *-pyridin-2-yl-(2,2-dimethyl)oxazolidin |
| I-28 | hydrogen | 2-chlorobenzyl | *-pyridin-2-yl-(2,2,5-trimethyl)oxazolidin |

TABLE 1-continued
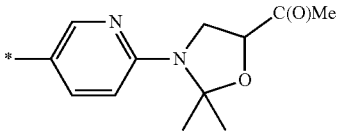
| Compound | R₁ | R₂ | R₃ |
|---|---|---|---|
| I-29 | hydrogen | 2-chlorobenzyl | 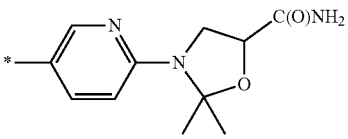 |
| I-30 | hydrogen | 2-chlorobenzyl | 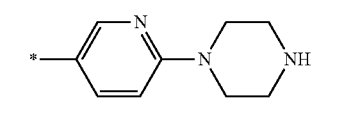 [SMILES: *c1ccc(N2CCNCC2)nc1] |
| I-31 | hydrogen | 2-methylbenzyl | 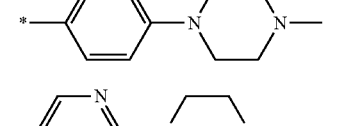 |
| I-32 | hydrogen | 2-methylbenzyl | 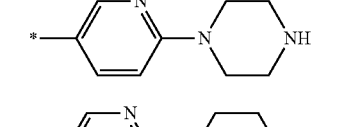 |
| I-33 | hydrogen | 2-methylbenzyl | 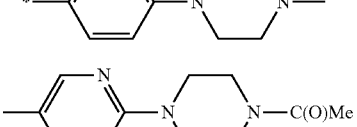 |
| I-34 | hydrogen | 2-methylbenzyl | 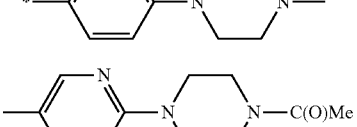 |
| I-35 | hydrogen | 2-methylbenzyl | 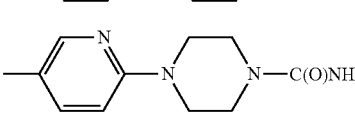 |
| I-36 | hydrogen | 2-methylbenzyl | 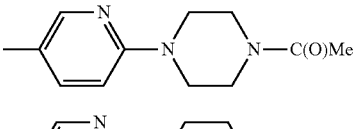 |
| I-37 | hydrogen | 2-methylbenzyl | 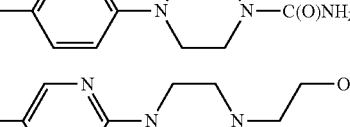 |
| I-38 | hydrogen | 2-methylbenzyl | 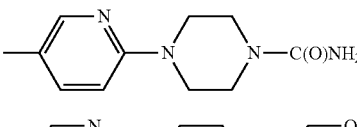 |
| I-39 | hydrogen | 2-methylbenzyl | 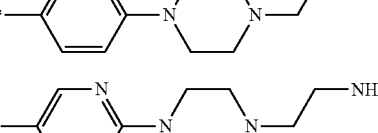 |
| I-40 | hydrogen | 2-methylbenzyl | 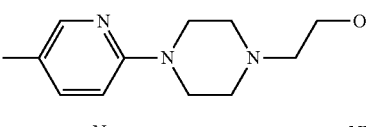 |

TABLE 1-continued

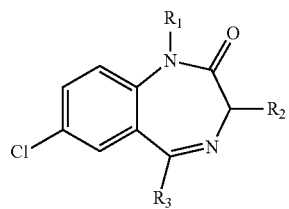

| Compound | R₁ | R₂ | R₃ |
|---|---|---|---|
| I-41 | hydrogen | 2-methylbenzyl | *-pyridine-piperidine-Me |
| I-42 | hydrogen | 2-methylbenzyl | *-pyridine-piperidine-C(O)Me |
| I-43 | hydrogen | 2-methylbenzyl | *-pyridine-piperidine-C(O)NH₂ |
| I-44 | hydrogen | 2-methylbenzyl | *-pyridine-piperidine-OH |
| I-45 | hydrogen | 2-methylbenzyl | *-pyridine-piperidine-NH₂ |
| I-46 | hydrogen | 2-methylbenzyl | *-pyridine-pyrrolidine |
| I-47 | hydrogen | 2-methylbenzyl | *-pyridine-pyrrolidine-Me |
| I-48 | hydrogen | 2-methylbenzyl | *-pyridine-pyrrolidine-C(O)Me |
| I-49 | hydrogen | 2-methylbenzyl | *-pyridine-pyrrolidine-C(O)NH₂ |
| I-50 | hydrogen | 2-methylbenzyl | *-pyridine-pyrrolidine-OH |
| I-51 | hydrogen | 2-methylbenzyl | *-pyridine-pyrrolidine-NH₂ |
| I-52 | hydrogen | 2-methylbenzyl | *-pyridine-imidazolidine-(Me)₂-NH |

TABLE 1-continued
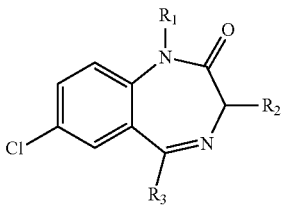
| Compound | R₁ | R₂ | R₃ |
|---|---|---|---|
| I-53 | hydrogen | 2-methylbenzyl | 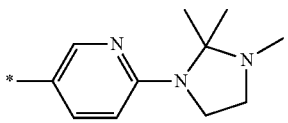 [SMILES: *c1ccc(N2CCN(C)C2(C)C)nc1] |
| I-54 | hydrogen | 2-methylbenzyl | 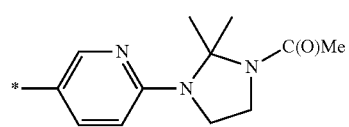 |
| I-55 | hydrogen | 2-methylbenzyl | 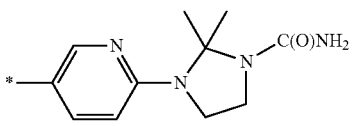 |
| I-56 | hydrogen | 2-methylbenzyl | 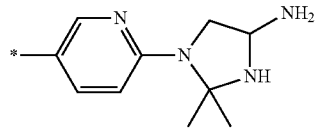 [SMILES: *c1ccc(N2CC(N)NC2(C)C)nc1] |
| I-57 | hydrogen | 2-methylbenzyl | 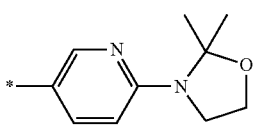 [SMILES: *c1ccc(N2CCOC2(C)C)nc1] |
| I-58 | hydrogen | 2-methylbenzyl | 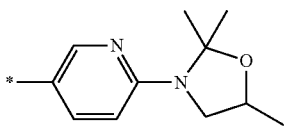 |
| I-59 | hydrogen | 2-methylbenzyl | 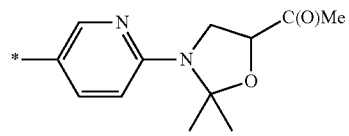 |
| I-60 | hydrogen | 2-methylbenzyl | 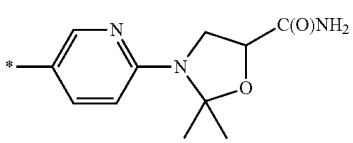 |
| I-61 | methyl | 2-chlorobenzyl | 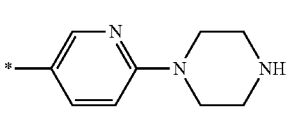 |
| I-62 | methyl | 2-chlorobenzyl | 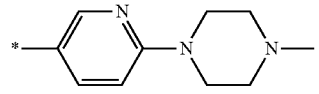 [SMILES: *c1ccc(N2CCN(C)CC2)nc1] |

TABLE 1-continued

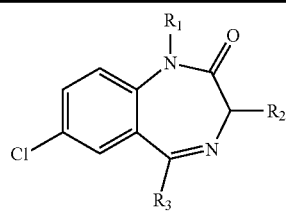

| Compound | R₁ | R₂ | R₃ |
|---|---|---|---|
| I-63 | methyl | 2-chlorobenzyl | *-pyridine-piperazine-N-C(O)Me |
| I-64 | methyl | 2-chlorobenzyl | *-pyridine-piperazine-N-C(O)NH₂ |
| I-65 | methyl | 2-chlorobenzyl | *-pyridine-piperazine-N-CH₂CH₂OH |
| I-66 | methyl | 2-chlorobenzyl | *-pyridine-piperazine-N-CH₂CH₂NH₂ |
| I-67 | methyl | 2-chlorobenzyl | *-pyridine-piperazine-N-CH₂CH₂C(O)NH₂ |
| I-68 | methyl | 2-chlorobenzyl | *-pyridine-piperazine-N-SO₂Me |
| I-69 | methyl | 2-chlorobenzyl | *-pyridine-piperazine-N-SO₂Me |
| I-70 | methyl | 2-chlorobenzyl | *-pyridine-piperidine |
| I-71 | methyl | 2-chlorobenzyl | *-pyridine-piperidine-Me |
| I-72 | methyl | 2-chlorobenzyl | *-pyridine-piperidine-C(O)Me |
| I-73 | methyl | 2-chlorobenzyl | *-pyridine-piperidine-C(O)NH₂ |
| I-74 | methyl | 2-chlorobenzyl | *-pyridine-piperidine-OH |
| I-75 | methyl | 2-chlorobenzyl | *-pyridine-piperidine-NH₂ |

TABLE 1-continued

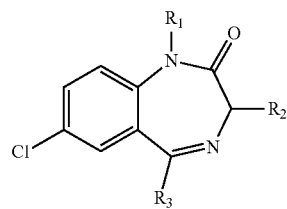

| Compound | R₁ | R₂ | R₃ |
|---|---|---|---|
| I-76 | methyl | 2-chlorobenzyl | 5-(pyrrolidin-1-yl)pyridin-2-yl |
| I-77 | methyl | 2-chlorobenzyl | 5-(3-methylpyrrolidin-1-yl)pyridin-2-yl |
| I-78 | methyl | 2-chlorobenzyl | 5-(3-C(O)Me-pyrrolidin-1-yl)pyridin-2-yl |
| I-79 | methyl | 2-chlorobenzyl | 5-(3-C(O)NH₂-pyrrolidin-1-yl)pyridin-2-yl |
| I-80 | methyl | 2-chlorobenzyl | 5-(3-hydroxypyrrolidin-1-yl)pyridin-2-yl |
| I-81 | methyl | 2-chlorobenzyl | 5-(3-aminopyrrolidin-1-yl)pyridin-2-yl |
| I-82 | methyl | 2-chlorobenzyl | 5-(2,2-dimethylimidazolidin-1-yl)pyridin-2-yl |
| I-83 | methyl | 2-chlorobenzyl | 5-(2,2,3-trimethylimidazolidin-1-yl)pyridin-2-yl |
| I-84 | methyl | 2-chlorobenzyl | 5-(3-C(O)Me-2,2-dimethylimidazolidin-1-yl)pyridin-2-yl |
| I-85 | methyl | 2-chlorobenzyl | 5-(3-C(O)NH₂-2,2-dimethylimidazolidin-1-yl)pyridin-2-yl |
| I-86 | methyl | 2-chlorobenzyl | 5-(4-amino-2,2-dimethylimidazolidin-1-yl)pyridin-2-yl |

TABLE 1-continued
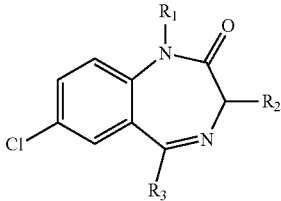
| Compound | R₁ | R₂ | R₃ |
|---|---|---|---|
| I-87 | methyl | 2-chlorobenzyl | 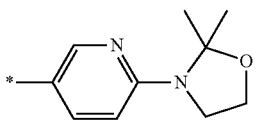 [SMILES: *c1ccc(N2CCOC2(C)C)nc1] |
| I-88 | methyl | 2-chlorobenzyl | 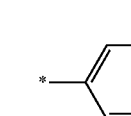 |
| I-89 | methyl | 2-chlorobenzyl | 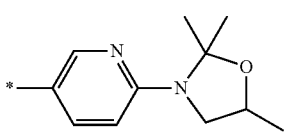 |
| I-90 | methyl | 2-chlorobenzyl | 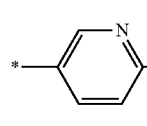 |
| I-91 | hydrogen | 2,4-dichlorobenzyl |  |
| I-92 | hydrogen | 2,4-dichlorobenzyl | 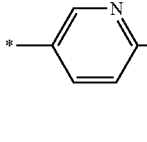 |
| I-93 | hydrogen | 2,4-dichlorobenzyl | 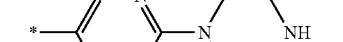 |
| I-94 | hydrogen | 2,4-dichlorobenzyl | 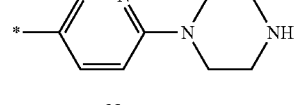 |
| I-95 | hydrogen | 2,4-dichlorobenzyl | 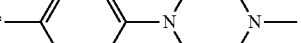 |
| I-96 | hydrogen | 2,4-dichlorobenzyl |  |
| I-97 | hydrogen | 2,4-dichlorobenzyl |  |

TABLE 1-continued

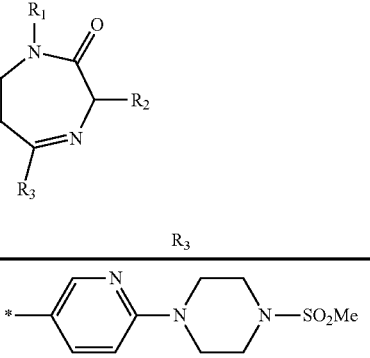

| Compound | R₁ | R₂ | R₃ |
|---|---|---|---|
| I-98 | hydrogen | 2,4-dichlorobenzyl | 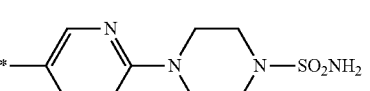 |
| I-99 | hydrogen | 2,4-dichlorobenzyl | 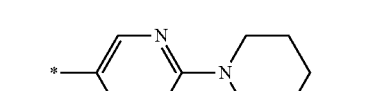 |
| I-100 | hydrogen | 2,4-dichlorobenzyl | 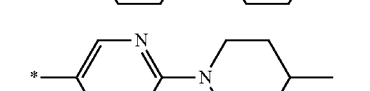 |
| I-101 | hydrogen | 2,4-dichlorobenzyl | 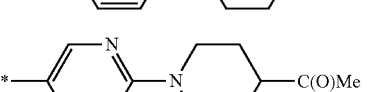 |
| I-102 | hydrogen | 2,4-dichlorobenzyl | 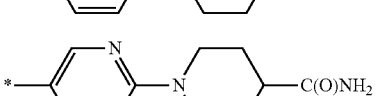 |
| I-103 | hydrogen | 2,4-dichlorobenzyl | 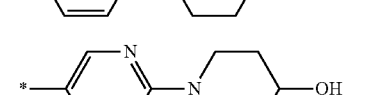 |
| I-104 | hydrogen | 2,4-dichlorobenzyl | 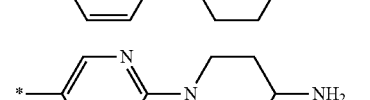 |
| I-105 | hydrogen | 2,4-dichlorobenzyl | 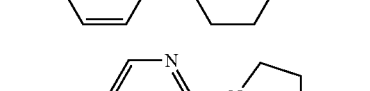 |
| I-106 | hydrogen | 2,4-dichlorobenzyl | 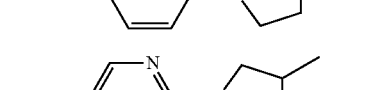 |
| I-107 | hydrogen | 2,4-dichlorobenzyl | 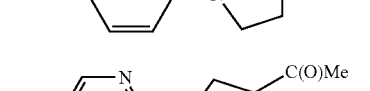 |
| I-108 | hydrogen | 2,4-dichlorobenzyl | 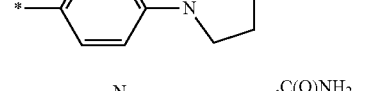 |
| I-109 | hydrogen | 2,4-dichlorobenzyl | 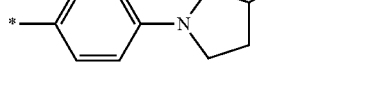 |
| I-110 | hydrogen | 2,4-dichlorobenzyl | |

TABLE 1-continued
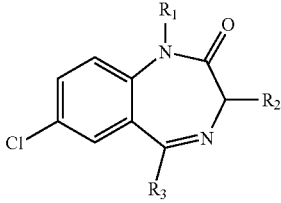
| Compound | R₁ | R₂ | R₃ |
|---|---|---|---|
| I-111 | hydrogen | 2,4-dichlorobenzyl | 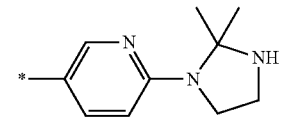 [SMILES: *c1ccc(N2CCNC2(C)C)nc1] |
| I-112 | hydrogen | 2,4-dichlorobenzyl | 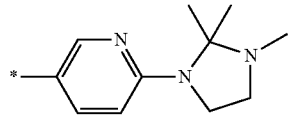 [SMILES: *c1ccc(N2CCN(C)C2(C)C)nc1] |
| I-113 | hydrogen | 2,4-dichlorobenzyl | 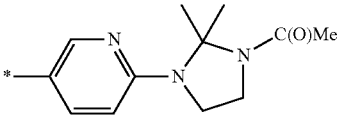 |
| I-114 | hydrogen | 2,4-dichlorobenzyl | 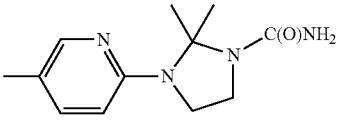 |
| I-115 | hydrogen | 2,4-dichlorobenzyl | 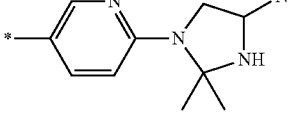 |
| I-116 | hydrogen | 2,4-dichlorobenzyl | 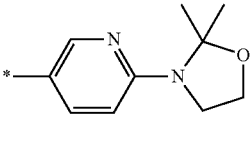 |
| I-117 | hydrogen | 2,4-dichlorobenzyl | 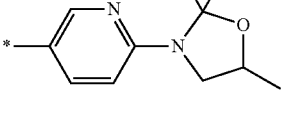 |
| I-118 | hydrogen | 2,4-dichlorobenzyl | 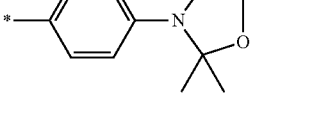 |
| I-119 | hydrogen | 2,4-dichlorobenzyl | 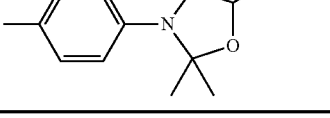 |
| I-120 | hydrogen | 2,4-dichlorobenzyl |  |

TABLE 2

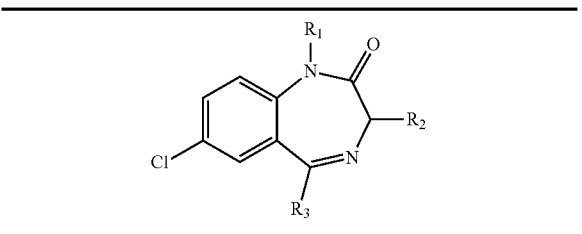

| Compound | R₁ | R₂ | R₃ |
|---|---|---|---|
| II-1 | hydrogen | 2-chlorobenzyl | 1H-pyrazol-4-yl |
| II-2 | hydrogen | 2-chlorobenzyl | 1-methyl-1H-pyrazol-4-yl |
| II-3 | hydrogen | 2-chlorobenzyl | 5-methyl-1H-pyrazol-4-yl |
| II-4 | hydrogen | 2-chlorobenzyl | 1-(C(O)Me)-1H-pyrazol-4-yl |
| II-5 | hydrogen | 2-chlorobenzyl | 1-(C(O)NH₂)-1H-pyrazol-4-yl |
| II-6 | hydrogen | 2-chlorobenzyl | 1H-pyrrol-3-yl |
| II-7 | hydrogen | 2-chlorobenzyl | 1-methyl-1H-pyrrol-3-yl |
| II-8 | hydrogen | 2-chlorobenzyl | 1-(C(O)Me)-1H-pyrrol-3-yl |
| II-9 | hydrogen | 2-chlorobenzyl | 5-(C(O)Me)-1H-pyrrol-3-yl |
| II-10 | hydrogen | 2-chlorobenzyl | thiazol-4-yl |
| II-11 | hydrogen | 2-methylbenzyl | 1H-pyrazol-4-yl |
| II-12 | hydrogen | 2-methylbenzyl | 1-methyl-1H-pyrazol-4-yl |
| II-13 | hydrogen | 2-methylbenzyl | 5-methyl-1H-pyrazol-4-yl |
| II-14 | hydrogen | 2-methylbenzyl | 1-(C(O)Me)-1H-pyrazol-4-yl |
| II-15 | hydrogen | 2-methylbenzyl | 1-(C(O)NH₂)-1H-pyrazol-4-yl |
| II-16 | hydrogen | 2-methylbenzyl | 1H-pyrrol-3-yl |
| II-17 | hydrogen | 2-methylbenzyl | 1-methyl-1H-pyrrol-3-yl |
| II-18 | hydrogen | 2-methylbenzyl | 1-(C(O)Me)-1H-pyrrol-3-yl |
| II-19 | hydrogen | 2-methylbenzyl | 5-(C(O)Me)-1H-pyrrol-3-yl |
| II-20 | hydrogen | 2-methylbenzyl | thiazol-4-yl |
| II-21 | hydrogen | 2,4-dichlorobenzyl | 1H-pyrazol-4-yl |
| II-22 | hydrogen | 2,4-dichlorobenzyl | 1-methyl-1H-pyrazol-4-yl |
| II-23 | hydrogen | 2,4-dichlorobenzyl | 5-methyl-1H-pyrazol-4-yl |

TABLE 2-continued

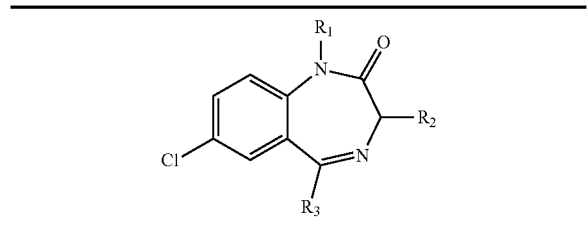

| Compound | R₁ | R₂ | R₃ |
|---|---|---|---|
| II-24 | hydrogen | 2,4-dichlorobenzyl | *pyrazol-4-yl, N-C(O)Me |
| II-25 | hydrogen | 2,4-dichlorobenzyl | *pyrazol-4-yl, N-C(O)NH₂ |
| II-26 | hydrogen | 2,4-dichlorobenzyl | *pyrrol-3-yl, NH |
| II-27 | hydrogen | 2,4-dichlorobenzyl | *pyrrol-3-yl, N-Me |
| II-28 | hydrogen | 2,4-dichlorobenzyl | *pyrrol-3-yl, N-C(O)Me |
| II-29 | hydrogen | 2,4-dichlorobenzyl | *pyrrol-4-yl, NH, 5-C(O)Me |
| II-30 | hydrogen | 2,4-dichlorobenzyl | *thiazol-4-yl |
| II-31 | methyl | 2-chlorobenzyl | *pyrazol-4-yl, NH |
| II-32 | methyl | 2-chlorobenzyl | *pyrazol-4-yl, N-Me |
| II-33 | methyl | 2-chlorobenzyl | *pyrazol-4-yl, 3-Me, NH |
| II-34 | methyl | 2-chlorobenzyl | *pyrazol-4-yl, N-C(O)Me |
| II-35 | methyl | 2-chlorobenzyl | *pyrazol-4-yl, N-C(O)NH₂ |
| II-36 | methyl | 2-chlorobenzyl | *pyrrol-3-yl, NH |

TABLE 2-continued

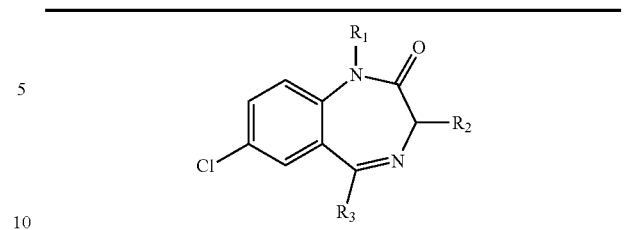

| Compound | R₁ | R₂ | R₃ |
|---|---|---|---|
| II-37 | methyl | 2-chlorobenzyl | *pyrrol-3-yl, N-Me |
| II-38 | methyl | 2-chlorobenzyl | *pyrrol-3-yl, N-C(O)Me |
| II-39 | methyl | 2-chlorobenzyl | *pyrrol-4-yl, NH, 5-C(O)Me |
| II-40 | methyl | 2-chlorobenzyl | *thiazol-4-yl |
| II-41 | hydrogen | naphthalen-2-ylmethyl | *pyrazol-4-yl, NH |
| II-42 | hydrogen | naphthalen-2-ylmethyl | *pyrazol-4-yl, N-Me |
| II-43 | hydrogen | naphthalen-2-ylmethyl | *pyrazol-4-yl, 3-Me, NH |
| II-44 | hydrogen | naphthalen-2-ylmethyl | *pyrazol-4-yl, N-C(O)Me |
| II-45 | hydrogen | naphthalen-2-ylmethyl | *pyrazol-4-yl, N-C(O)NH₂ |
| II-46 | hydrogen | naphthalen-2-ylmethyl | *pyrrol-3-yl, NH |
| II-47 | hydrogen | naphthalen-2-ylmethyl | *pyrrol-3-yl, N-Me |
| II-48 | hydrogen | naphthalen-2-ylmethyl | *pyrrol-3-yl, N-C(O)Me |

TABLE 2-continued
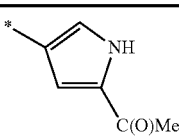
| Compound | R₁ | R₂ | R₃ |
|---|---|---|---|
| II-49 | hydrogen | naphthalen-2-ylmethyl | 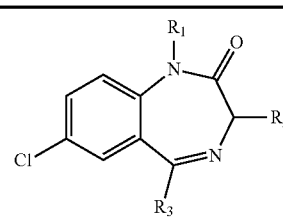 |
| II-50 | hydrogen | naphthalen-2-ylmethyl | 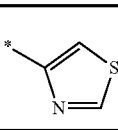 |
TABLE 3
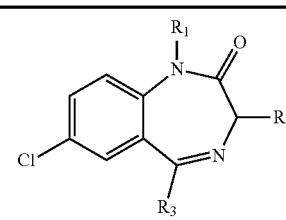
| Compound | R₁ | R₂ | R₃ |
|---|---|---|---|
| III-1 | hydrogen | 2-chlorobenzyl | 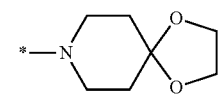 |
| III-2 | hydrogen | 2-chlorobenzyl | 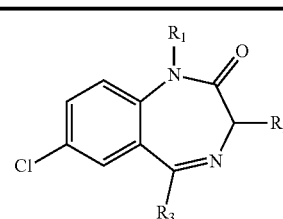 |
| III-3 | hydrogen | 2-chlorobenzyl |  |
| III-4 | hydrogen | 2-chlorobenzyl | 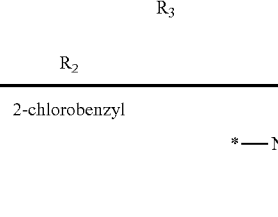 |
| III-5 | hydrogen | 2-chlorobenzyl | 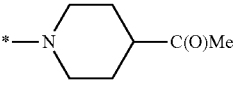 |
| III-6 | hydrogen | 2-chlorobenzyl | 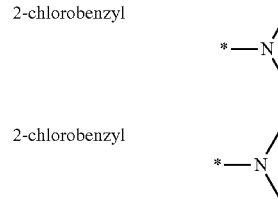 |
| III-7 | hydrogen | 2-chlorobenzyl | 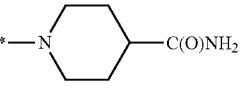 |
| III-8 | hydrogen | 2-chlorobenzyl | 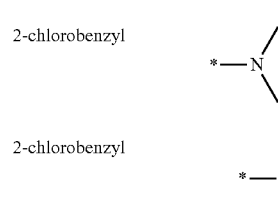 |

TABLE 3-continued

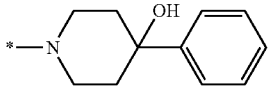

| Compound | R₁ | R₂ | R₃ |
|---|---|---|---|
| III-9 | hydrogen | 2-chlorobenzyl |  |
| III-10 | hydrogen | 2-chlorobenzyl | 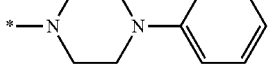 |
| III-11 | hydrogen | 2-chlorobenzyl | 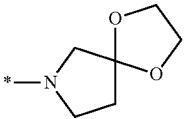 [SMILES: *N1CCC2(C1)OCCO2] |
| III-12 | hydrogen | 2-chlorobenzyl |  |
| III-13 | hydrogen | 2-chlorobenzyl |  |
| III-14 | hydrogen | 2-methylbenzyl |  |
| III-15 | hydrogen | 2-methylbenzyl | 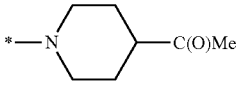 |
| III-16 | hydrogen | 2-methylbenzyl | 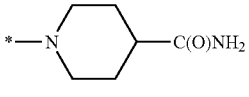 |
| III-17 | hydrogen | 2-methylbenzyl | 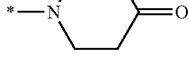 |
| III-18 | hydrogen | 2-methylbenzyl | 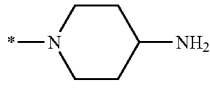 |
| III-19 | hydrogen | 2-methylbenzyl | 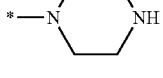 |
| III-20 | hydrogen | 2-methylbenzyl | 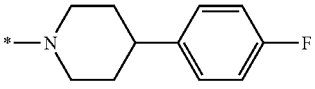 |
| III-21 | hydrogen | 2-methylbenzyl | |

TABLE 3-continued

| Compound | R₁ | R₂ | R₃ |
|---|---|---|---|
| III-22 | hydrogen | 2-methylbenzyl | *—N(piperidine)-C(OH)(phenyl) |
| III-23 | hydrogen | 2-methylbenzyl | *—N(piperidine)-C(NH₂)(phenyl) |
| III-24 | hydrogen | 2-methylbenzyl | *—N(piperazine)-phenyl |
| III-25 | hydrogen | 2-methylbenzyl | *—N(pyrrolidine spiro 1,3-dioxolane) |
| III-26 | hydrogen | 2-methylbenzyl | *—N(3-oxopyrrolidine) |
| III-27 | hydrogen | 2,4-dichlorobenzyl | *—N(piperidine spiro 1,3-dioxolane) |
| III-28 | hydrogen | 2,4-dichlorobenzyl | *—N(piperidine spiro 1,3-dioxane) |
| III-29 | hydrogen | 2,4-dichlorobenzyl | *—N(piperidine)-C(O)Me |
| III-30 | hydrogen | 2,4-dichlorobenzyl | *—N(piperidine)-C(O)NH₂ |
| III-31 | hydrogen | 2,4-dichlorobenzyl | *—N(4-oxopiperidine) |
| III-32 | hydrogen | 2,4-dichlorobenzyl | *—N(piperidine)-NH₂ |
| III-33 | hydrogen | 2,4-dichlorobenzyl | *—N(piperazine)-NH |
| III-34 | hydrogen | 2,4-dichlorobenzyl | *—N(piperidine)-(4-fluorophenyl) |

TABLE 3-continued

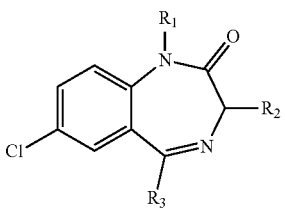

| Compound | R₁ | R₂ | R₃ |
|---|---|---|---|
| III-35 | hydrogen | 2,4-dichlorobenzyl | 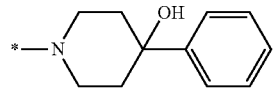 [SMILES: *N1CCC(O)(c2ccccc2)CC1] |
| III-36 | hydrogen | 2,4-dichlorobenzyl | 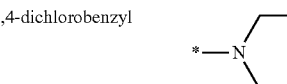 |
| III-37 | hydrogen | 2,4-dichlorobenzyl | 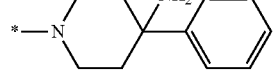 |
| III-38 | hydrogen | 2,4-dichlorobenzyl | 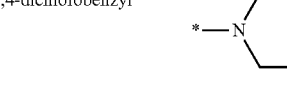 |
| III-39 | hydrogen | 2,4-dichlorobenzyl | 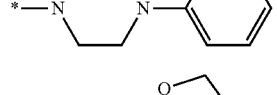 |
| III-40 | methyl | 2-chlorobenzyl |  |
| III-41 | methyl | 2-chlorobenzyl | 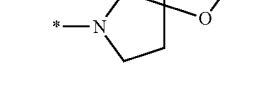 |
| III-42 | methyl | 2-chlorobenzyl |  |
| III-43 | methyl | 2-chlorobenzyl | 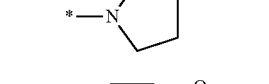 |
| III-44 | methyl | 2-chlorobenzyl |  |
| III-45 | methyl | 2-chlorobenzyl | 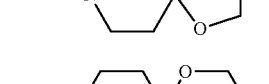 |
| III-46 | methyl | 2-chlorobenzyl | 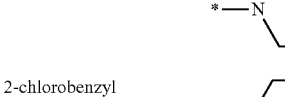 |
| III-47 | methyl | 2-chlorobenzyl |  |

TABLE 3-continued

| Compound | R₁ | R₂ | R₃ |
|---|---|---|---|
| III-48 | methyl | 2-chlorobenzyl | *—N-piperidinyl-4-OH-4-phenyl |
| III-49 | methyl | 2-chlorobenzyl | *—N-piperidinyl-4-NH₂-4-phenyl |
| III-50 | methyl | 2-chlorobenzyl | *—N-piperazinyl-4-phenyl |
| III-51 | methyl | 2-chlorobenzyl | *—N-pyrrolidinyl-1,4-dioxaspiro |
| III-52 | methyl | 2-chlorobenzyl | *—N-3-oxopyrrolidinyl |

TABLE 4

| Compound | R₁ | R₂ | R₃ |
|---|---|---|---|
| IV-1 | hydrogen | 2-chlorobenzyl | *-pyridin-2-ol |
| IV-2 | hydrogen | 2-chlorobenzyl | *-pyridin-NH-CH₂CH₂-morpholine |
| IV-3 | hydrogen | 2-chlorobenzyl | *-pyridin-NH-CH₂CH₂-piperazine-NH |
| IV-4 | hydrogen | 2-chlorobenzyl | *-pyridin-NH-CH₂CH₂-N(Et)₂ |

TABLE 4-continued

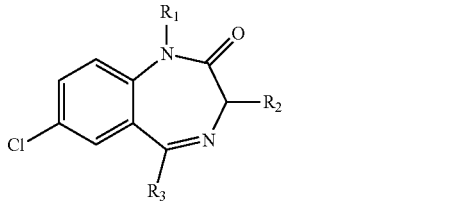

| Compound | R₁ | R₂ | R₃ |
|---|---|---|---|
| IV-5 | cyclopropyl | 2-chlorobenzyl | 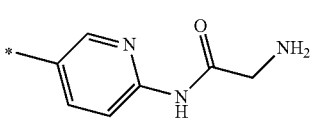 |
| IV-6 | hydrogen | 2-chlorobenzyl | 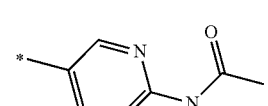 |
| IV-7 | hydrogen | 2-chlorobenzyl | 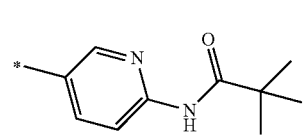 |
| IV-8 | hydrogen | 2-chlorobenzyl | 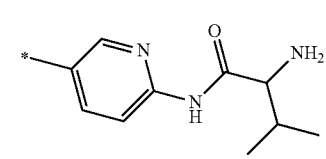 |
| IV-9 | hydrogen | 2-chlorobenzyl | 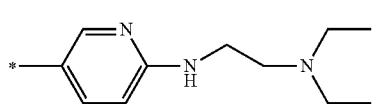 |
| IV-10 | hydrogen | 2-(methylsulfonyl)benzyl | 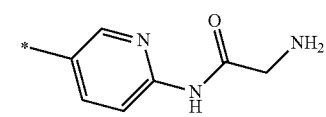 |
| IV-11 | hydrogen | 2-chloro-3-fluorobenzyl | 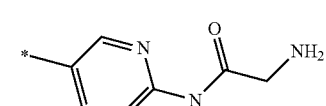 |
| IV-12 | hydrogen | 2-chloro-3-fluorobenzyl | 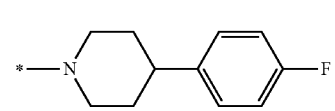 |
| IV-13 | hydrogen | 2-(methylsulfonyl)benzyl | 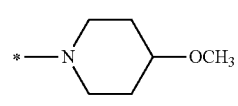 |
| IV-14 | hydrogen | 2-chlorobenzyl | 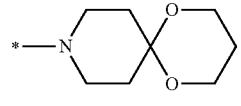 |
| IV-15 | hydrogen | 2-chlorobenzyl |  |

TABLE 4-continued

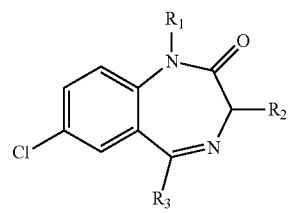

| Compound | R₁ | R₂ | R₃ |
|---|---|---|---|
| IV-16 | hydrogen | 2-chlorobenzyl | 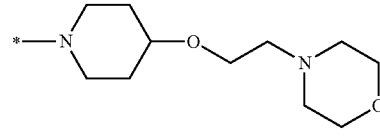 |
| IV-17 | hydrogen | 2-chlorobenzyl | 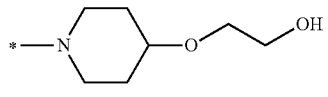 |
| IV-18 | hydrogen | 2-chlorobenzyl | 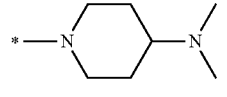 |
| IV-19 | hydrogen | 2-chlorobenzyl | 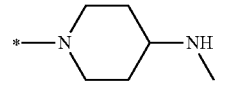 |
| IV-20 | hydrogen | 2-(methylsulfonyl)benzyl | 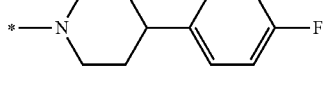 |
| IV-21 | hydrogen | 2-chlorobenzyl | 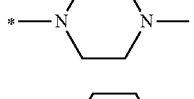 |
| IV-22 | hydrogen | 2-chlorobenzyl | 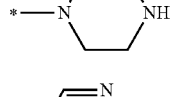 |
| IV-23 | hydrogen | 2-chlorobenzyl | 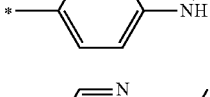 |
| IV-24 | hydrogen | 2-chlorobenzyl | 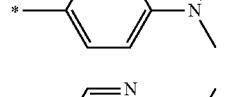 |
| IV-25 | hydrogen | 2-(N,N-dimethylsulfamoyl)benzyl | 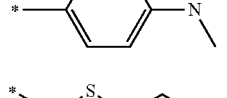 |
| IV-26 | hydrogen | 2-chlorobenzyl | 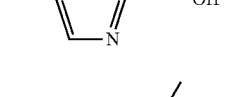 |
| IV-27 | hydrogen | 2-chlorobenzyl | 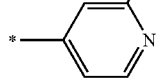 |

TABLE 4-continued
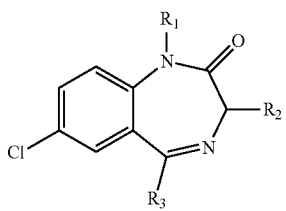
| Compound | R₁ | R₂ | R₃ |
|---|---|---|---|
| IV-28 | hydrogen | 2-chlorobenzyl | 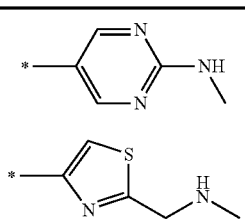 |
| IV-29 | hydrogen | 2-chlorobenzyl | 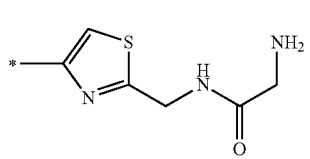 |
| IV-30 | hydrogen | 2-chlorobenzyl | 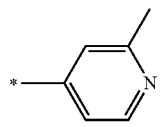 |
| IV-31 | hydrogen | 2-fluorobenzyl | 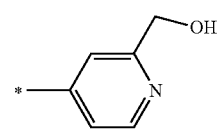 |
| IV-32 | hydrogen | 2-fluorobenzyl | 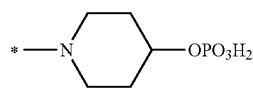 |
| IV-33 | hydrogen | 2-chlorobenzyl | 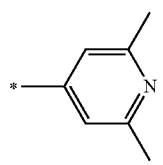 |
| IV-34 | hydrogen | 2-cyanobenzyl | 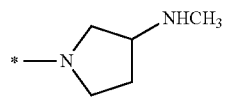 |
| IV-35 | hydrogen | 2-chlorobenzyl | 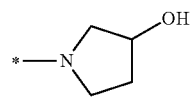 |
| IV-36 | hydrogen | 2-chlorobenzyl | 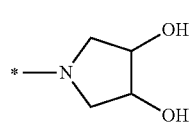 |
| IV-37 | hydrogen | 2-chlorobenzyl | 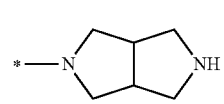 |
| IV-38 | hydrogen | 2-chlorobenzyl | |

TABLE 4-continued

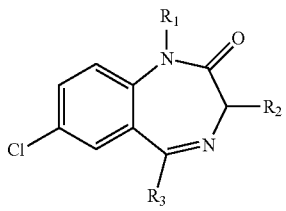

| Compound | R₁ | R₂ | R₃ |
|---|---|---|---|
| IV-39 | hydrogen | 2-chloro-3-fluorobenzyl | 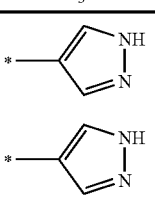 |
| IV-40 | methyl | 2-chlorobenzyl | 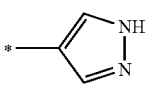 |
| IV-41 | —(CH₂)₂OH | 2-chlorobenzyl | 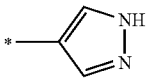 |
| IV-42 | cyclopropyl | 2-chlorobenzyl | 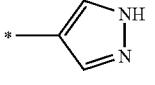 |
| IV-43 | —(CH₂)₂N(CH₃)₂ | 2-chlorobenzyl | 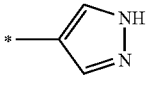 |
| IV-44 | —(CH₂)₂N(CH₃)₂ | 2-(methylsulfonyl)benzyl | 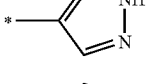 |
| IV-45 | cyclopropyl | 2-cyanobenzyl | 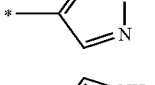 |
| IV-46 | —(CH₂)₂OH | 2-methylbenzyl | 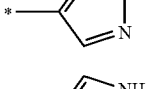 |
| IV-47 | —(CH₂)₂OH | 2-phenylbenzyl | 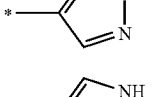 |
| IV-48 | Methyl | 2-methylbenzyl | 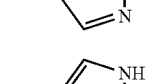 |
| IV-49 | hydrogen | 2-phenylbenzyl | 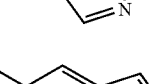 |
| IV-50 | hydrogen | 2-t-butylbenzyl | 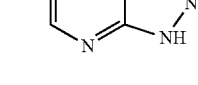 |
| IV-51 | hydrogen | 2-chloro-3-flurobenzyl | 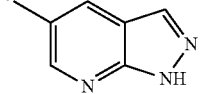 |
| IV-52 | hydrogen | 2-chlorobenzyl |  |

TABLE 4-continued
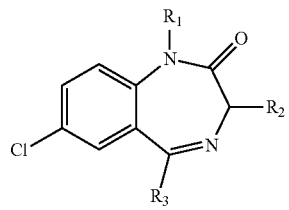
| Compound | R₁ | R₂ | R₃ |
|---|---|---|---|
| IV-53 | hydrogen | 2-chlorobenzyl | 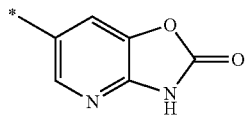 |
| IV-54 | hydrogen | 2-chlorobenzyl | 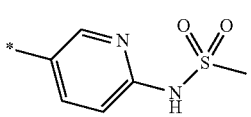 [SMILES: *c1ccc(NS(C)(=O)=O)nc1] |
| IV-55 | hydrogen | 2-chlorobenzyl | 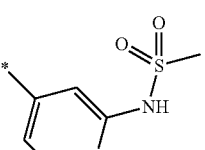 |
| IV-56 | hydrogen | 2-chlorobenzyl | 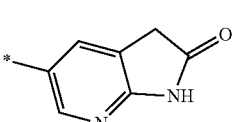 |
| IV-57 | hydrogen | 2-chlorobenzyl | 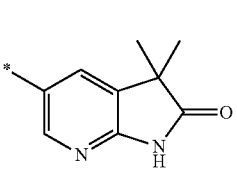 [SMILES: *c1cnc2c(c1)C(C)(C)C(=O)N2] |
TABLE 5
| Compound | Chemical Structure |
|---|---|
| V-1 | 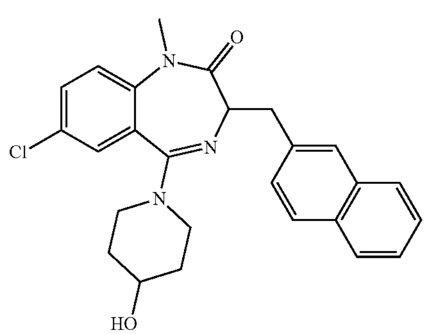 [SMILES: CN1C(=O)C(Cc2ccc3ccccc3c2)N=C(N2CCC(O)CC2)c2cc(Cl)ccc21] |

TABLE 5-continued
| Compound | Chemical Structure |
|---|---|
| V-2 | 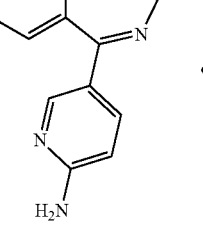 |
| V-3 | 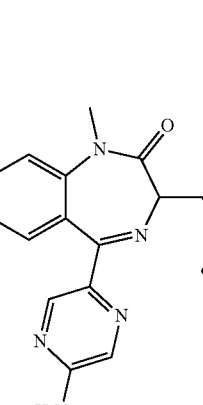 |
| V-4 | 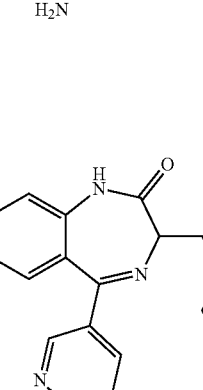 |
| V-5 | 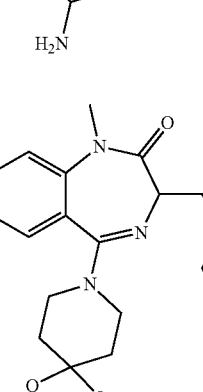 |

TABLE 5-continued

| Compound | Chemical Structure |
|---|---|
| V-6 | 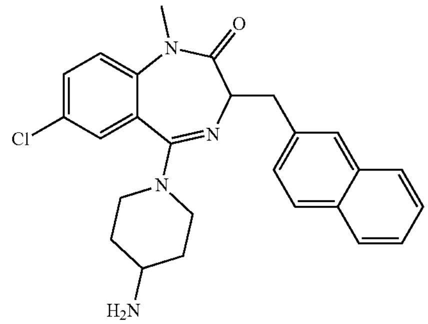 [SMILES: CN1C(=O)C(Cc2ccc3ccccc3c2)N=C(N2CCC(N)CC2)c2cc(Cl)ccc21] |
| V-7 | 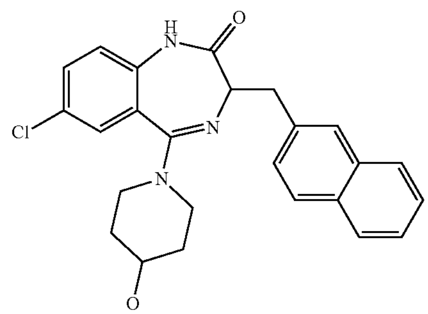 [SMILES: O=C1Nc2ccc(Cl)cc2C(N2CCC(O)CC2)=NC1Cc1ccc2ccccc2c1] |
| V-8 | 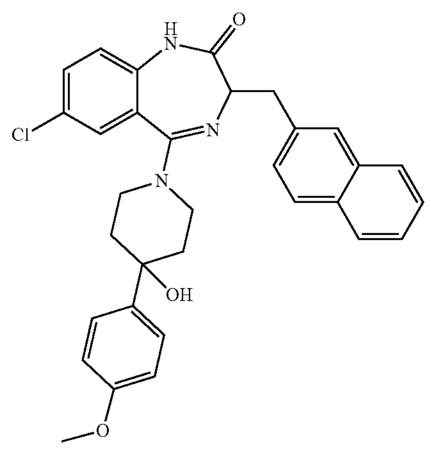 [SMILES: COc1ccc(C2(O)CCN(C3=NC(Cc4ccc5ccccc5c4)C(=O)Nc4ccc(Cl)cc43)CC2)cc1] |
| V-9 | 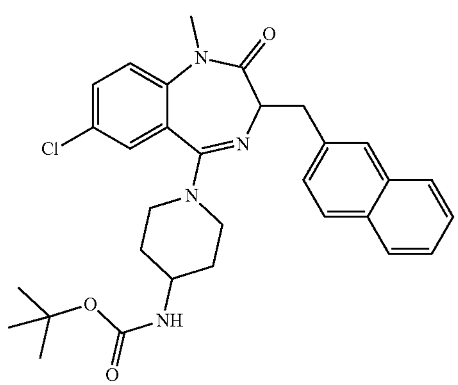 [SMILES: CN1C(=O)C(Cc2ccc3ccccc3c2)N=C(N2CCC(NC(=O)OC(C)(C)C)CC2)c2cc(Cl)ccc21] |

TABLE 5-continued

| Compound | Chemical Structure |
|---|---|
| V-10 | 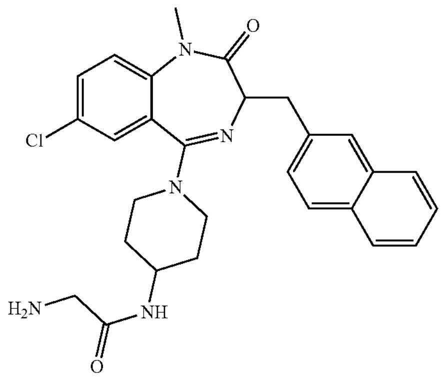 [SMILES: CN1C(=O)C(Cc2ccc3ccccc3c2)N=C(N2CCC(NC(=O)CN)CC2)c2cc(Cl)ccc21] |
| V-11 | 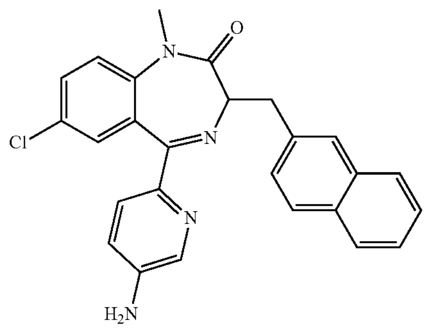 [SMILES: CN1C(=O)C(Cc2ccc3ccccc3c2)N=C(c2ccc(N)cn2)c2cc(Cl)ccc21] |
| V-12 | 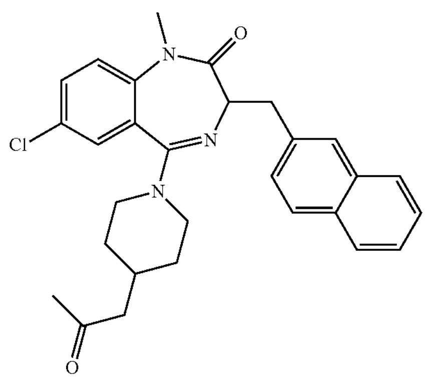 [SMILES: CC(=O)CC1CCN(C2=NC(Cc3ccc4ccccc4c3)C(=O)N(C)c3ccc(Cl)cc32)CC1] |
| V-13 | 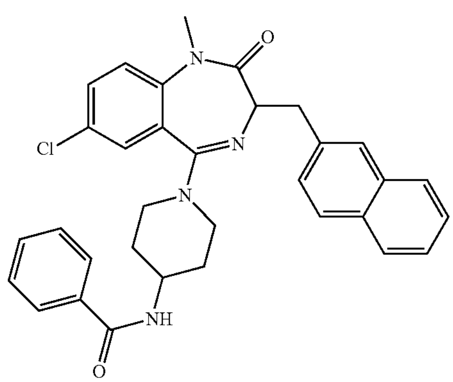 [SMILES: CN1C(=O)C(Cc2ccc3ccccc3c2)N=C(N2CCC(NC(=O)c3ccccc3)CC2)c2cc(Cl)ccc21] |

TABLE 5-continued

| Compound | Chemical Structure |
|---|---|
| V-14 | 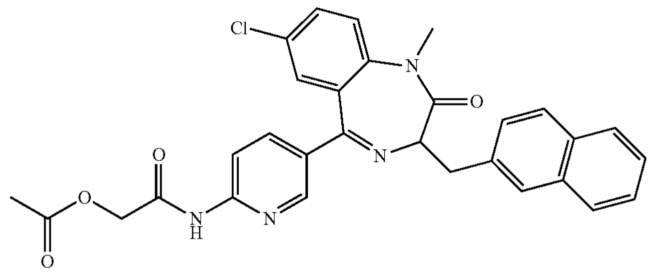 [SMILES: CC(=O)OCC(=O)Nc1ccc(C2=NC(Cc3ccc4ccccc4c3)C(=O)N(C)c3ccc(Cl)cc32)cn1] |
| V-15 | 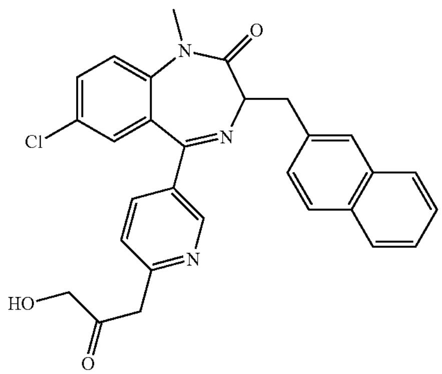 [SMILES: CN1C(=O)C(Cc2ccc3ccccc3c2)N=C(c2ccc(CC(=O)CO)nc2)c2cc(Cl)ccc21] |
| V-16 | 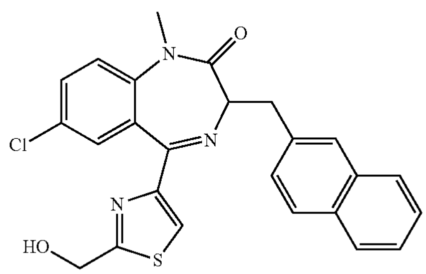 [SMILES: CN1C(=O)C(Cc2ccc3ccccc3c2)N=C(c2csc(CO)n2)c2cc(Cl)ccc21] |
| V-17 | 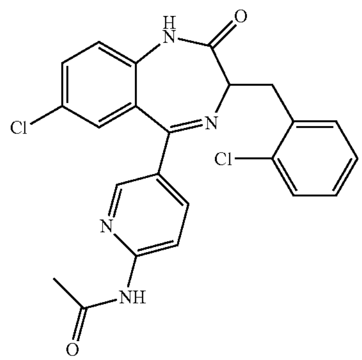 [SMILES: CC(=O)Nc1ccc(C2=NC(Cc3ccccc3Cl)C(=O)Nc3ccc(Cl)cc32)cn1] |
| V-18 | 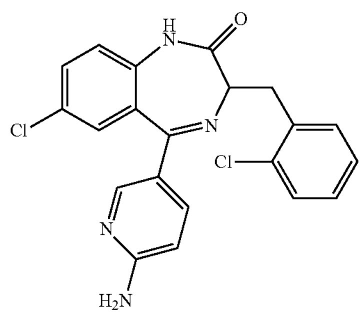 [SMILES: Nc1ccc(C2=NC(Cc3ccccc3Cl)C(=O)Nc3ccc(Cl)cc32)cn1] |

TABLE 5-continued
| Compound | Chemical Structure |
|---|---|
| V-19 | 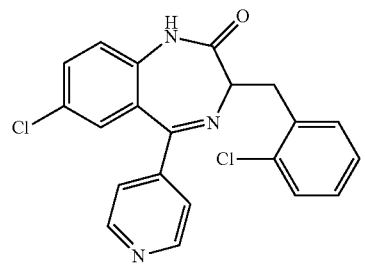 [SMILES: O=C1Nc2ccc(Cl)cc2C(c2ccncc2)=NC1Cc1ccccc1Cl] |
| V-20 | 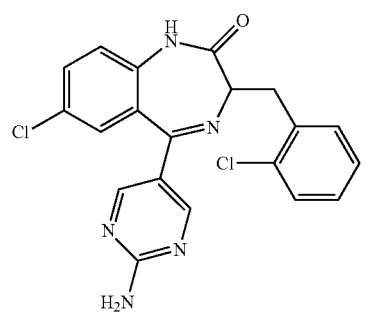 [SMILES: Nc1ncc(C2=NC(Cc3ccccc3Cl)C(=O)Nc3ccc(Cl)cc32)cn1] |
| V-21 | 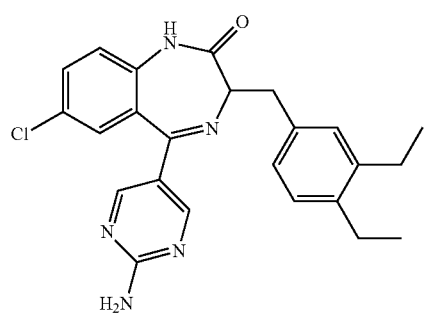 [SMILES: CCc1ccc(CC2N=C(c3cnc(N)nc3)c3cc(Cl)ccc3NC2=O)cc1CC] |
| V-22 | 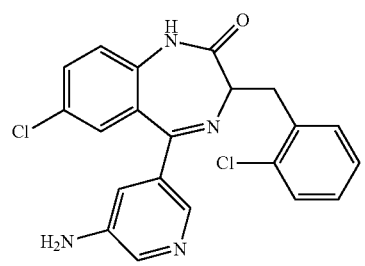 [SMILES: Nc1cncc(C2=NC(Cc3ccccc3Cl)C(=O)Nc3ccc(Cl)cc32)c1] |
| V-23 | 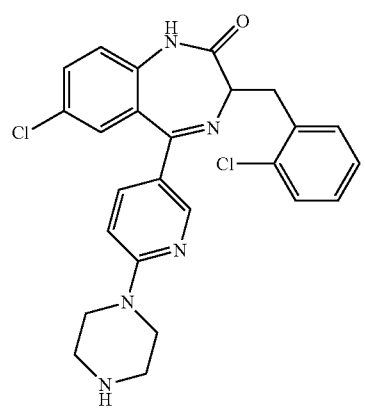 [SMILES: O=C1Nc2ccc(Cl)cc2C(c2ccc(N3CCNCC3)nc2)=NC1Cc1ccccc1Cl] |

TABLE 5-continued

| Compound | Chemical Structure |
|---|---|
| V-24 | 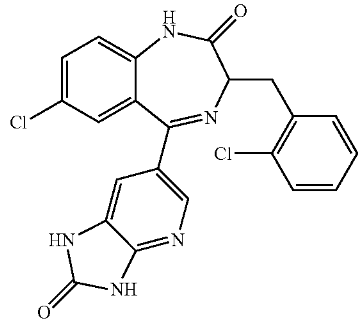 [SMILES: O=C1Nc2ccc(Cl)cc2C(c2cnc3[nH]c(=O)[nH]c3c2)=NC1Cc1ccccc1Cl] |
| V-25 | 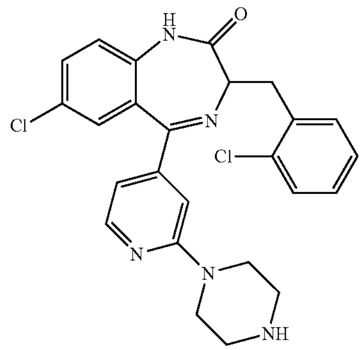 [SMILES: O=C1Nc2ccc(Cl)cc2C(c2ccnc(N3CCNCC3)c2)=NC1Cc1ccccc1Cl] |
| V-26 | 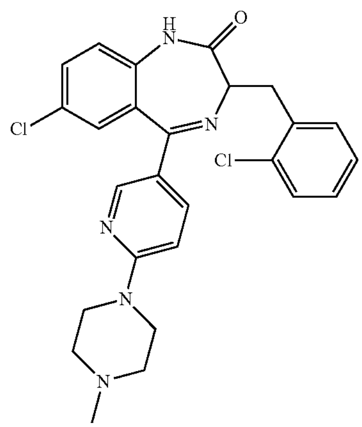 [SMILES: CN1CCN(c2ccc(C3=NC(Cc4ccccc4Cl)C(=O)Nc4ccc(Cl)cc43)cn2)CC1] |
| V-27 | 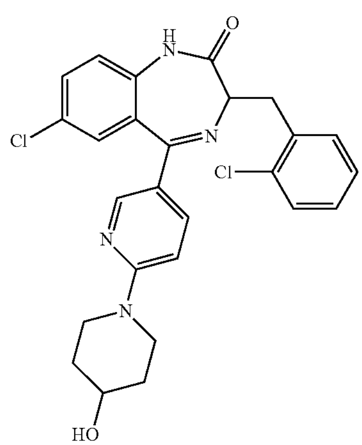 [SMILES: O=C1Nc2ccc(Cl)cc2C(c2ccc(N3CCC(O)CC3)nc2)=NC1Cc1ccccc1Cl] |

TABLE 5-continued
| Compound | Chemical Structure |
|---|---|
| V-28 | 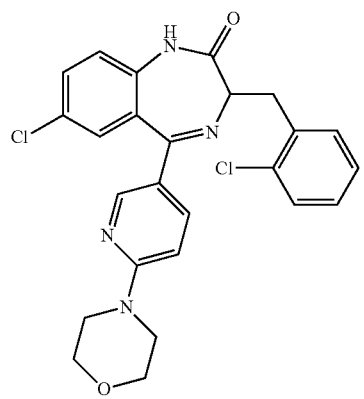 [SMILES: O=C1Nc2ccc(Cl)cc2C(c2ccc(N3CCOCC3)nc2)=NC1Cc1ccccc1Cl] |
| V-29 | 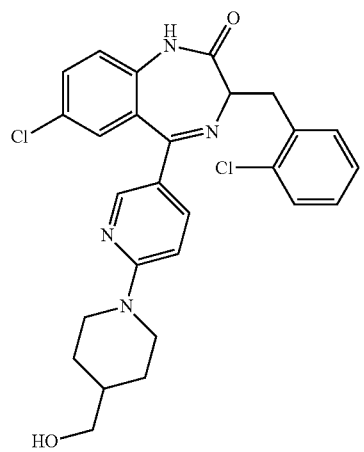 [SMILES: O=C1Nc2ccc(Cl)cc2C(c2ccc(N3CCC(CO)CC3)nc2)=NC1Cc1ccccc1Cl] |
| V-30 | 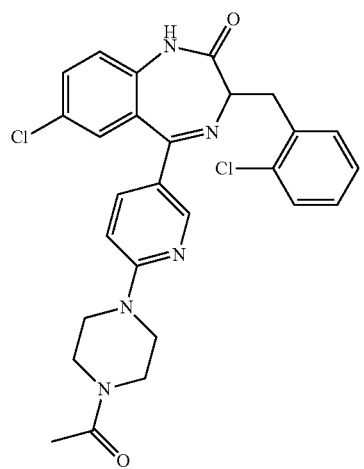 [SMILES: CC(=O)N1CCN(c2ccc(C3=NC(Cc4ccccc4Cl)C(=O)Nc4ccc(Cl)cc43)cn2)CC1] |

TABLE 5-continued
| Compound | Chemical Structure |
|---|---|
| V-31 | 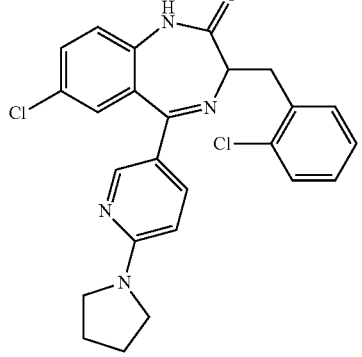 |
| V-32 | 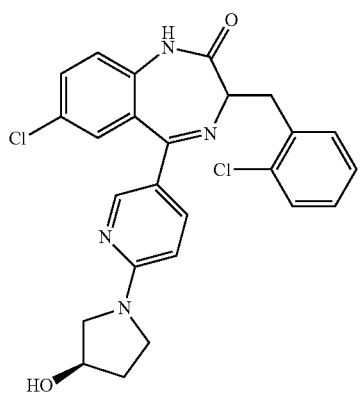 [SMILES: O=C1Nc2ccc(Cl)cc2C(c2ccc(N3CC[C@@H](O)C3)nc2)=NC1Cc1ccccc1Cl] |
| V-33 | 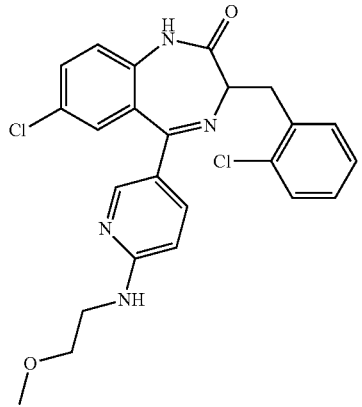 [SMILES: COCCNc1ccc(C2=NC(Cc3ccccc3Cl)C(=O)Nc3ccc(Cl)cc32)cn1] |
| V-34 | 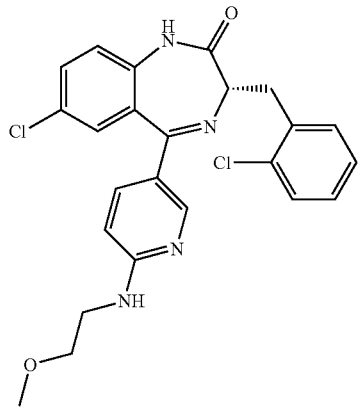 [SMILES: COCCNc1ccc(C2=N[C@@H](Cc3ccccc3Cl)C(=O)Nc3ccc(Cl)cc32)cn1] |

TABLE 5-continued

| Compound | Chemical Structure |
|---|---|
| V-35 | 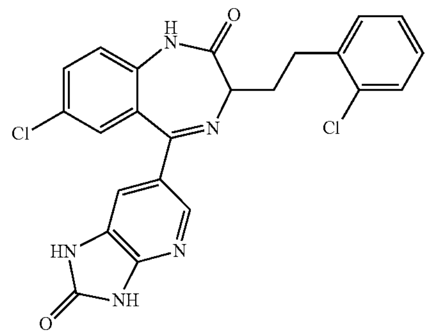 [SMILES: O=C1Nc2ccc(Cl)cc2C(c2cnc3[nH]c(=O)[nH]c3c2)=NC1CCc1ccccc1Cl] |
| V-36 | 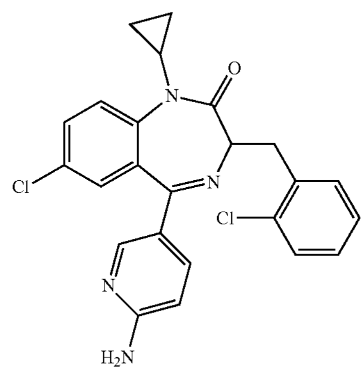 [SMILES: Nc1ccc(C2=NC(Cc3ccccc3Cl)C(=O)N(C3CC3)c3ccc(Cl)cc32)cn1] |
| V-37 | 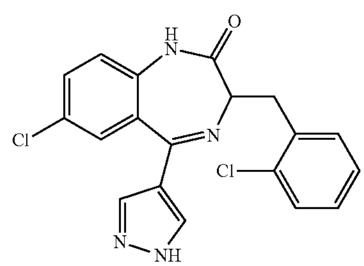 [SMILES: O=C1Nc2ccc(Cl)cc2C(c2cn[nH]c2)=NC1Cc1ccccc1Cl] |
| V-38 | 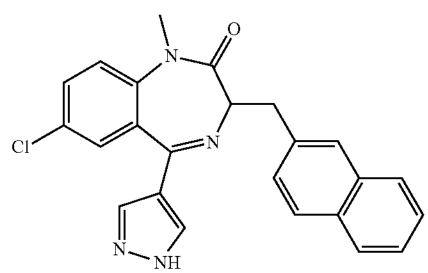 [SMILES: CN1C(=O)C(Cc2ccc3ccccc3c2)N=C(c2cn[nH]c2)c2cc(Cl)ccc21] |
| V-39 | 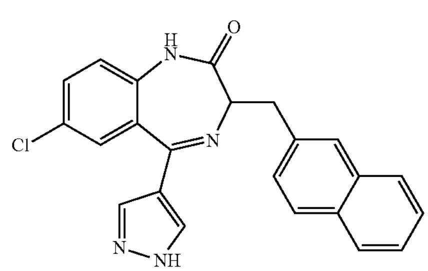 [SMILES: O=C1Nc2ccc(Cl)cc2C(c2cn[nH]c2)=NC1Cc1ccc2ccccc2c1] |

TABLE 5-continued

| Compound | Chemical Structure |
| --- | --- |
| V-40 | 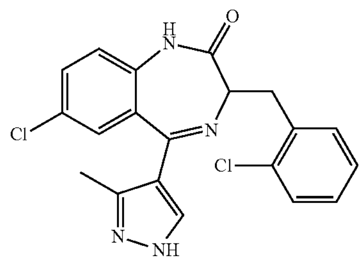 [SMILES: Cc1n[nH]cc1C1=NC(Cc2ccccc2Cl)C(=O)Nc2ccc(Cl)cc21] |
| V-41 | | or a pharmaceutically acceptable salt thereof.

22. A pharmaceutical composition, comprising a compound of claim 1 and a pharmaceutically acceptable carrier.

23. A method of treating cancer in a subject, comprising administering to a subject in need thereof a compound of claim 1, wherein the cancer is breast cancer, colon cancer, small-cell lung cancer, non-small cell lung cancer, prostate cancer, renal cancer, ovarian cancer, melanoma, cancer of the central nervous system tissue, pancreatic cancer, cervical cancer, testicular cancer, bladder cancer, brain cancer, skin cancer, thyroid cancer, Hodgkin's lymphoma, non-Hodgkin's lymphoma, cutaneous T-Cell lymphoma, cutaneous B-Cell lymphoma, or diffuse large B-Cell lymphoma.

24. The method of claim 23, wherein the cancer is breast cancer, colon cancer, small-cell lung cancer, non-small cell lung cancer, prostate cancer, renal cancer, ovarian cancer, melanoma, or cancer of the central nervous system tissue.

* * * * *

UNITED STATES PATENT AND TRADEMARK OFFICE
CERTIFICATE OF CORRECTION

PATENT NO.      : 8,604,023 B2
APPLICATION NO. : 13/263962
DATED           : December 10, 2013
INVENTOR(S)     : Gary D. Glick et al.

It is certified that error appears in the above-identified patent and that said Letters Patent is hereby corrected as shown below:

Title Page:

Column 2 (56) Other Publications), line 5, delete "derivaties" and insert -- derivatives --, therefor.

In the Claims:

Column 195 (Table 1 Compound I-69), line 1, in Claim 21, delete "  " and insert -- --, therefor.

Column 219 (Table 4 Compound IV-12), line 14, in Claim 21, delete " 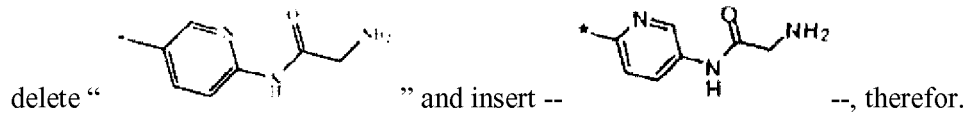 " and insert -- --, therefor.

Column 225 (Table 4 Compound IV-51), line 1, in Claim 21, delete "2-chloro-3-flurobenzyl" and insert -- 2-chloro-3-fluorobenzyl --, therefor.

Column 231 (Table 5 Compound V-7), line 1, in Claim 21, delete " 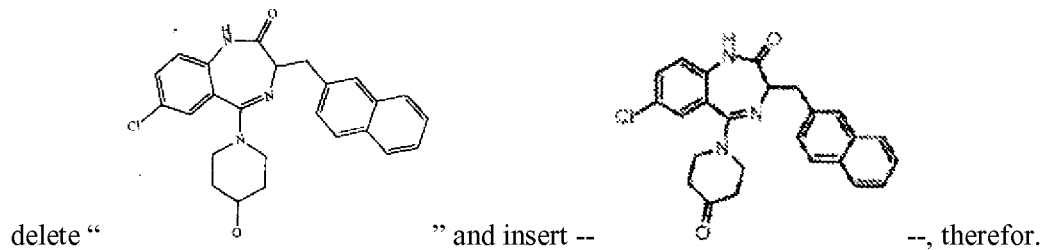 " and insert -- --, therefor.

Signed and Sealed this
Twenty-seventh Day of May, 2014

Michelle K. Lee
*Deputy Director of the United States Patent and Trademark Office*

CERTIFICATE OF CORRECTION (continued)
U.S. Pat. No. 8,604,023 B2

Column 233 (Table 5 Compound V-12), line 1, in Claim 21,

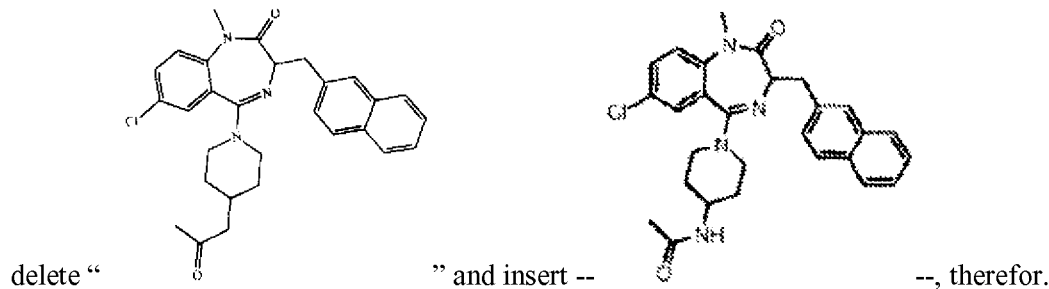

delete " " and insert -- --, therefor.

Column 235 (Table 5 Compound V-15), line 1, in Claim 21,

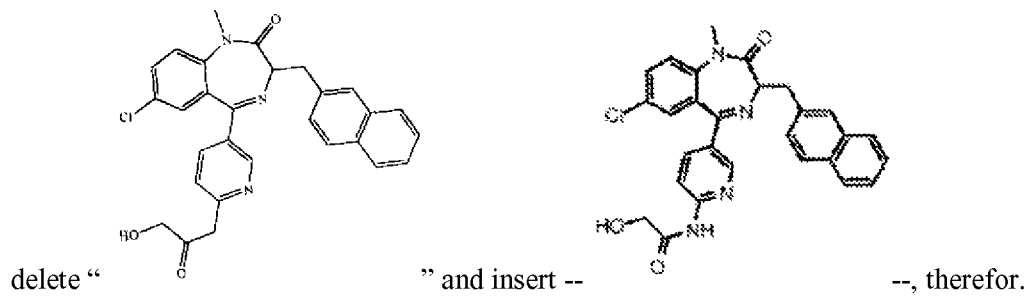

delete " " and insert -- --, therefor.